(12) United States Patent
Lee et al.

(10) Patent No.: US 10,253,016 B2
(45) Date of Patent: Apr. 9, 2019

(54) HETEROCYCLIC COMPOUND AND ORGANIC LIGHT-EMITTING DEVICE COMPRISING SAME

(71) Applicant: LG CHEM, LTD., Seoul (KR)

(72) Inventors: Hoyong Lee, Daejeon (KR); Seongmi Cho, Daejeon (KR); Kongkyeom Kim, Daejeon (KR); Sang Young Jeon, Daejeon (KR); Minseung Chun, Daejeon (KR); Hyoung Seok Kim, Daejeon (KR); Dongheon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 7 days.

(21) Appl. No.: 14/908,095

(22) PCT Filed: Jul. 10, 2014

(86) PCT No.: PCT/KR2014/006184
§ 371 (c)(1),
(2) Date: Jan. 27, 2016

(87) PCT Pub. No.: WO2015/016498
PCT Pub. Date: Feb. 5, 2015

(65) Prior Publication Data
US 2016/0204359 A1 Jul. 14, 2016

(30) Foreign Application Priority Data
Jul. 29, 2013 (KR) .................. 10-2013-0089869

(51) Int. Cl.
*C07D 401/14* (2006.01)
*C09K 11/02* (2006.01)
*C07D 403/14* (2006.01)
*C09K 11/06* (2006.01)
(Continued)

(52) U.S. Cl.
CPC ......... *C07D 401/14* (2013.01); *C07D 403/14* (2013.01); *C09K 11/025* (2013.01); *C09K 11/06* (2013.01); *H01L 51/0067* (2013.01); *H01L 51/0072* (2013.01); *H01L 51/5016* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/185* (2013.01); *H01L 51/006* (2013.01); *H01L 51/0052* (2013.01); *H01L 51/0085* (2013.01)

(58) Field of Classification Search
None
See application file for complete search history.

(56) References Cited

U.S. PATENT DOCUMENTS

2011/0210318 A1   9/2011   Bae et al.
2012/0086329 A1   4/2012   Dyatkin
2012/0211736 A1   8/2012   Kim et al.
(Continued)

FOREIGN PATENT DOCUMENTS

CN   103155195 A   6/2013
EP   2568030 A2    3/2013
(Continued)

*Primary Examiner* — Eli S Mekhlin
(74) *Attorney, Agent, or Firm* — Dentons US LLP

(57) ABSTRACT

The present specification provides a heterocyclic compound and an organic light emitting device comprising the same.

11 Claims, 8 Drawing Sheets

(51) Int. Cl.
  *H01L 51/00*   (2006.01)
  *H01L 51/50*   (2006.01)

(56) References Cited

U.S. PATENT DOCUMENTS

| | | | |
|---|---|---|---|
| 2012/0223276 A1 | 9/2012 | Parham et al. | |
| 2014/0158999 A1* | 6/2014 | Jung | C09K 11/06 257/40 |
| 2015/0126736 A1* | 5/2015 | Cho | C07D 401/14 544/212 |
| 2015/0171342 A1* | 6/2015 | Jung | C07D 405/14 257/40 |

FOREIGN PATENT DOCUMENTS

| | | |
|---|---|---|
| EP | 2 878 599 A1 | 6/2015 |
| JP | 2009021336 A | 1/2009 |
| JP | 2010040830 A | 2/2010 |
| JP | 2013-510141 A | 3/2013 |
| KR | 20120104246 A | 9/2012 |
| KR | 20130069431 A | 6/2013 |
| WO | 2010021524 A3 | 2/2010 |
| WO | 2011/139055 A2 | 11/2011 |
| WO | 2012048266 A1 | 4/2012 |
| WO | 2013/073874 A1 | 5/2013 |
| WO | 2013/100540 A1 | 7/2013 |

* cited by examiner

[Figure 1]
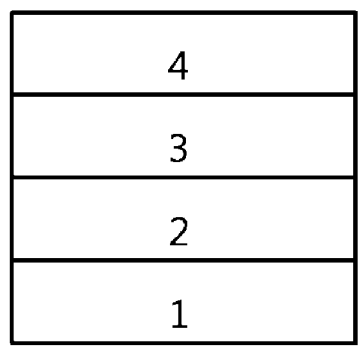
[Figure 2]
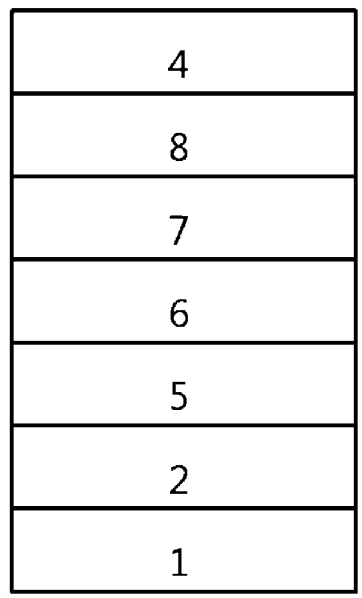

[Figure 3]
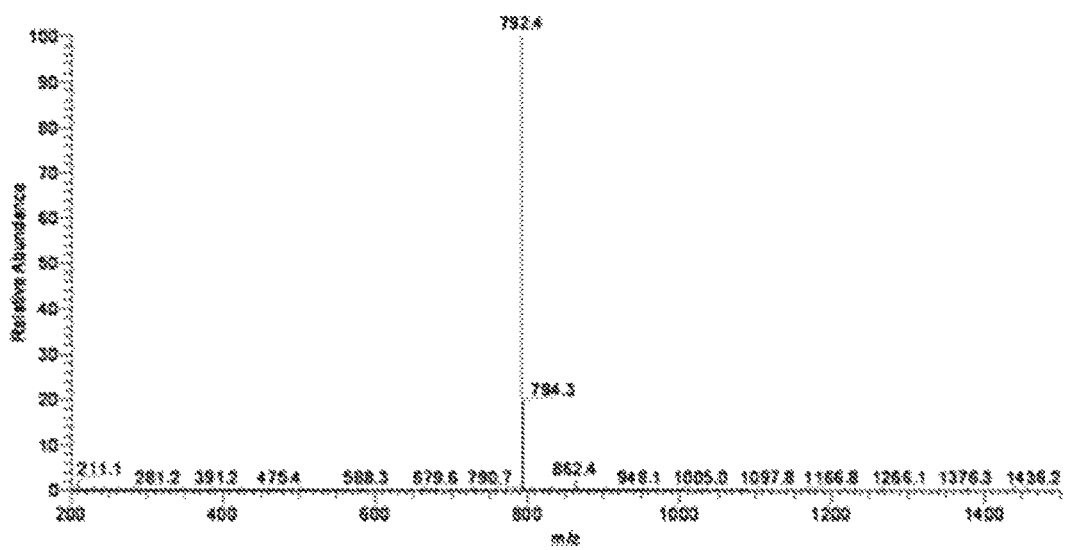
Mass spectrum of chemical Formula 1-1
[Figure 4]
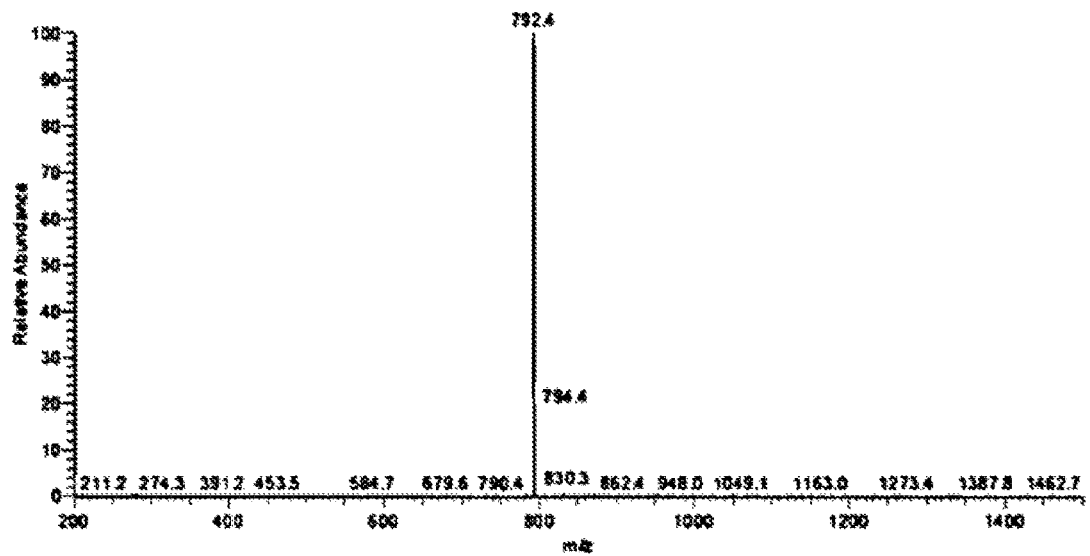
Mass spectrum of chemical Formula 1-2

[Figure 5]
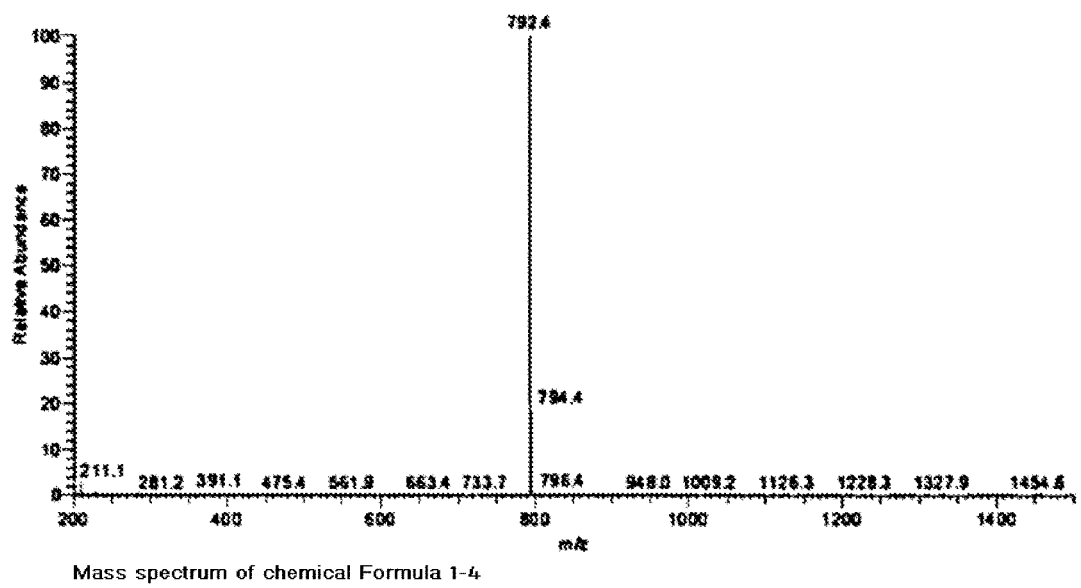
Mass spectrum of chemical Formula 1-4
[Figure 6]
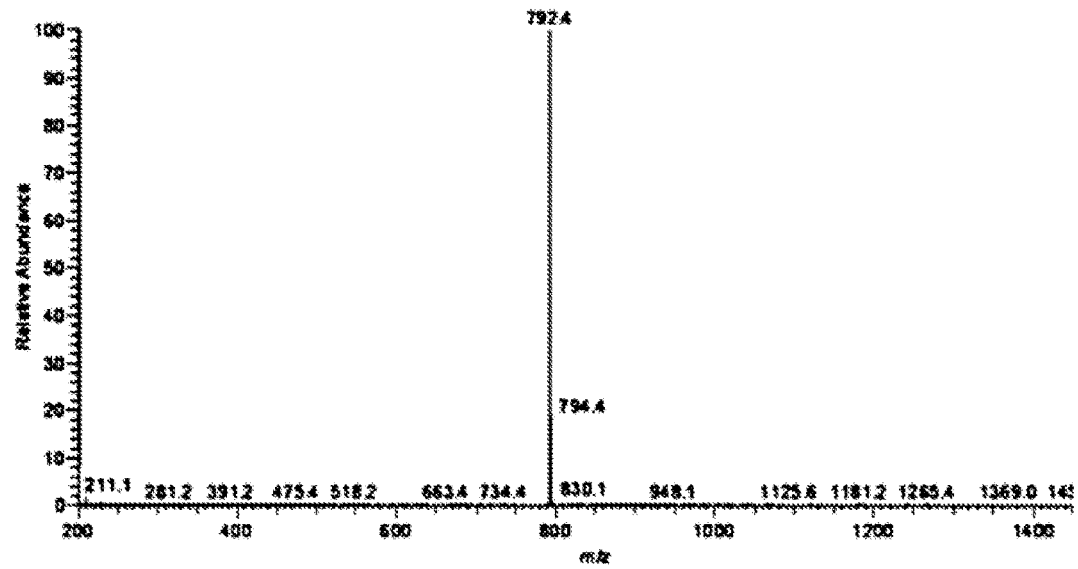
Mass spectrum of chemical Formula 1-5

[Figure 7]
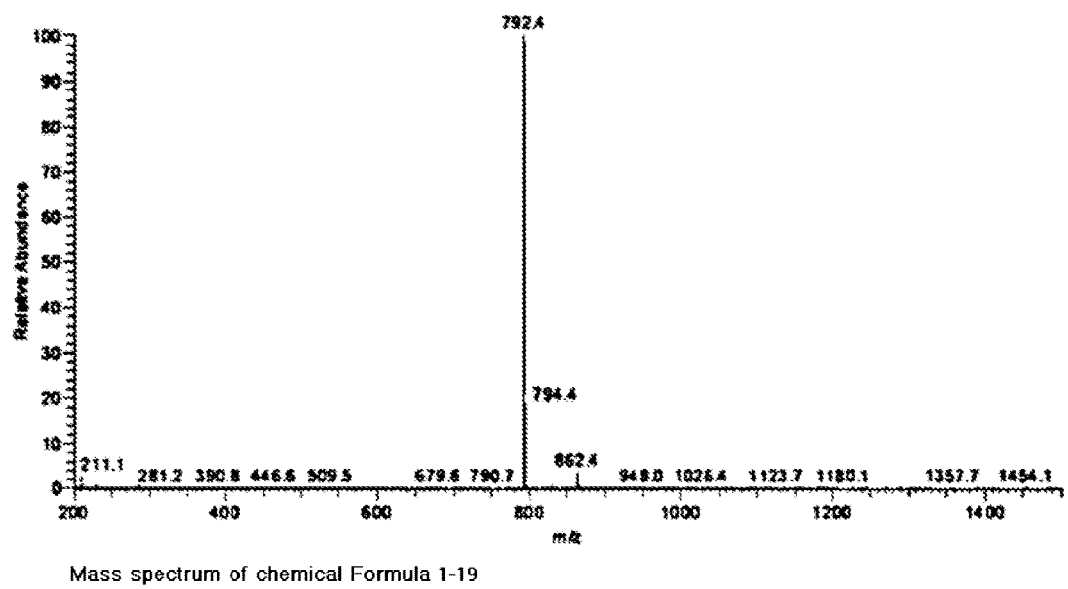
Mass spectrum of chemical Formula 1-19
[Figure 8]
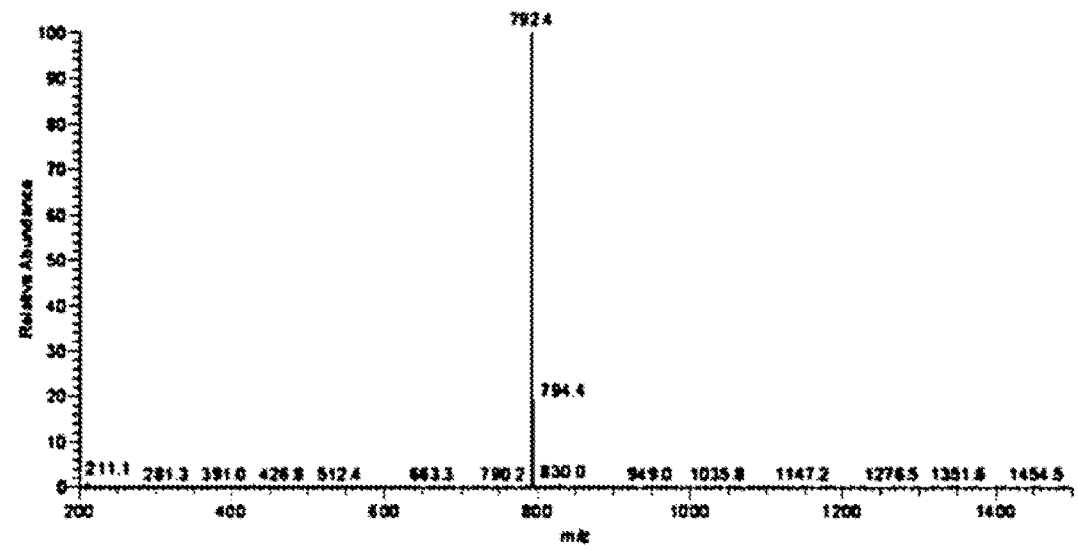
Mass spectrum of chemical Formula 1-23

[Figure 9]
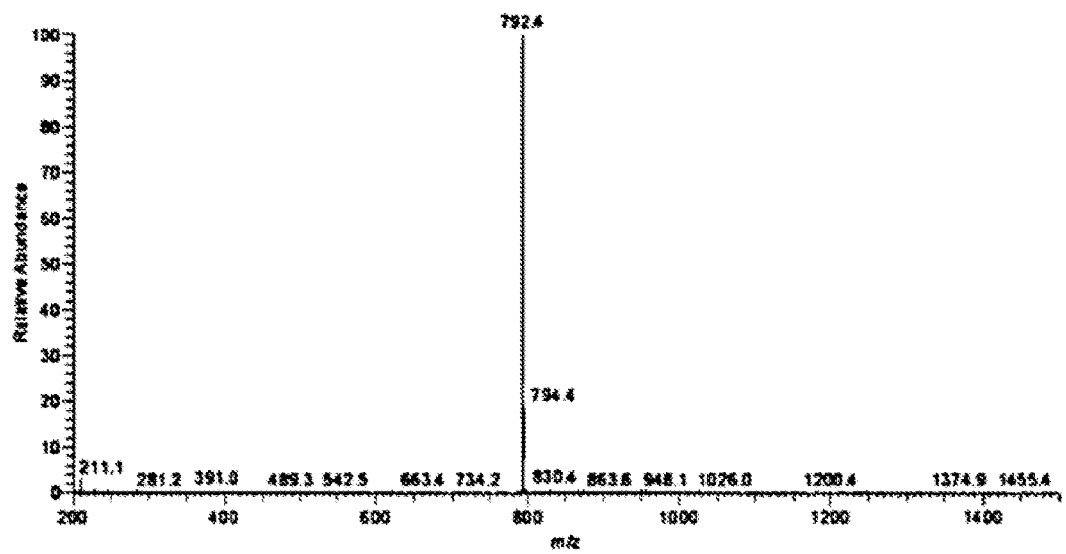
Mass spectrum of chemical Formula 1-70
[Figure 10]
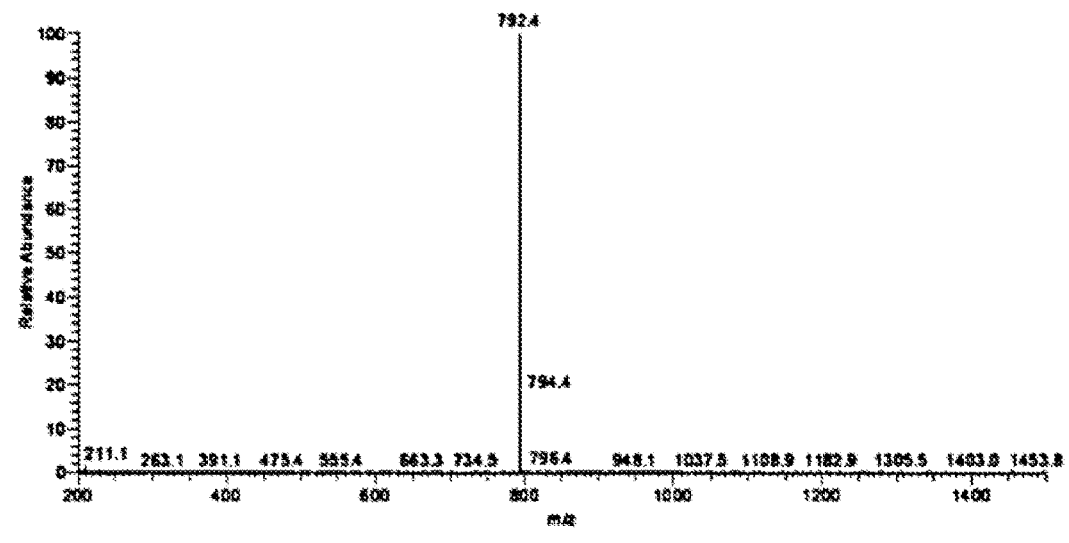
Mass spectrum of chemical Formula 1-71

[Figure 11]
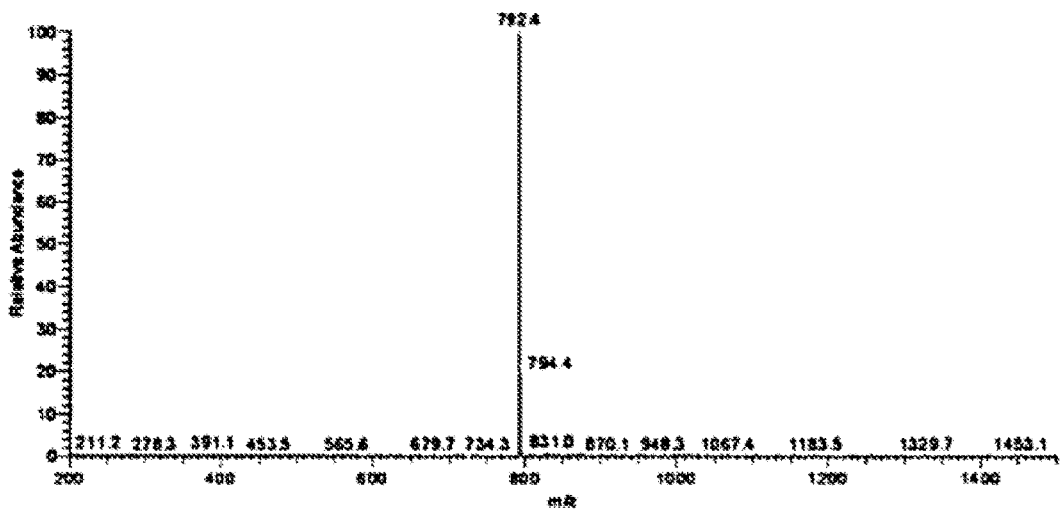
Mass spectrum of chemical Formula 1-74
[Figure 12]
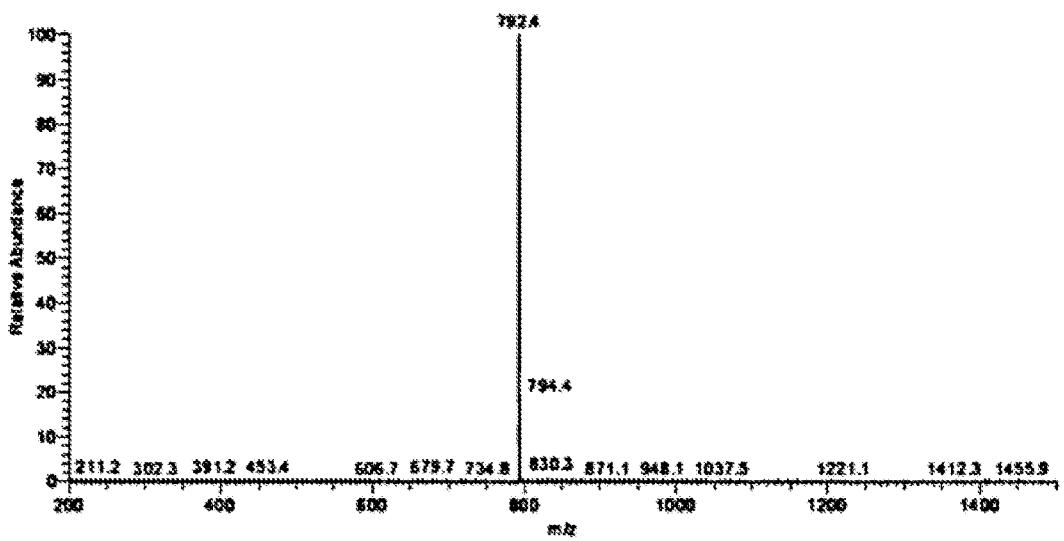
Mass spectrum of chemical Formula 1-142

[Figure 13]
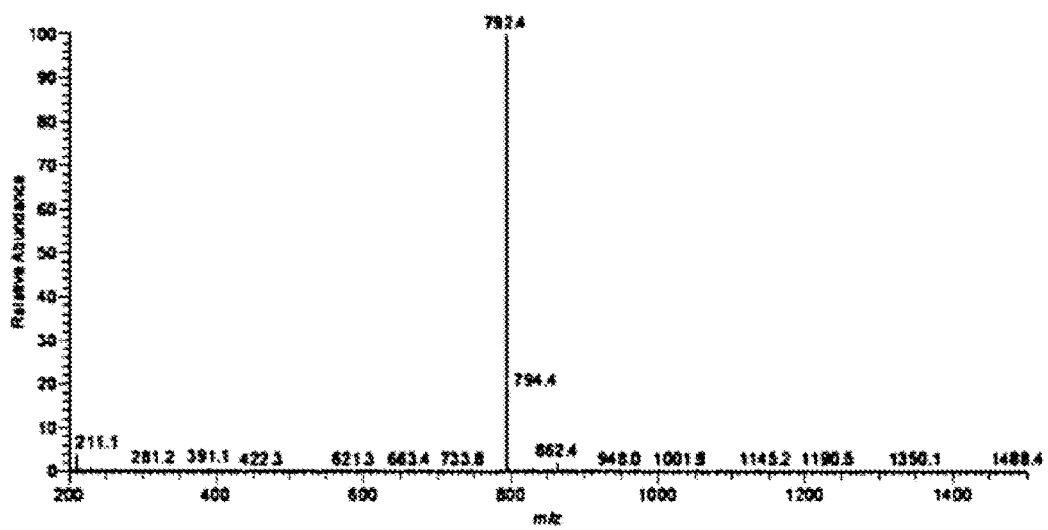
Mass spectrum of chemical Formula 1-160
[Figure 14]
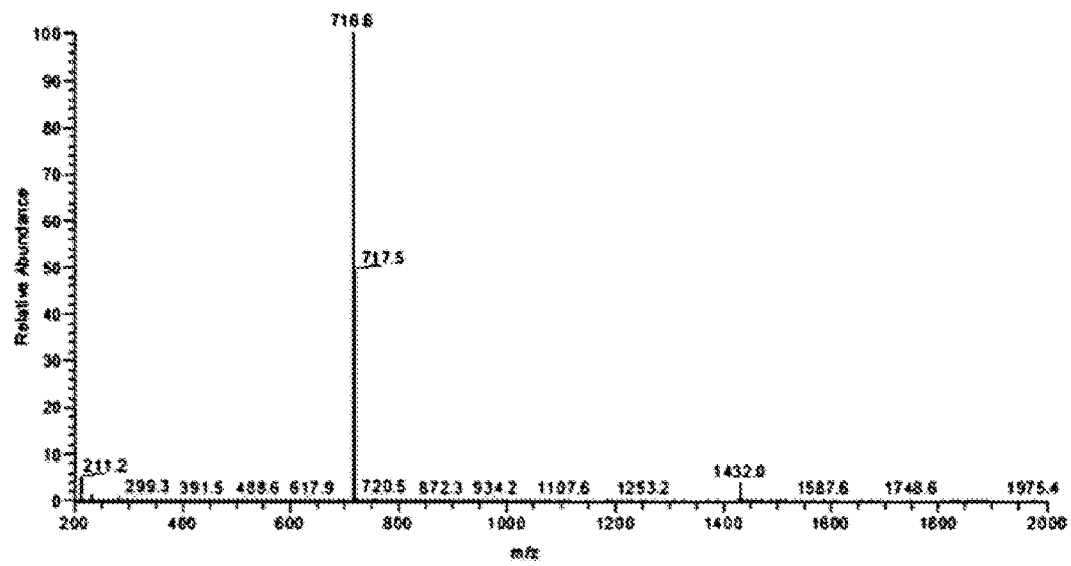
Mass spectrum of chemical Formula 1-219

[Figure 15]
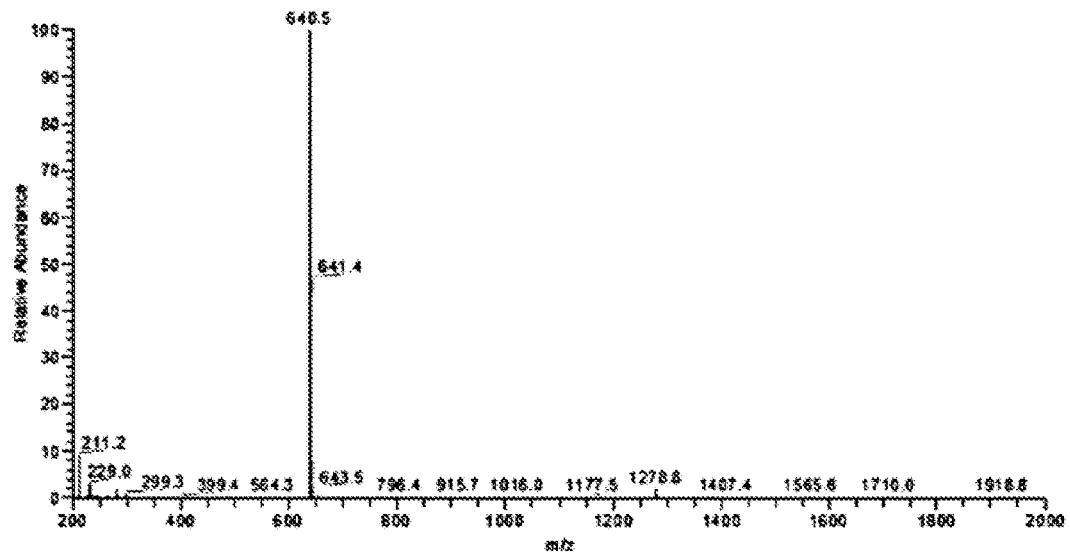
Mass spectrum of chemical Formula 1-227
[Figure 16]
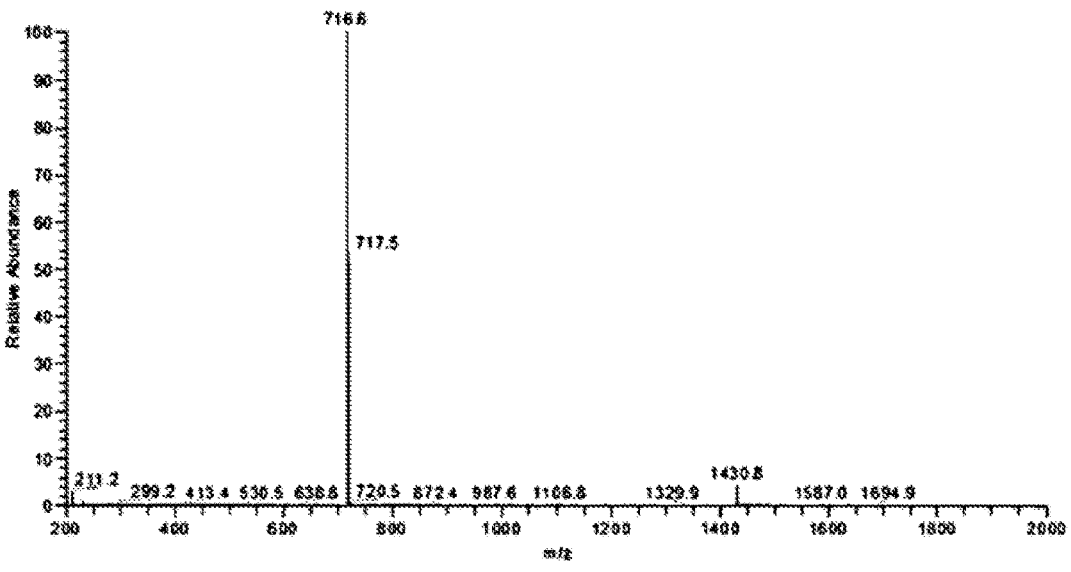
Mass spectrum of chemical Formula 1-228

HETEROCYCLIC COMPOUND AND ORGANIC LIGHT-EMITTING DEVICE COMPRISING SAME

CROSS-REFERENCE

This application is a National Stage Application of International Application No. PCT/KR2014/006184, filed Jul. 10, 2014, and claims priority to and the benefit of Korean Patent Application No. 10-2013-0089869, filed on Jul. 29, 2013, the contents of each which is incorporated by reference in its entirety for all purposes as if fully set forth below.

TECHNICAL FIELD

The present specification relates to a heterocyclic compound and an organic light emitting device comprising the same.

BACKGROUND ART

In general, an organic light emitting phenomenon means a phenomenon where electric energy is converted into light energy by using an organic material. An organic light emitting device using the organic light emitting phenomenon has a structure generally including an anode, a cathode, and an organic material layer interposed therebetween. Herein, in many cases, the organic material layer has a multilayered structure constituted by different materials in order to increase efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from the anode to the organic material layer and the electrons are injected from the cathode to the organic material layer, and when the injected holes and electrons meet each other, an exciton is formed, and light is emitted when the exciton falls to a bottom state again.

There is a continuous demand for developing a novel material for the aforementioned organic light emitting device.

DISCLOSURE

Technical Problem

The present specification describes a novel heterocyclic compound and an organic light emitting device comprising the same.

Technical Solution

An exemplary embodiment of the present specification provides a compound represented by the following Chemical Formula 1.

[Chemical Formula 1]

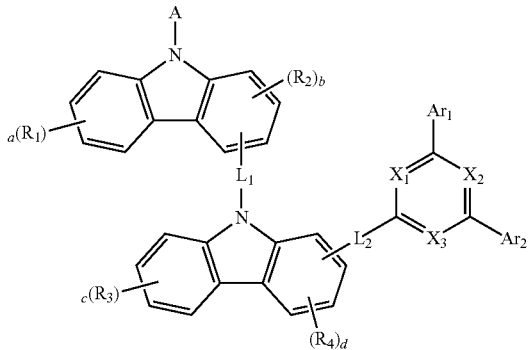

In Chemical Formula 1, $L_1$ is a direct bond; substituted or unsubstituted phenylene; or a substituted or unsubstituted divalent monocyclic heterocyclic group including one or more of N, O, and S atoms, $L_2$ is a direct bond; a substituted or unsubstituted arylene group; or a substituted or unsubstituted divalent heterocyclic group including one or more of N, O, and S atoms, $X_1$ is N or $CR_{11}$, $X_2$ is N or $CR_{12}$, $X_3$ is N or $CR_{13}$, A is hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted phenyl group; a substituted or unsubstituted biphenyl group; or a substituted or unsubstituted aromatic or aliphatic monocyclic six-membered heterocyclic group including one or more of N, O, and S atoms, $Ar_1$ and $Ar_2$ are the same as or different from each other, and are each independently hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted aryl group; a substituted or unsubstituted fluorenyl group; or a substituted or unsubstituted aromatic or aliphatic heterocyclic group including one or more of N, O, and S atoms, but do not include a carbazole group, $R_1$ to $R_4$ and $R_{11}$ to $R_{13}$ are the same as or different from each other, and are each independently hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted aryl group; a substituted or unsubstituted fluorenyl group; or a substituted or unsubstituted aromatic or aliphatic heterocyclic group including one or more of N, O, and S atoms, a and c are each an integer of 0 to 4, b and d are each an integer of 0 to 3, in the case where a is 2 or more, $R_1$s are the same as or different from each other, in the case where b is 2 or more, $R_2$s are the same as or different from each other, in the case where c is 2 or more, $R_3$s are the same as or different from each other, and in the case where d is 2 or more, $R_4$s are the same as or different from each other.

Another exemplary embodiment of the present specification provides an organic light emitting device including: a first electrode; a second electrode provided to face the first electrode; and one or more organic material layers provided between the first electrode and the second electrode, in which one or more of the organic material layers include the compound of Chemical Formula 1.

Advantageous Effects

A compound described in the present specification may be used as a material of an organic material layer of an organic light emitting device. The compound according to at least some exemplary embodiments can improve efficiency, and low driving voltage and/or life-span characteristics in the organic light emitting device. Particularly, in the case where the compound described in the present specification is used as a host of a phosphorescent light emitting layer or an electron transport material adjacent to a light emitting layer, it is possible to provide the organic light emitting device having high efficiency and/or a long life-span.

DESCRIPTION OF DRAWINGS

FIG. 1 illustrates an example of an organic light emitting device including a substrate 1, an anode 2, a light emitting layer 3, and a cathode 4.

FIG. 2 illustrates an example of an organic light emitting device including a substrate 1, an anode 2, a hole injection layer 5, a hole transport layer 6, a light emitting layer 7, an electron transport layer 8, and a cathode 4.

FIGS. 3 to 16 illustrate data for confirming synthesis of main compounds.

MODE FOR INVENTION

Hereinafter, the present specification will be described in more detail.

An exemplary embodiment of the present specification provides a compound represented by Chemical Formula 1.

In the present specification, { means a bond connected to another substituent group.

Examples of the substituent groups will be described below, but are not limited thereto.

In the present specification, the term "substituted or unsubstituted" means that substitution is performed by one or more substituent groups selected from the group consisting of deuterium; a halogen group; a nitrile group; a nitro group; an imide group; an amide group; a hydroxy group; a thiol group; an alkyl group; an alkenyl group; an alkoxy group; a cycloalkyl group; a silyl group; an arylalkenyl group; an aryl group; an aryloxy group; an alkylthioxy group; an arylthioxy group; an alkylsulfoxy group; an arylsulfoxy group; a silyl group; a boron group; a carbazole group; an aryl group; a fluorenyl group; an arylalkyl group; an arylalkenyl group; and a heterocyclic group including one or more of O, N, and S as a heteroatom, or there is no substituent group, or substitution is performed by a substituent group where two or more substituent groups of the exemplified substituent groups are connected or there is no substituent group. For example, the term "substituent group where two or more substituent groups are connected" may be a biphenyl group. That is, the biphenyl group may be an aryl group, or may be interpreted as a substituent group where two phenyl groups are connected.

In the present specification, examples of a halogen group include fluorine, chlorine, bromine, or iodine.

In the present specification, the number of carbon atoms of a carbonyl group is not particularly limited but is preferably 1 to 50. Specifically, the carbonyl group may be compounds having the following structures, but is not limited thereto.

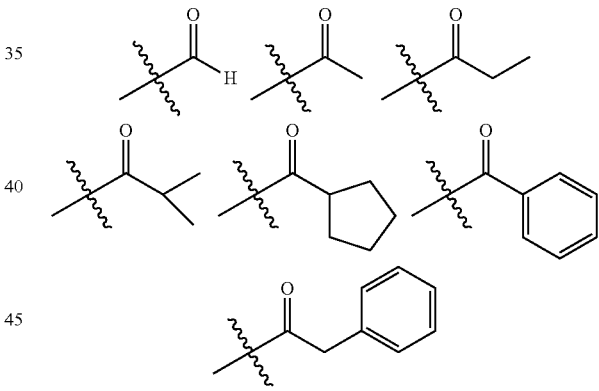

In the present specification, oxygen of an ester group may be substituted by a straight-chained, branched-chained, or cyclic-chained alkyl group having 1 to 25 carbon atoms, or an aryl group having 6 to 25 carbon atoms. Specifically, the ester group may be compounds having the following Structural Formulas, but is not limited thereto.

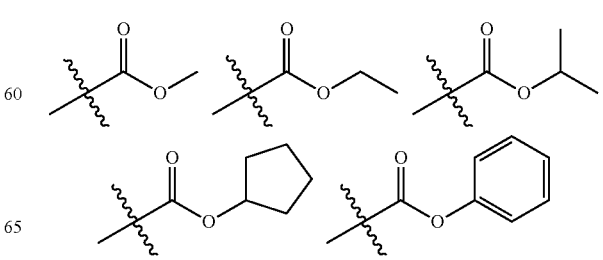

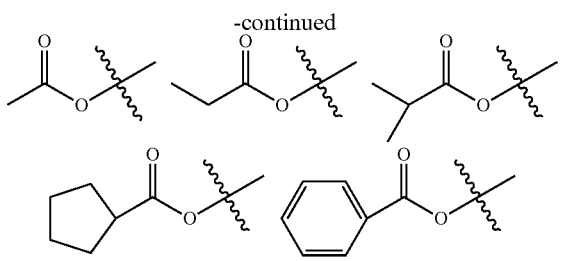

In the present specification, the number of carbon atoms of an imide group is not particularly limited but is preferably 1 to 25. Specifically, the imide group may be compounds having the following structures, but is not limited thereto.

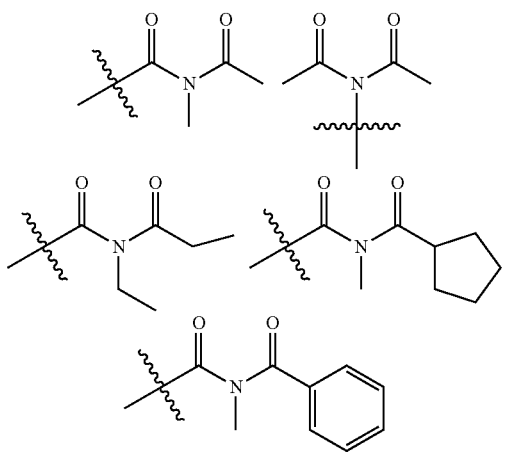

In the present specification, one or two nitrogen atoms of an amide group may be substituted by hydrogen, a straight-chained, branched-chained, or cyclic-chained alkyl group having 1 to 25 carbon atoms, or an aryl group having 6 to 25 carbon atoms. Specifically, the amide group may be compounds having the following Structural Formulas, but is not limited thereto.

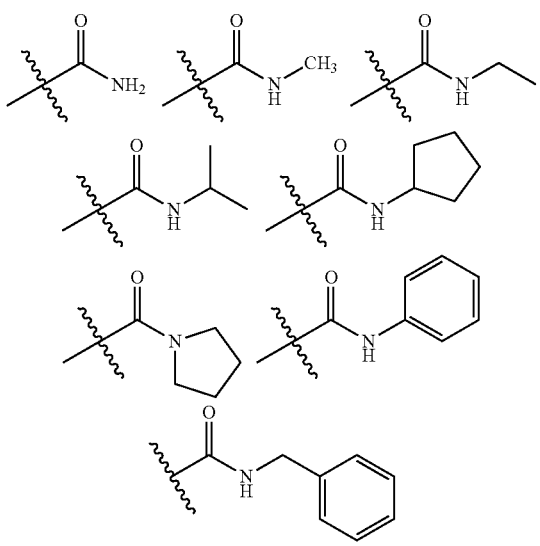

In the present specification, an alkyl group may be a straight or branched chain, and the number of carbon atoms thereof is not particularly limited but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohectylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be a straight, branched, or cyclic chain. The number of carbon atoms of the alkoxy group is not particularly limited, but preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be a straight or branched chain, and the number of carbon atoms thereof is not particularly limited but is preferably 2 to 40. Specific examples thereof include vinyl, 1-prophenyl, iso-prophenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the aryl group may be a monocyclic aryl group or a polycyclic aryl group, and includes the case where an alkyl group having 1 to 25 carbon atoms or an alkoxy group having 1 to 25 carbon atoms is substituted. Further, in the present specification, the aryl group may mean an aromatic cycle.

In the case where the aryl group is the monocyclic aryl group, the number of carbon atoms is not particularly limited but is preferably 6 to 25. Specific examples of the monocyclic aryl group may include a phenyl group, a biphenyl group, a terphenyl group, a stilbenyl group, or the like, but are not limited thereto.

In the case where the aryl group is the polycyclic aryl group, the number of carbon atoms thereof is not particularly limited but is preferably 10 to 24. Specific examples of the polycyclic aryl group may include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and two substituent groups may be bonded to each other to form a spiro structure.

In the case where the fluorenyl group is substituted,

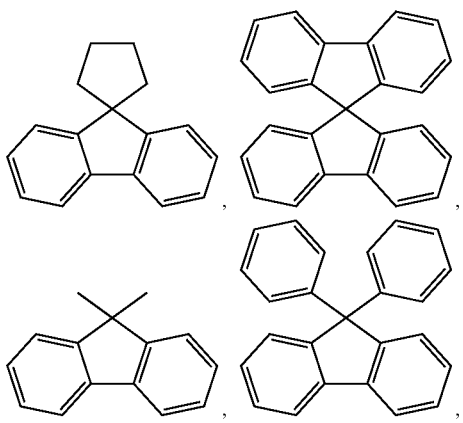

and the like may be formed. However, the structure is not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the heterocyclic group is a heterocyclic group including one or more of O, N, and S as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group of the aryloxy group, the arylthioxy group, and the arylsulfoxy group is the same as the aforementioned examples of the aryl group. Specific examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, specific examples of the arylthioxy group include a phenylthioxy group, a 2-methylphenylthioxy group, a 4-tert-butylphenylthioxy group, and the like, and specific examples of the arylsulfoxy group include a benzenesulfoxy group, a p-toluenesulfoxy group, and the like, but the examples are not limited thereto.

In the present specification, the alkyl group of an alkylthioxy group and an alkylsulfoxy group is the same as the aforementioned examples of the alkyl group. Specific examples of the alkylthioxy group include a methylthioxy group, an ethylthioxy group, a tert-butylthioxy group, a hexylthioxy group, an octylthioxy group, and the like, and specific examples of the alkylsulfoxy group include a methylsulfoxy group, an ethylsulfoxy group, a propylsulfoxy group, a butylsulfoxy group, and the like, but the examples are not limited thereto.

In the present specification, an arylene group means a matter where two bonding positions exist at the aryl group, that is, a divalent group. Excepting that the groups are each the divalent group, the aforementioned description of the aryl group may be applied.

In the present specification, a divalent heterocyclic group means a matter where two bonding positions exist at the heterocyclic group, that is, a divalent group. Excepting that the groups are each the divalent group, the aforementioned description of the heterocyclic group may be applied.

According to the exemplary embodiment of the present specification, A of Chemical Formula 1 is a substituted or unsubstituted phenyl group; a substituted or unsubstituted biphenyl group; or a substituted or unsubstituted aromatic or aliphatic monocyclic six-membered heterocyclic group including one or more of N, O, and S atoms. In the case where the polycycle is positioned at a position A, synthesis is not easy and a molecular weight is excessively increased, and thus a deposition temperature is excessively high, and in this case, processability is not good.

According to the exemplary embodiment of the present specification, A of Chemical Formula 1 is a substituted or unsubstituted phenyl group; a substituted or unsubstituted biphenyl group; or a substituted or unsubstituted monocyclic six-membered heterocyclic group including N.

According to the exemplary embodiment of the present specification, Chemical Formula 1 may be represented by the following Chemical Formula 2.

[Chemical Formula 2]

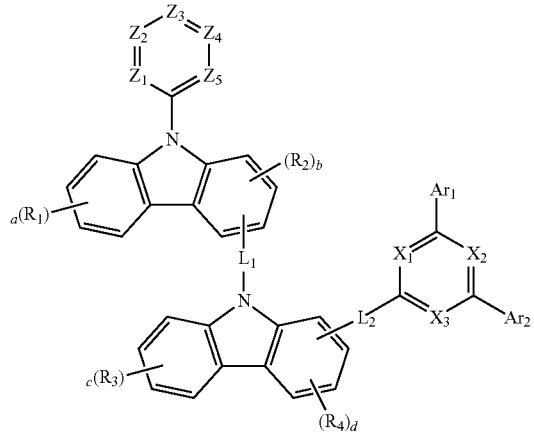

In Chemical Formula 2, $Z_1$ to $Z_5$ are the same as or different from each other, and are each independently $CR_5$ or N, herein, $R_5$ is the same as definitions of $R_1$ to $R_4$, in the case where at least two of $Z_1$ to $Z_5$ are $CR_5$, $R_5$s are the same as or different from each other, and a residual substituent group is the same as the matter defined in Chemical Formula 1.

According to the exemplary embodiment of the present specification, A of Chemical Formula 1 is a phenyl group unsubstituted or substituted by an alkyl group, an aryl group, or a heterocyclic group; a biphenyl group unsubstituted or substituted by an alkyl group, an aryl group, or a heterocyclic group; or a monocyclic six-membered heterocyclic group unsubstituted or substituted by an alkyl group, an aryl group, or a heterocyclic group and including one or more of N, O, and S atoms. In the case where the monocycle is positioned at A, since triplet energy is high, the compound of Chemical Formula 1 is suitable as yellowish green, green, and blue phosphorescent hosts.

According to the exemplary embodiment of the present specification, A of Chemical Formula 1 is a phenyl group unsubstituted or substituted by an alkyl group, a phenyl group, or a N-containing monocyclic six-membered heterocyclic group; a biphenyl group unsubstituted or substituted by an alkyl group, a phenyl group, or a N-containing monocyclic six-membered heterocyclic group; or a N-containing monocyclic six-membered heterocyclic group unsubstituted or substituted by an alkyl group, a phenyl group, or a N-containing monocyclic six-membered heterocyclic group. Herein, the N-containing monocyclic six-membered heterocyclic group may be a monocyclic structure having 1 to 5 nitrogen atoms and preferably 1 to 3 nitrogen atoms, for example, a pyridine group, a pyrimidine group, a pyridazine group, a pyrazine group, or a triazine group. The alkyl group may be a $C_1$ to $C_6$ alkyl group, for example, methyl, ethyl, propyl, butyl, or the like.

According to the exemplary embodiment of the present specification, A of Chemical Formula 1 is a phenyl group unsubstituted or substituted by an alkyl group; or a biphenyl group unsubstituted or substituted by an alkyl group.

According to the exemplary embodiment of the present specification, $L_1$ of Chemical Formula 1 is substituted or unsubstituted phenylene; or a substituted or unsubstituted divalent monocyclic heterocyclic group including one or more of N, O, and S atoms. In the case where the polycycle is positioned at a position $L_1$, synthesis is not easy and a molecular weight is excessively increased, and thus a deposition temperature is excessively high, and in this case, processability is not good. In the case where the monocycle is positioned at $L_1$, since triplet energy is high, the compound of Chemical Formula 1 is suitable as yellowish green, green, and blue phosphorescent hosts.

According to the exemplary embodiment of the present specification, $L_1$ of Chemical Formula 1 is substituted or unsubstituted phenylene; or a substituted or unsubstituted divalent monocyclic heterocyclic group including N.

According to the exemplary embodiment of the present specification, $L_1$ of Chemical Formula 1 is phenylene unsubstituted or substituted by a halogen group, a nitrile group, an alkyl group, an aryl group, or a heterocyclic group; or a divalent monocyclic N-containing heterocyclic group unsubstituted or substituted by a halogen group, a nitrile group, an alkyl group, an aryl group, or a heterocyclic group.

According to the exemplary embodiment of the present specification, $L_1$ of Chemical Formula 1 is phenylene unsubstituted or substituted by a halogen group, a nitrile group, an alkyl group, a phenyl group, or a N-containing heterocyclic group; or a divalent N-containing monocyclic heterocyclic group unsubstituted or substituted by a halogen group, a nitrile group, an alkyl group, a phenyl group, or a N-containing heterocyclic group.

According to the exemplary embodiment of the present specification, $L_1$ of Chemical Formula 1 is phenylene unsubstituted or substituted by a halogen group, a nitrile group, an alkyl group, a phenyl group, or a N-containing monocyclic heterocyclic group; or a divalent N-containing monocyclic heterocyclic group unsubstituted or substituted by a halogen group, a nitrile group, an alkyl group, a phenyl group, or a N-containing monocyclic heterocyclic group. Herein, the N-containing monocyclic heterocyclic group may be a monocyclic structure having 1 to 5 nitrogen atoms and preferably 1 to 3 nitrogen atoms, for example, a pyridine group, a pyrimidine group, a pyridazine group, a pyrazine group, or a triazine group. The alkyl group may be a $C_1$ to $C_6$ alkyl group, for example, methyl, ethyl, propyl, butyl, or the like.

According to the exemplary embodiment of the present specification, $L_1$ of Chemical Formula 1 does not include a carbazole structure.

According to the exemplary embodiment of the present specification, $L_2$ of Chemical Formula 1 is a substituted or unsubstituted arylene group; or a substituted or unsubstituted divalent heterocyclic group including one or more of N, O, and S atoms.

According to the exemplary embodiment of the present specification, $L_2$ of Chemical Formula 1 is a substituted or unsubstituted monocyclic arylene group; or a substituted or unsubstituted divalent monocyclic heterocyclic group including one or more of N, O, and S atoms.

According to the exemplary embodiment of the present specification, $L_2$ of Chemical Formula 1 is a substituted or unsubstituted monocyclic arylene group; or a substituted or unsubstituted divalent monocyclic N-containing heterocyclic group.

According to the exemplary embodiment of the present specification, Chemical Formula 1 may be represented by the following Chemical Formula 3.

[Chemical Formula 3]

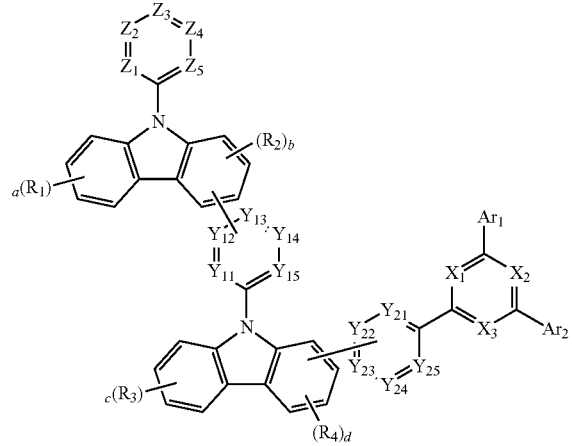

In Chemical Formula 3, $Z_1$ to $Z_5$ are the same as or different from each other, and are each independently $CR_5$ or N, herein, $R_5$ is the same as definitions of $R_1$ to $R_4$, in the case where at least two of $Z_1$ to $Z_5$ are $CR_5$, $R_5$s are the same as or different from each other, $Y_{11}$ to $Y_{15}$ and $Y_{21}$ to $Y_{25}$ are the same as or different from each other, and are each independently $CR_6$ or N, herein, $R_6$ is the same as definitions of $R_1$ to $R_4$, in the case where at least two of $Y_{11}$ to $Y_{15}$ and $Y_{21}$ to $Y_{25}$ are $CR_6$, $R_6$s are the same as or different from each other, but one of $Y_{11}$ to $Y_{15}$ and one of $Y_{21}$ to $Y_{25}$ are carbon atoms bonded to an adjacent carbazole group, and a residual substituent group is the same as the matter defined in Chemical Formula 1.

According to the exemplary embodiment of the present specification, $L_1$ and $L_2$ of Chemical Formula 1 are the same as or different from each other, and are each independently a phenyl group unsubstituted or substituted by a halogen group, a nitrile group, an alkyl group, or an aryl group; or a monocyclic N-containing heterocyclic group unsubstituted or substituted by a halogen group, a nitrile group, an alkyl group, or an aryl group.

According to the exemplary embodiment of the present specification, $L_1$ and $L_2$ of Chemical Formula 1 are the same as or different from each other, and are each independently a phenyl group unsubstituted or substituted by a fluorine group, a nitrile group, an alkyl group, or a phenyl group; or a monocyclic N-containing heterocyclic group unsubstituted or substituted by a fluorine group, a nitrile group, an alkyl group, or a phenyl group. Herein, the N-containing heterocyclic group may be a monocyclic structure having 1 to 5 nitrogen atoms and preferably 1 to 3 nitrogen atoms, for example, a pyridine group, a pyrimidine group, a pyridazine group, a pyrazine group, or a triazine group. The alkyl group may be a $C_1$ to $C_6$ alkyl group, for example, methyl, ethyl, propyl, butyl, or the like.

According to the exemplary embodiment of the present specification, $L_1$ and $L_2$ of Chemical Formula 1 are the same as or different from each other, and are each independently a phenyl group unsubstituted or substituted by a fluorine group, a nitrile group, or an alkyl group.

According to the exemplary embodiment of the present specification, in Chemical Formula 1, $L_1$ and $L_2$ may be each represented as below.

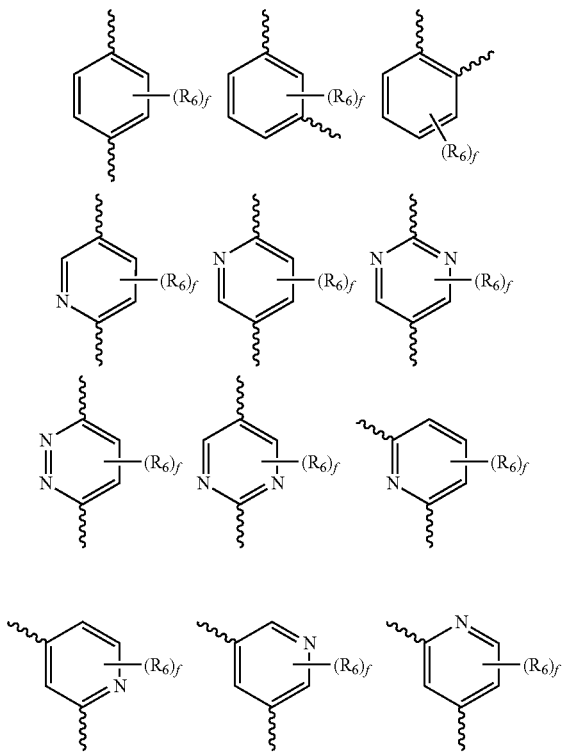

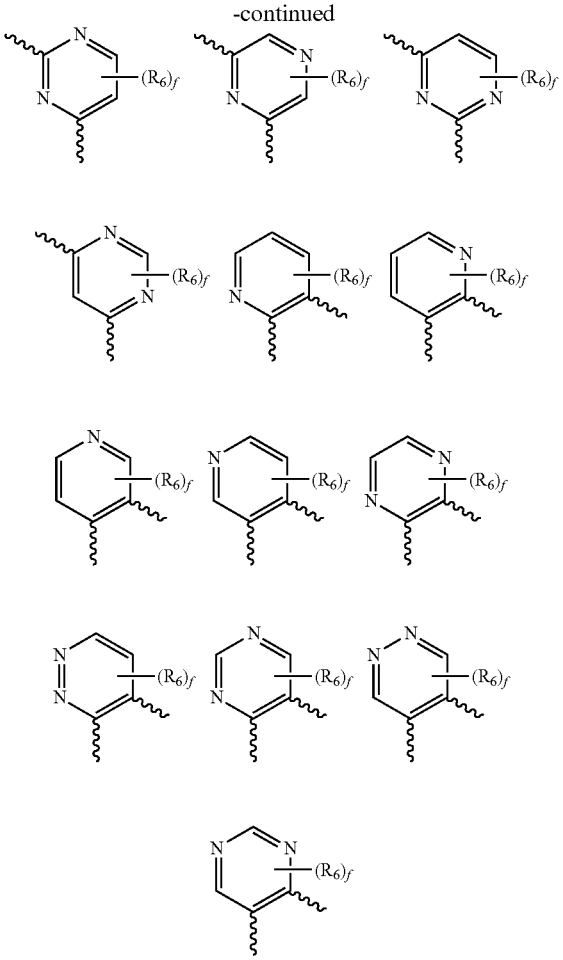

$R_6$ is hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted arylphosphine group; a substituted or unsubstituted phosphine oxide group; a substituted or unsubstituted aryl group; a substituted or unsubstituted fluorenyl group; or a substituted or unsubstituted aromatic or aliphatic heterocyclic group including one or more of N, O, and S atoms, f is an integer of 0 to 4, and in the case where f is 2 or more, $R_6$s are the same as or different from each other.

According to one exemplary embodiment of the present specification, in the aforementioned Structural Formulas, $R_6$ is a halogen group, a nitrile group, an alkyl group, or an aryl group.

In Chemical Formulas 1 to 3, the Structural Formula

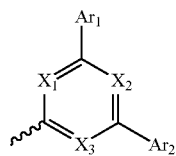

may be selected from the following Structural Formulas.

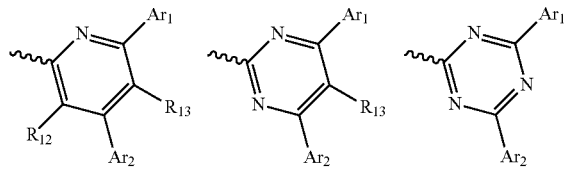

According to the exemplary embodiment of the present specification, $Ar_1$ and $Ar_2$ are the same as or different from each other, and are a substituted or unsubstituted aryl group; or a substituted or unsubstituted heterocyclic group including one or more of N, O, and S atoms. However, $Ar_1$ and $Ar_2$ do not include a carbazole structure. In the case where carbazole is positioned at positions $Ar_1$ or $Ar_2$, synthesis is not easy.

According to the exemplary embodiment of the present specification, $Ar_1$ and $Ar_2$ are the same as or different from each other, and are each independently an aryl group unsubstituted or substituted by an alkyl group, an aryl group, or a N-containing heterocyclic group; or a substituted or unsubstituted heterocyclic group unsubstituted or substituted by an alkyl group, an aryl group, or a N-containing heterocyclic group and including one or more of N, O, and S atoms. Herein, the N-containing heterocyclic group may be a monocyclic structure having 1 to 5 nitrogen atoms and preferably 1 to 3 nitrogen atoms, for example, a pyridine group, a pyrimidine group, a pyridazine group, a pyrazine group, or a triazine group. The alkyl group may be a $C_1$ to $C_6$ alkyl group, for example, methyl, ethyl, propyl, butyl, or the like.

According to the exemplary embodiment of the present specification, $Ar_1$ and $Ar_2$ are the same as or different from each other, and are each independently a phenyl group unsubstituted or substituted by an alkyl group, a phenyl group, or a N-containing heterocyclic group; a fluorenyl group unsubstituted or substituted by an alkyl group, a phenyl group, or a N-containing heterocyclic group; or a N-containing heterocyclic group unsubstituted or substituted by an alkyl group, a phenyl group, or a N-containing heterocyclic group. Herein, the N-containing heterocyclic group may be a monocyclic structure having 1 to 5 nitrogen atoms and preferably 1 to 3 nitrogen atoms, for example, a pyridine group, a pyrimidine group, a pyridazine group, a pyrazine group, or a triazine group. The alkyl group may be a $C_1$ to $C_6$ alkyl group, for example, methyl, ethyl, propyl, butyl, or the like.

According to the exemplary embodiment of the present specification, $Ar_1$ and $Ar_2$ are the same as or different from each other, and are each independently a phenyl group unsubstituted or substituted by an alkyl group or a phenyl group; a fluorenyl group unsubstituted or substituted by an alkyl group or a phenyl group; or a N-containing monocyclic heterocyclic group unsubstituted or substituted by an alkyl group or a phenyl group. Herein, the N-containing monocyclic heterocyclic group may be a pyridine group, a pyrimidine group, a pyridazine group, a pyrazine group, or a triazine group. The alkyl group may be a $C_1$ to $C_6$ alkyl group, for example, methyl, ethyl, propyl, butyl, or the like.

According to the exemplary embodiment of the present specification, Chemical Formula 1 may be represented by the following Chemical Formula 4.

[Chemical Formula 4]

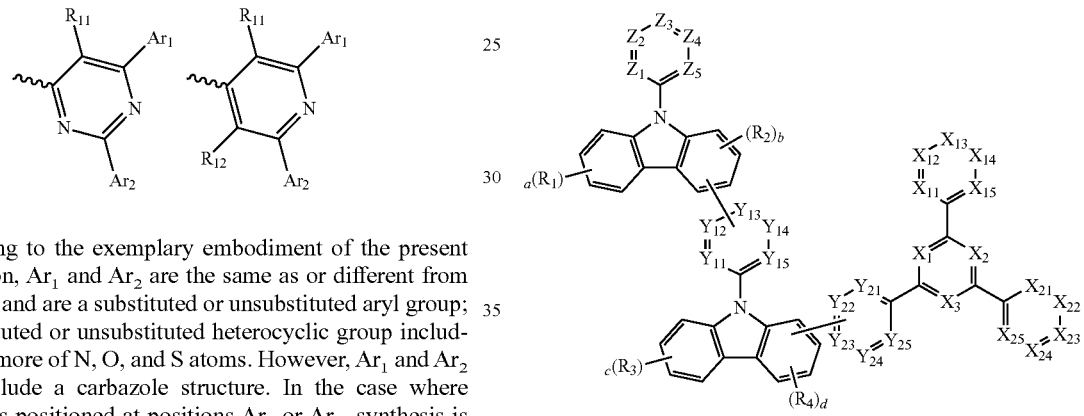

In Chemical Formula 4, $Z_1$ to $Z_5$ are the same as or different from each other, and are each independently $CR_5$ or N, herein, $R_5$ is the same as definitions of $R_1$ to $R_4$, in the case where at least two of $Z_1$ to $Z_5$ are $CR_5$, $R_5$s are the same as or different from each other, $Y_{11}$ to $Y_{15}$ and $Y_{21}$ to $Y_{25}$ are the same as or different from each other, and are each independently $CR_6$ or N, herein, $R_6$ is the same as definitions of $R_1$ to $R_4$, in the case where at least two of $Y_{11}$ to $Y_{15}$ and $Y_{21}$ to $Y_{25}$ are $CR_6$, $R_6$s are the same as or different from each other, but one of $Y_{11}$ to $Y_{15}$ and one of $Y_{21}$ to $Y_{25}$ are carbon atoms bonded to an adjacent carbazole group, $X_{11}$ to $X_{15}$ and $X_{21}$ to $X_{25}$ are the same as or different from each other, and each independently $CR_7$ or N, herein, $R_7$ is the same as definitions of $R_1$ to $R_4$, in the case where at least two of $X_{11}$ to $X_{15}$ and $X_{21}$ to $X_{25}$ are $CR_7$, $R_7$s are the same as or different from each other, and a residual substituent group is the same as a matter defined in Chemical Formula 1.

According to the exemplary embodiment of the present specification, $R_1$ to $R_4$ of Chemical Formula 1 are hydrogen.

According to the exemplary embodiment of the present specification, the compound of Chemical Formula 1 may be represented by the following Structural Formulas.

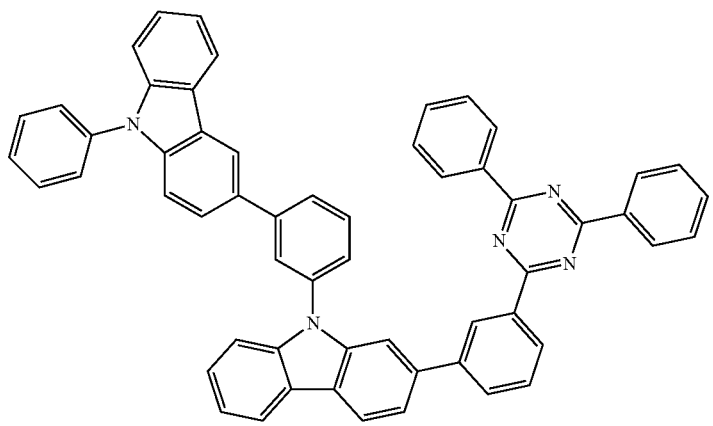
Chemical Formula 1-1
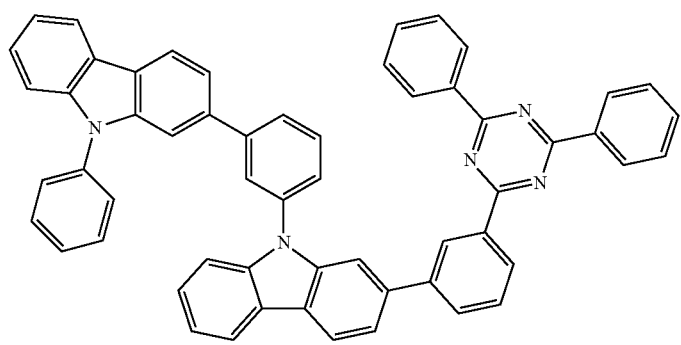 [SMILES: c1ccc(-c2nc(-c3ccccc3)nc(-c3cccc(-c4ccc5c6ccccc6n(-c6cccc(-c7ccc8c9ccccc9n(-c9ccccc9)c8c7)c6)c5c4)c3)n2)cc1]
Chemical Formula 1-2
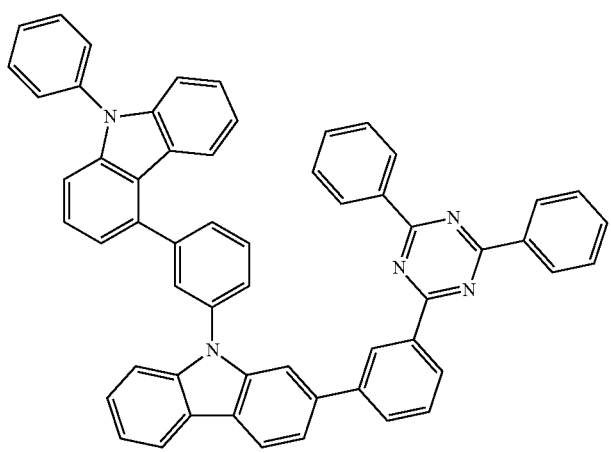 [SMILES: c1ccc(-c2nc(-c3ccccc3)nc(-c3cccc(-c4ccc5c6ccccc6n(-c6cccc(-c7cccc8c7c7ccccc7n8-c7ccccc7)c6)c5c4)c3)n2)cc1]
Chemical Formula 1-3

-continued
Chemical Formula 1-4
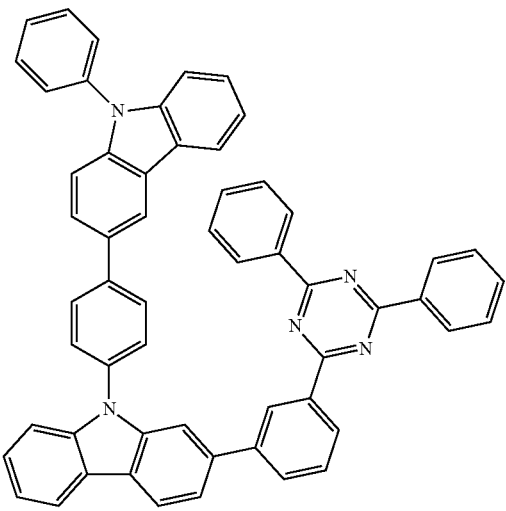 [SMILES: c1ccc(-c2nc(-c3ccccc3)nc(-c3cccc(-c4ccc5c6ccccc6n(-c6ccc(-c7ccc8c(c7)c7ccccc7n8-c7ccccc7)cc6)c5c4)c3)n2)cc1]
Chemical Formula 1-5
Chemical Formula 1-6
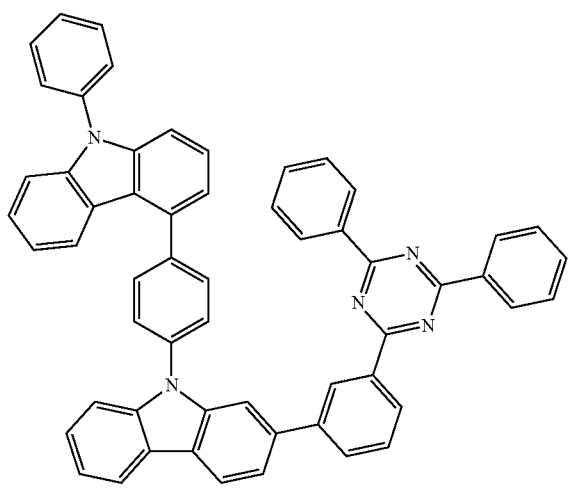 [SMILES: c1ccc(-c2nc(-c3ccccc3)nc(-c3cccc(-c4ccc5c6ccccc6n(-c6ccc(-c7cccc8c7c7ccccc7n8-c7ccccc7)cc6)c5c4)c3)n2)cc1]

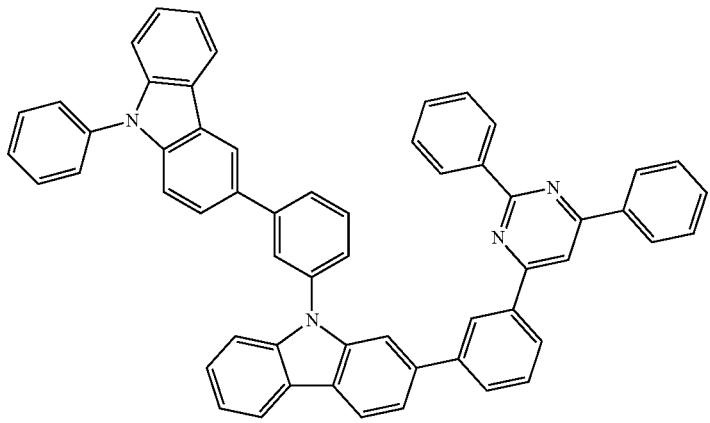 [SMILES: c1ccc(-c2cc(-c3cccc(-c4ccc5c6ccccc6n(-c6cccc(-c7ccc8c(c7)c7ccccc7n8-c7ccccc7)c6)c5c4)c3)nc(-c3ccccc3)n2)cc1]
Chemical Formula 1-7
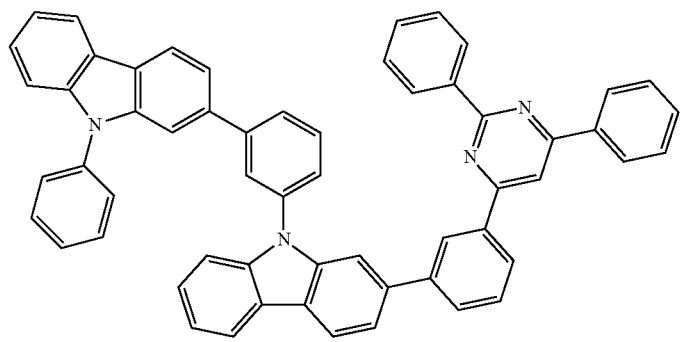 [SMILES: c1ccc(-c2cc(-c3cccc(-c4ccc5c6ccccc6n(-c6cccc(-c7ccc8c9ccccc9n(-c9ccccc9)c8c7)c6)c5c4)c3)nc(-c3ccccc3)n2)cc1]
Chemical Formula 1-8
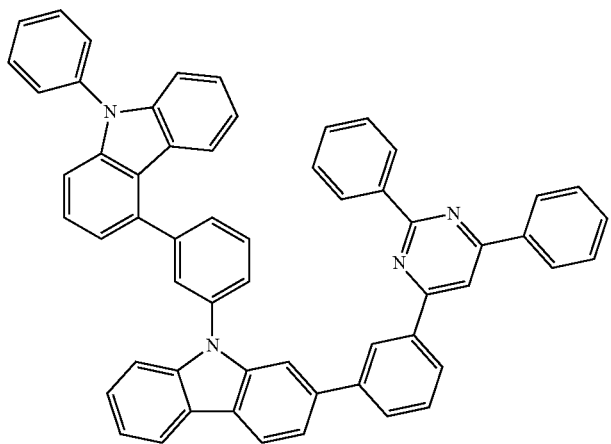 [SMILES: c1ccc(-c2cc(-c3cccc(-c4ccc5c6ccccc6n(-c6cccc(-c7cccc8c7c7ccccc7n8-c7ccccc7)c6)c5c4)c3)nc(-c3ccccc3)n2)cc1]
Chemical Formula 1-9

Chemical Formula 1-10
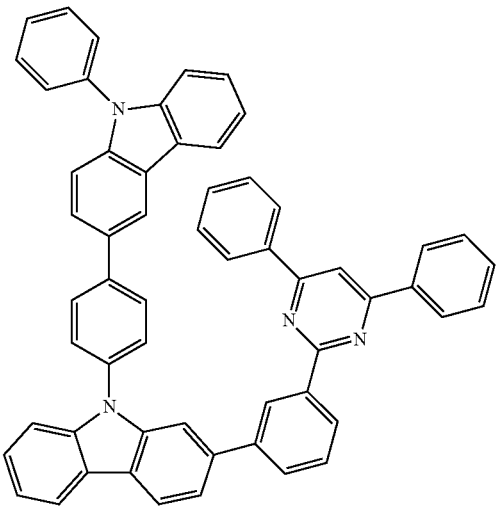
Chemical Formula 1-11
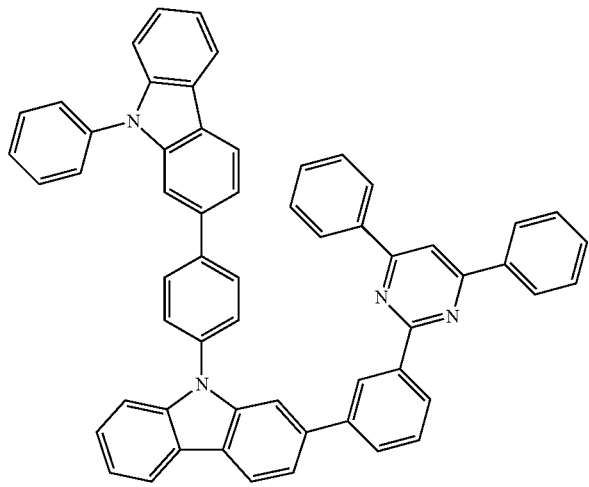 [SMILES: c1ccc(-c2cc(-c3ccccc3)nc(-c3cccc(-c4ccc5c6ccccc6n(-c6ccc(-c7ccc8c9ccccc9n(-c9ccccc9)c8c7)cc6)c5c4)c3)n2)cc1]
Chemical Formula 1-12
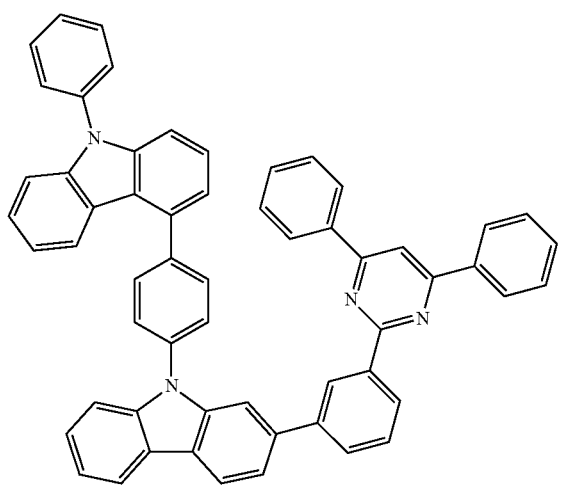 [SMILES: c1ccc(-c2cc(-c3ccccc3)nc(-c3cccc(-c4ccc5c6ccccc6n(-c6ccc(-c7cccc8c7c7ccccc7n8-c7ccccc7)cc6)c5c4)c3)n2)cc1]

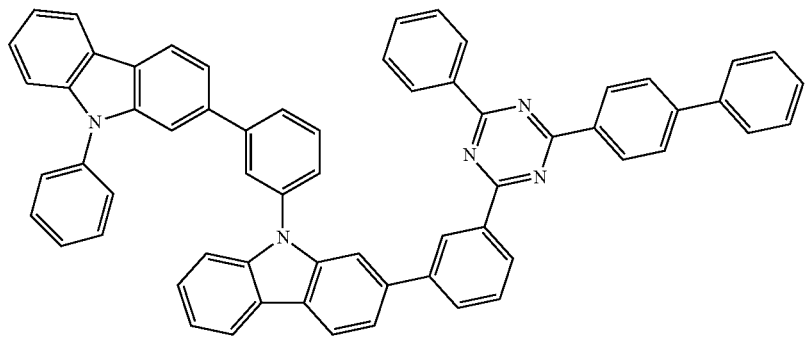 [SMILES: c1ccc(-c2ccc(-c3nc(-c4ccccc4)nc(-c4cccc(-c5ccc6c7ccccc7n(-c7cccc(-c8ccc9c%10ccccc%10n(-c%10ccccc%10)c9c8)c7)c6c5)c4)n3)cc2)cc1]
Chemical Formula 1-13
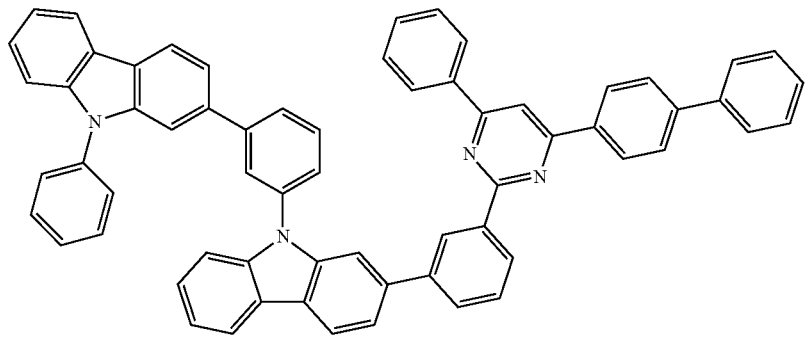 [SMILES: c1ccc(-c2ccc(-c3cc(-c4ccccc4)nc(-c4cccc(-c5ccc6c7ccccc7n(-c7cccc(-c8ccc9c%10ccccc%10n(-c%10ccccc%10)c9c8)c7)c6c5)c4)n3)cc2)cc1]
Chemical Formula 1-14
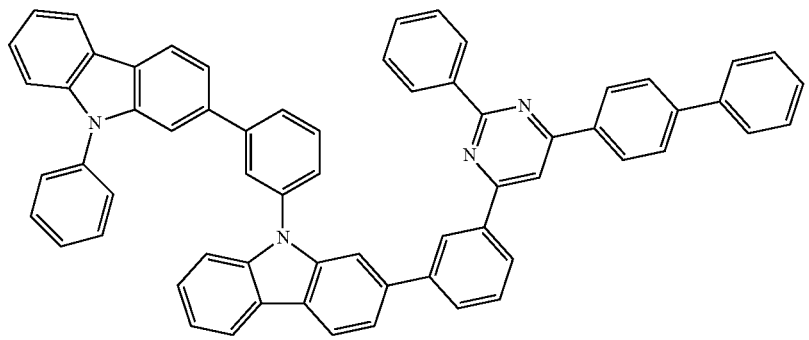 [SMILES: c1ccc(-c2ccc(-c3cc(-c4cccc(-c5ccc6c7ccccc7n(-c7cccc(-c8ccc9c%10ccccc%10n(-c%10ccccc%10)c9c8)c7)c6c5)c4)nc(-c4ccccc4)n3)cc2)cc1]
Chemical Formula 1-15
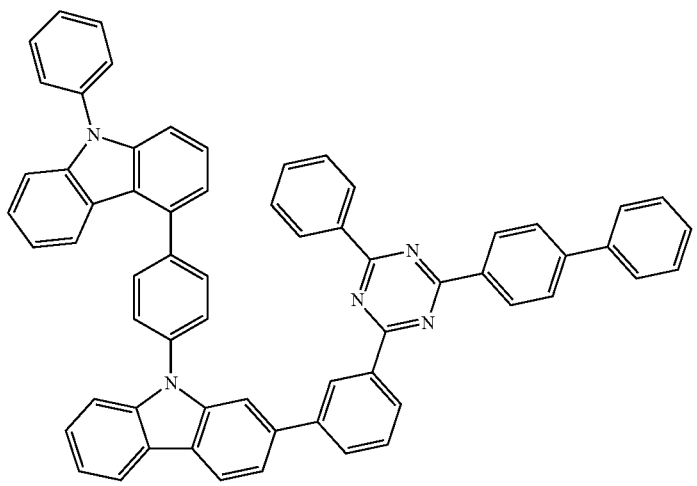 [SMILES: c1ccc(-c2ccc(-c3nc(-c4ccccc4)nc(-c4cccc(-c5ccc6c7ccccc7n(-c7ccc(-c8cccc9c8c8ccccc8n9-c8ccccc8)cc7)c6c5)c4)n3)cc2)cc1]
Chemical Formula 1-16

Chemical Formula 1-17
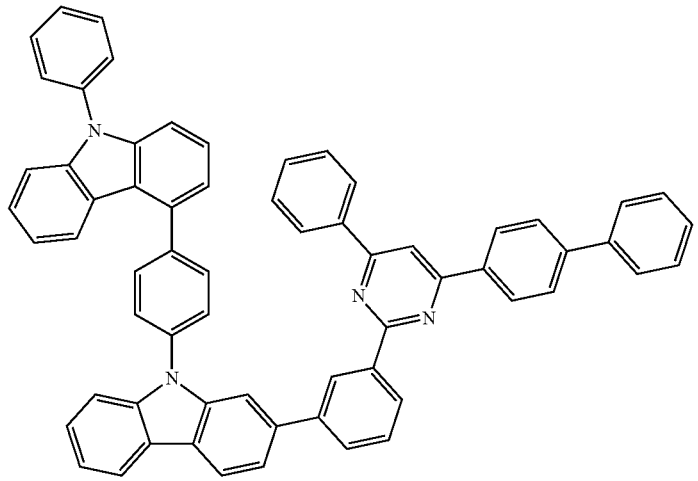 [SMILES: c1ccc(-c2ccc(-c3cc(-c4ccccc4)nc(-c4cccc(-c5ccc6c7ccccc7n(-c7ccc(-c8cccc9c8c8ccccc8n9-c8ccccc8)cc7)c6c5)c4)n3)cc2)cc1]
Chemical Formula 1-18
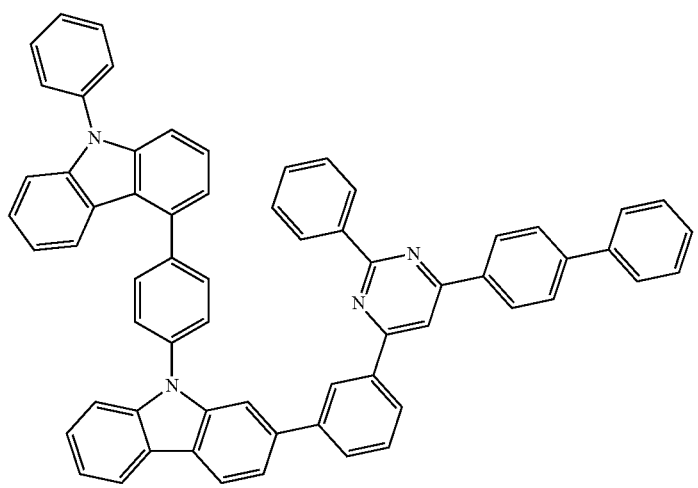 [SMILES: c1ccc(-c2ccc(-c3cc(-c4cccc(-c5ccc6c7ccccc7n(-c7ccc(-c8cccc9c8c8ccccc8n9-c8ccccc8)cc7)c6c5)c4)nc(-c4ccccc4)n3)cc2)cc1]
Chemical Formula 1-19
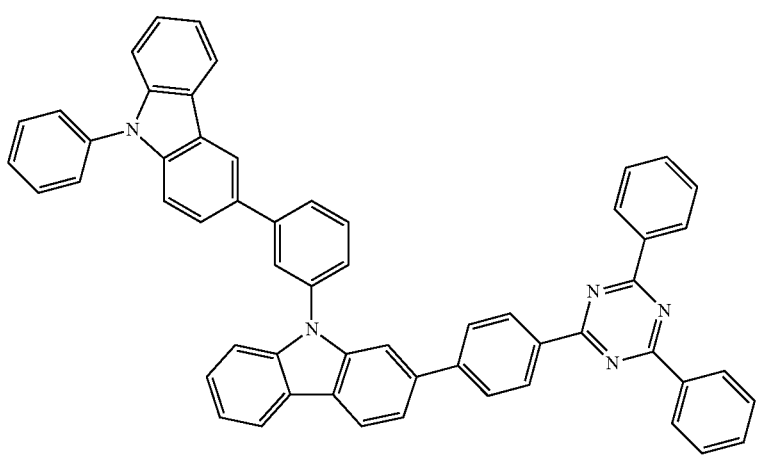

Chemical Formula 1-20
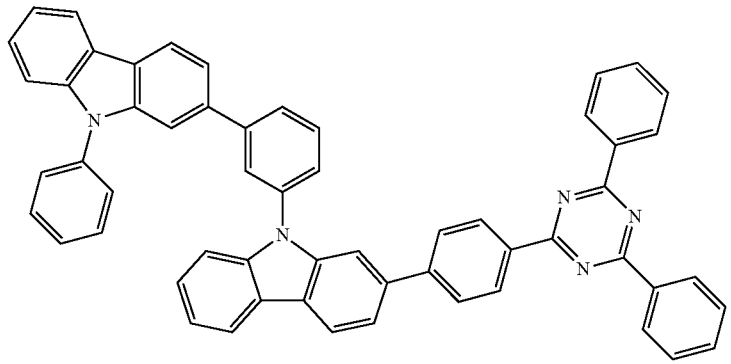 [SMILES: c1ccc(-c2nc(-c3ccccc3)nc(-c3ccc(-c4ccc5c6ccccc6n(-c6cccc(-c7ccc8c9ccccc9n(-c9ccccc9)c8c7)c6)c5c4)cc3)n2)cc1]
Chemical Formula 1-21
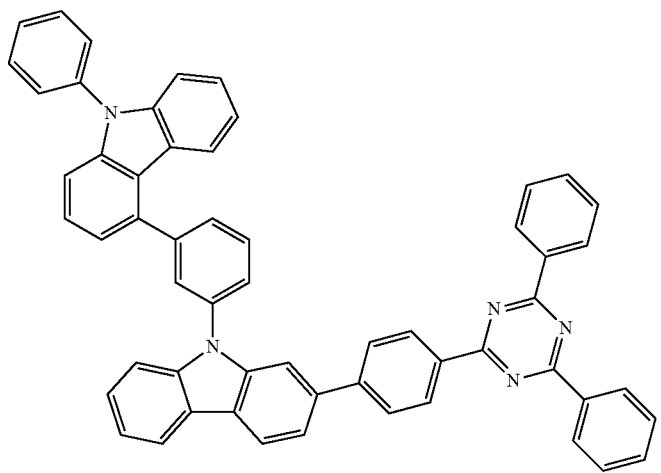 [SMILES: c1ccc(-c2nc(-c3ccccc3)nc(-c3ccc(-c4ccc5c6ccccc6n(-c6cccc(-c7cccc8c7c7ccccc7n8-c7ccccc7)c6)c5c4)cc3)n2)cc1]
Chemical Formula 1-22
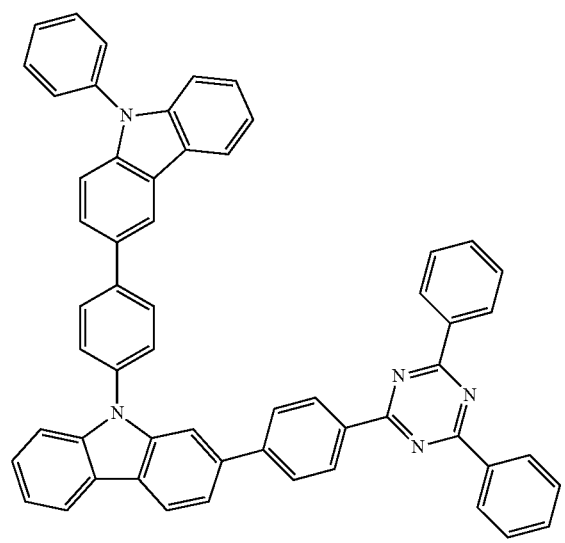 [SMILES: c1ccc(-c2nc(-c3ccccc3)nc(-c3ccc(-c4ccc5c6ccccc6n(-c6ccc(-c7ccc8c(c7)c7ccccc7n8-c7ccccc7)cc6)c5c4)cc3)n2)cc1]

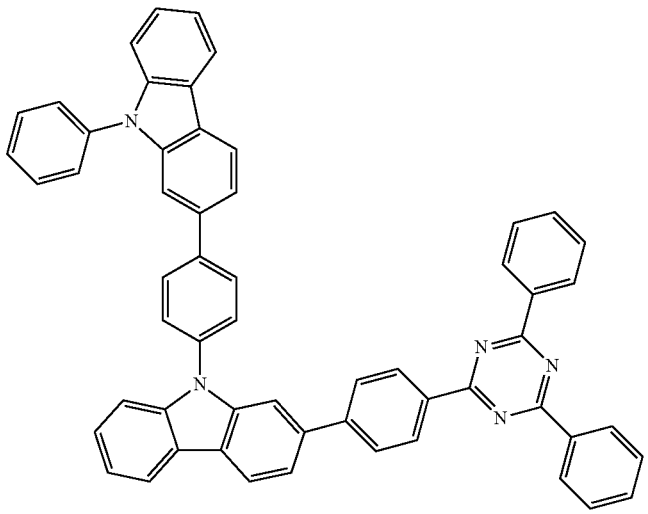
Chemical Formula 1-23
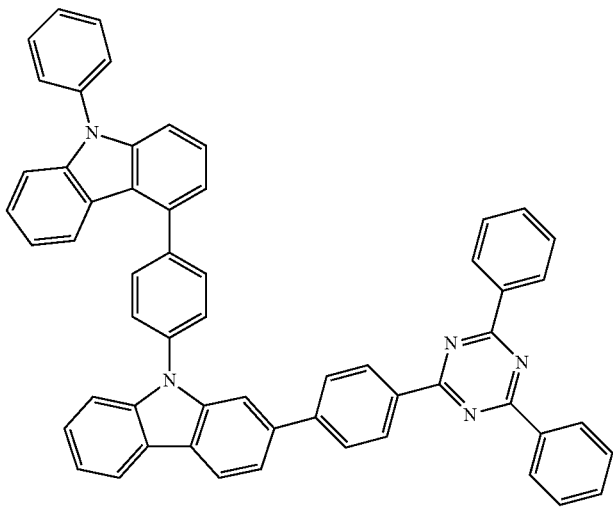 [SMILES: c1ccc(-c2nc(-c3ccccc3)nc(-c3ccc(-c4ccc5c6ccccc6n(-c6ccc(-c7cccc8c7c7ccccc7n8-c7ccccc7)cc6)c5c4)cc3)n2)cc1]
Chemical Formula 1-24
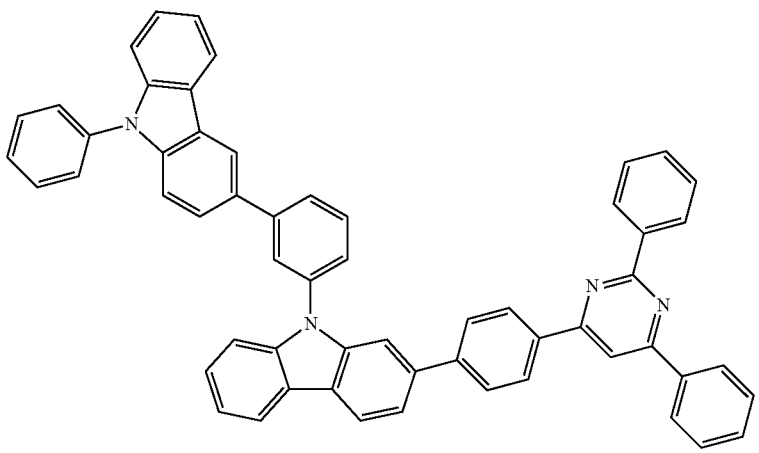
Chemical Formula 1-25

Chemical Formula 1-26
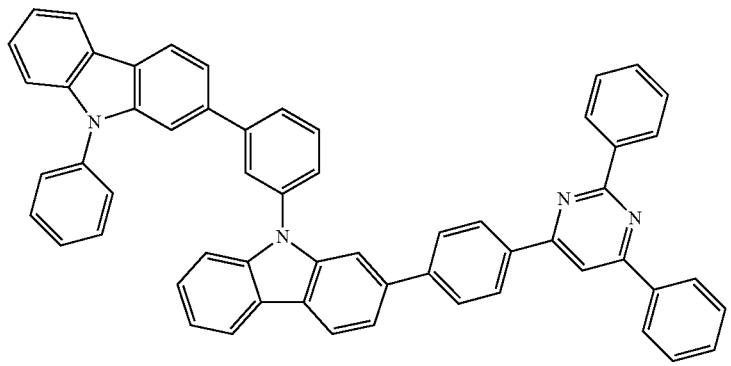 [SMILES: c1ccc(-c2cc(-c3ccc(-c4ccc5c6ccccc6n(-c6cccc(-c7ccc8c9ccccc9n(-c9ccccc9)c8c7)c6)c5c4)cc3)nc(-c3ccccc3)n2)cc1]
Chemical Formula 1-27
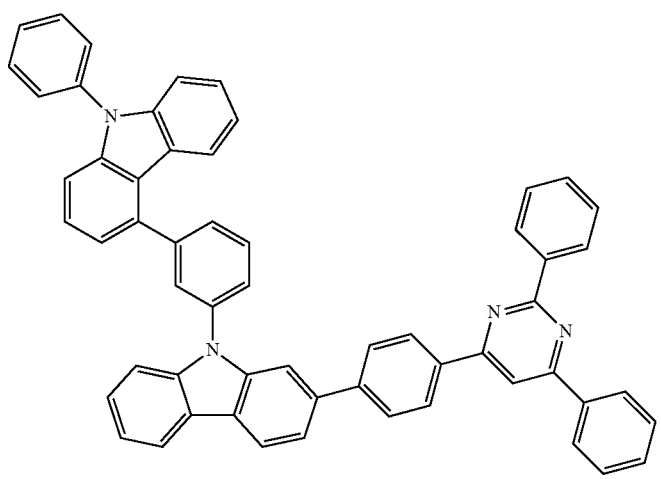 [SMILES: c1ccc(-c2cc(-c3ccc(-c4ccc5c6ccccc6n(-c6cccc(-c7cccc8c7c7ccccc7n8-c7ccccc7)c6)c5c4)cc3)nc(-c3ccccc3)n2)cc1]
Chemical Formula 1-28
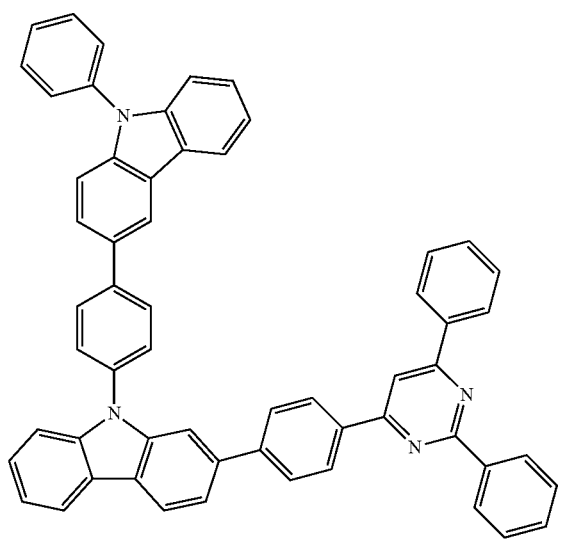

Chemical Formula 1-29
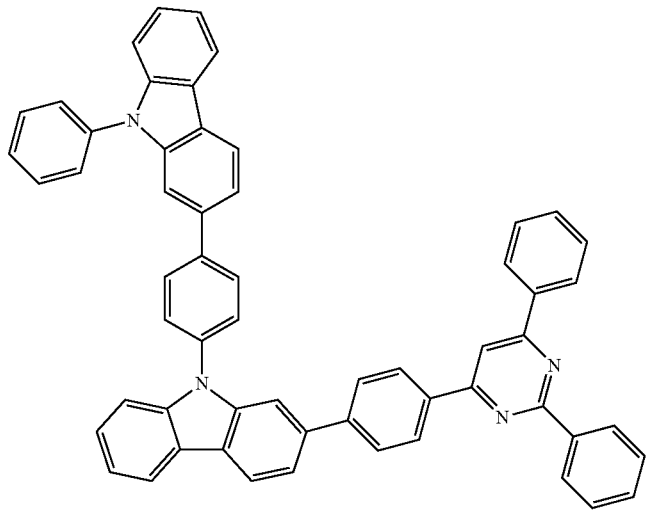
Chemical Formula 1-30
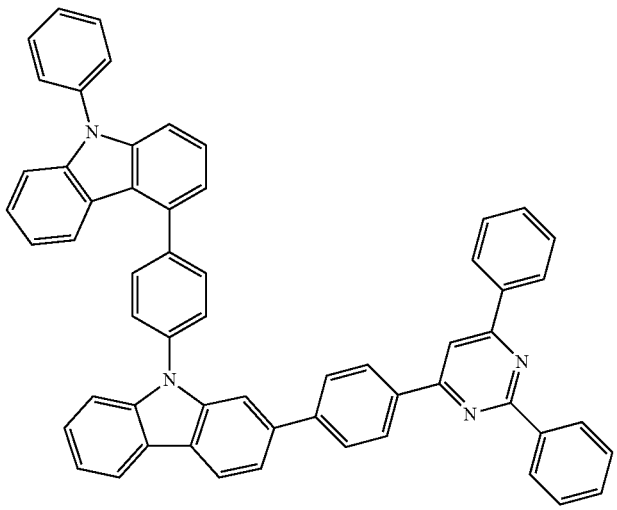 [SMILES: c1ccc(-c2cc(-c3ccc(-c4ccc5c6ccccc6n(-c6ccc(-c7cccc8c7c7ccccc7n8-c7ccccc7)cc6)c5c4)cc3)nc(-c3ccccc3)n2)cc1]
Chemical Formula 1-31
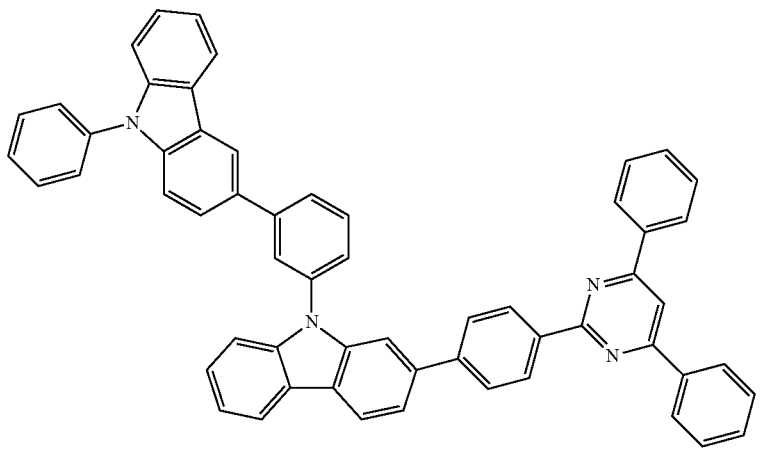

Chemical Formula 1-32
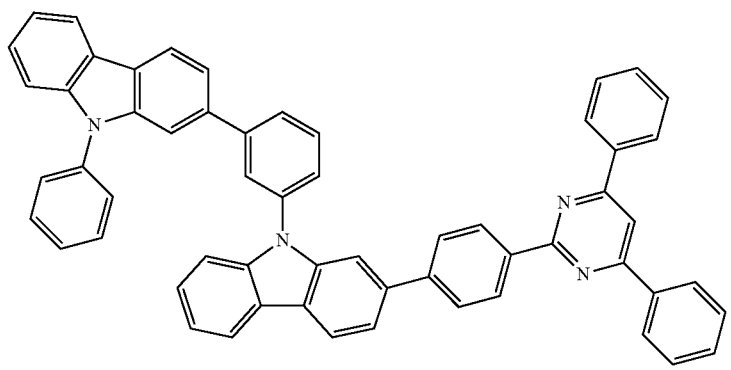 [SMILES: c1ccc(-c2cc(-c3ccccc3)nc(-c3ccc(-c4ccc5c6ccccc6n(-c6cccc(-c7ccc8c9ccccc9n(-c9ccccc9)c8c7)c6)c5c4)cc3)n2)cc1]
Chemical Formula 1-33
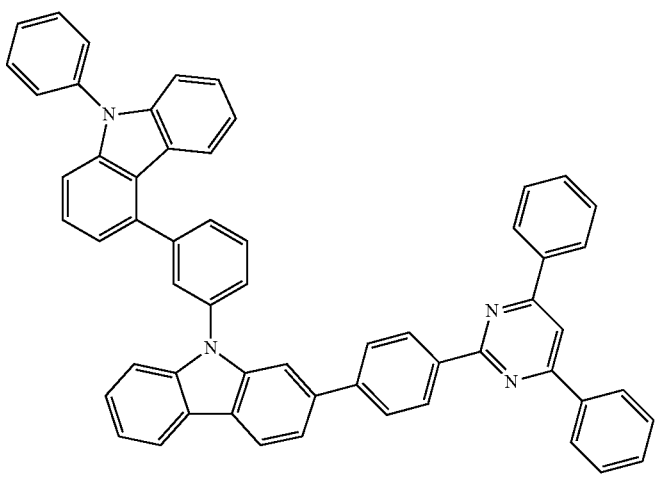 [SMILES: c1ccc(-c2cc(-c3ccccc3)nc(-c3ccc(-c4ccc5c6ccccc6n(-c6cccc(-c7cccc8c7c7ccccc7n8-c7ccccc7)c6)c5c4)cc3)n2)cc1]
Chemical Formula 1-34
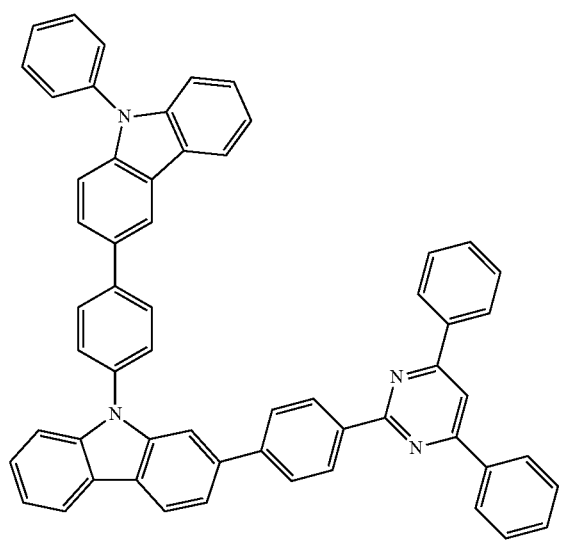

Chemical Formula 1-35
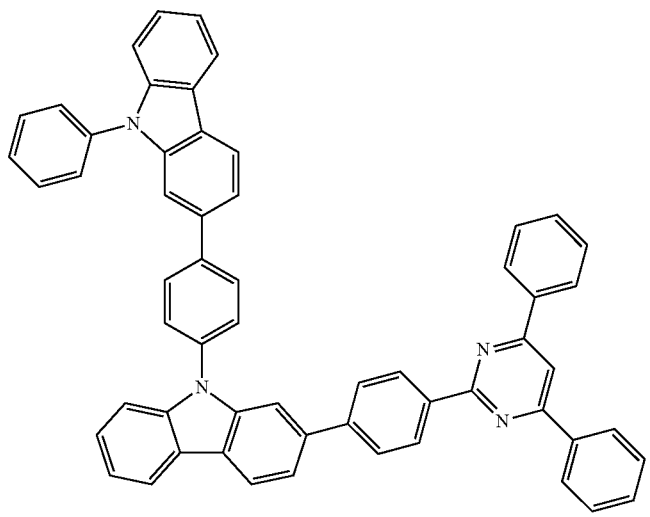 [SMILES: c1ccc(-c2cc(-c3ccccc3)nc(-c3ccc(-c4ccc5c6ccccc6n(-c6ccc(-c7ccc8c9ccccc9n(-c9ccccc9)c8c7)cc6)c5c4)cc3)n2)cc1]
Chemical Formula 1-36
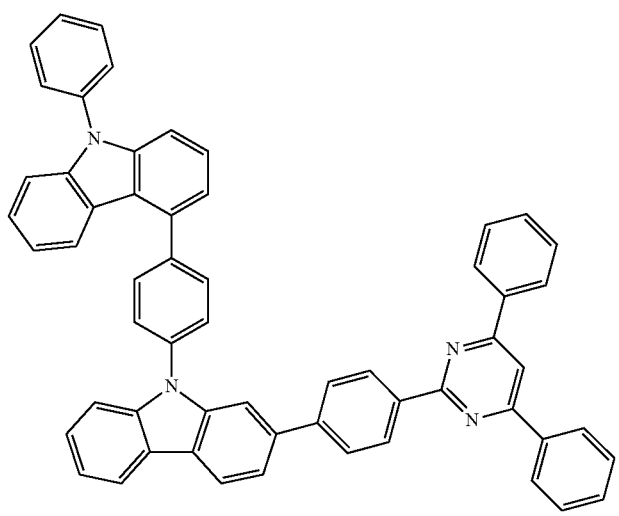 [SMILES: c1ccc(-c2cc(-c3ccccc3)nc(-c3ccc(-c4ccc5c6ccccc6n(-c6ccc(-c7cccc8c7c7ccccc7n8-c7ccccc7)cc6)c5c4)cc3)n2)cc1]
Chemical Formula 1-37
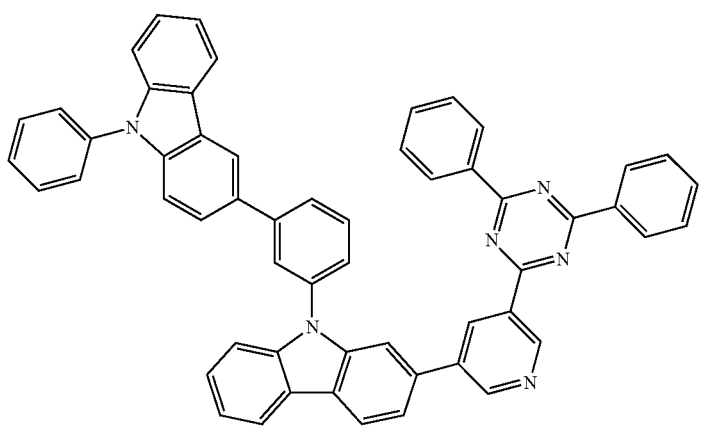 [SMILES: c1ccc(-c2nc(-c3ccccc3)nc(-c3cncc(-c4ccc5c6ccccc6n(-c6cccc(-c7ccc8c(c7)c7ccccc7n8-c7ccccc7)c6)c5c4)c3)n2)cc1]

Chemical Formula 1-38
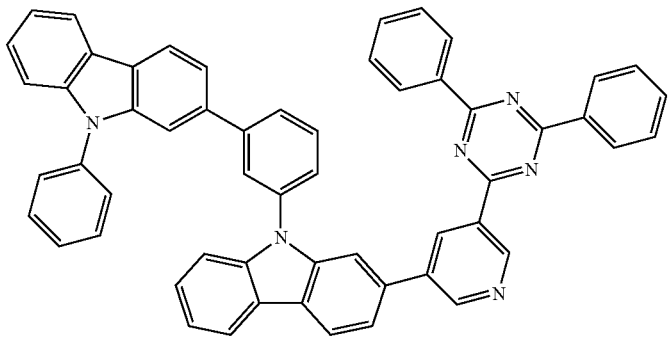 [SMILES: c1ccc(-c2nc(-c3ccccc3)nc(-c3cncc(-c4ccc5c6ccccc6n(-c6cccc(-c7ccc8c9ccccc9n(-c9ccccc9)c8c7)c6)c5c4)c3)n2)cc1]
Chemical Formula 1-39
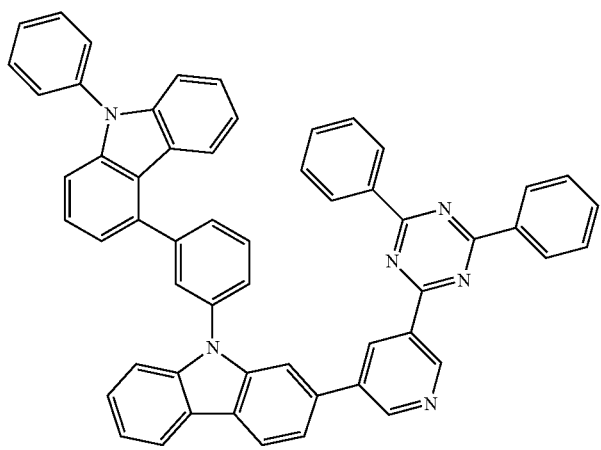 [SMILES: c1ccc(-c2nc(-c3ccccc3)nc(-c3cncc(-c4ccc5c6ccccc6n(-c6cccc(-c7cccc8c7c7ccccc7n8-c7ccccc7)c6)c5c4)c3)n2)cc1]
Chemical Formula 1-40
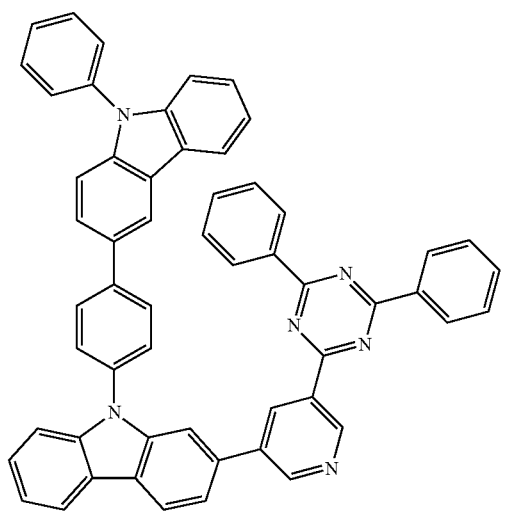 [SMILES: c1ccc(-c2nc(-c3ccccc3)nc(-c3cncc(-c4ccc5c6ccccc6n(-c6ccc(-c7ccc8c(c7)c7ccccc7n8-c7ccccc7)cc6)c5c4)c3)n2)cc1]

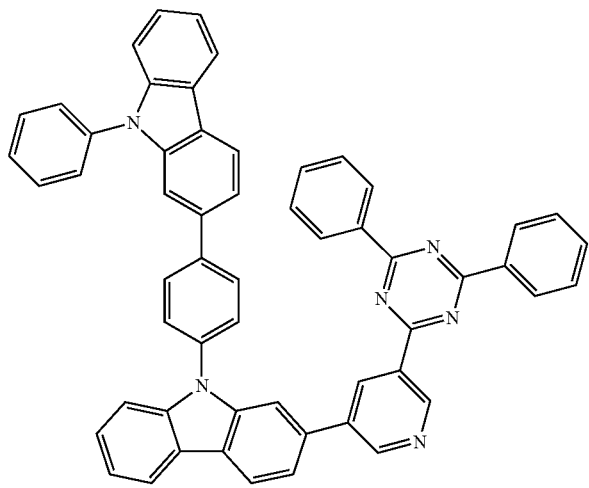 [SMILES: c1ccc(-c2nc(-c3ccccc3)nc(-c3cncc(-c4ccc5c6ccccc6n(-c6ccc(-c7ccc8c9ccccc9n(-c9ccccc9)c8c7)cc6)c5c4)c3)n2)cc1]
Chemical Formula 1-41
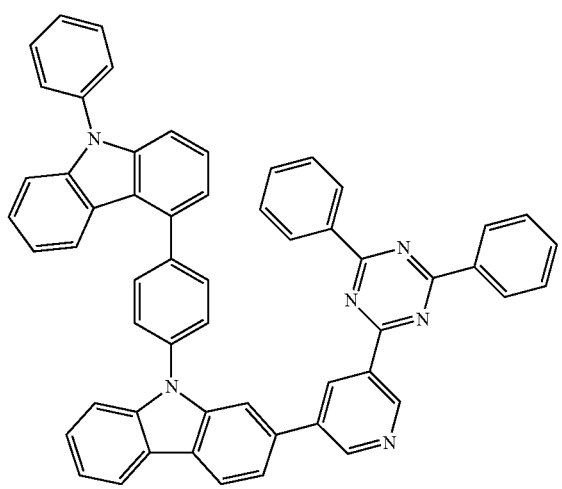 [SMILES: c1ccc(-c2nc(-c3ccccc3)nc(-c3cncc(-c4ccc5c6ccccc6n(-c6ccc(-c7cccc8c7c7ccccc7n8-c7ccccc7)cc6)c5c4)c3)n2)cc1]
Chemical Formula 1-42
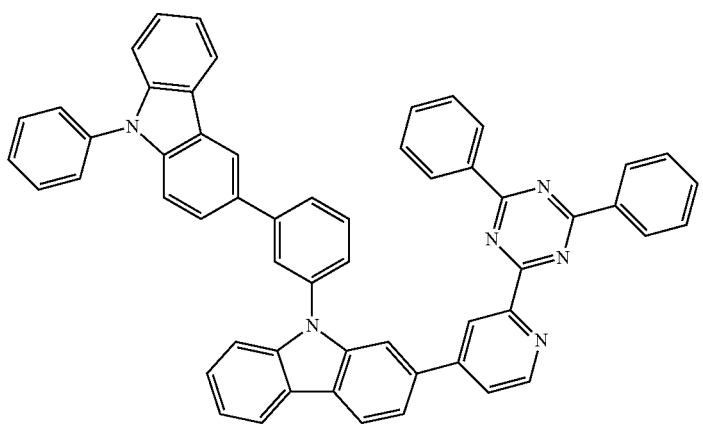 [SMILES: c1ccc(-c2nc(-c3ccccc3)nc(-c3cc(-c4ccc5c6ccccc6n(-c6cccc(-c7ccc8c(c7)c7ccccc7n8-c7ccccc7)c6)c5c4)ccn3)n2)cc1]
Chemical Formula 1-43

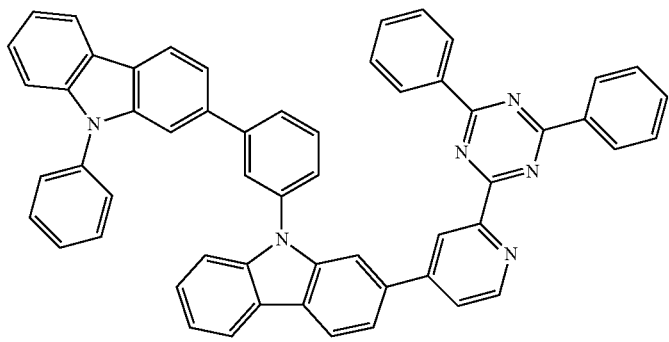 [SMILES: c1ccc(-c2nc(-c3ccccc3)nc(-c3cc(-c4ccc5c6ccccc6n(-c6cccc(-c7ccc8c9ccccc9n(-c9ccccc9)c8c7)c6)c5c4)ccn3)n2)cc1]
Chemical Formula 1-44
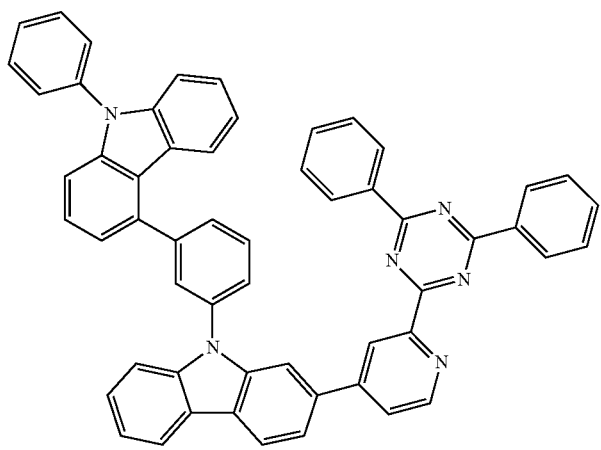
Chemical Formula 1-45
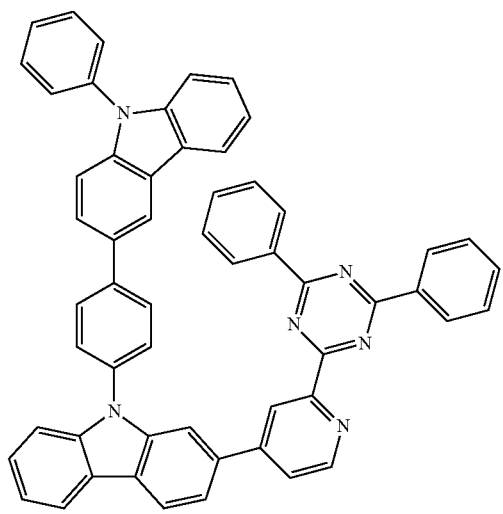 [SMILES: c1ccc(-c2nc(-c3ccccc3)nc(-c3cc(-c4ccc5c6ccccc6n(-c6ccc(-c7ccc8c(c7)c7ccccc7n8-c7ccccc7)cc6)c5c4)ccn3)n2)cc1]
Chemical Formula 1-46

Chemical Formula 1-47
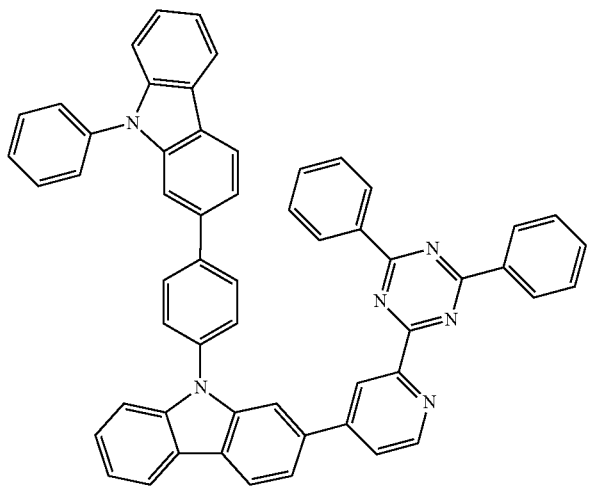 [SMILES: c1ccc(-c2nc(-c3ccccc3)nc(-c3cc(-c4ccc5c6ccccc6n(-c6ccc(-c7ccc8c9ccccc9n(-c9ccccc9)c8c7)cc6)c5c4)ccn3)n2)cc1]
Chemical Formula 1-48
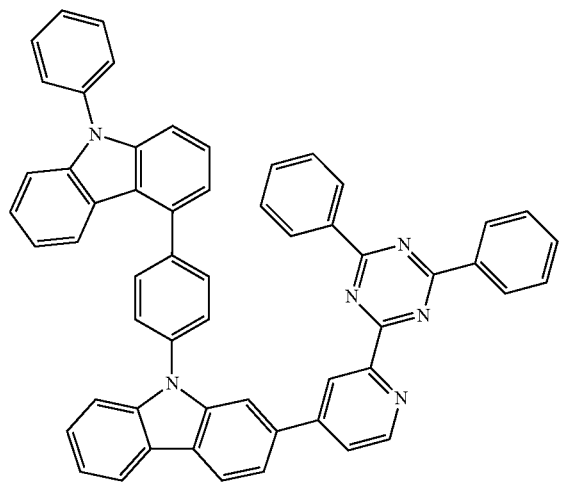 [SMILES: c1ccc(-c2nc(-c3ccccc3)nc(-c3cc(-c4ccc5c6ccccc6n(-c6ccc(-c7cccc8c7c7ccccc7n8-c7ccccc7)cc6)c5c4)ccn3)n2)cc1]
Chemical Formula 1-49
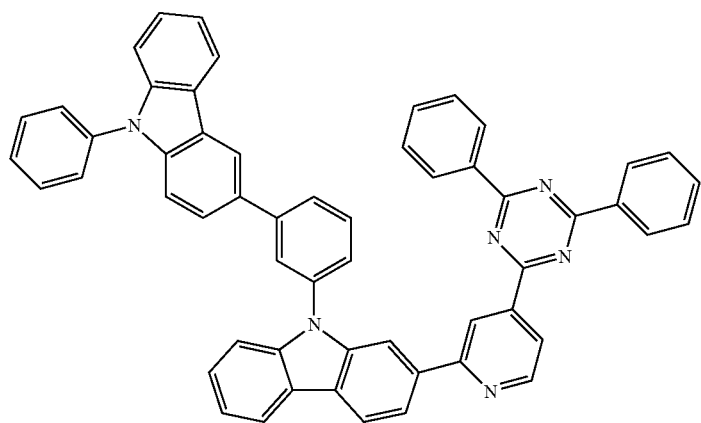

Chemical Formula 1-50
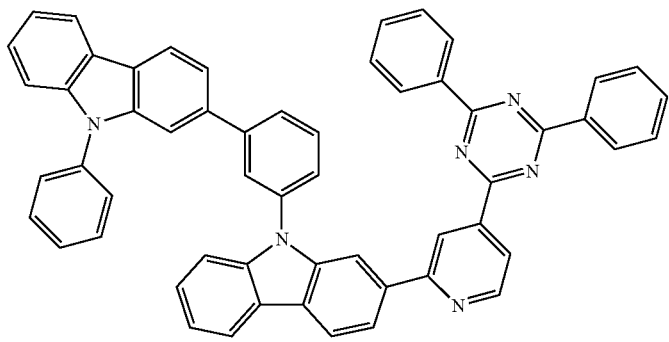 [SMILES: c1ccc(-c2nc(-c3ccccc3)nc(-c3ccnc(-c4ccc5c6ccccc6n(-c6cccc(-c7ccc8c9ccccc9n(-c9ccccc9)c8c7)c6)c5c4)c3)n2)cc1]
Chemical Formula 1-51
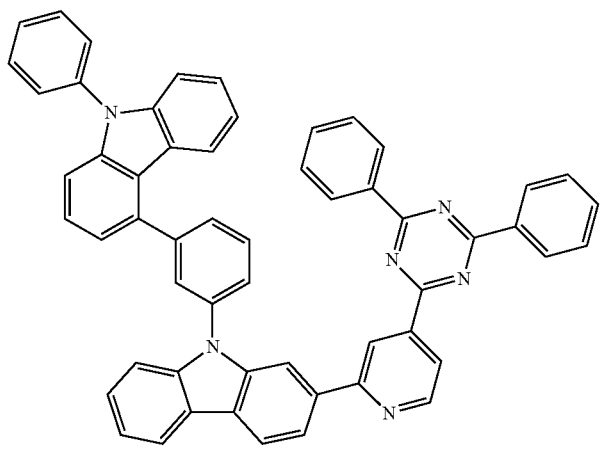 [SMILES: c1ccc(-c2nc(-c3ccccc3)nc(-c3ccnc(-c4ccc5c6ccccc6n(-c6cccc(-c7cccc8c7c7ccccc7n8-c7ccccc7)c6)c5c4)c3)n2)cc1]
Chemical Formula 1-52
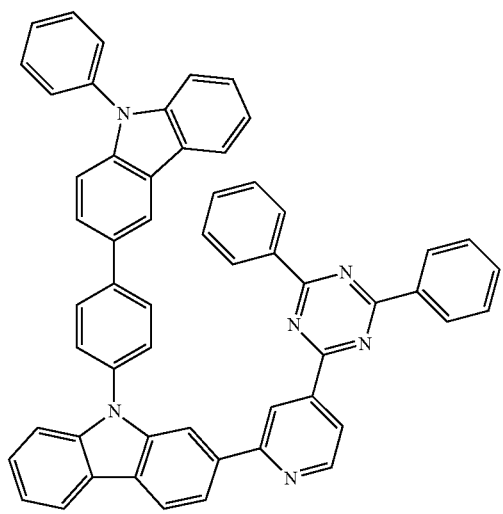 [SMILES: c1ccc(-c2nc(-c3ccccc3)nc(-c3ccnc(-c4ccc5c6ccccc6n(-c6ccc(-c7ccc8c(c7)c7ccccc7n8-c7ccccc7)cc6)c5c4)c3)n2)cc1]

Chemical Formula 1-53
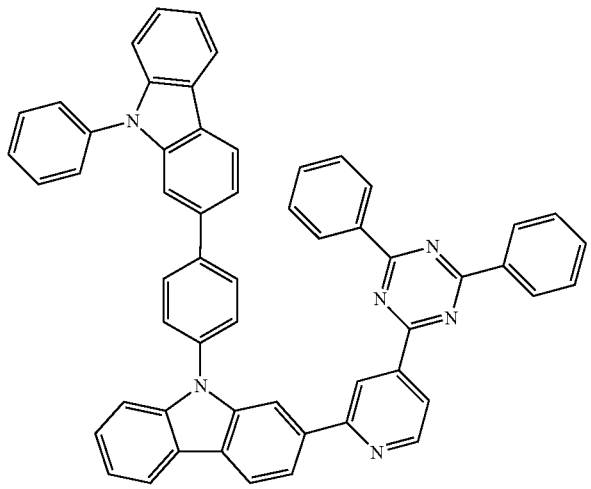 [SMILES: c1ccc(-c2nc(-c3ccccc3)nc(-c3ccnc(-c4ccc5c6ccccc6n(-c6ccc(-c7ccc8c9ccccc9n(-c9ccccc9)c8c7)cc6)c5c4)c3)n2)cc1]
Chemical Formula 1-54
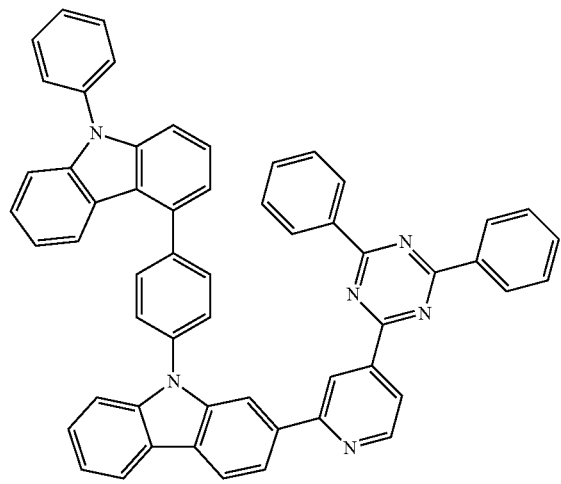 [SMILES: c1ccc(-c2nc(-c3ccccc3)nc(-c3ccnc(-c4ccc5c6ccccc6n(-c6ccc(-c7cccc8c7c7ccccc7n8-c7ccccc7)cc6)c5c4)c3)n2)cc1]
Chemical Formula 1-55
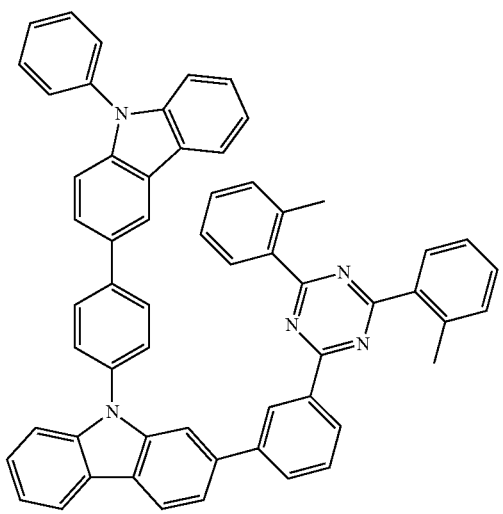 [SMILES: Cc1ccccc1-c1nc(-c2cccc(-c3ccc4c5ccccc5n(-c5ccc(-c6ccc7c(c6)c6ccccc6n7-c6ccccc6)cc5)c4c3)c2)nc(-c2ccccc2C)n1]

-continued
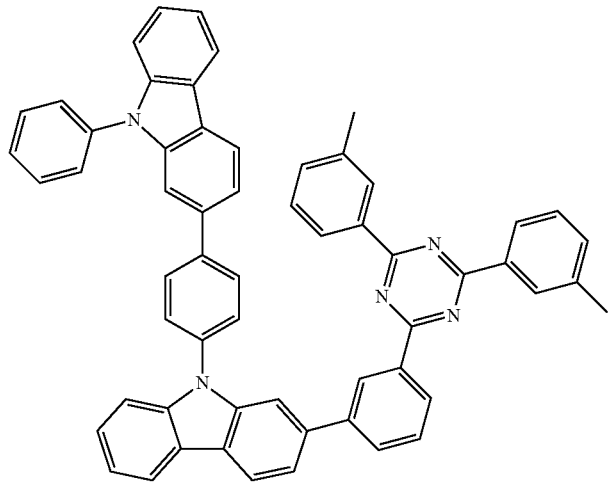 [SMILES: Cc1cccc(-c2nc(-c3cccc(C)c3)nc(-c3cccc(-c4ccc5c6ccccc6n(-c6ccc(-c7ccc8c9ccccc9n(-c9ccccc9)c8c7)cc6)c5c4)c3)n2)c1]
Chemical Formula 1-56
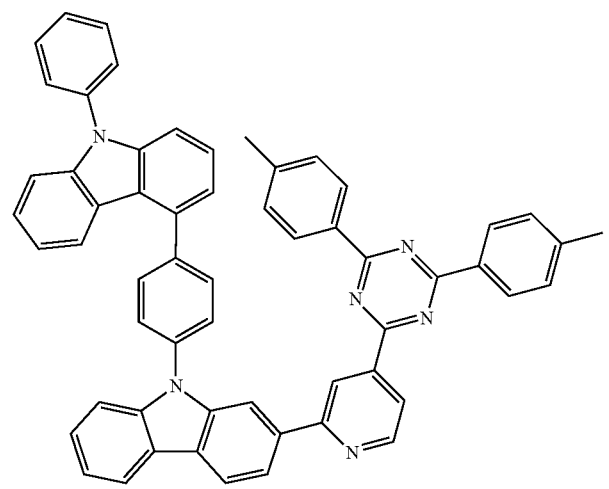 [SMILES: Cc1ccc(-c2nc(-c3ccc(C)cc3)nc(-c3ccnc(-c4ccc5c6ccccc6n(-c6ccc(-c7cccc8c7c7ccccc7n8-c7ccccc7)cc6)c5c4)c3)n2)cc1]
Chemical Formula 1-57
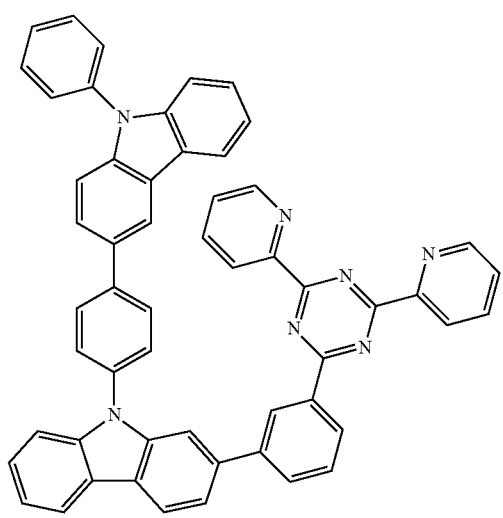 [SMILES: c1ccc(-n2c3ccccc3c3cc(-c4ccc(-n5c6ccccc6c6ccc(-c7cccc(-c8nc(-c9ccccn9)nc(-c9ccccn9)n8)c7)cc65)cc4)ccc32)cc1]
Chemical Formula 1-58

Chemical Formula 1-59
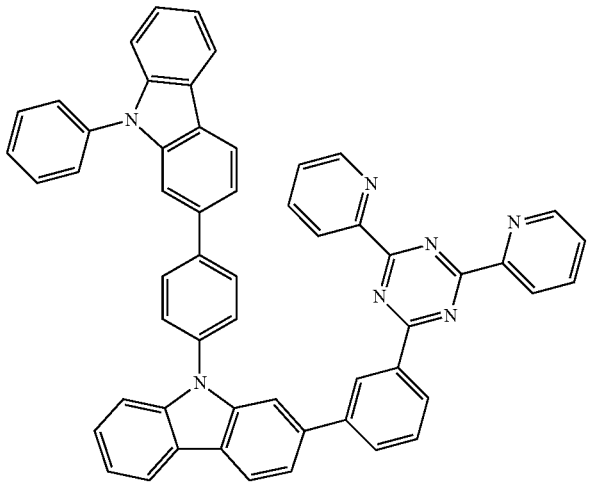 [SMILES: c1ccc(-n2c3ccccc3c3ccc(-c4ccc(-n5c6ccccc6c6ccc(-c7cccc(-c8nc(-c9ccccn9)nc(-c9ccccn9)n8)c7)cc65)cc4)cc32)cc1]
Chemical Formula 1-60
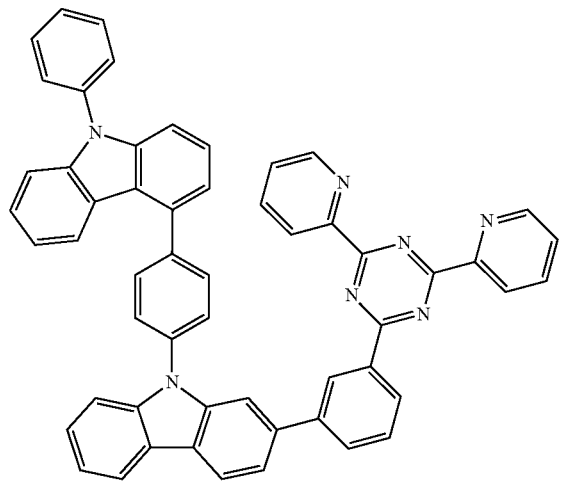 [SMILES: c1ccc(-n2c3ccccc3c3c(-c4ccc(-n5c6ccccc6c6ccc(-c7cccc(-c8nc(-c9ccccn9)nc(-c9ccccn9)n8)c7)cc65)cc4)cccc32)cc1]
Chemical Formula 1-61
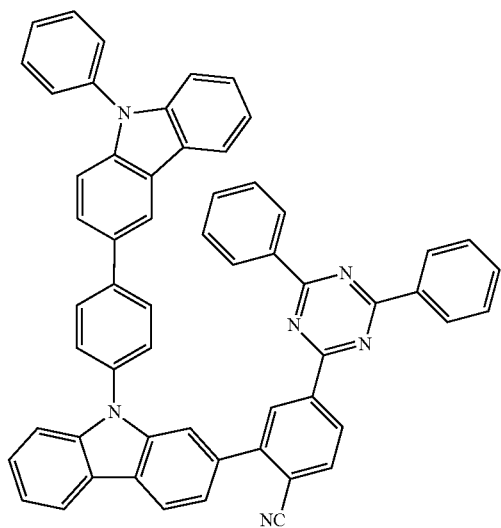 [SMILES: N#Cc1ccc(-c2nc(-c3ccccc3)nc(-c3ccccc3)n2)cc1-c1ccc2c3ccccc3n(-c3ccc(-c4ccc5c(c4)c4ccccc4n5-c4ccccc4)cc3)c2c1]

Chemical Formula 1-62
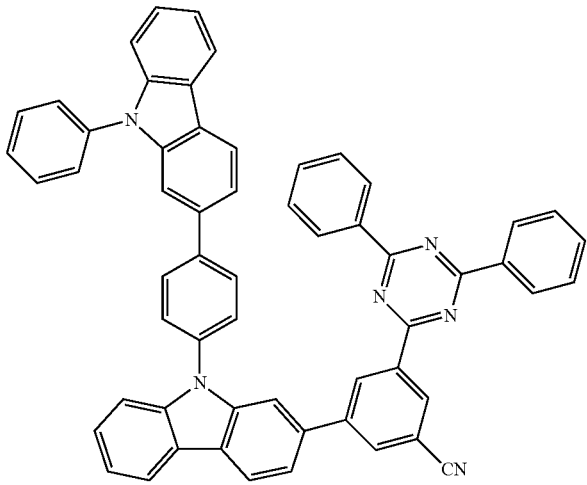 [SMILES: N#Cc1cc(-c2ccc3c4ccccc4n(-c4ccc(-c5ccc6c7ccccc7n(-c7ccccc7)c6c5)cc4)c3c2)cc(-c2nc(-c3ccccc3)nc(-c3ccccc3)n2)c1]
Chemical Formula 1-63
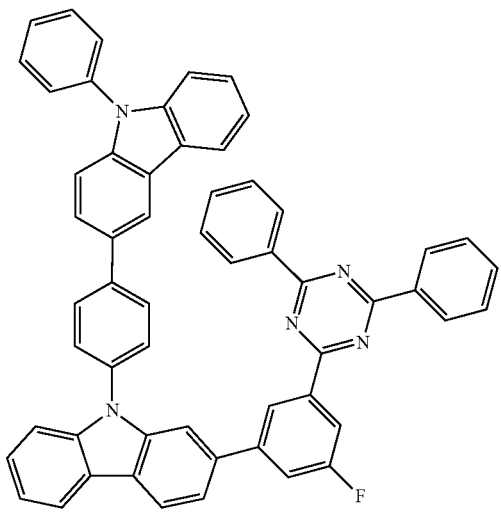 [SMILES: Fc1cc(-c2ccc3c4ccccc4n(-c4ccc(-c5ccc6c(c5)c5ccccc5n6-c5ccccc5)cc4)c3c2)cc(-c2nc(-c3ccccc3)nc(-c3ccccc3)n2)c1]
Chemical Formula 1-64
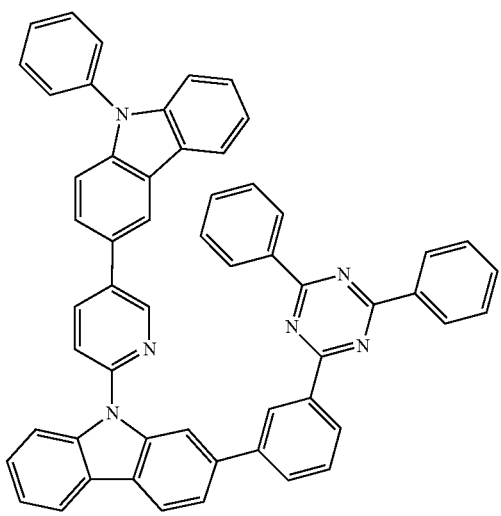 [SMILES: c1ccc(-c2nc(-c3ccccc3)nc(-c3cccc(-c4ccc5c6ccccc6n(-c6ccc(-c7ccc8c(c7)c7ccccc7n8-c7ccccc7)cn6)c5c4)c3)n2)cc1]

Chemical Formula 1-65
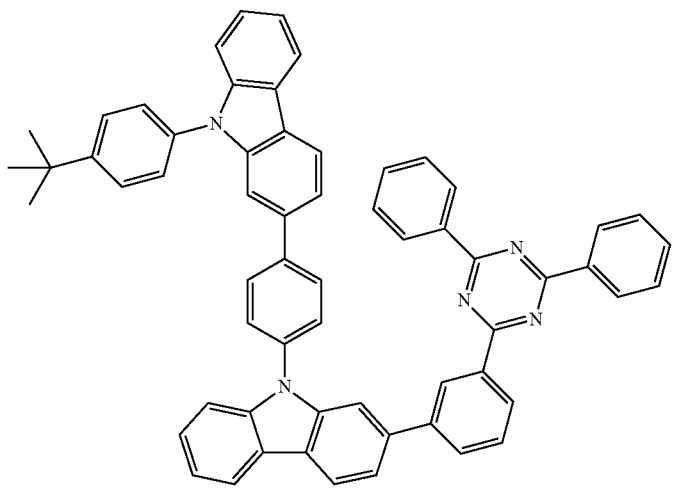 [SMILES: CC(C)(C)c1ccc(-n2c3ccccc3c3ccc(-c4ccc(-n5c6ccccc6c6ccc(-c7cccc(-c8nc(-c9ccccc9)nc(-c9ccccc9)n8)c7)cc65)cc4)cc32)cc1]
Chemical Formula 1-66
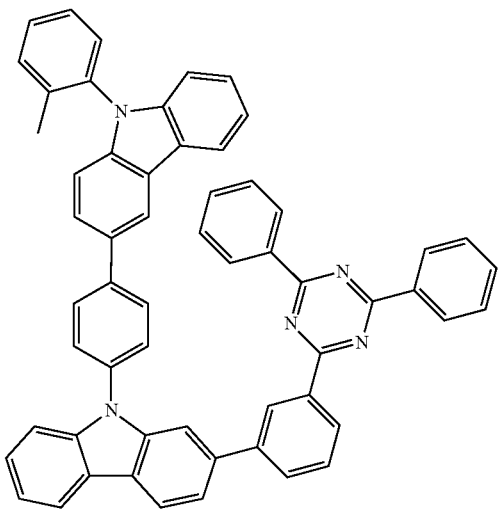 [SMILES: Cc1ccccc1-n1c2ccccc2c2cc(-c3ccc(-n4c5ccccc5c5ccc(-c6cccc(-c7nc(-c8ccccc8)nc(-c8ccccc8)n7)c6)cc54)cc3)ccc21]
Chemical Formula 1-67
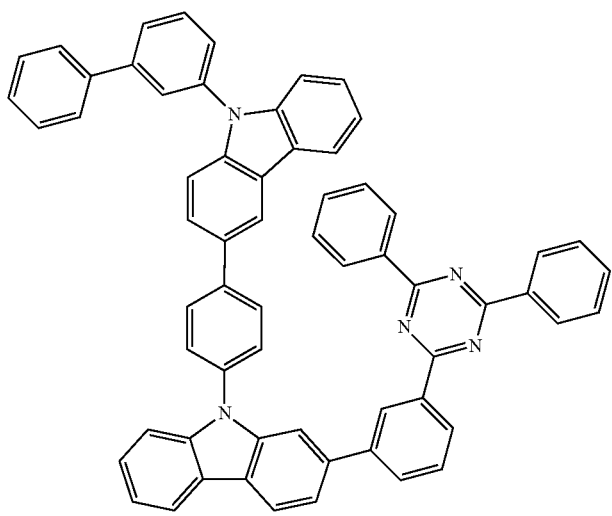 [SMILES: c1ccc(-c2cccc(-n3c4ccccc4c4cc(-c5ccc(-n6c7ccccc7c7ccc(-c8cccc(-c9nc(-c%10ccccc%10)nc(-c%10ccccc%10)n9)c8)cc76)cc5)ccc43)c2)cc1]

Chemical Formula 1-68
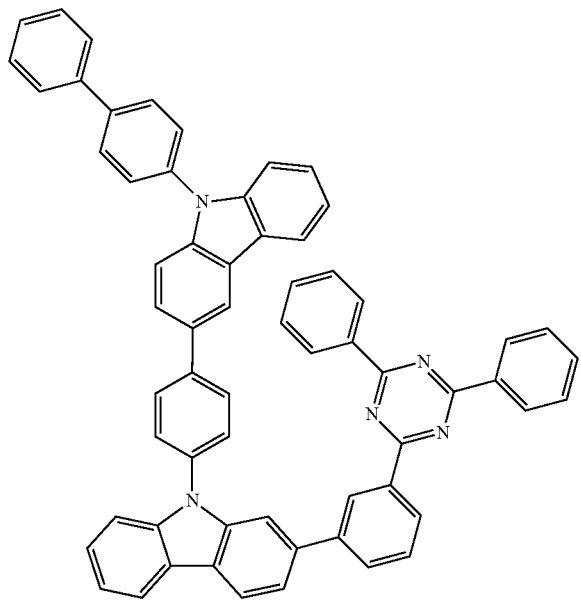 [SMILES: c1ccc(-c2ccc(-n3c4ccccc4c4cc(-c5ccc(-n6c7ccccc7c7ccc(-c8cccc(-c9nc(-c%10ccccc%10)nc(-c%10ccccc%10)n9)c8)cc76)cc5)ccc43)cc2)cc1]
Chemical Formula 1-69
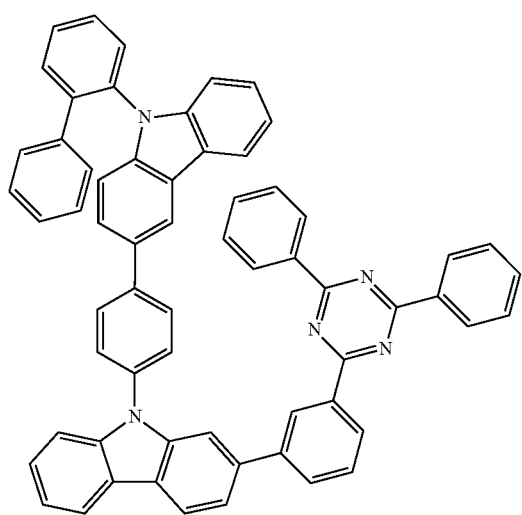 [SMILES: c1ccc(-c2nc(-c3ccccc3)nc(-c3cccc(-c4ccc5c6ccccc6n(-c6ccc(-c7ccc8c(c7)c7ccccc7n8-c7ccccc7-c7ccccc7)cc6)c5c4)c3)n2)cc1]

Chemical Formula 1-70
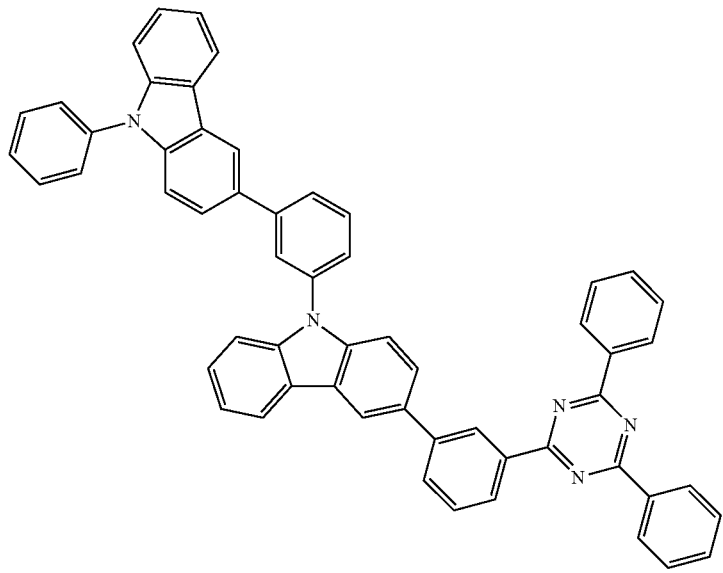
Chemical Formula 1-71
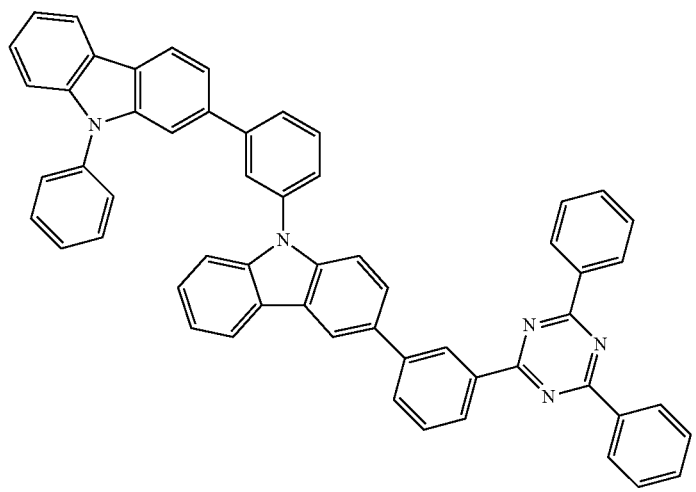
Chemical Formula 1-72
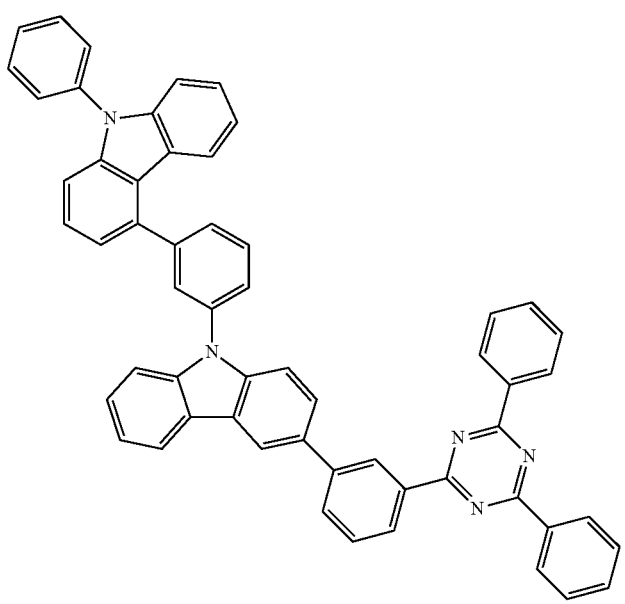 [SMILES: c1ccc(-c2nc(-c3ccccc3)nc(-c3cccc(-c4ccc5c(c4)c4ccccc4n5-c4cccc(-c5cccc6c5c5ccccc5n6-c5ccccc5)c4)c3)n2)cc1]

Chemical Formula 1-73
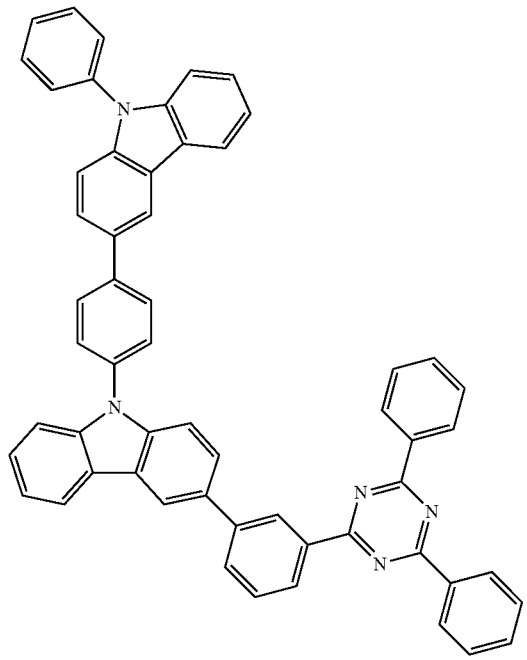 [SMILES: c1ccc(-c2nc(-c3ccccc3)nc(-c3cccc(-c4ccc5c(c4)c4ccccc4n5-c4ccc(-c5ccc6c(c5)c5ccccc5n6-c5ccccc5)cc4)c3)n2)cc1]
Chemical Formula 1-74
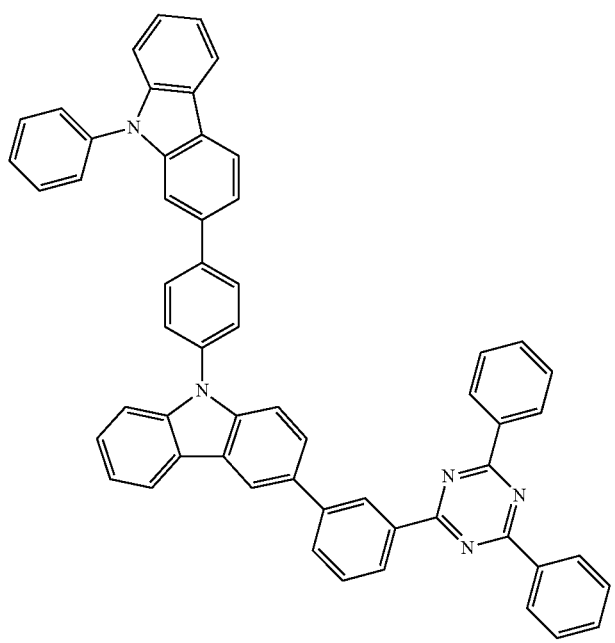

Chemical Formula 1-75
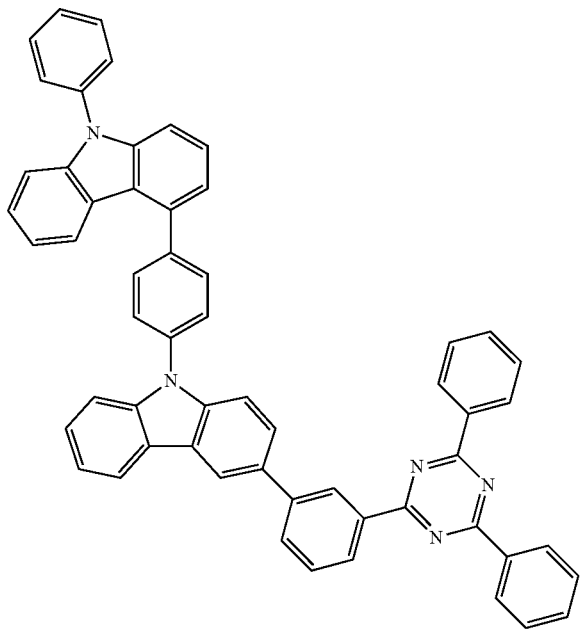 [SMILES: c1ccc(-c2nc(-c3ccccc3)nc(-c3cccc(-c4ccc5c(c4)c4ccccc4n5-c4ccc(-c5cccc6c5c5ccccc5n6-c5ccccc5)cc4)c3)n2)cc1]
Chemical Formula 1-76
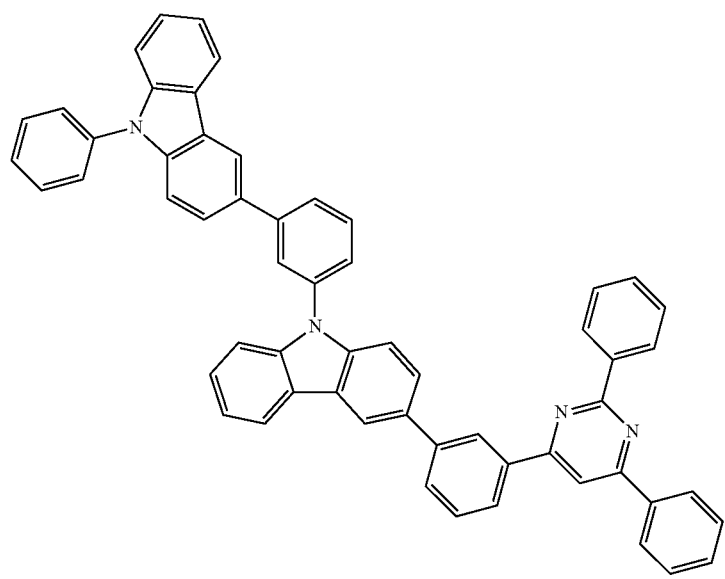

Chemical Formula 1-77
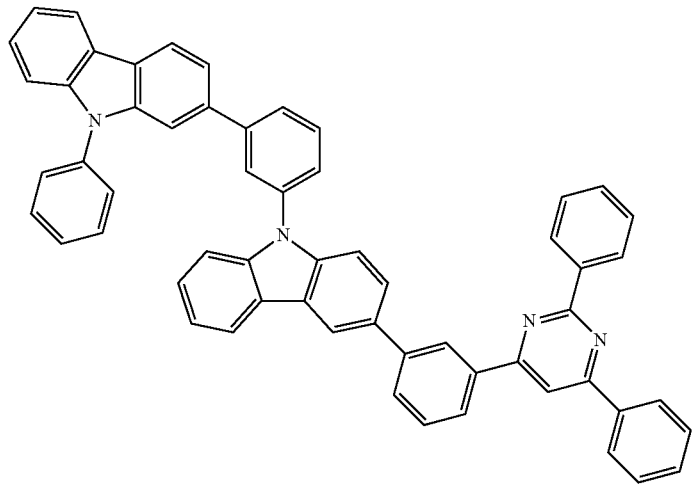
Chemical Formula 1-78
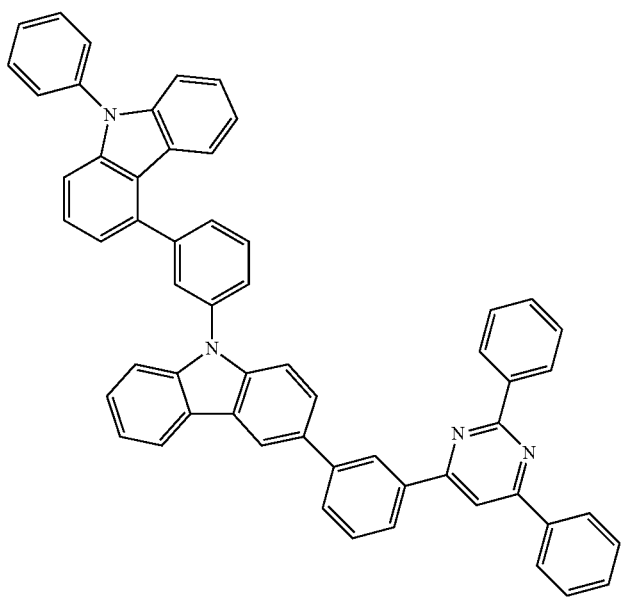 [SMILES: c1ccc(-c2cc(-c3cccc(-c4ccc5c(c4)c4ccccc4n5-c4cccc(-c5cccc6c5c5ccccc5n6-c5ccccc5)c4)c3)nc(-c3ccccc3)n2)cc1]

Chemical Formula 1-79
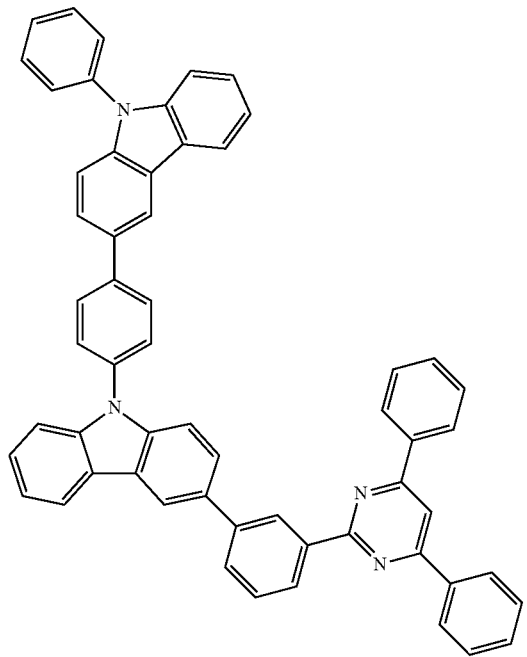
Chemical Formula 1-80
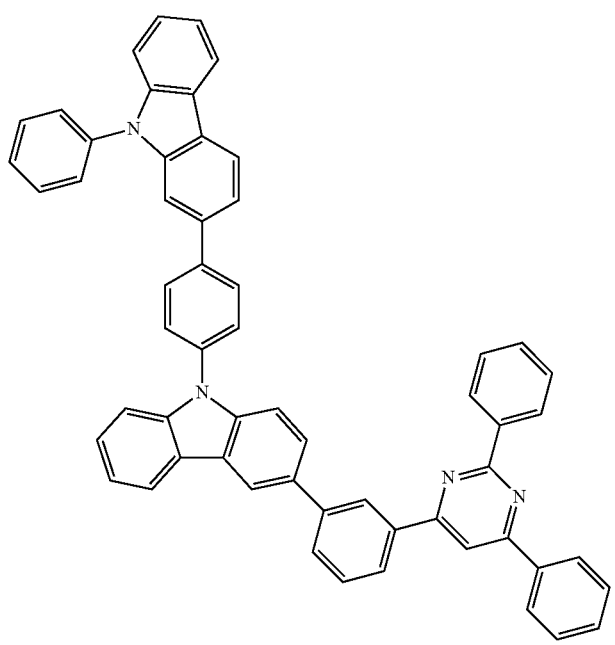 [SMILES: c1ccc(-c2cc(-c3cccc(-c4ccc5c(c4)c4ccccc4n5-c4ccc(-c5ccc6c7ccccc7n(-c7ccccc7)c6c5)cc4)c3)nc(-c3ccccc3)n2)cc1]

Chemical Formula 1-81
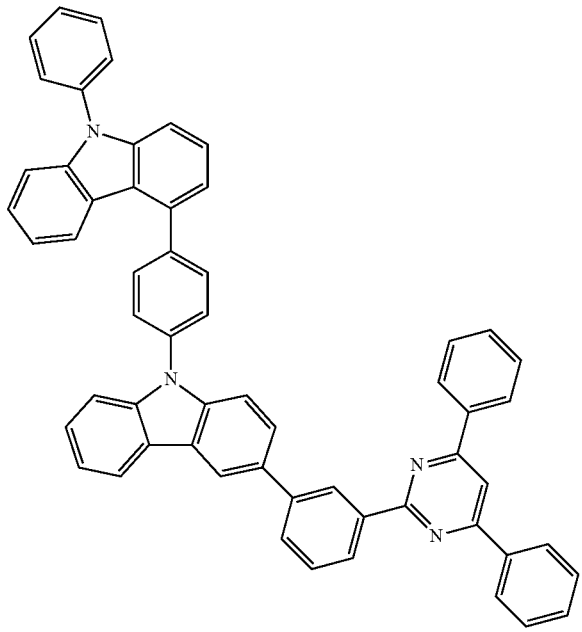 [SMILES: c1ccc(-c2cc(-c3ccccc3)nc(-c3cccc(-c4ccc5c(c4)c4ccccc4n5-c4ccc(-c5cccc6c5c5ccccc5n6-c5ccccc5)cc4)c3)n2)cc1]
Chemical Formula 1-82
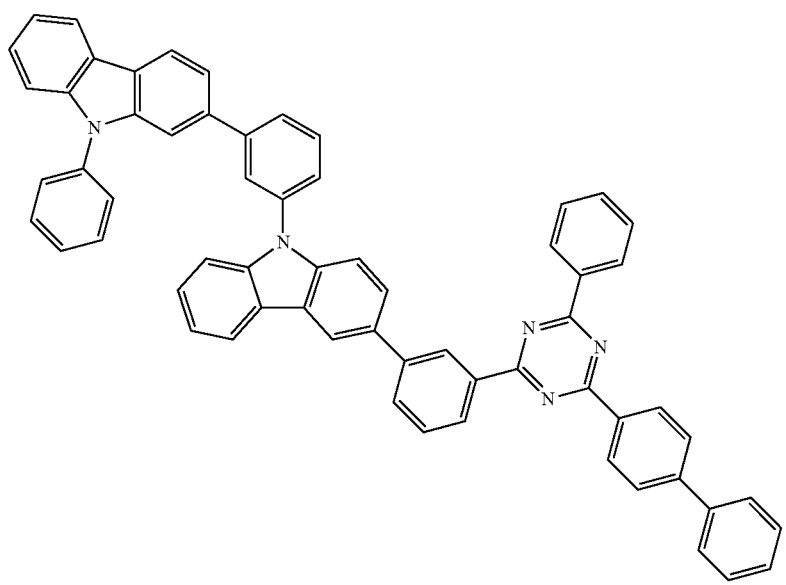 [SMILES: c1ccc(-c2ccc(-c3nc(-c4ccccc4)nc(-c4cccc(-c5ccc6c(c5)c5ccccc5n6-c5cccc(-c6ccc7c8ccccc8n(-c8ccccc8)c7c6)c5)c4)n3)cc2)cc1]

Chemical Formula 1-83
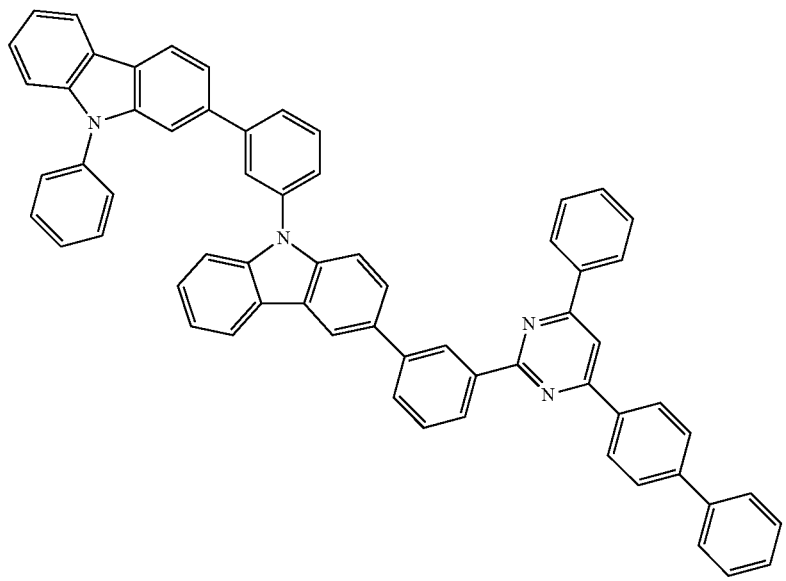 [SMILES: c1ccc(-c2ccc(-c3cc(-c4ccccc4)nc(-c4cccc(-c5ccc6c(c5)c5ccccc5n6-c5cccc(-c6ccc7c8ccccc8n(-c8ccccc8)c7c6)c5)c4)n3)cc2)cc1]
Chemical Formula 1-84
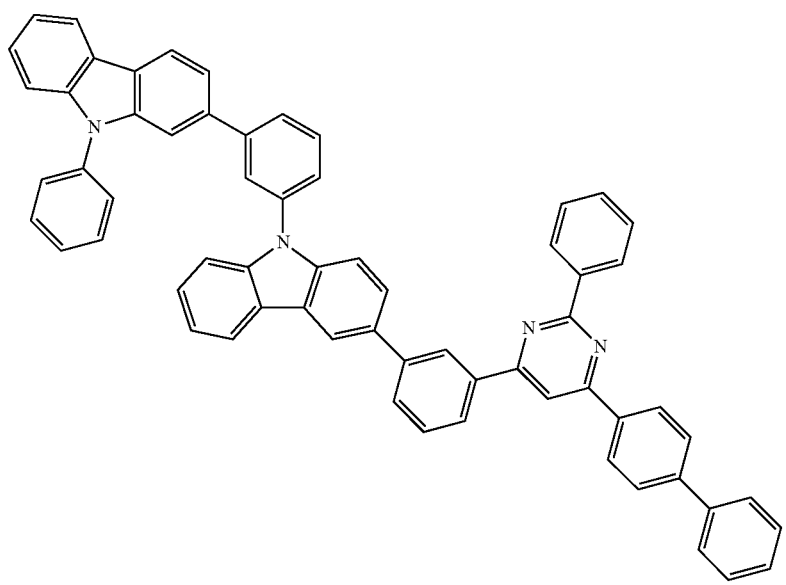 [SMILES: c1ccc(-c2ccc(-c3cc(-c4cccc(-c5ccc6c(c5)c5ccccc5n6-c5cccc(-c6ccc7c8ccccc8n(-c8ccccc8)c7c6)c5)c4)nc(-c4ccccc4)n3)cc2)cc1]

Chemical Formula 1-85
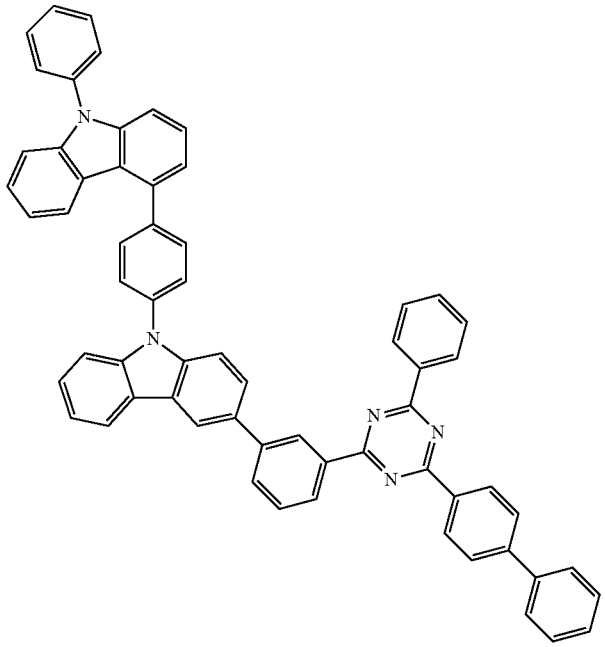 [SMILES: c1ccc(-c2ccc(-c3nc(-c4ccccc4)nc(-c4cccc(-c5ccc6c(c5)c5ccccc5n6-c5ccc(-c6cccc7c6c6ccccc6n7-c6ccccc6)cc5)c4)n3)cc2)cc1]
Chemical Formula 1-86
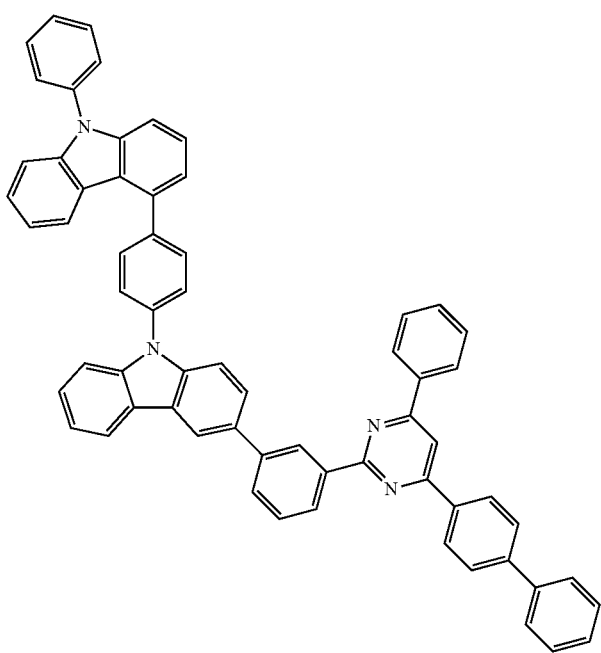 [SMILES: c1ccc(-c2ccc(-c3cc(-c4ccccc4)nc(-c4cccc(-c5ccc6c(c5)c5ccccc5n6-c5ccc(-c6cccc7c6c6ccccc6n7-c6ccccc6)cc5)c4)n3)cc2)cc1]

Chemical Formula 1-87
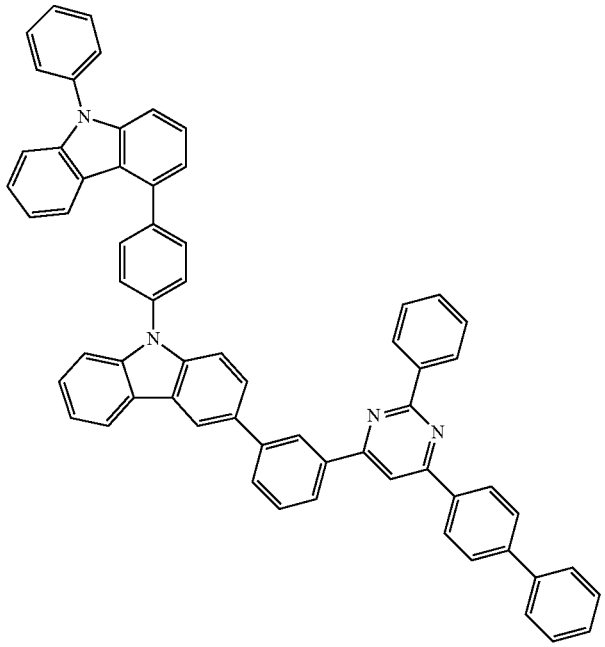 [SMILES: c1ccc(-c2ccc(-c3cc(-c4cccc(-c5ccc6c(c5)c5ccccc5n6-c5ccc(-c6cccc7c6c6ccccc6n7-c6ccccc6)cc5)c4)nc(-c4ccccc4)n3)cc2)cc1]
Chemical Formula 1-88
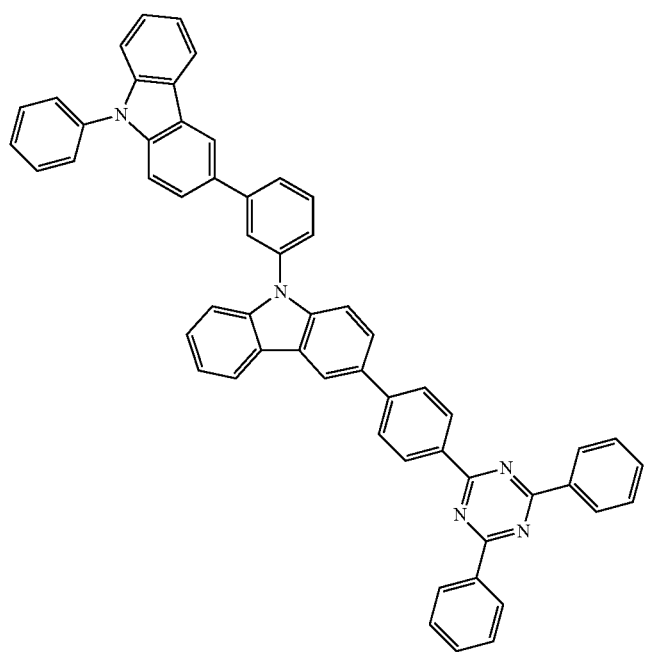 [SMILES: c1ccc(-c2nc(-c3ccccc3)nc(-c3ccc(-c4ccc5c(c4)c4ccccc4n5-c4cccc(-c5ccc6c(c5)c5ccccc5n6-c5ccccc5)c4)cc3)n2)cc1]

Chemical Formula 1-89
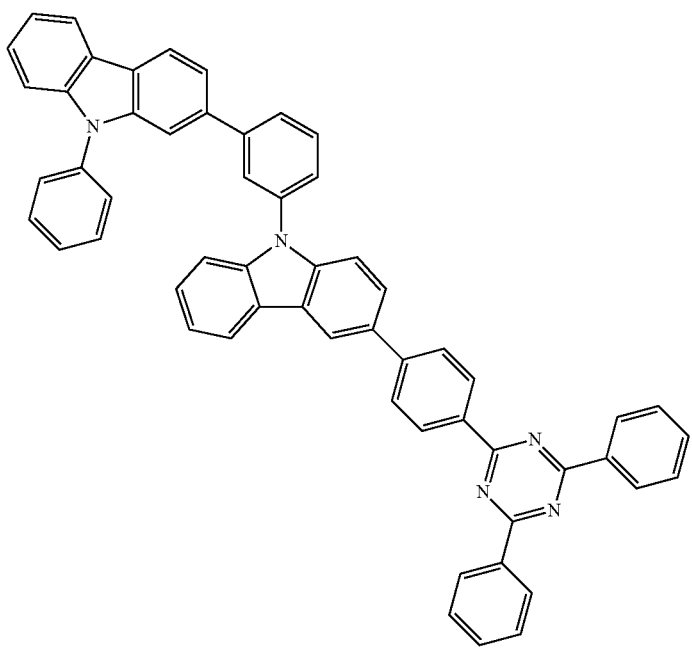
Chemical Formula 1-90
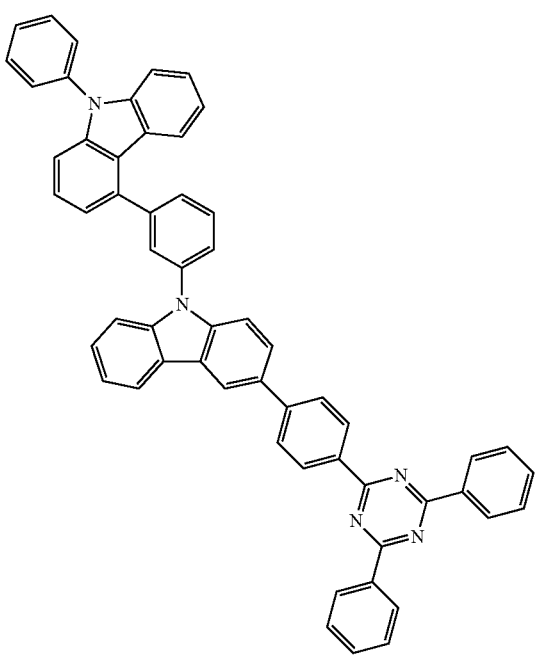 [SMILES: c1ccc(-c2nc(-c3ccccc3)nc(-c3ccc(-c4ccc5c(c4)c4ccccc4n5-c4cccc(-c5cccc6c5c5ccccc5n6-c5ccccc5)c4)cc3)n2)cc1]

Chemical Formula 1-91
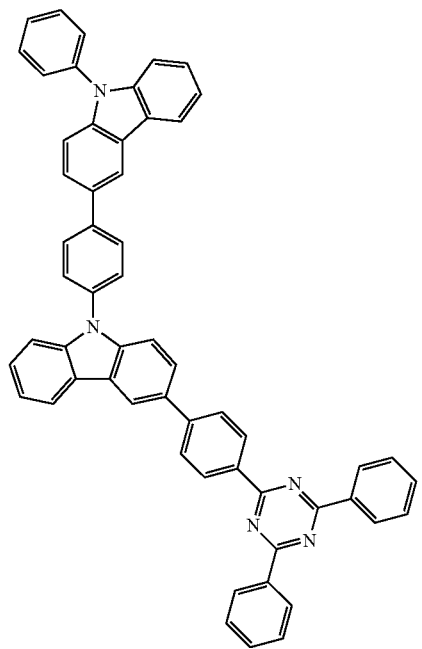 [SMILES: c1ccc(-c2nc(-c3ccccc3)nc(-c3ccc(-c4ccc5c(c4)c4ccccc4n5-c4ccc(-c5ccc6c(c5)c5ccccc5n6-c5ccccc5)cc4)cc3)n2)cc1]
Chemical Formula 1-92
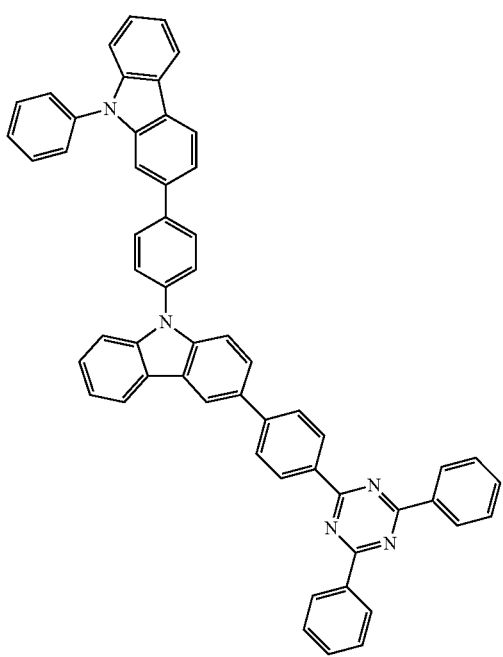 [SMILES: c1ccc(-c2nc(-c3ccccc3)nc(-c3ccc(-c4ccc5c(c4)c4ccccc4n5-c4ccc(-c5ccc6c7ccccc7n(-c7ccccc7)c6c5)cc4)cc3)n2)cc1]

Chemical Formula 1-93
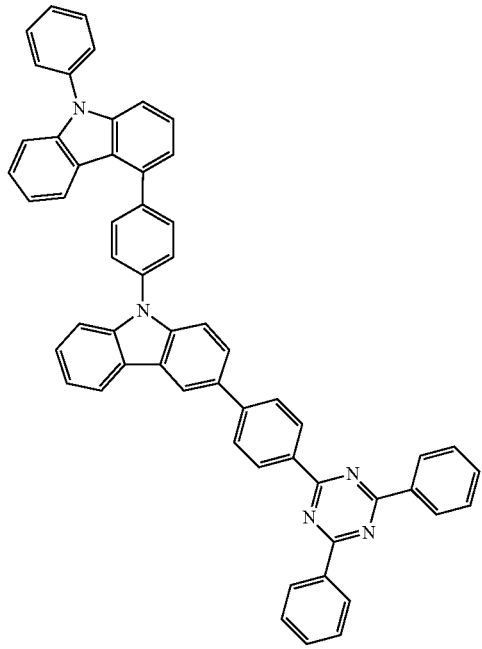 [SMILES: c1ccc(-c2nc(-c3ccccc3)nc(-c3ccc(-c4ccc5c(c4)c4ccccc4n5-c4ccc(-c5cccc6c5c5ccccc5n6-c5ccccc5)cc4)cc3)n2)cc1]
Chemical Formula 1-94
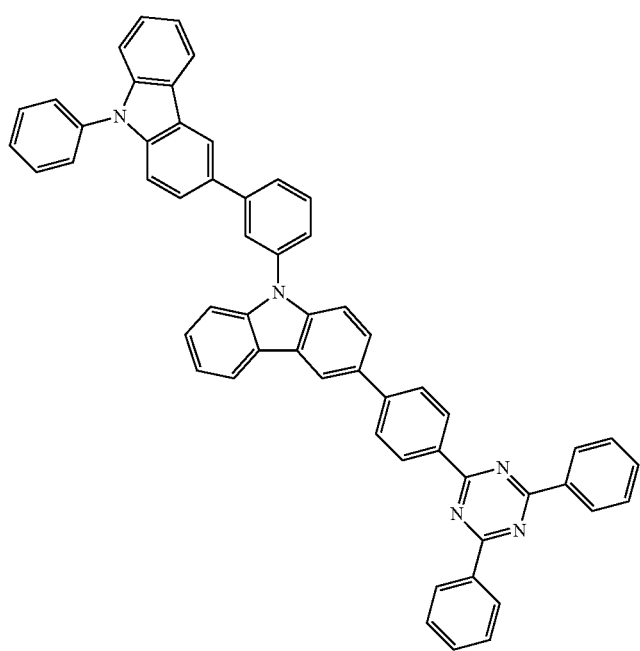 [SMILES: c1ccc(-c2nc(-c3ccccc3)nc(-c3ccc(-c4ccc5c(c4)c4ccccc4n5-c4cccc(-c5ccc6c(c5)c5ccccc5n6-c5ccccc5)c4)cc3)n2)cc1]

Chemical Formula 1-95
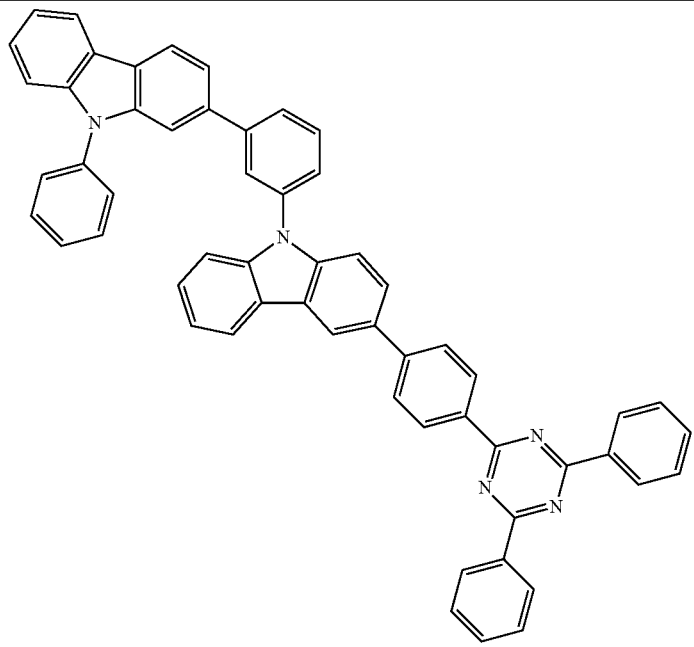
Chemical Formula 1-96
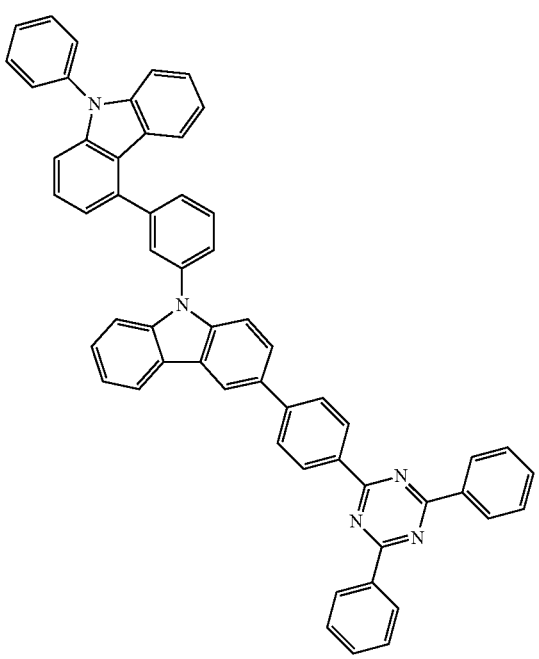

Chemical Formula 1-97
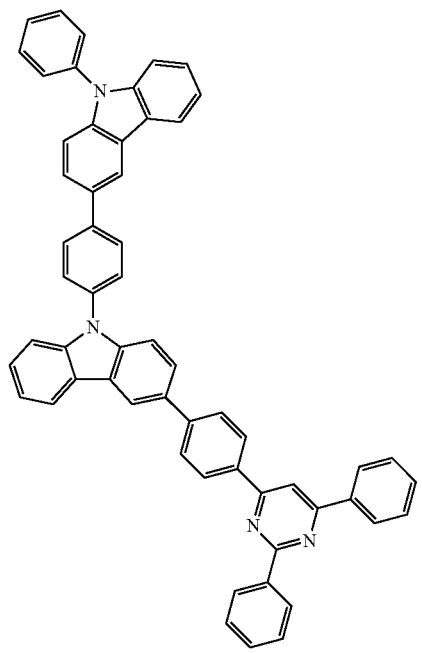
Chemical Formula 1-98
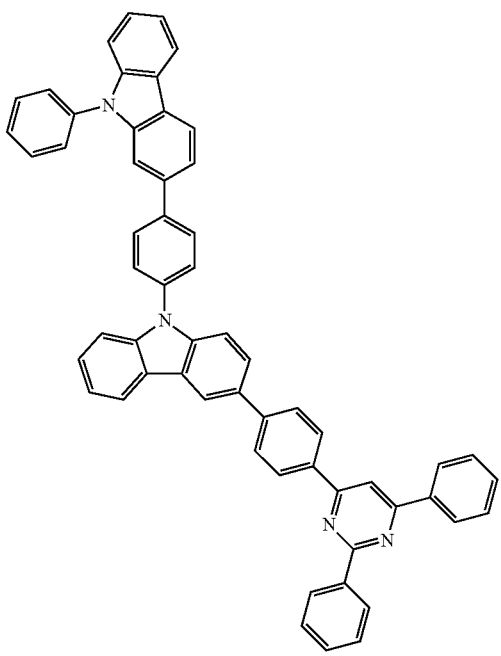 [SMILES: c1ccc(-c2cc(-c3ccc(-c4ccc5c(c4)c4ccccc4n5-c4ccc(-c5ccc6c7ccccc7n(-c7ccccc7)c6c5)cc4)cc3)nc(-c3ccccc3)n2)cc1]

Chemical Formula 1-99
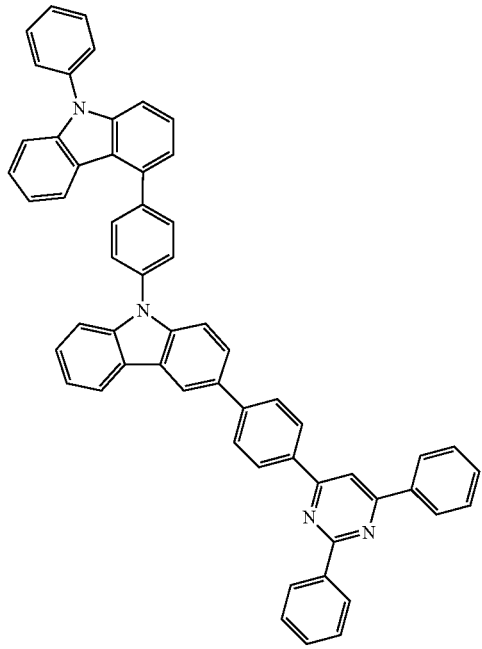 [SMILES: c1ccc(-c2cc(-c3ccc(-c4ccc5c(c4)c4ccccc4n5-c4ccc(-c5cccc6c5c5ccccc5n6-c5ccccc5)cc4)cc3)nc(-c3ccccc3)n2)cc1]
Chemical Formula 1-100
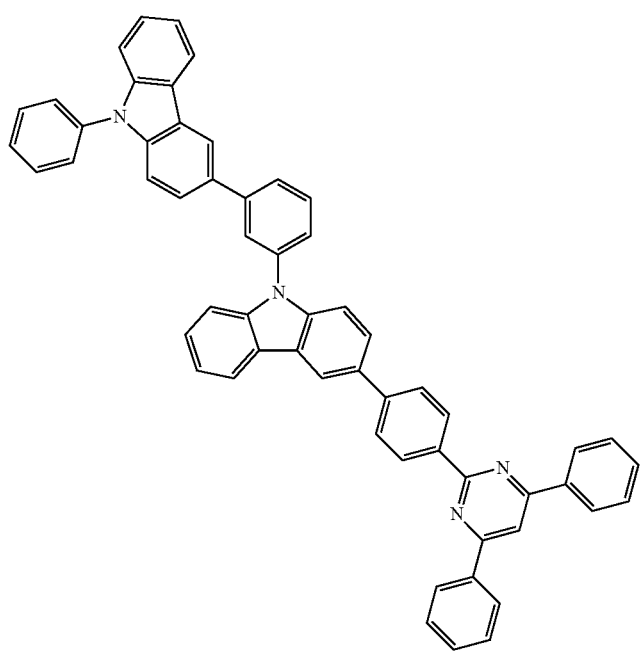 [SMILES: c1ccc(-c2cc(-c3ccccc3)nc(-c3ccc(-c4ccc5c(c4)c4ccccc4n5-c4cccc(-c5ccc6c(c5)c5ccccc5n6-c5ccccc5)c4)cc3)n2)cc1]

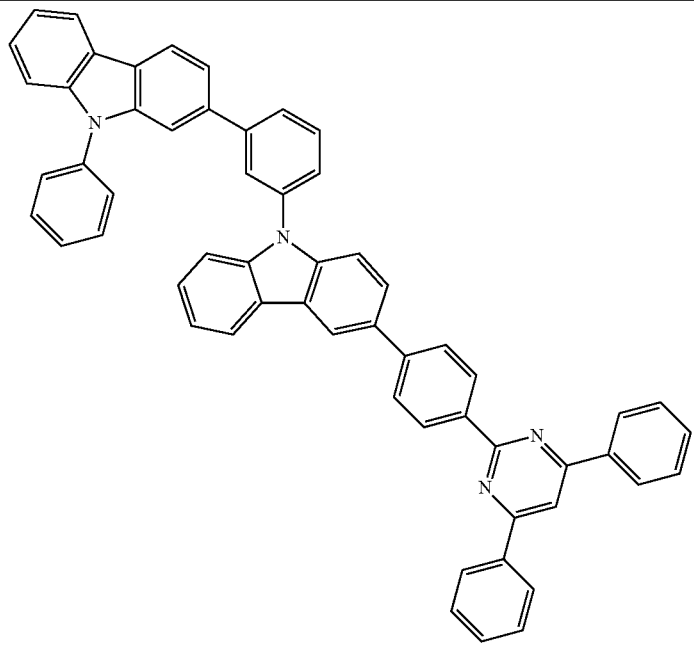
Chemical Formula 1-101
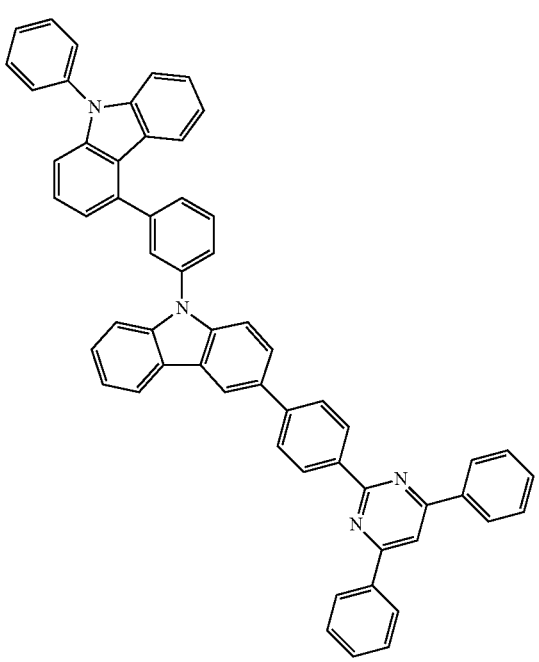 [SMILES: c1ccc(-c2cc(-c3ccccc3)nc(-c3ccc(-c4ccc5c(c4)c4ccccc4n5-c4cccc(-c5cccc6c5c5ccccc5n6-c5ccccc5)c4)cc3)n2)cc1]
Chemical Formula 1-102

Chemical Formula 1-103
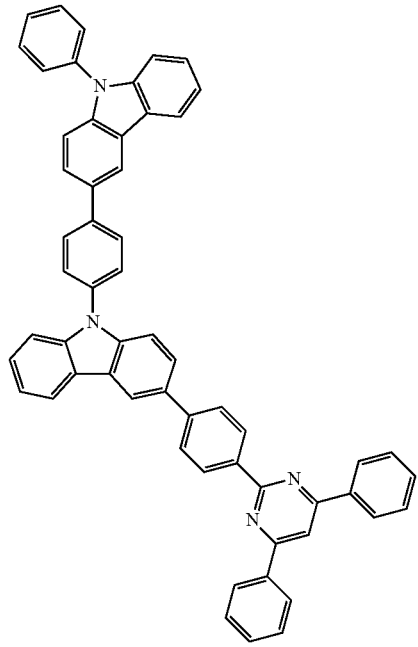
Chemical Formula 1-104
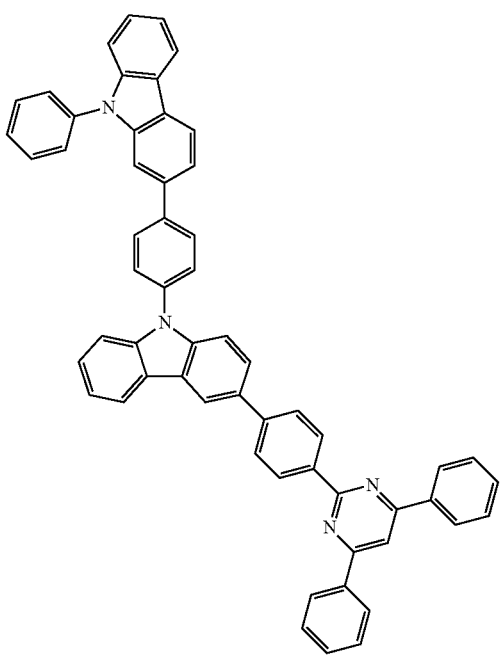

Chemical Formula 1-105
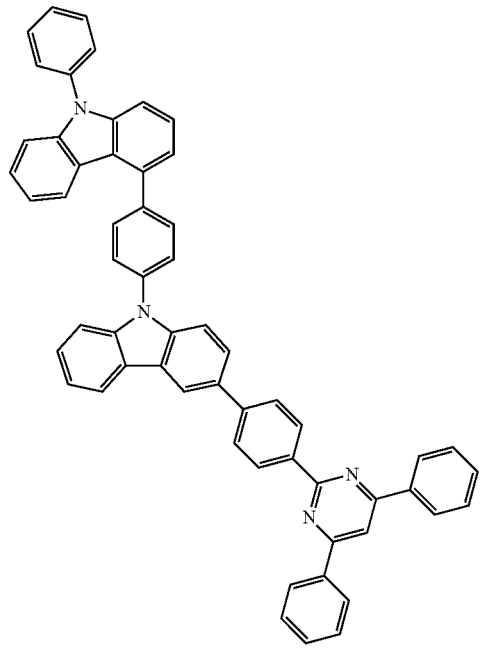 [SMILES: c1ccc(-c2cc(-c3ccccc3)nc(-c3ccc(-c4ccc5c(c4)c4ccccc4n5-c4ccc(-c5cccc6c5c5ccccc5n6-c5ccccc5)cc4)cc3)n2)cc1]
Chemical Formula 1-106
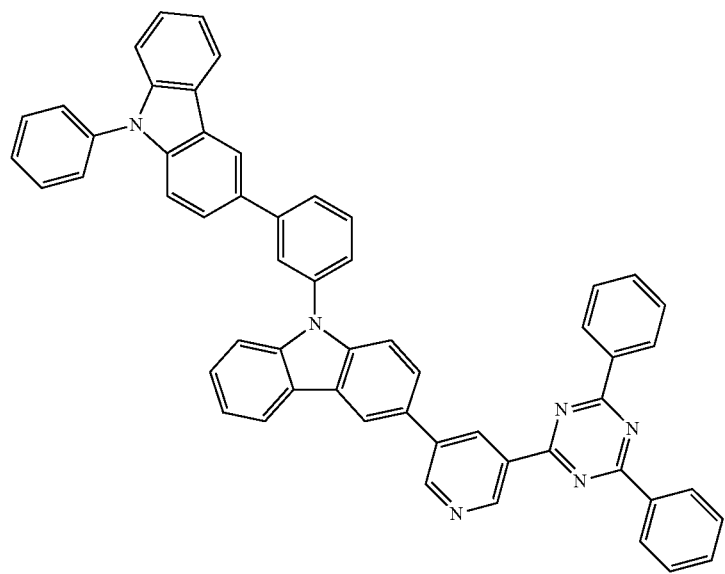

Chemical Formula 1-107
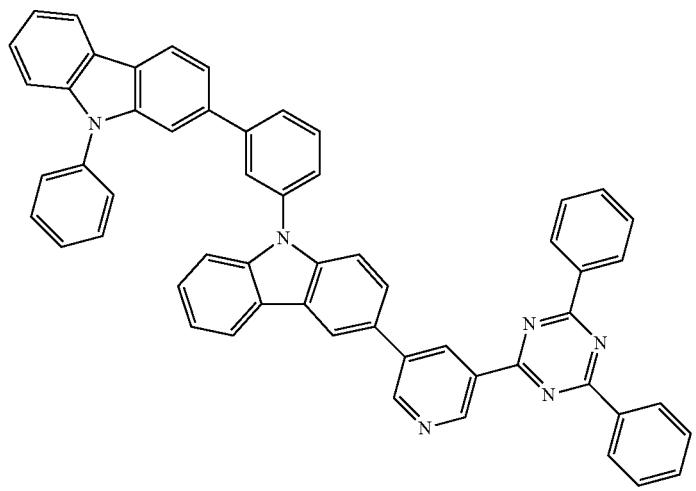
Chemical Formula 1-108
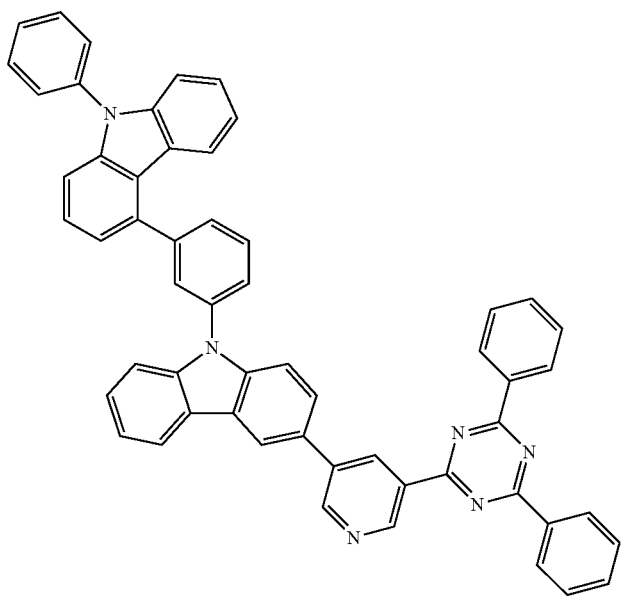

Chemical Formula 1-109
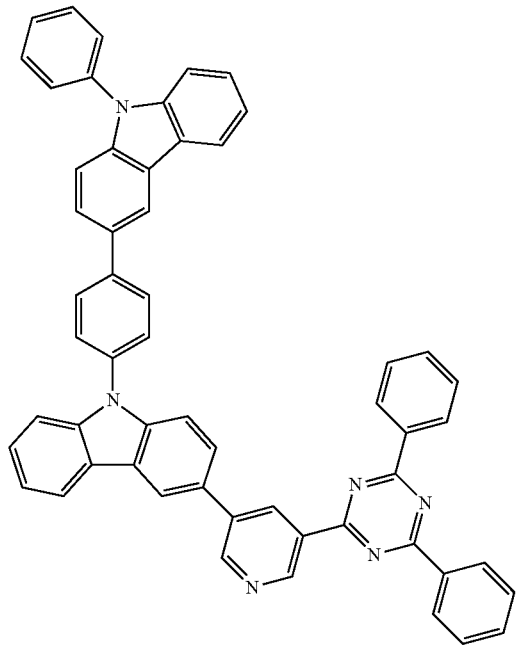
Chemical Formula 1-110
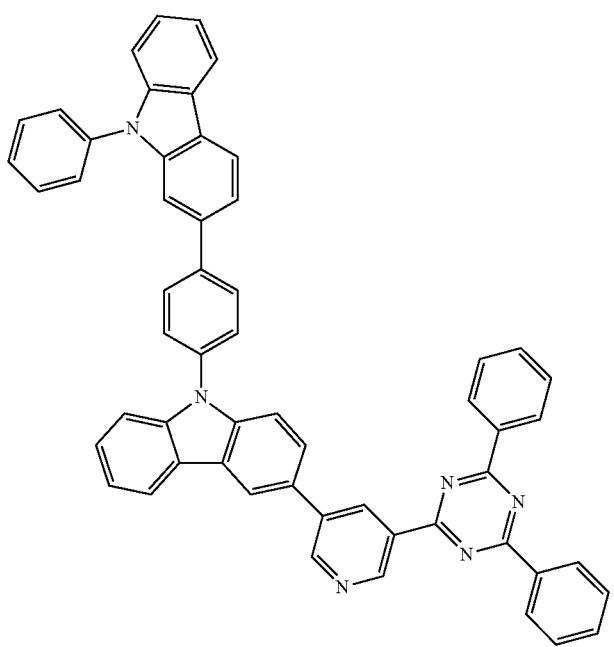 [SMILES: c1ccc(-c2nc(-c3ccccc3)nc(-c3cncc(-c4ccc5c(c4)c4ccccc4n5-c4ccc(-c5ccc6c7ccccc7n(-c7ccccc7)c6c5)cc4)c3)n2)cc1]

Chemical Formula 1-111
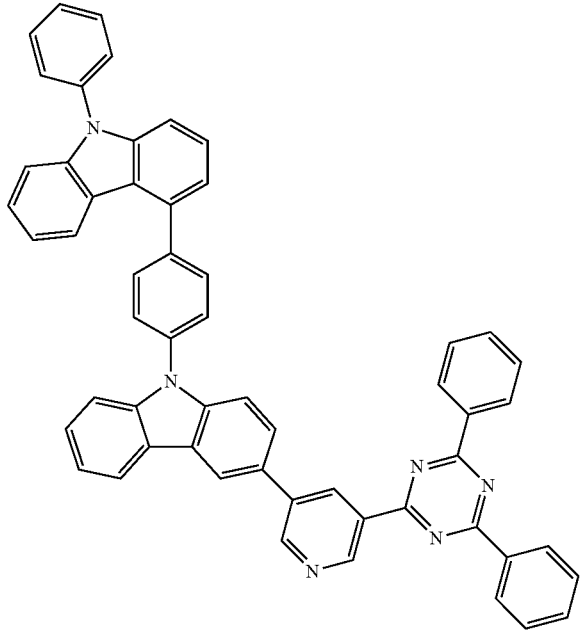 [SMILES: c1ccc(-c2nc(-c3ccccc3)nc(-c3cncc(-c4ccc5c(c4)c4ccccc4n5-c4ccc(-c5cccc6c5c5ccccc5n6-c5ccccc5)cc4)c3)n2)cc1]
Chemical Formula 1-112
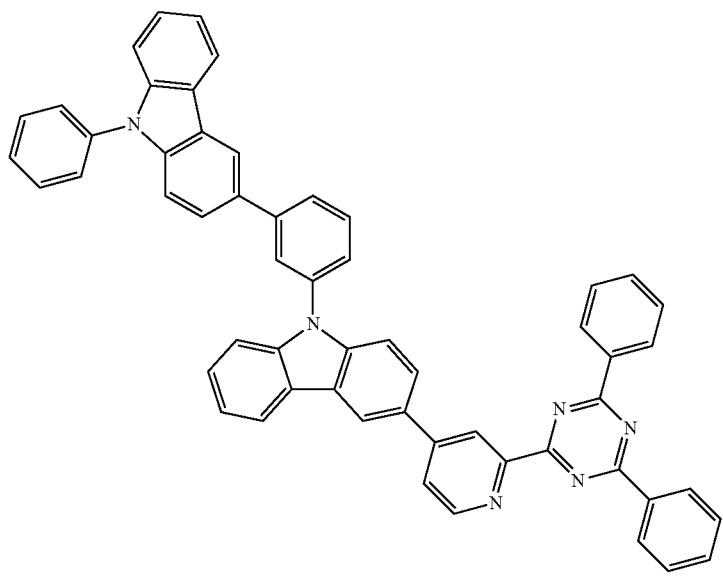

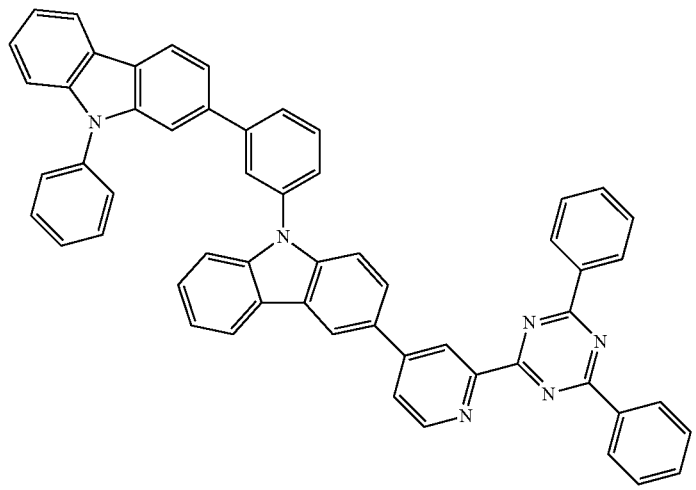
Chemical Formula 1-113
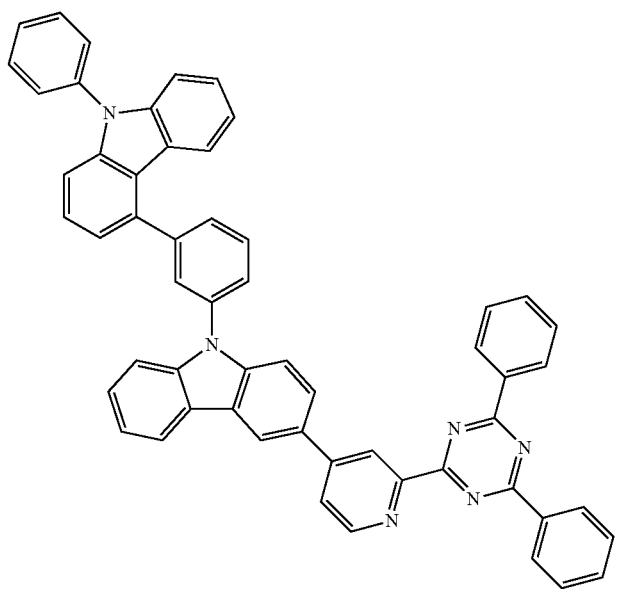
Chemical Formula 1-114

Chemical Formula 1-115
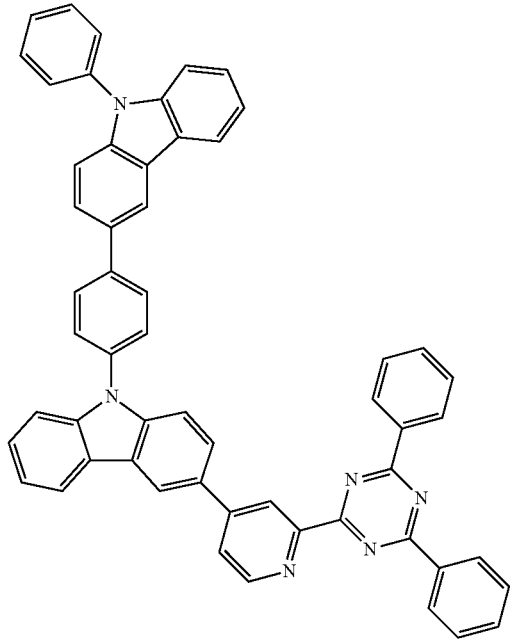 [SMILES: c1ccc(-c2nc(-c3ccccc3)nc(-c3cc(-c4ccc5c(c4)c4ccccc4n5-c4ccc(-c5ccc6c(c5)c5ccccc5n6-c5ccccc5)cc4)ccn3)n2)cc1]
Chemical Formula 1-116
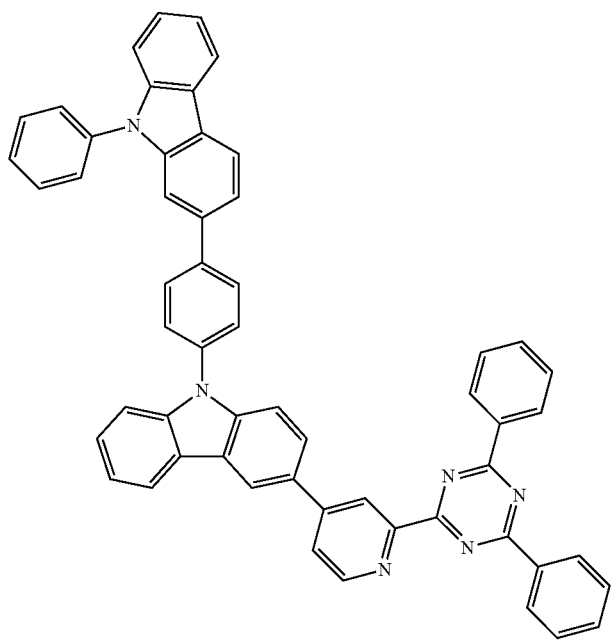 [SMILES: c1ccc(-c2nc(-c3ccccc3)nc(-c3cc(-c4ccc5c(c4)c4ccccc4n5-c4ccc(-c5ccc6c7ccccc7n(-c7ccccc7)c6c5)cc4)ccn3)n2)cc1]

Chemical Formula 1-117
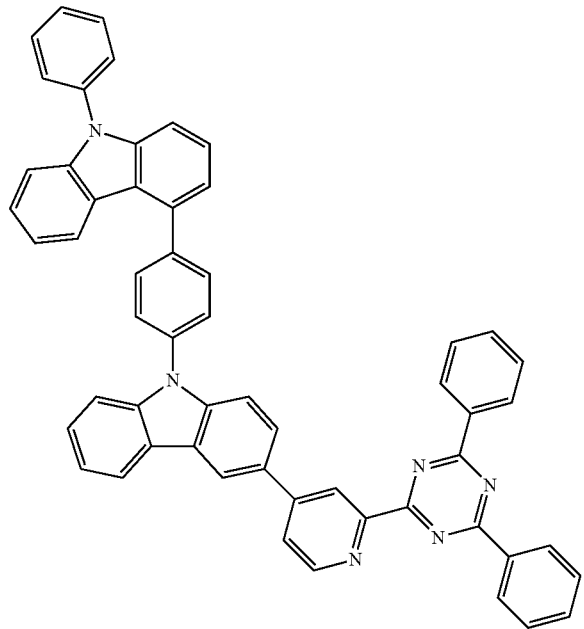 [SMILES: c1ccc(-c2nc(-c3ccccc3)nc(-c3cc(-c4ccc5c(c4)c4ccccc4n5-c4ccc(-c5cccc6c5c5ccccc5n6-c5ccccc5)cc4)ccn3)n2)cc1]
Chemical Formula 1-118
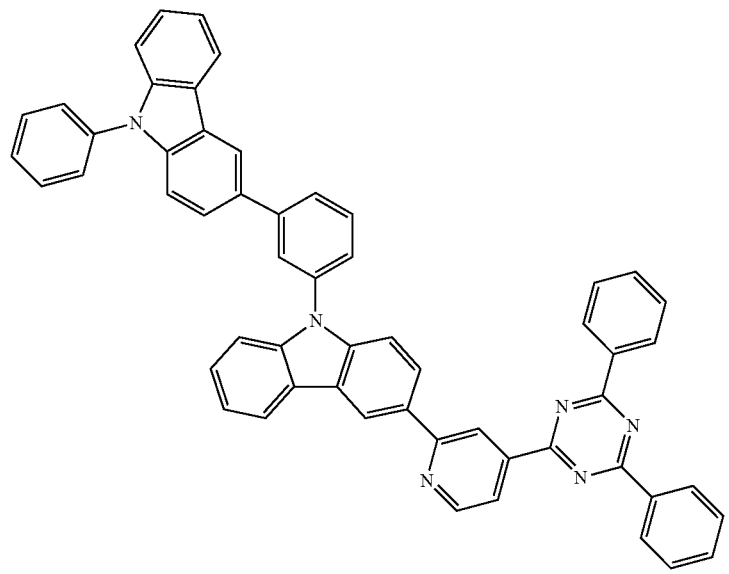 [SMILES: c1ccc(-c2nc(-c3ccccc3)nc(-c3ccnc(-c4ccc5c(c4)c4ccccc4n5-c4cccc(-c5ccc6c(c5)c5ccccc5n6-c5ccccc5)c4)c3)n2)cc1]

Chemical Formula 1-119
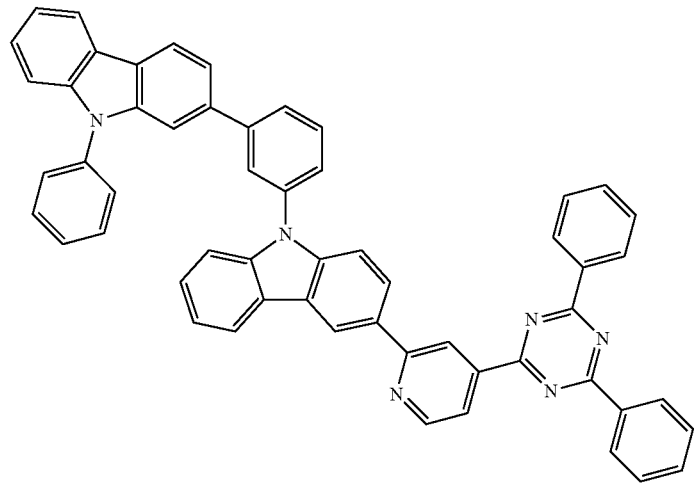 [SMILES: c1ccc(-c2nc(-c3ccccc3)nc(-c3ccnc(-c4ccc5c(c4)c4ccccc4n5-c4cccc(-c5ccc6c7ccccc7n(-c7ccccc7)c6c5)c4)c3)n2)cc1]
Chemical Formula 1-120
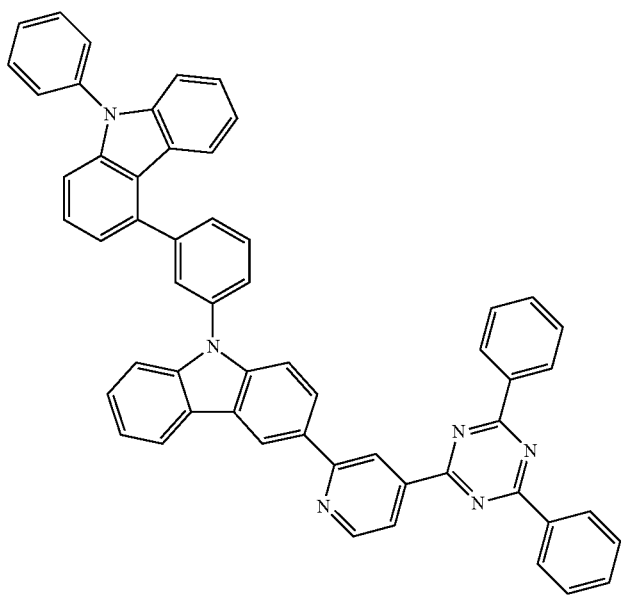 [SMILES: c1ccc(-c2nc(-c3ccccc3)nc(-c3ccnc(-c4ccc5c(c4)c4ccccc4n5-c4cccc(-c5cccc6c5c5ccccc5n6-c5ccccc5)c4)c3)n2)cc1]

Chemical Formula 1-121
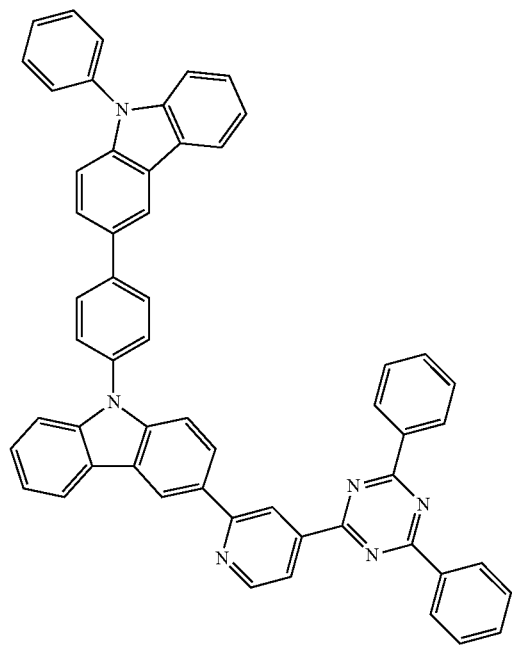 [SMILES: c1ccc(-c2nc(-c3ccccc3)nc(-c3ccnc(-c4ccc5c(c4)c4ccccc4n5-c4ccc(-c5ccc6c(c5)c5ccccc5n6-c5ccccc5)cc4)c3)n2)cc1]
Chemical Formula 1-122
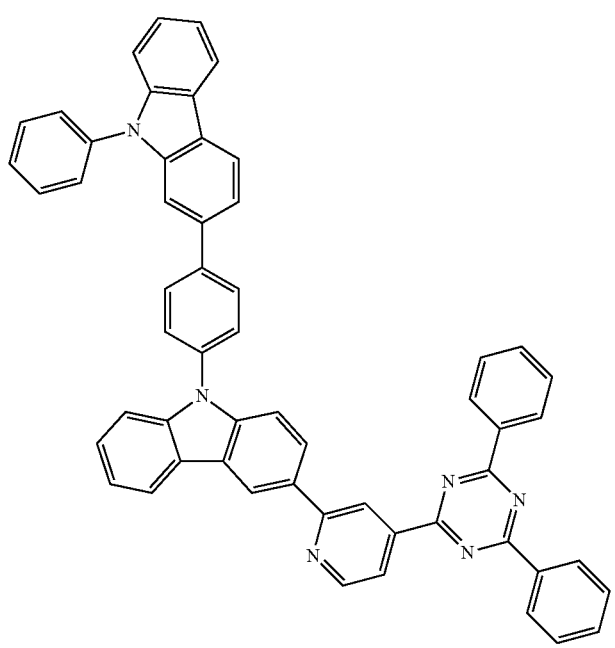 [SMILES: c1ccc(-c2nc(-c3ccccc3)nc(-c3ccnc(-c4ccc5c(c4)c4ccccc4n5-c4ccc(-c5ccc6c7ccccc7n(-c7ccccc7)c6c5)cc4)c3)n2)cc1]

Chemical Formula 1-123
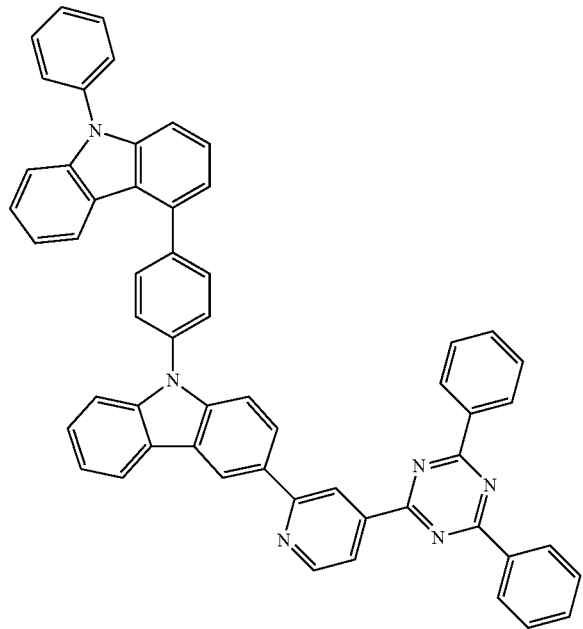 [SMILES: c1ccc(-c2nc(-c3ccccc3)nc(-c3ccnc(-c4ccc5c(c4)c4ccccc4n5-c4ccc(-c5cccc6c5c5ccccc5n6-c5ccccc5)cc4)c3)n2)cc1]
Chemical Formula 1-124
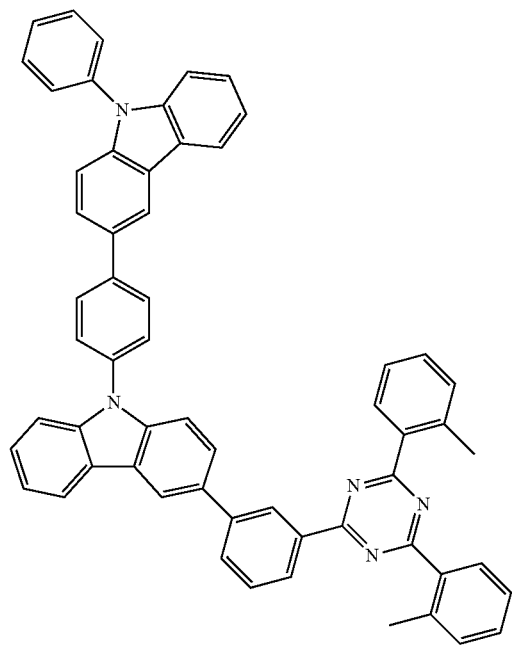 [SMILES: Cc1ccccc1-c1nc(-c2cccc(-c3ccc4c(c3)c3ccccc3n4-c3ccc(-c4ccc5c(c4)c4ccccc4n5-c4ccccc4)cc3)c2)nc(-c2ccccc2C)n1]

Chemical Formula 1-125
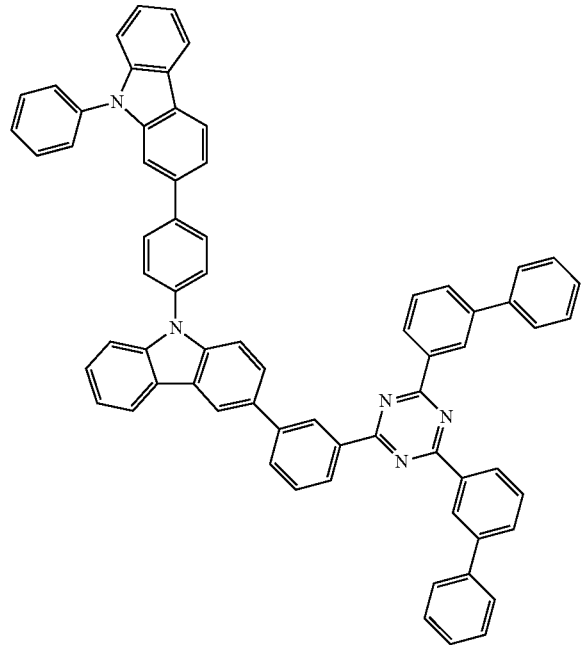 [SMILES: c1ccc(-c2cccc(-c3nc(-c4cccc(-c5ccccc5)c4)nc(-c4cccc(-c5ccc6c(c5)c5ccccc5n6-c5ccc(-c6ccc7c8ccccc8n(-c8ccccc8)c7c6)cc5)c4)n3)c2)cc1]
Chemical Formula 1-126
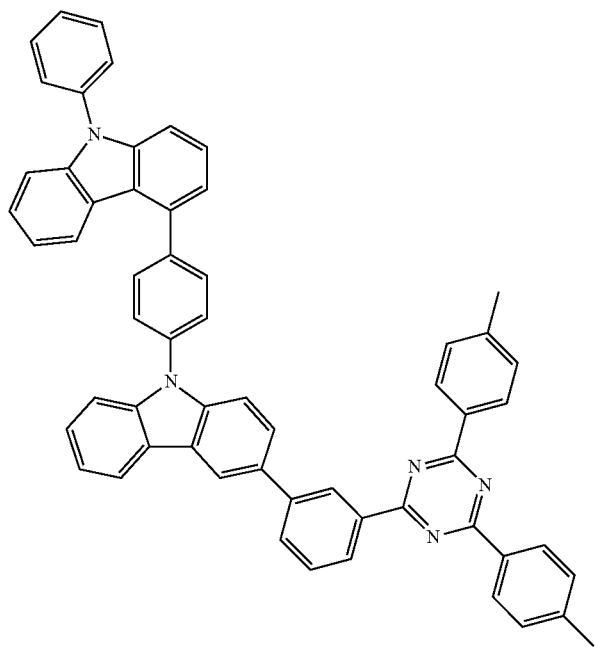 [SMILES: Cc1ccc(-c2nc(-c3ccc(C)cc3)nc(-c3cccc(-c4ccc5c(c4)c4ccccc4n5-c4ccc(-c5cccc6c5c5ccccc5n6-c5ccccc5)cc4)c3)n2)cc1]

Chemical Formula 1-127
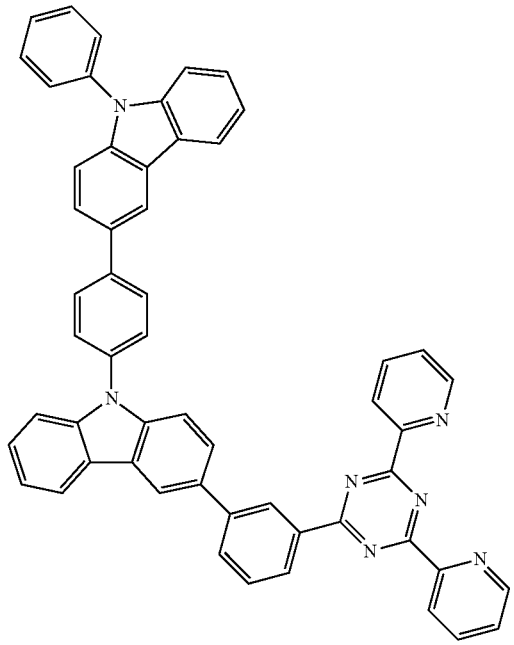 [SMILES: c1ccc(-n2c3ccccc3c3cc(-c4ccc(-n5c6ccccc6c6cc(-c7cccc(-c8nc(-c9ccccn9)nc(-c9ccccn9)n8)c7)ccc65)cc4)ccc32)cc1]
Chemical Formula 1-128
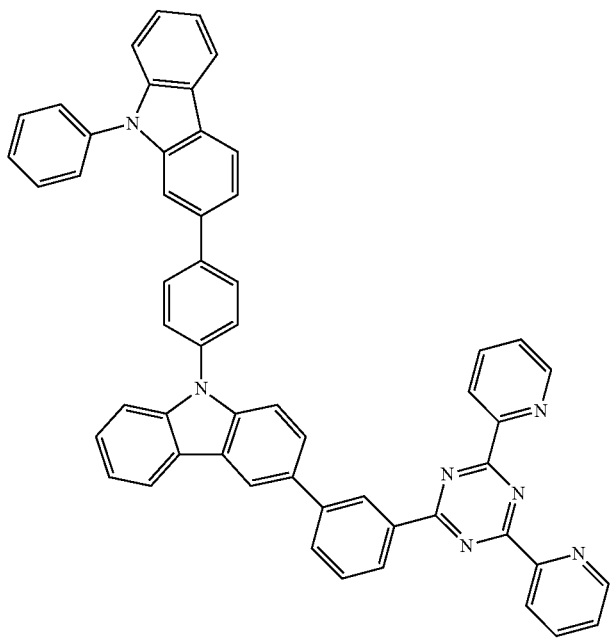 [SMILES: c1ccc(-n2c3ccccc3c3ccc(-c4ccc(-n5c6ccccc6c6cc(-c7cccc(-c8nc(-c9ccccn9)nc(-c9ccccn9)n8)c7)ccc65)cc4)cc32)cc1]

Chemical Formula 1-129
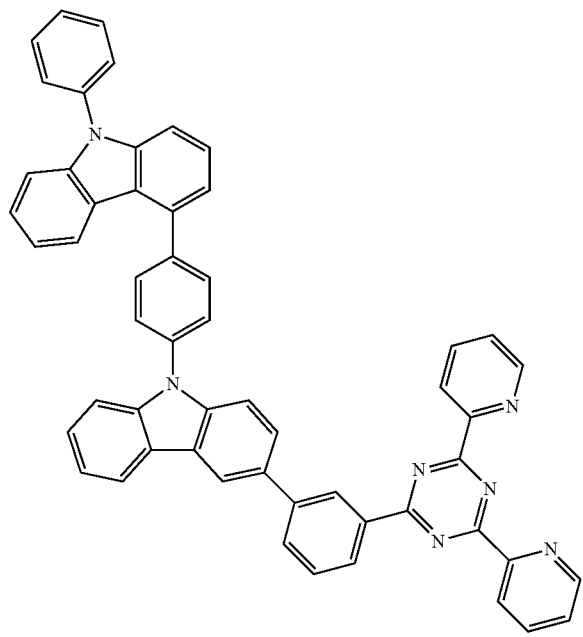 [SMILES: c1ccc(-n2c3ccccc3c3c(-c4ccc(-n5c6ccccc6c6cc(-c7cccc(-c8nc(-c9ccccn9)nc(-c9ccccn9)n8)c7)ccc65)cc4)cccc32)cc1]
Chemical Formula 1-130
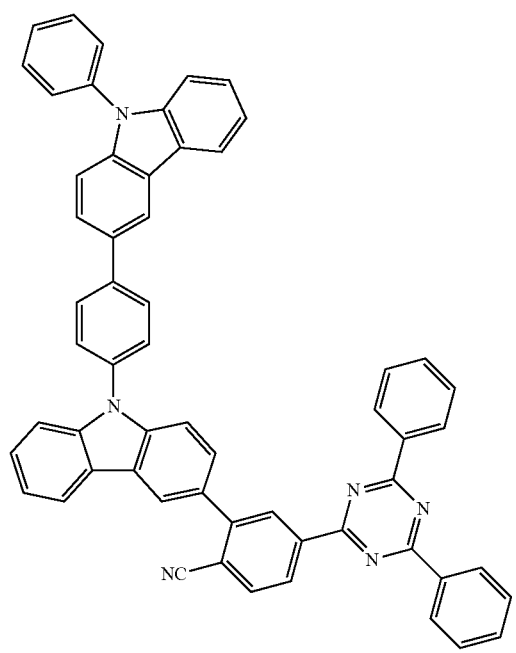 [SMILES: N#Cc1ccc(-c2nc(-c3ccccc3)nc(-c3ccccc3)n2)cc1-c1ccc2c(c1)c1ccccc1n2-c1ccc(-c2ccc3c(c2)c2ccccc2n3-c2ccccc2)cc1]

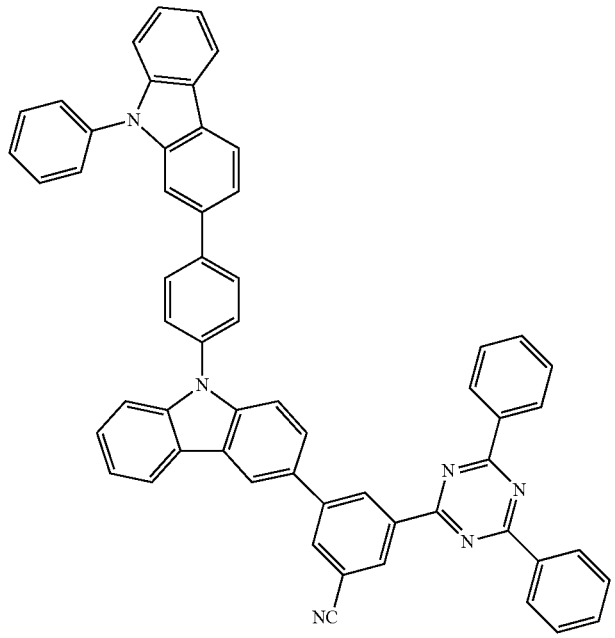 [SMILES: N#Cc1cc(-c2ccc3c(c2)c2ccccc2n3-c2ccc(-c3ccc4c5ccccc5n(-c5ccccc5)c4c3)cc2)cc(-c2nc(-c3ccccc3)nc(-c3ccccc3)n2)c1]
Chemical Formula 1-131
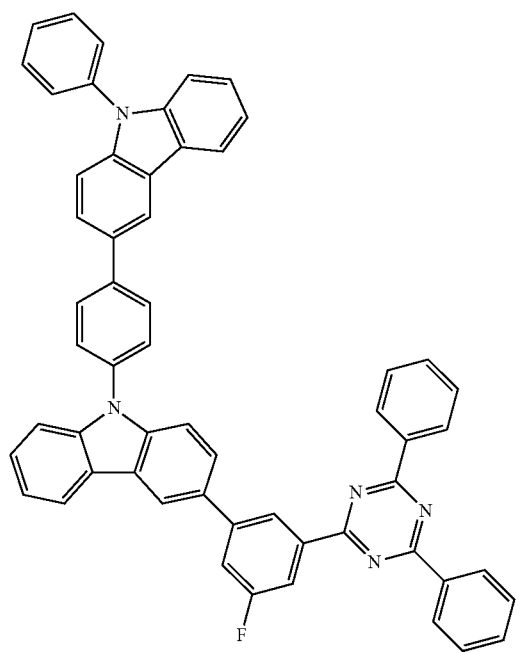 [SMILES: Fc1cc(-c2ccc3c(c2)c2ccccc2n3-c2ccc(-c3ccc4c(c3)c3ccccc3n4-c3ccccc3)cc2)cc(-c2nc(-c3ccccc3)nc(-c3ccccc3)n2)c1]
Chemical Formula 1-132

Chemical Formula 1-133
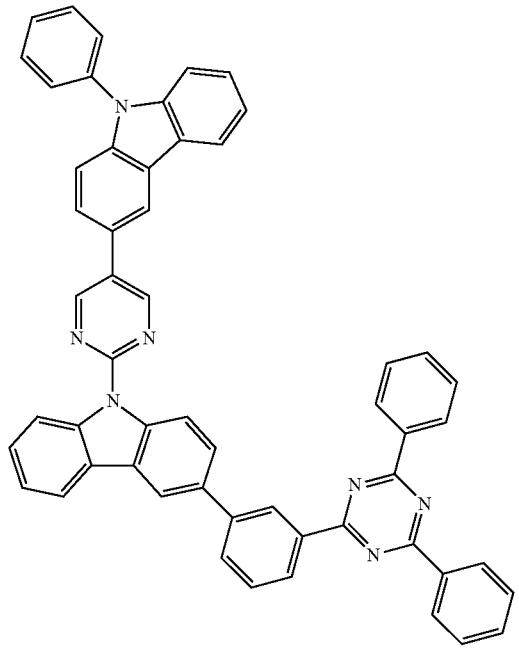 [SMILES: c1ccc(-c2nc(-c3ccccc3)nc(-c3cccc(-c4ccc5c(c4)c4ccccc4n5-c4ncc(-c5ccc6c(c5)c5ccccc5n6-c5ccccc5)cn4)c3)n2)cc1]
Chemical Formula 1-134
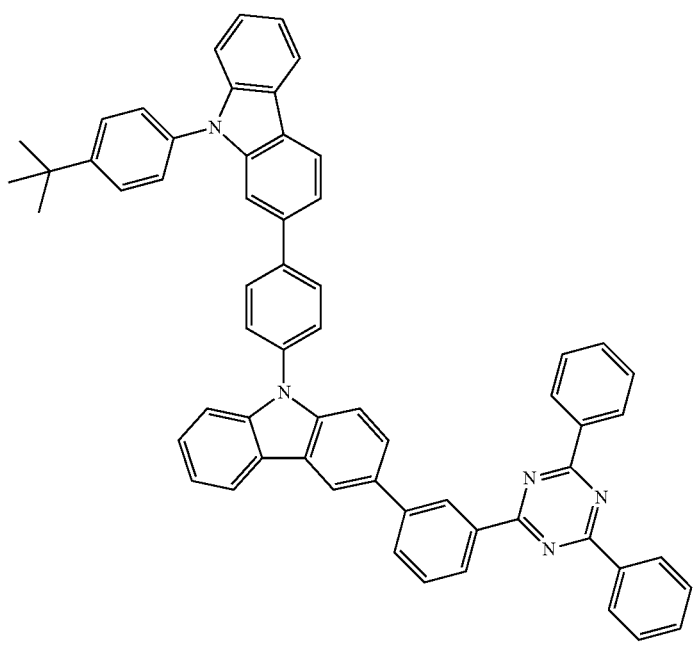 [SMILES: CC(C)(C)c1ccc(-n2c3ccccc3c3ccc(-c4ccc(-n5c6ccccc6c6cc(-c7cccc(-c8nc(-c9ccccc9)nc(-c9ccccc9)n8)c7)ccc65)cc4)cc32)cc1]

Chemical Formula 1-135
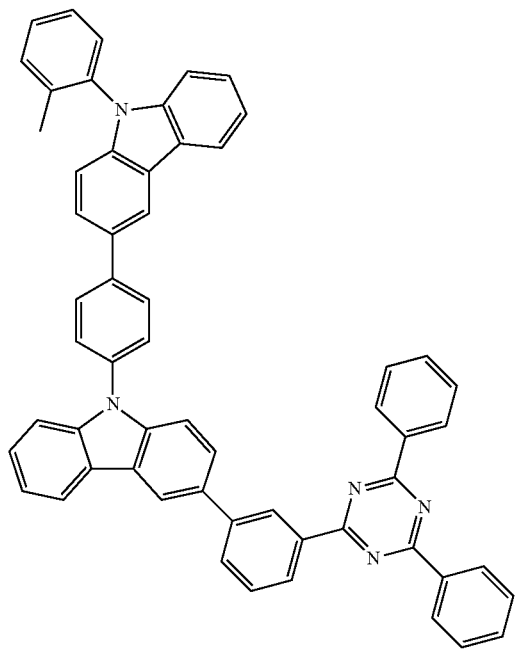 [SMILES: Cc1ccccc1-n1c2ccccc2c2cc(-c3ccc(-n4c5ccccc5c5cc(-c6cccc(-c7nc(-c8ccccc8)nc(-c8ccccc8)n7)c6)ccc54)cc3)ccc21]
Chemical Formula 1-136
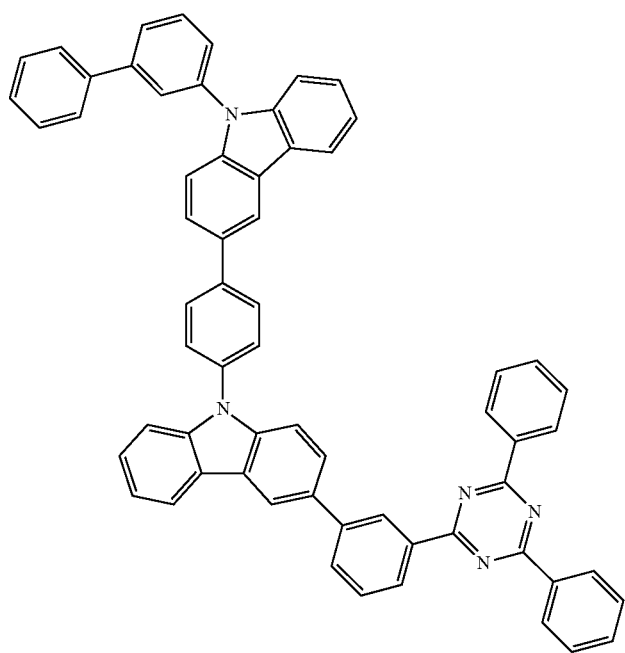 [SMILES: c1ccc(-c2cccc(-n3c4ccccc4c4cc(-c5ccc(-n6c7ccccc7c7cc(-c8cccc(-c9nc(-c%10ccccc%10)nc(-c%10ccccc%10)n9)c8)ccc76)cc5)ccc43)c2)cc1]

Chemical Formula 1-137
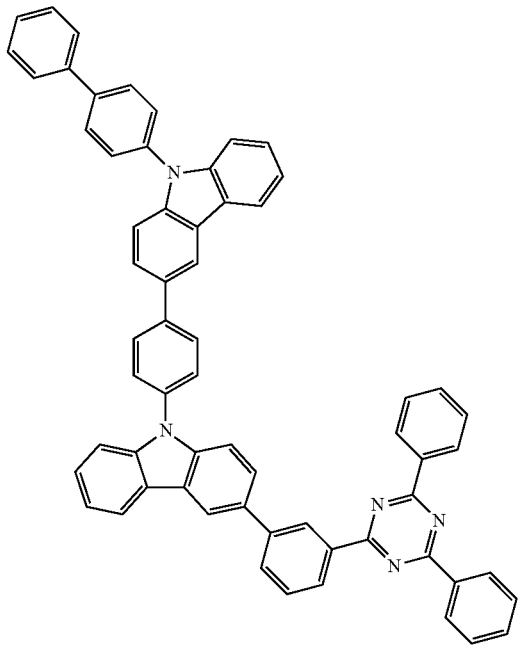 [SMILES: c1ccc(-c2ccc(-n3c4ccccc4c4cc(-c5ccc(-n6c7ccccc7c7cc(-c8cccc(-c9nc(-c%10ccccc%10)nc(-c%10ccccc%10)n9)c8)ccc76)cc5)ccc43)cc2)cc1]
Chemical Formula 1-138
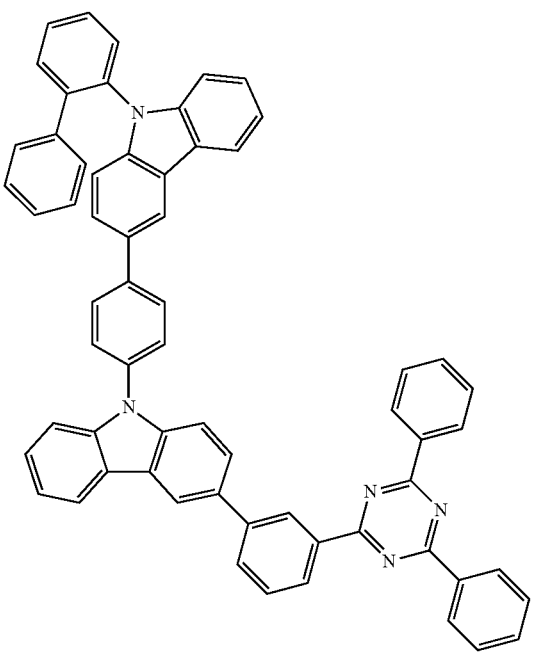 [SMILES: c1ccc(-c2nc(-c3ccccc3)nc(-c3cccc(-c4ccc5c(c4)c4ccccc4n5-c4ccc(-c5ccc6c(c5)c5ccccc5n6-c5ccccc5-c5ccccc5)cc4)c3)n2)cc1]

Chemical Formula 1-139
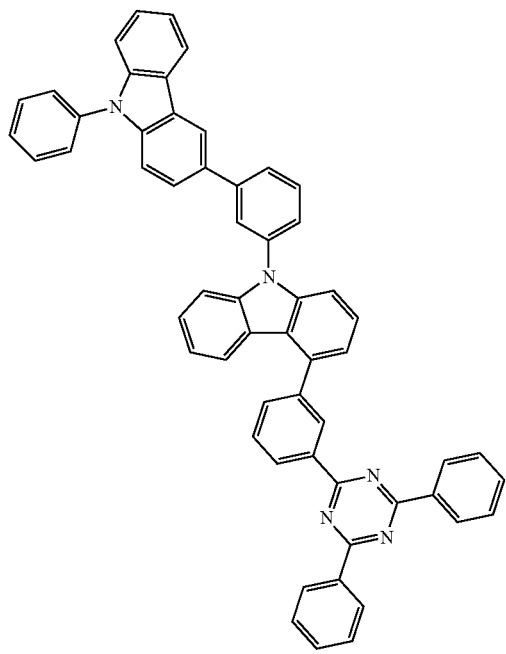 [SMILES: c1ccc(-c2nc(-c3ccccc3)nc(-c3cccc(-c4cccc5c4c4ccccc4n5-c4cccc(-c5ccc6c(c5)c5ccccc5n6-c5ccccc5)c4)c3)n2)cc1]
Chemical Formula 1-140
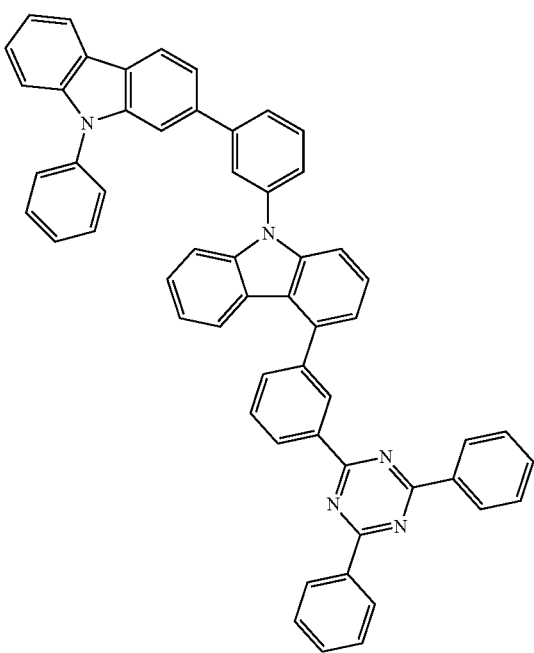

Chemical Formula 1-141
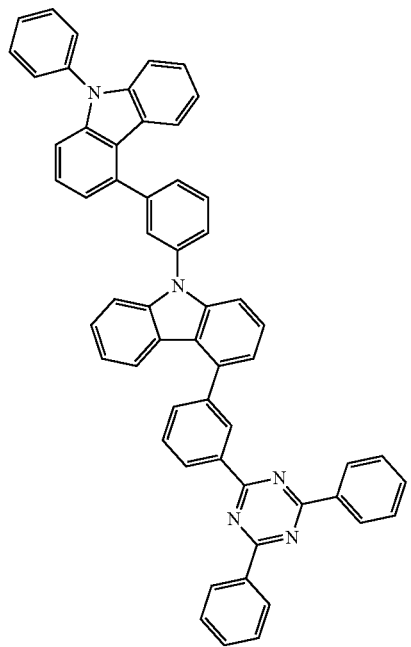 [SMILES: c1ccc(-c2nc(-c3ccccc3)nc(-c3cccc(-c4cccc5c4c4ccccc4n5-c4cccc(-c5cccc6c5c5ccccc5n6-c5ccccc5)c4)c3)n2)cc1]
Chemical Formula 1-142
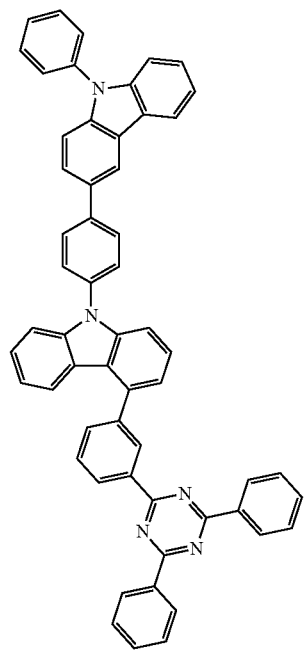

Chemical Formula 1-143
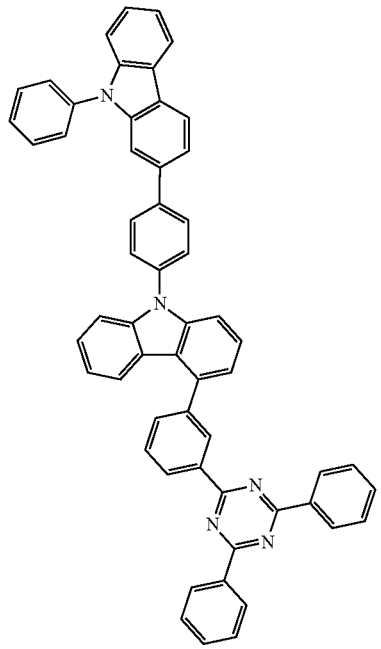 [SMILES: c1ccc(-c2nc(-c3ccccc3)nc(-c3cccc(-c4cccc5c4c4ccccc4n5-c4ccc(-c5ccc6c7ccccc7n(-c7ccccc7)c6c5)cc4)c3)n2)cc1]
Chemical Formula 1-144
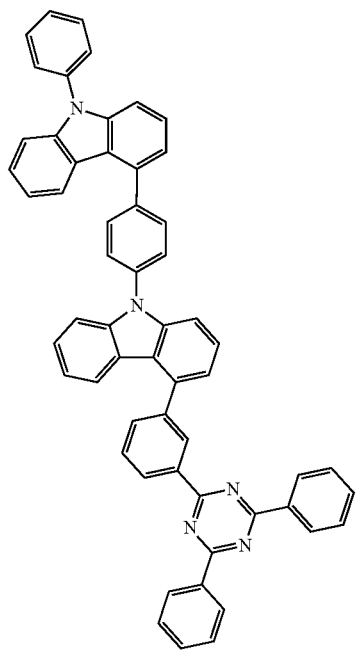 [SMILES: c1ccc(-c2nc(-c3ccccc3)nc(-c3cccc(-c4cccc5c4c4ccccc4n5-c4ccc(-c5cccc6c5c5ccccc5n6-c5ccccc5)cc4)c3)n2)cc1]

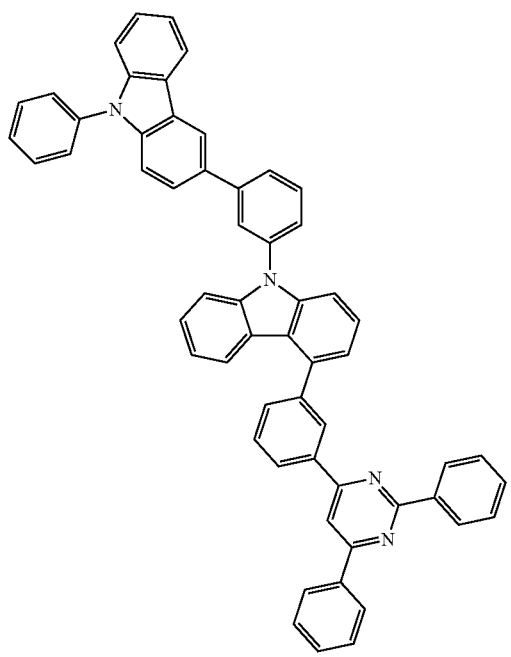 [SMILES: c1ccc(-c2cc(-c3cccc(-c4cccc5c4c4ccccc4n5-c4cccc(-c5ccc6c(c5)c5ccccc5n6-c5ccccc5)c4)c3)nc(-c3ccccc3)n2)cc1]
Chemical Formula 1-145
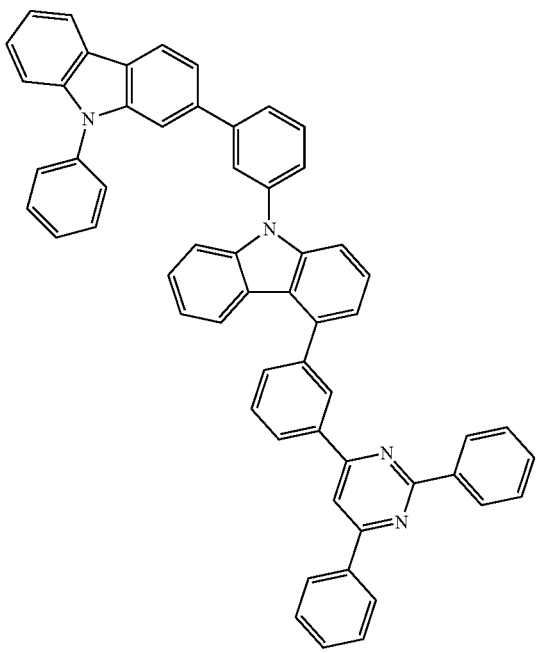
Chemical Formula 1-146

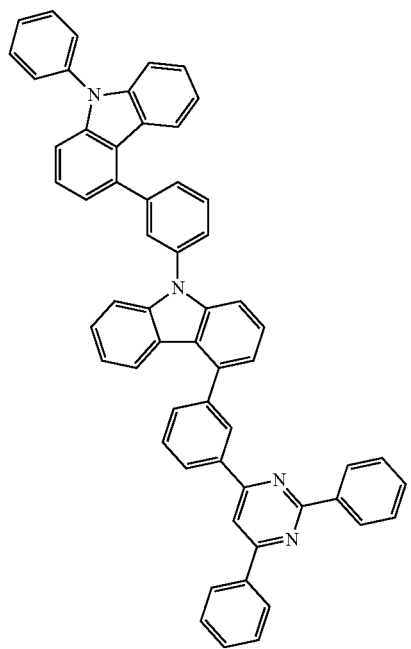 [SMILES: c1ccc(-c2cc(-c3cccc(-c4cccc5c4c4ccccc4n5-c4cccc(-c5cccc6c5c5ccccc5n6-c5ccccc5)c4)c3)nc(-c3ccccc3)n2)cc1]
Chemical Formula 1-147
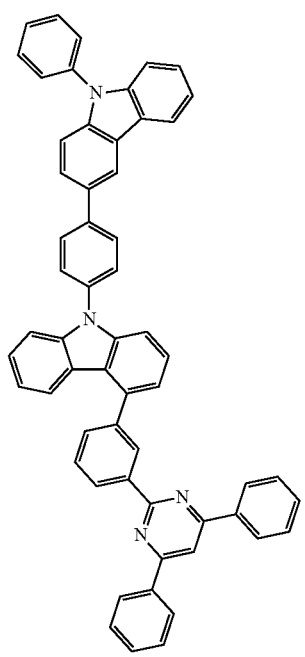 [SMILES: c1ccc(-c2cc(-c3ccccc3)nc(-c3cccc(-c4cccc5c4c4ccccc4n5-c4ccc(-c5ccc6c(c5)c5ccccc5n6-c5ccccc5)cc4)c3)n2)cc1]
Chemical Formula 1-148

Chemical Formula 1-149
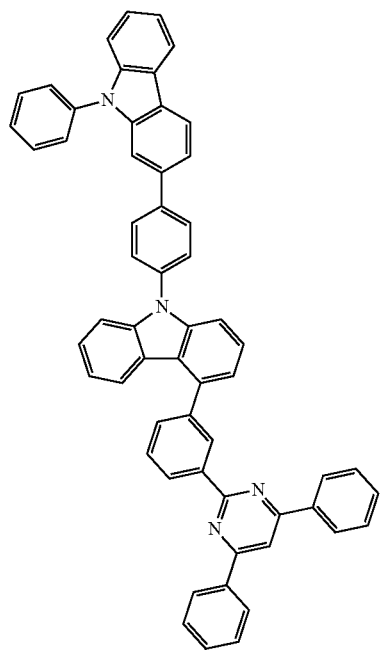
Chemical Formula 1-150
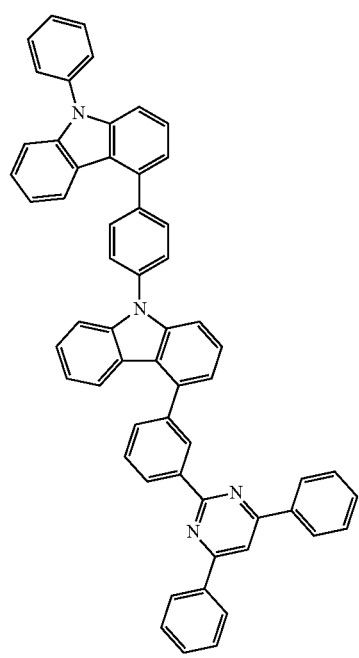 [SMILES: c1ccc(-c2cc(-c3ccccc3)nc(-c3cccc(-c4cccc5c4c4ccccc4n5-c4ccc(-c5cccc6c5c5ccccc5n6-c5ccccc5)cc4)c3)n2)cc1]

Chemical Formula 1-151
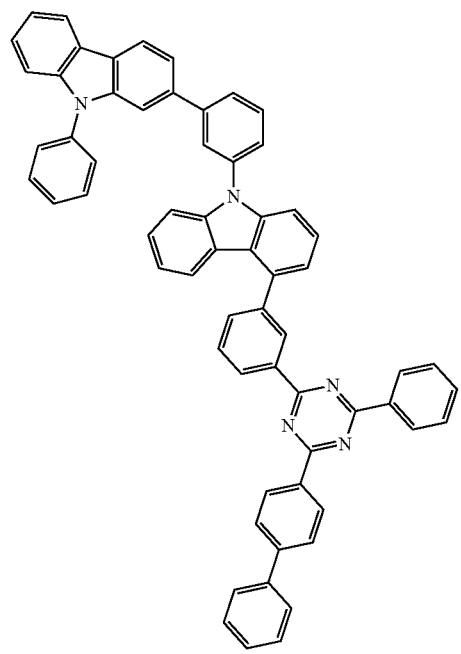 [SMILES: c1ccc(-c2ccc(-c3nc(-c4ccccc4)nc(-c4cccc(-c5cccc6c5c5ccccc5n6-c5cccc(-c6ccc7c8ccccc8n(-c8ccccc8)c7c6)c5)c4)n3)cc2)cc1]
Chemical Formula 1-152
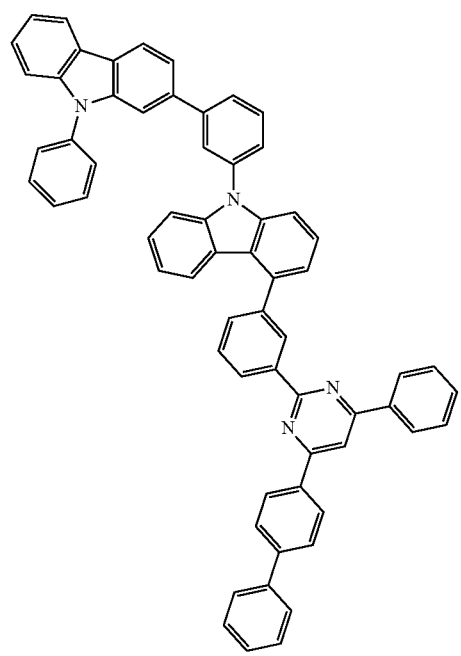 [SMILES: c1ccc(-c2ccc(-c3cc(-c4ccccc4)nc(-c4cccc(-c5cccc6c5c5ccccc5n6-c5cccc(-c6ccc7c8ccccc8n(-c8ccccc8)c7c6)c5)c4)n3)cc2)cc1]

Chemical Formula 1-153
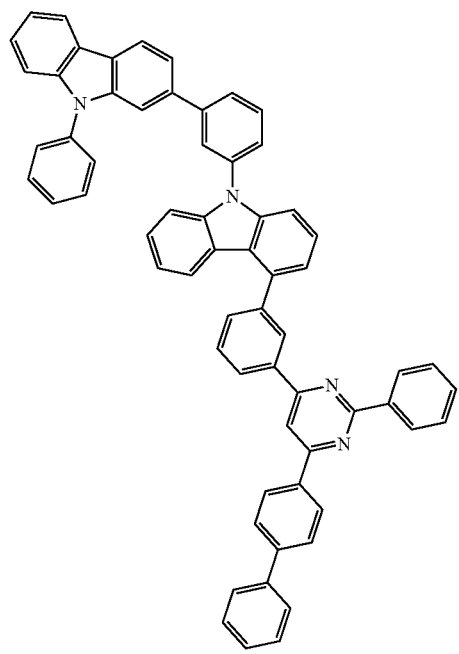 [SMILES: c1ccc(-c2ccc(-c3cc(-c4cccc(-c5cccc6c5c5ccccc5n6-c5cccc(-c6ccc7c8ccccc8n(-c8ccccc8)c7c6)c5)c4)nc(-c4ccccc4)n3)cc2)cc1]
Chemical Formula 1-154
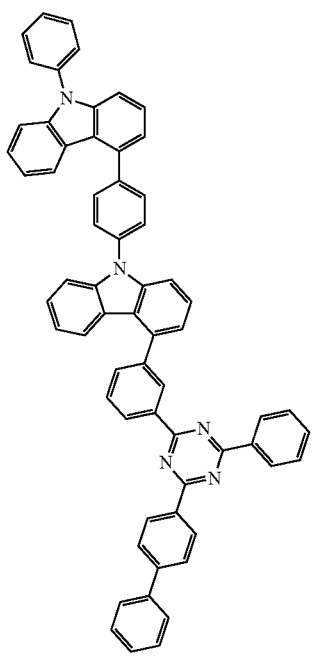 [SMILES: c1ccc(-c2ccc(-c3nc(-c4ccccc4)nc(-c4cccc(-c5cccc6c5c5ccccc5n6-c5ccc(-c6cccc7c6c6ccccc6n7-c6ccccc6)cc5)c4)n3)cc2)cc1]

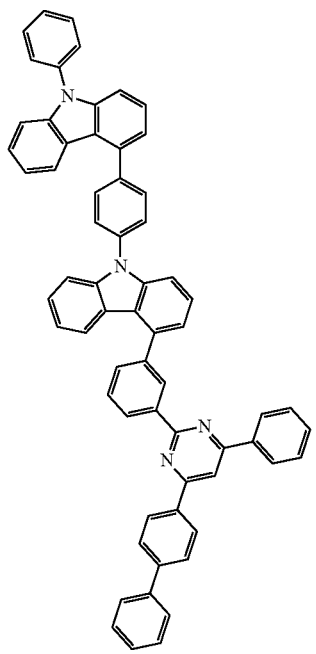 [SMILES: c1ccc(-c2ccc(-c3cc(-c4ccccc4)nc(-c4cccc(-c5cccc6c5c5ccccc5n6-c5ccc(-c6cccc7c6c6ccccc6n7-c6ccccc6)cc5)c4)n3)cc2)cc1]
Chemical Formula 1-155
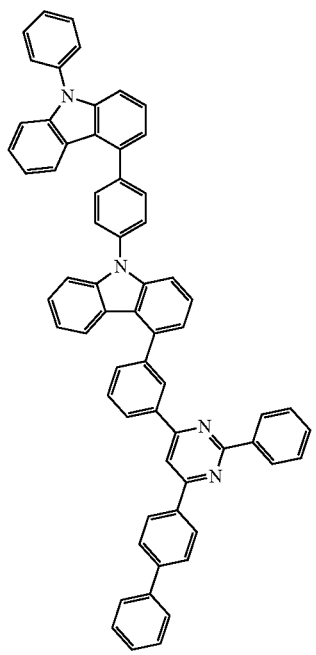 [SMILES: c1ccc(-c2ccc(-c3cc(-c4cccc(-c5cccc6c5c5ccccc5n6-c5ccc(-c6cccc7c6c6ccccc6n7-c6ccccc6)cc5)c4)nc(-c4ccccc4)n3)cc2)cc1]
Chemical Formula 1-156

Chemical Formula 1-157
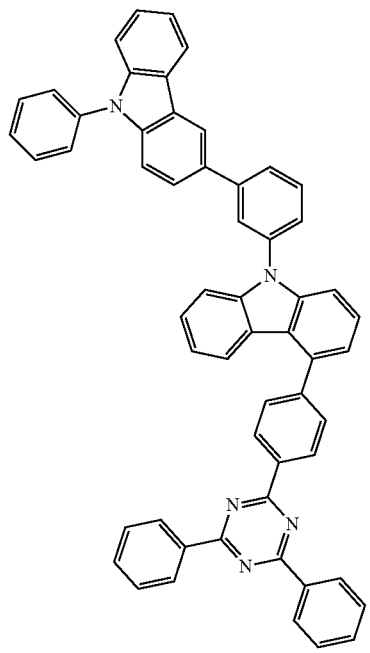 [SMILES: c1ccc(-c2nc(-c3ccccc3)nc(-c3ccc(-c4cccc5c4c4ccccc4n5-c4cccc(-c5ccc6c(c5)c5ccccc5n6-c5ccccc5)c4)cc3)n2)cc1]
Chemical Formula 1-158
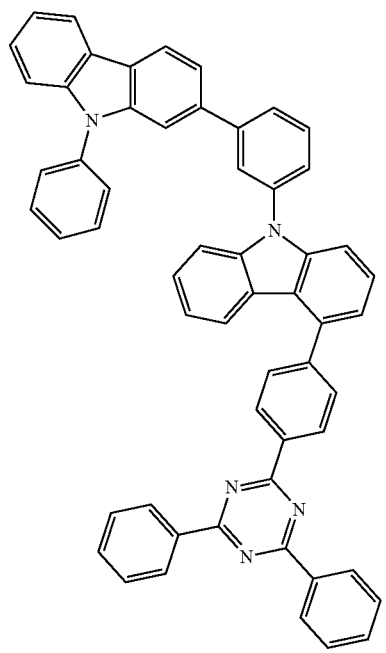 [SMILES: c1ccc(-c2nc(-c3ccccc3)nc(-c3ccc(-c4cccc5c4c4ccccc4n5-c4cccc(-c5ccc6c7ccccc7n(-c7ccccc7)c6c5)c4)cc3)n2)cc1]

Chemical Formula 1-159
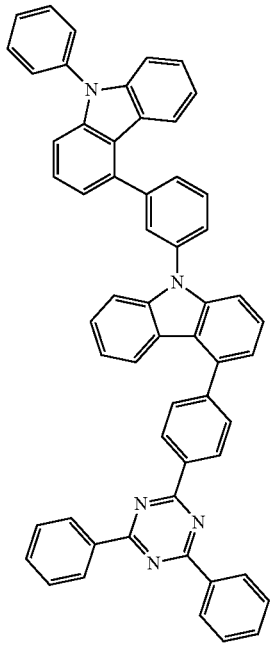 [SMILES: c1ccc(-c2nc(-c3ccccc3)nc(-c3ccc(-c4cccc5c4c4ccccc4n5-c4cccc(-c5cccc6c5c5ccccc5n6-c5ccccc5)c4)cc3)n2)cc1]
Chemical Formula 1-160
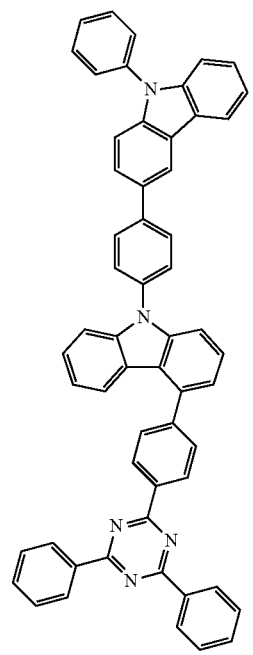

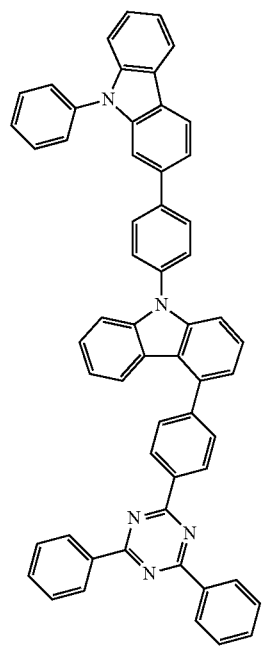 [SMILES: c1ccc(-c2nc(-c3ccccc3)nc(-c3ccc(-c4cccc5c4c4ccccc4n5-c4ccc(-c5ccc6c7ccccc7n(-c7ccccc7)c6c5)cc4)cc3)n2)cc1]
Chemical Formula 1-161
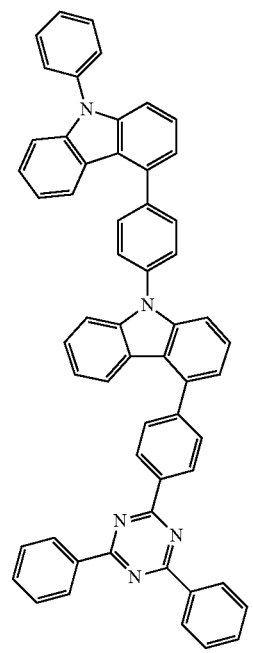 [SMILES: c1ccc(-c2nc(-c3ccccc3)nc(-c3ccc(-c4cccc5c4c4ccccc4n5-c4ccc(-c5cccc6c5c5ccccc5n6-c5ccccc5)cc4)cc3)n2)cc1]
Chemical Formula 1-162

Chemical Formula 1-163
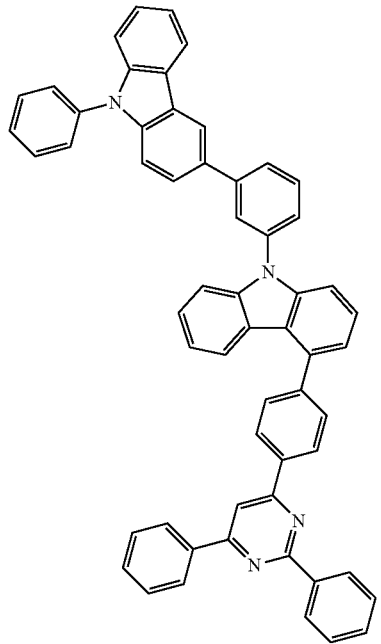
Chemical Formula 1-164
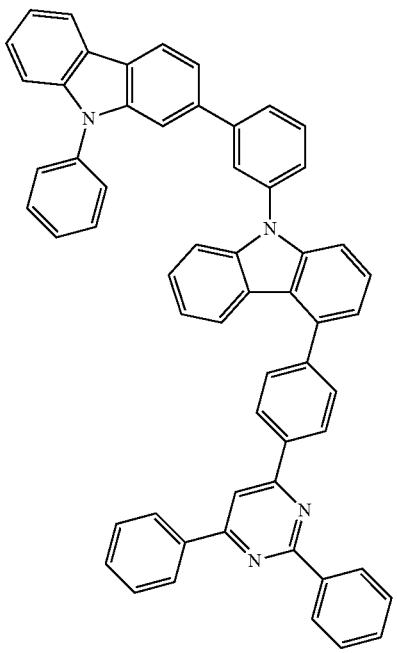 [SMILES: c1ccc(-c2cc(-c3ccc(-c4cccc5c4c4ccccc4n5-c4cccc(-c5ccc6c7ccccc7n(-c7ccccc7)c6c5)c4)cc3)nc(-c3ccccc3)n2)cc1]

-continued
Chemical Formula 1-165
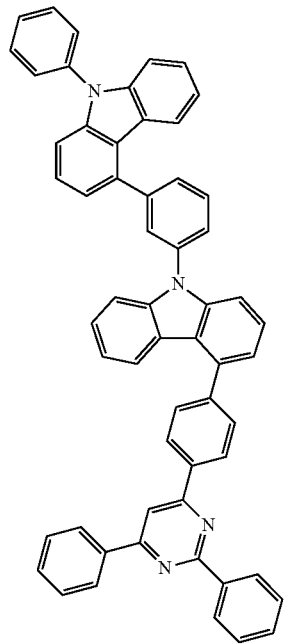 [SMILES: c1ccc(-c2cc(-c3ccc(-c4cccc5c4c4ccccc4n5-c4cccc(-c5cccc6c5c5ccccc5n6-c5ccccc5)c4)cc3)nc(-c3ccccc3)n2)cc1]
Chemical Formula 1-166
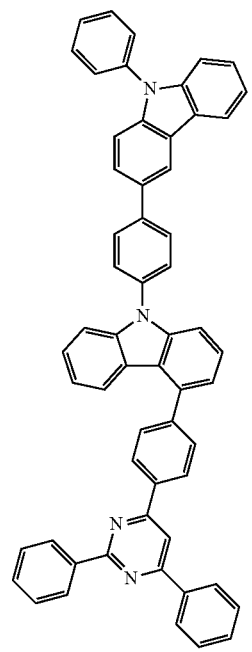 [SMILES: c1ccc(-c2cc(-c3ccc(-c4cccc5c4c4ccccc4n5-c4ccc(-c5ccc6c(c5)c5ccccc5n6-c5ccccc5)cc4)cc3)nc(-c3ccccc3)n2)cc1]

Chemical Formula 1-167
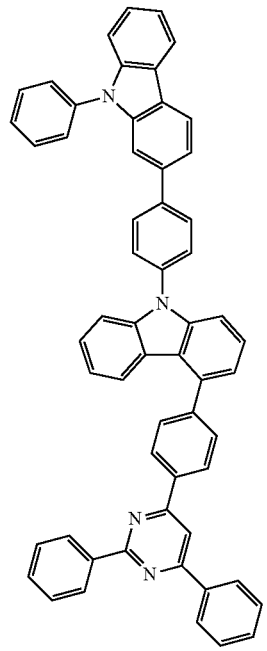
Chemical Formula 1-168
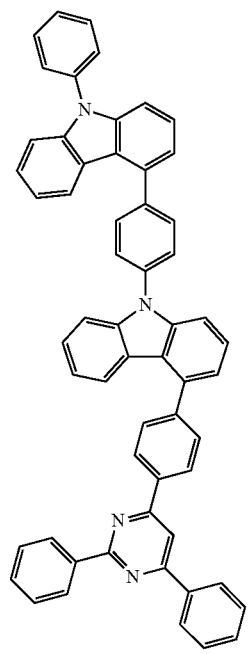 [SMILES: c1ccc(-c2cc(-c3ccc(-c4cccc5c4c4ccccc4n5-c4ccc(-c5cccc6c5c5ccccc5n6-c5ccccc5)cc4)cc3)nc(-c3ccccc3)n2)cc1]

Chemical Formula 1-169
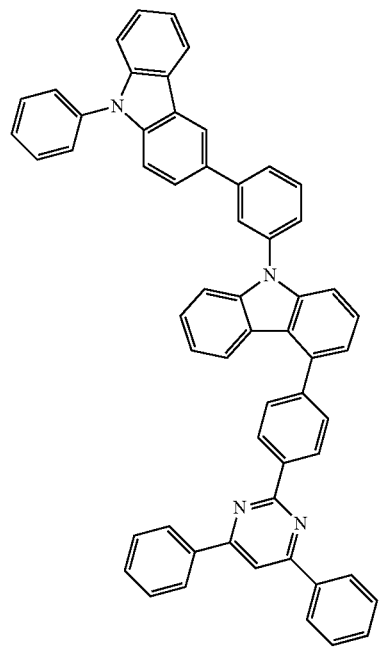 [SMILES: c1ccc(-c2cc(-c3ccccc3)nc(-c3ccc(-c4cccc5c4c4ccccc4n5-c4cccc(-c5ccc6c(c5)c5ccccc5n6-c5ccccc5)c4)cc3)n2)cc1]
Chemical Formula 1-170
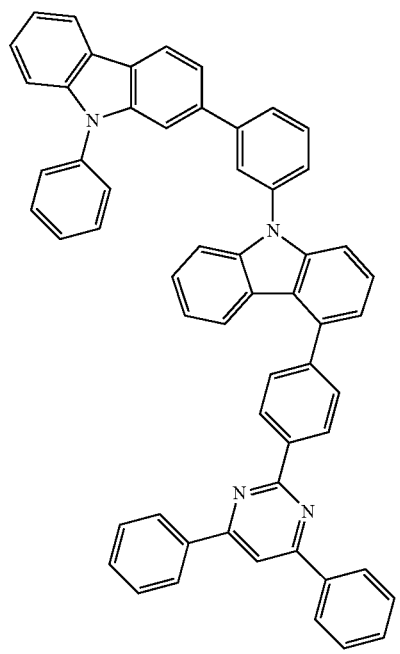

Chemical Formula 1-171
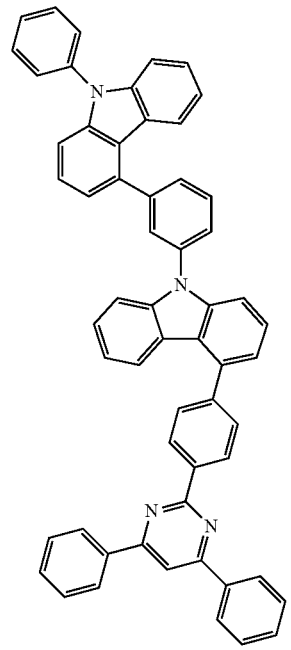 [SMILES: c1ccc(-c2cc(-c3ccccc3)nc(-c3ccc(-c4cccc5c4c4ccccc4n5-c4cccc(-c5cccc6c5c5ccccc5n6-c5ccccc5)c4)cc3)n2)cc1]
Chemical Formula 1-172
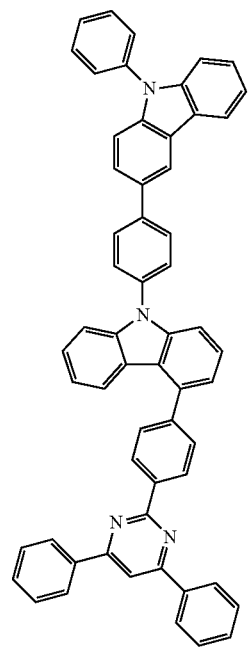 [SMILES: c1ccc(-c2cc(-c3ccccc3)nc(-c3ccc(-c4cccc5c4c4ccccc4n5-c4ccc(-c5ccc6c(c5)c5ccccc5n6-c5ccccc5)cc4)cc3)n2)cc1]

Chemical Formula 1-173
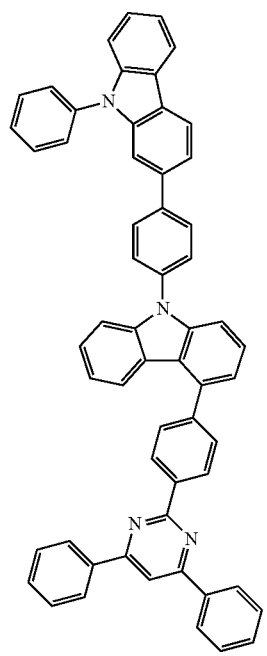
Chemical Formula 1-174
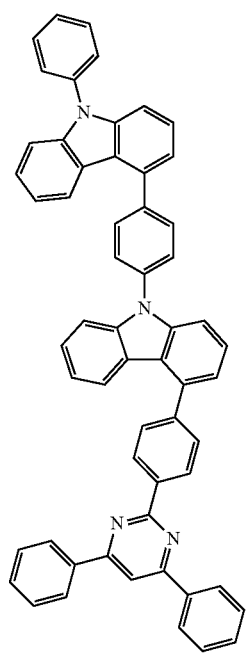 [SMILES: c1ccc(-c2cc(-c3ccccc3)nc(-c3ccc(-c4cccc5c4c4ccccc4n5-c4ccc(-c5cccc6c5c5ccccc5n6-c5ccccc5)cc4)cc3)n2)cc1]

-continued
Chemical Formula 1-175
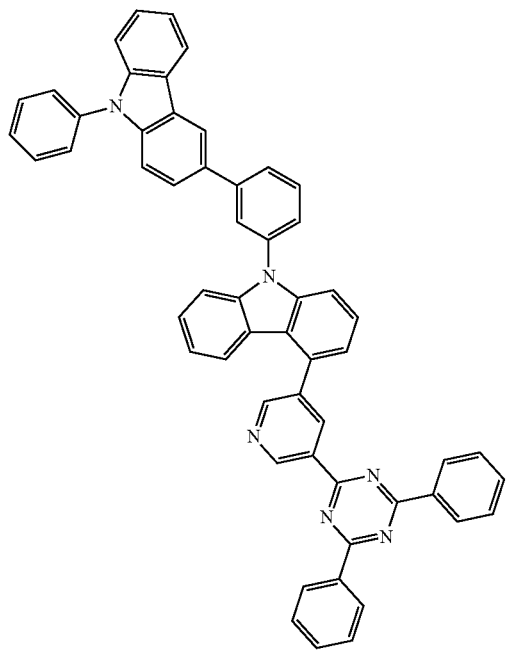 [SMILES: c1ccc(-c2nc(-c3ccccc3)nc(-c3cncc(-c4cccc5c4c4ccccc4n5-c4cccc(-c5ccc6c(c5)c5ccccc5n6-c5ccccc5)c4)c3)n2)cc1]
Chemical Formula 1-176
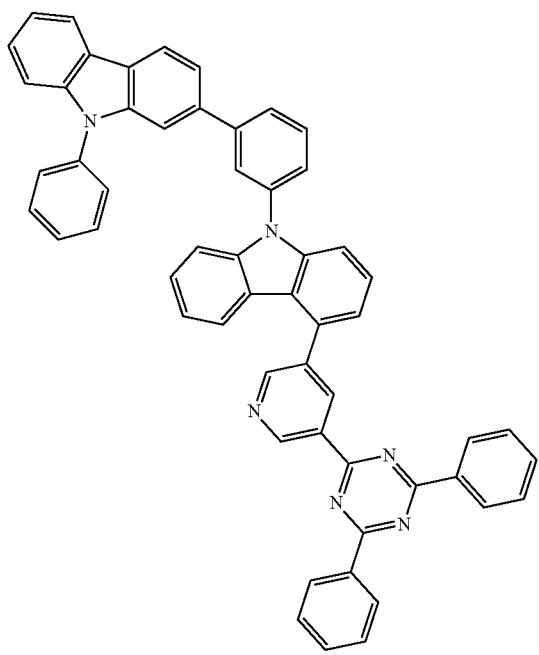 [SMILES: c1ccc(-c2nc(-c3ccccc3)nc(-c3cncc(-c4cccc5c4c4ccccc4n5-c4cccc(-c5ccc6c7ccccc7n(-c7ccccc7)c6c5)c4)c3)n2)cc1]

Chemical Formula 1-177
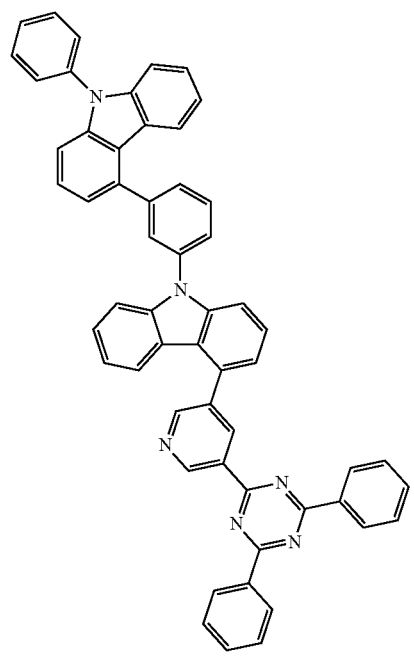 [SMILES: c1ccc(-c2nc(-c3ccccc3)nc(-c3cncc(-c4cccc5c4c4ccccc4n5-c4cccc(-c5cccc6c5c5ccccc5n6-c5ccccc5)c4)c3)n2)cc1]
Chemical Formula 1-178
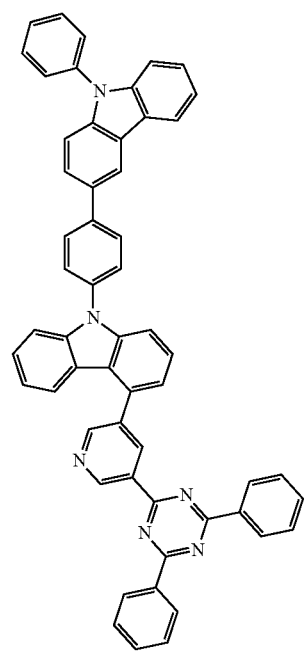

Chemical Formula 1-179
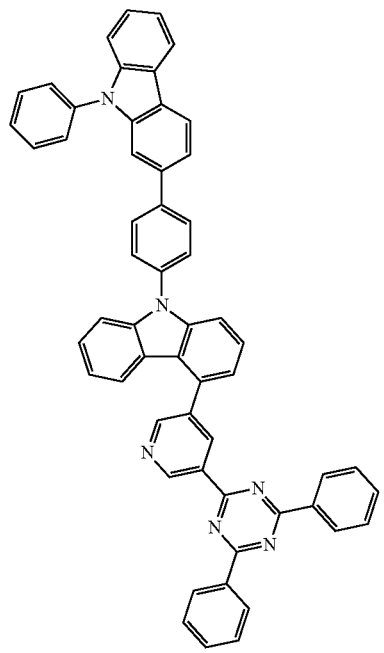
Chemical Formula 1-180
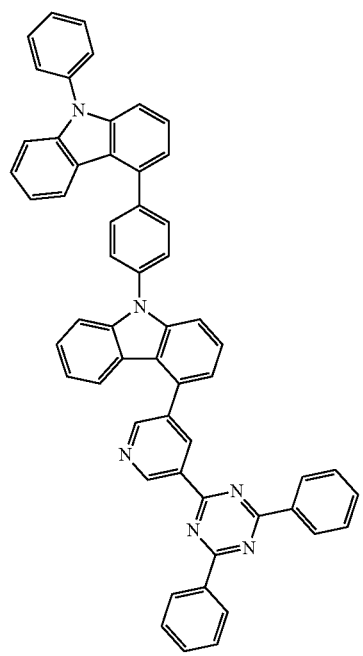 [SMILES: c1ccc(-c2nc(-c3ccccc3)nc(-c3cncc(-c4cccc5c4c4ccccc4n5-c4ccc(-c5cccc6c5c5ccccc5n6-c5ccccc5)cc4)c3)n2)cc1]

Chemical Formula 1-181
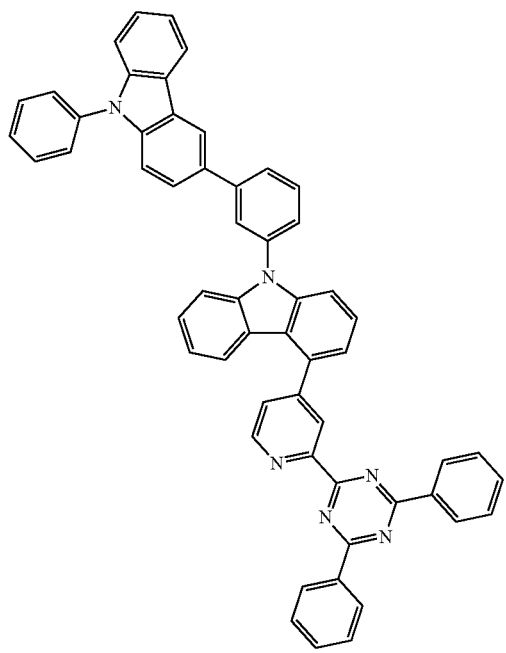
Chemical Formula 1-182
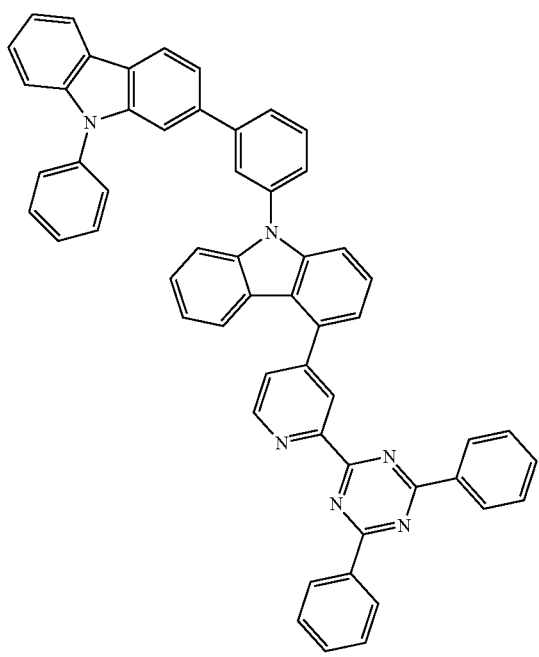 [SMILES: c1ccc(-c2nc(-c3ccccc3)nc(-c3cc(-c4cccc5c4c4ccccc4n5-c4cccc(-c5ccc6c7ccccc7n(-c7ccccc7)c6c5)c4)ccn3)n2)cc1]

Chemical Formula 1-183
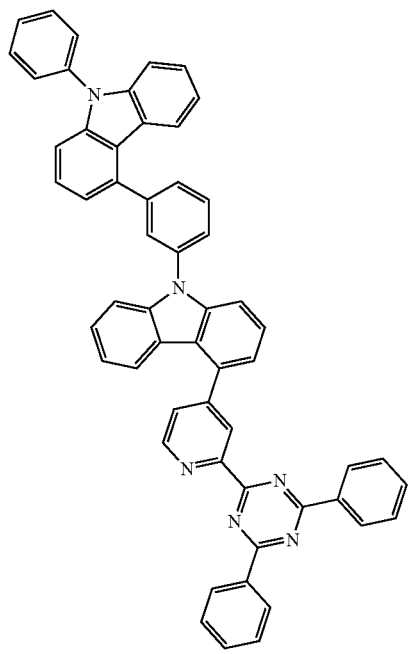 [SMILES: c1ccc(-c2nc(-c3ccccc3)nc(-c3cc(-c4cccc5c4c4ccccc4n5-c4cccc(-c5cccc6c5c5ccccc5n6-c5ccccc5)c4)ccn3)n2)cc1]
Chemical Formula 1-184
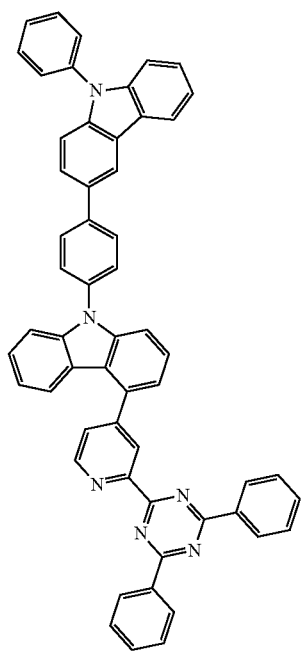

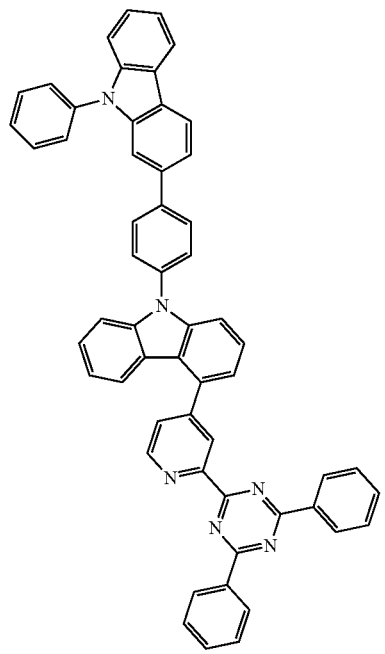
Chemical Formula 1-185
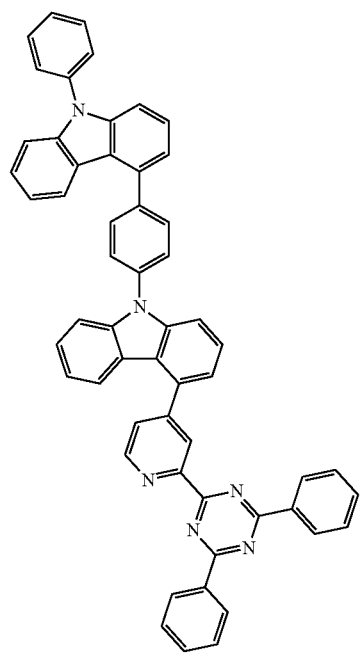
Chemical Formula 1-186

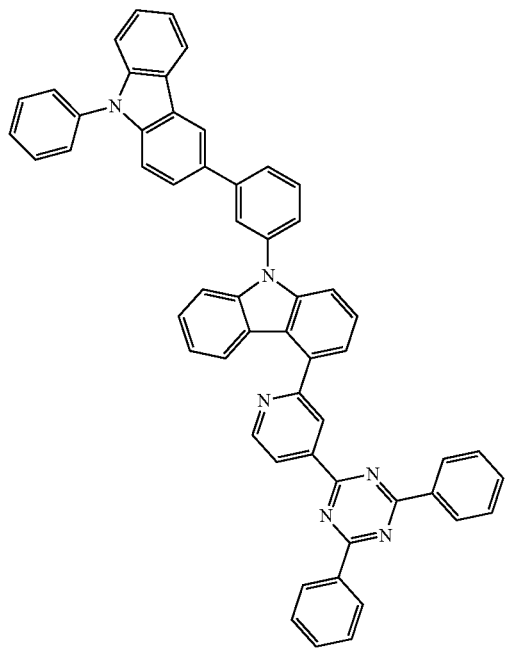
Chemical Formula 1-187
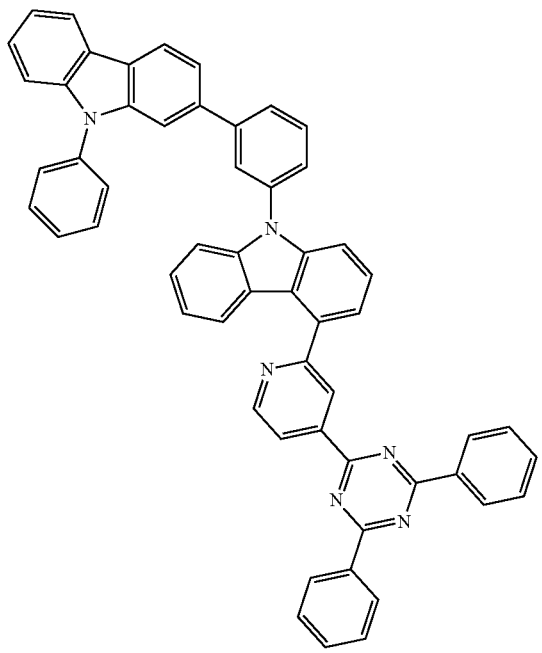 [SMILES: c1ccc(-c2nc(-c3ccccc3)nc(-c3ccnc(-c4cccc5c4c4ccccc4n5-c4cccc(-c5ccc6c7ccccc7n(-c7ccccc7)c6c5)c4)c3)n2)cc1]
Chemical Formula 1-188

-continued
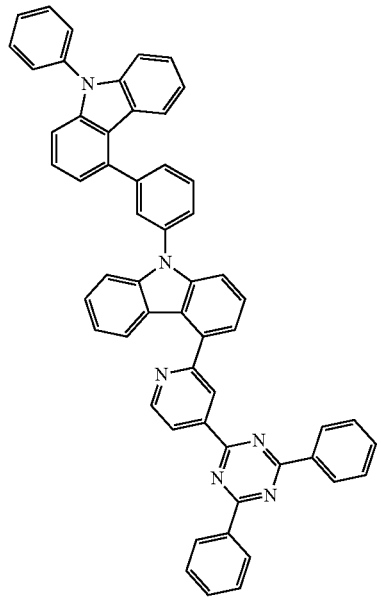 [SMILES: c1ccc(-c2nc(-c3ccccc3)nc(-c3ccnc(-c4cccc5c4c4ccccc4n5-c4cccc(-c5cccc6c5c5ccccc5n6-c5ccccc5)c4)c3)n2)cc1]
Chemical Formula 1-189
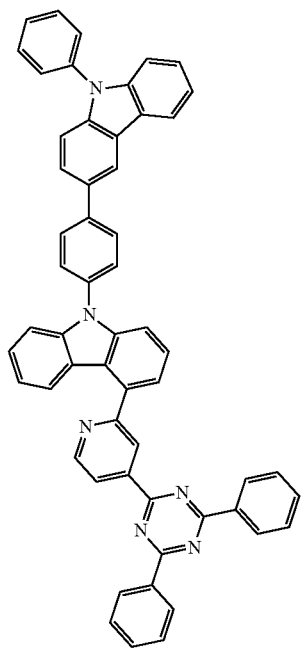
Chemical Formula 1-190

Chemical Formula 1-191
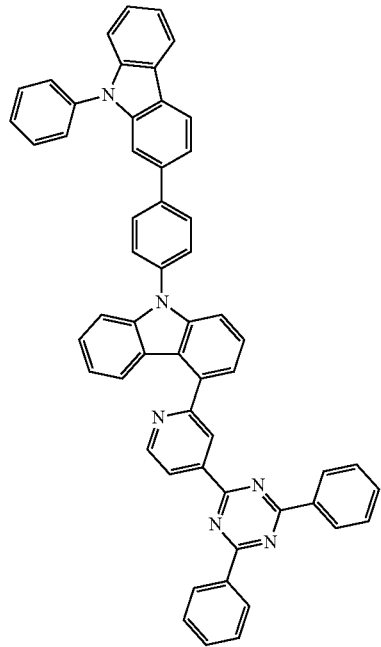
Chemical Formula 1-192
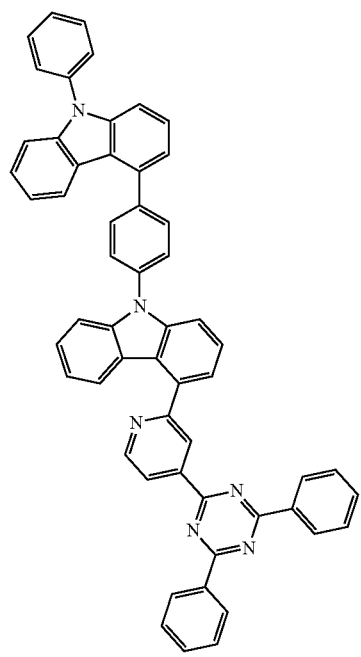

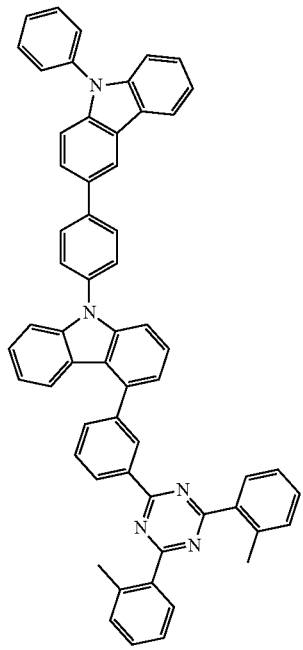
Chemical Formula 1-193
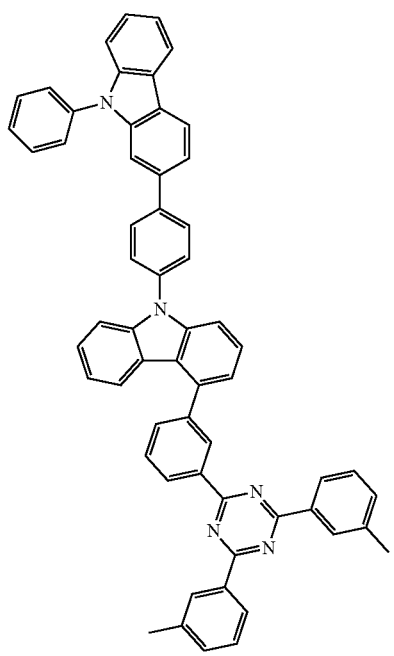 [SMILES: Cc1cccc(-c2nc(-c3cccc(C)c3)nc(-c3cccc(-c4cccc5c4c4ccccc4n5-c4ccc(-c5ccc6c7ccccc7n(-c7ccccc7)c6c5)cc4)c3)n2)c1]
Chemical Formula 1-194

Chemical Formula 1-195
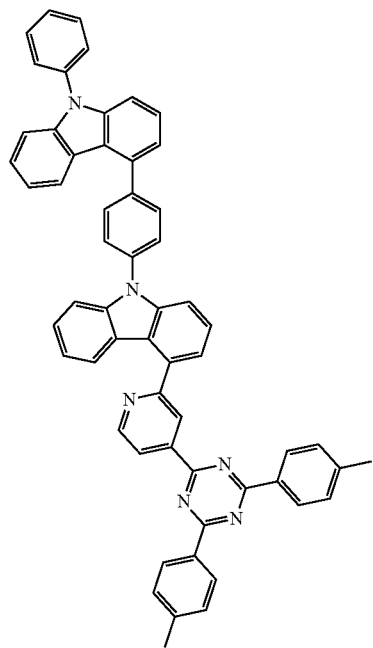 [SMILES: Cc1ccc(-c2nc(-c3ccc(C)cc3)nc(-c3ccnc(-c4cccc5c4c4ccccc4n5-c4ccc(-c5cccc6c5c5ccccc5n6-c5ccccc5)cc4)c3)n2)cc1]
Chemical Formula 1-196
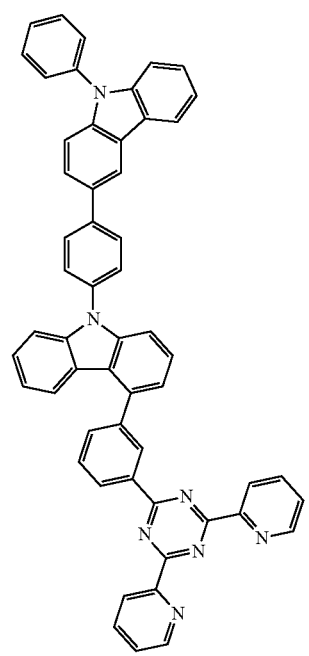 [SMILES: c1ccc(-n2c3ccccc3c3cc(-c4ccc(-n5c6ccccc6c6c(-c7cccc(-c8nc(-c9ccccn9)nc(-c9ccccn9)n8)c7)cccc65)cc4)ccc32)cc1]

Chemical Formula 1-197
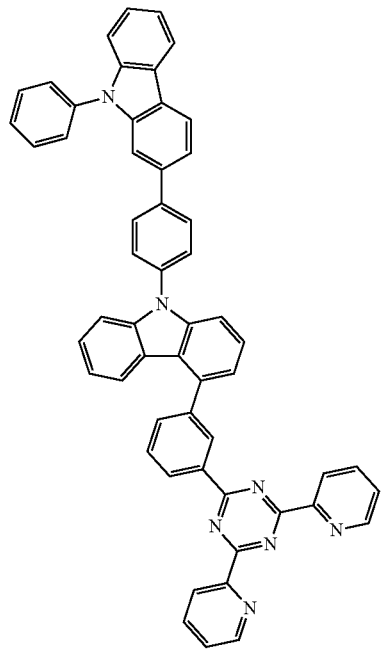 [SMILES: c1ccc(-n2c3ccccc3c3ccc(-c4ccc(-n5c6ccccc6c6c(-c7cccc(-c8nc(-c9ccccn9)nc(-c9ccccn9)n8)c7)cccc65)cc4)cc32)cc1]
Chemical Formula 1-198
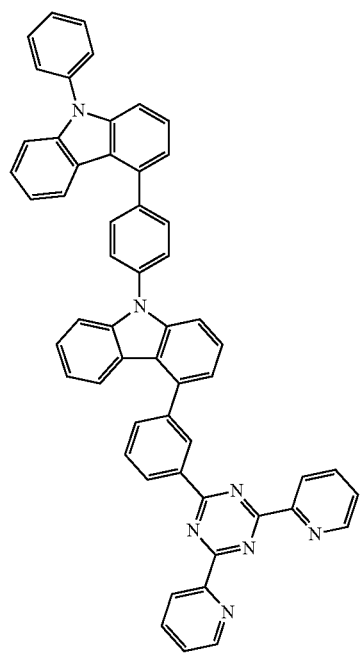 [SMILES: c1ccc(-n2c3ccccc3c3c(-c4ccc(-n5c6ccccc6c6c(-c7cccc(-c8nc(-c9ccccn9)nc(-c9ccccn9)n8)c7)cccc65)cc4)cccc32)cc1]

Chemical Formula 1-199
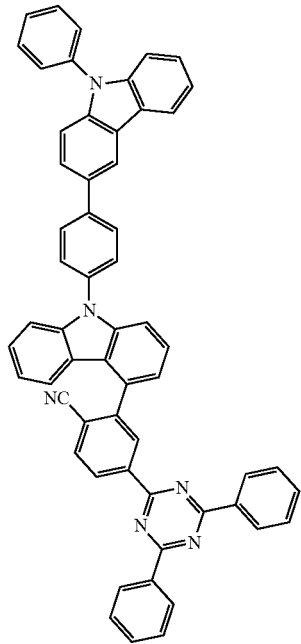 [SMILES: N#Cc1ccc(-c2nc(-c3ccccc3)nc(-c3ccccc3)n2)cc1-c1cccc2c1c1ccccc1n2-c1ccc(-c2ccc3c(c2)c2ccccc2n3-c2ccccc2)cc1]
Chemical Formula 1-200
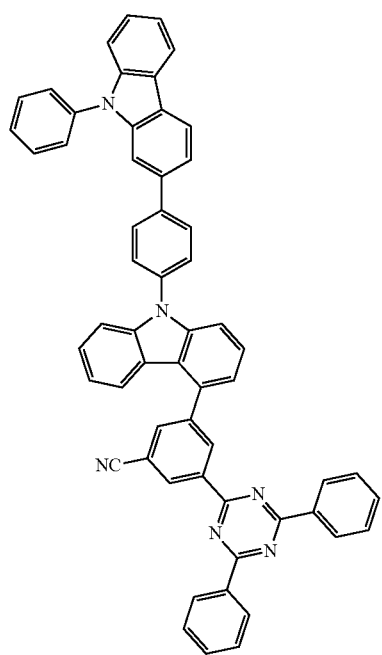 [SMILES: N#Cc1cc(-c2nc(-c3ccccc3)nc(-c3ccccc3)n2)cc(-c2cccc3c2c2ccccc2n3-c2ccc(-c3ccc4c5ccccc5n(-c5ccccc5)c4c3)cc2)c1]

Chemical Formula 1-201
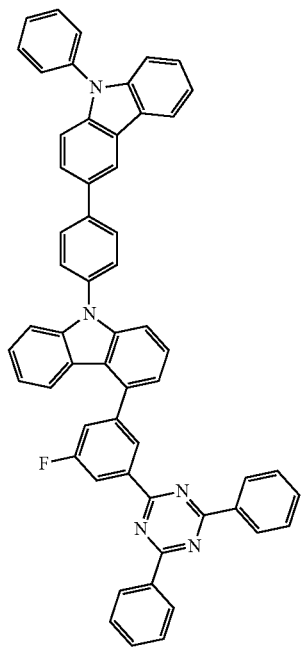
Chemical Formula 1-202
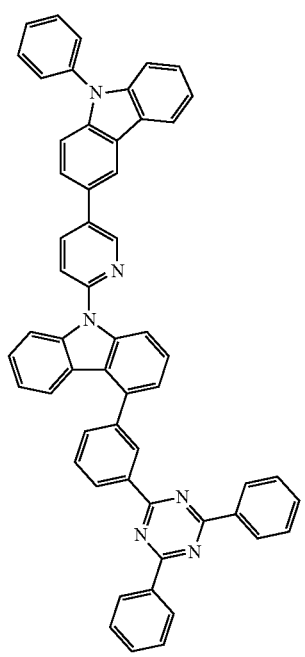

Chemical Formula 1-203
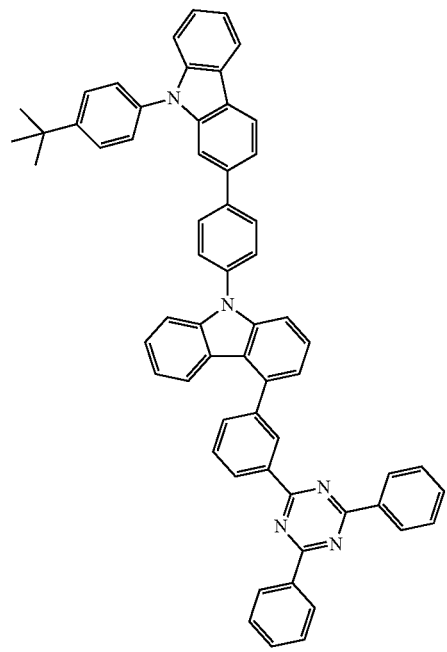 [SMILES: CC(C)(C)c1ccc(-n2c3ccccc3c3ccc(-c4ccc(-n5c6ccccc6c6c(-c7cccc(-c8nc(-c9ccccc9)nc(-c9ccccc9)n8)c7)cccc65)cc4)cc32)cc1]
Chemical Formula 1-204
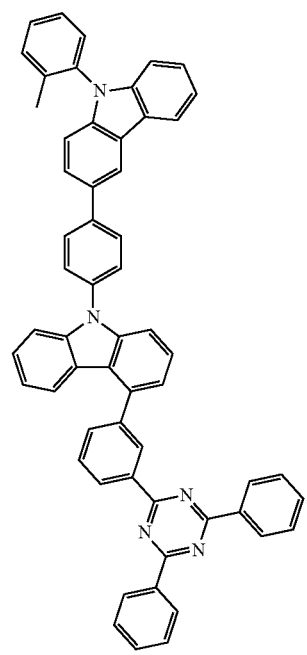 [SMILES: Cc1ccccc1-n1c2ccccc2c2cc(-c3ccc(-n4c5ccccc5c5c(-c6cccc(-c7nc(-c8ccccc8)nc(-c8ccccc8)n7)c6)cccc54)cc3)ccc21]

Chemical Formula 1-205
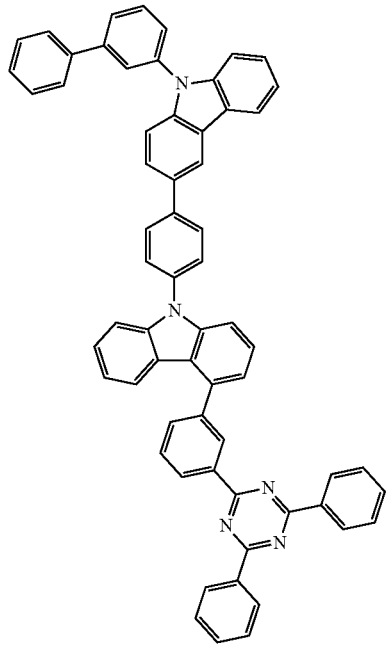 [SMILES: c1ccc(-c2cccc(-n3c4ccccc4c4cc(-c5ccc(-n6c7ccccc7c7c(-c8cccc(-c9nc(-c%10ccccc%10)nc(-c%10ccccc%10)n9)c8)cccc76)cc5)ccc43)c2)cc1]
Chemical Formula 1-206
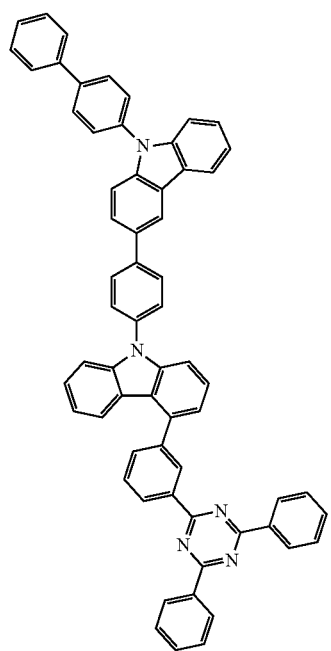 [SMILES: c1ccc(-c2ccc(-n3c4ccccc4c4cc(-c5ccc(-n6c7ccccc7c7c(-c8cccc(-c9nc(-c%10ccccc%10)nc(-c%10ccccc%10)n9)c8)cccc76)cc5)ccc43)cc2)cc1]

Chemical Formula 1-207
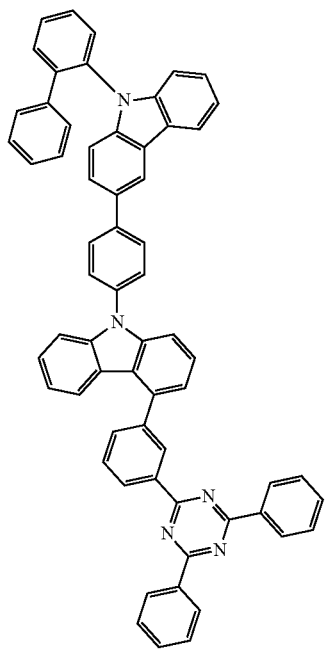 [SMILES: c1ccc(-c2nc(-c3ccccc3)nc(-c3cccc(-c4cccc5c4c4ccccc4n5-c4ccc(-c5ccc6c(c5)c5ccccc5n6-c5ccccc5-c5ccccc5)cc4)c3)n2)cc1]
Chemical Formula 1-208
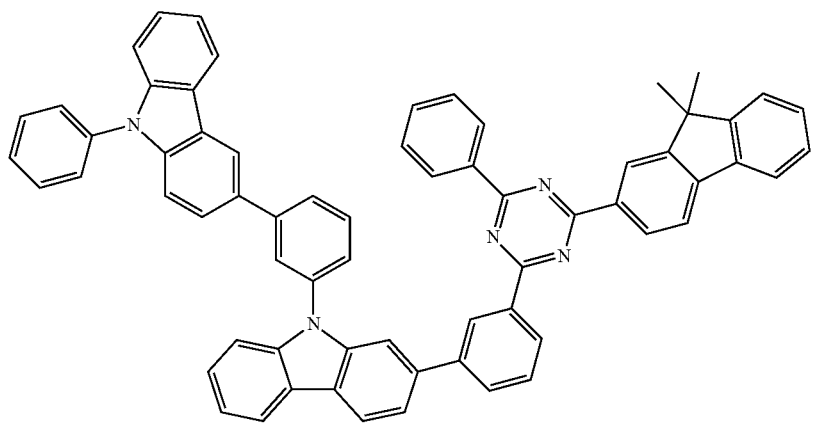 [SMILES: CC1(C)c2ccccc2-c2ccc(-c3nc(-c4ccccc4)nc(-c4cccc(-c5ccc6c7ccccc7n(-c7cccc(-c8ccc9c(c8)c8ccccc8n9-c8ccccc8)c7)c6c5)c4)n3)cc21]
Chemical Formula 1-209
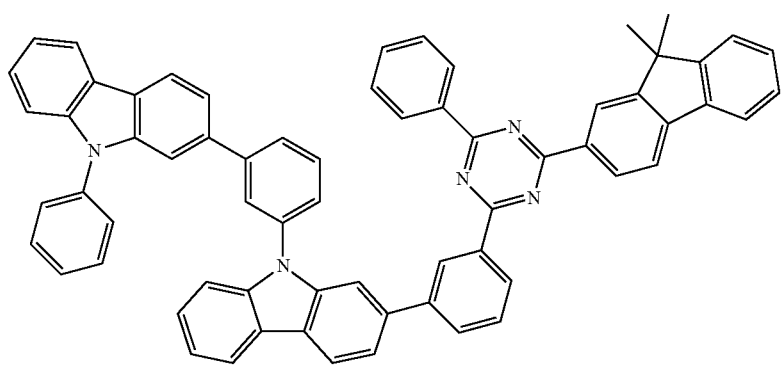 [SMILES: CC1(C)c2ccccc2-c2ccc(-c3nc(-c4ccccc4)nc(-c4cccc(-c5ccc6c7ccccc7n(-c7cccc(-c8ccc9c%10ccccc%10n(-c%10ccccc%10)c9c8)c7)c6c5)c4)n3)cc21]

-continued
Chemical Formula 1-210
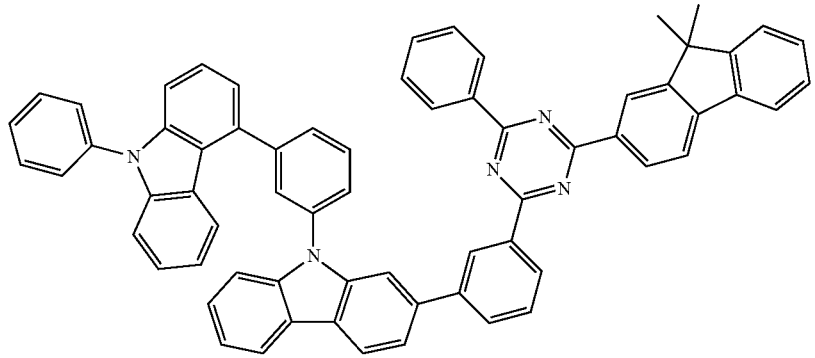 [SMILES: CC1(C)c2ccccc2-c2ccc(-c3nc(-c4ccccc4)nc(-c4cccc(-c5ccc6c7ccccc7n(-c7cccc(-c8cccc9c8c8ccccc8n9-c8ccccc8)c7)c6c5)c4)n3)cc21]
Chemical Formula 1-211
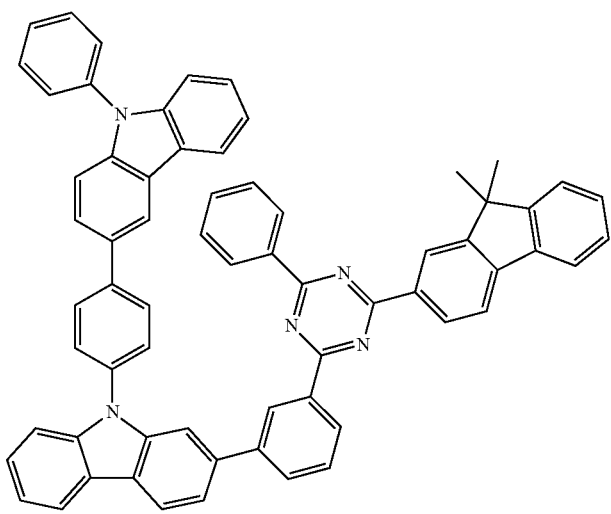 [SMILES: CC1(C)c2ccccc2-c2ccc(-c3nc(-c4ccccc4)nc(-c4cccc(-c5ccc6c7ccccc7n(-c7ccc(-c8ccc9c(c8)c8ccccc8n9-c8ccccc8)cc7)c6c5)c4)n3)cc21]
Chemical Formula 1-212
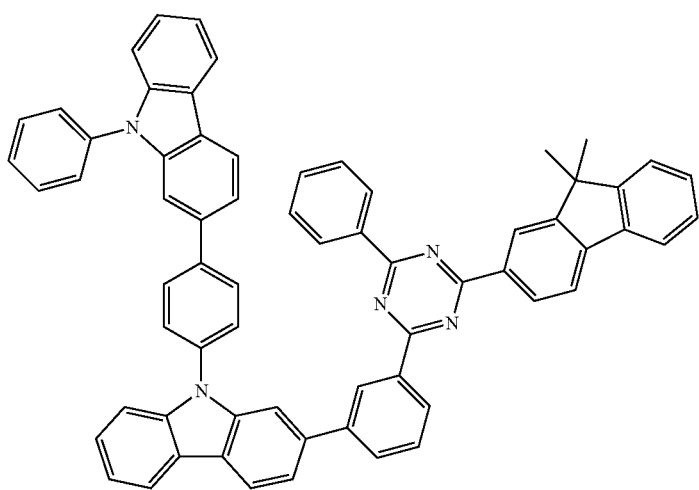 [SMILES: CC1(C)c2ccccc2-c2ccc(-c3nc(-c4ccccc4)nc(-c4cccc(-c5ccc6c7ccccc7n(-c7ccc(-c8ccc9c%10ccccc%10n(-c%10ccccc%10)c9c8)cc7)c6c5)c4)n3)cc21]

Chemical Formula 1-213
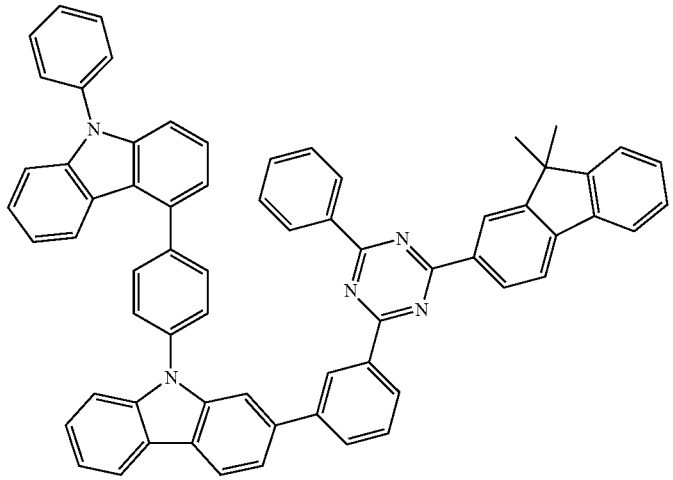 [SMILES: CC1(C)c2ccccc2-c2ccc(-c3nc(-c4ccccc4)nc(-c4cccc(-c5ccc6c7ccccc7n(-c7ccc(-c8cccc9c8c8ccccc8n9-c8ccccc8)cc7)c6c5)c4)n3)cc21]
Chemical Formula 1-214
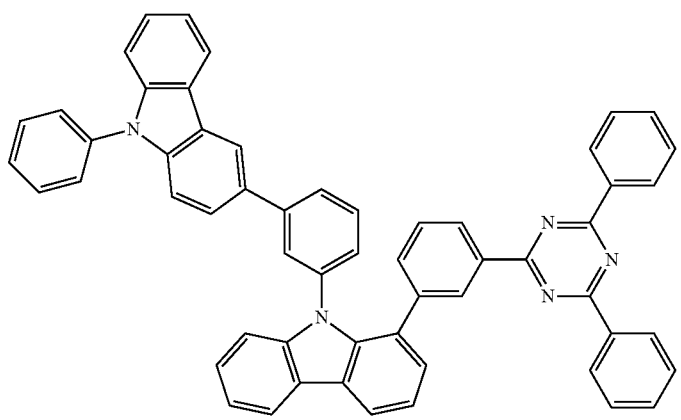 [SMILES: c1ccc(-c2nc(-c3ccccc3)nc(-c3cccc(-c4cccc5c6ccccc6n(-c6cccc(-c7ccc8c(c7)c7ccccc7n8-c7ccccc7)c6)c45)c3)n2)cc1]
Chemical Formula 1-215
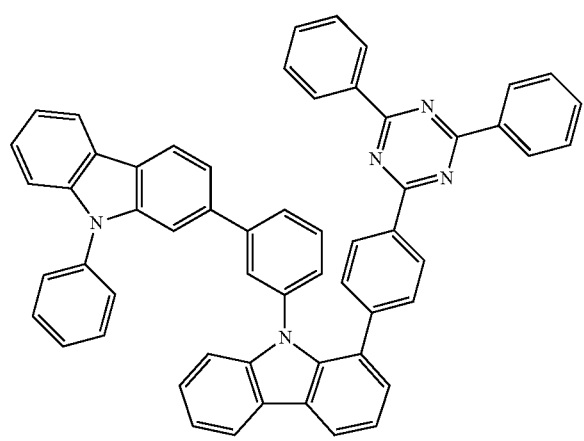 [SMILES: c1ccc(-c2nc(-c3ccccc3)nc(-c3ccc(-c4cccc5c6ccccc6n(-c6cccc(-c7ccc8c9ccccc9n(-c9ccccc9)c8c7)c6)c45)cc3)n2)cc1]

Chemical Formula 1-216
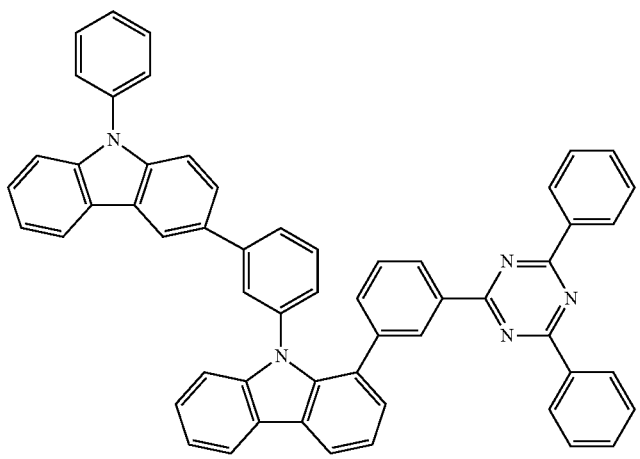 [SMILES: c1ccc(-c2nc(-c3ccccc3)nc(-c3cccc(-c4cccc5c6ccccc6n(-c6cccc(-c7ccc8c(c7)c7ccccc7n8-c7ccccc7)c6)c45)c3)n2)cc1]
Chemical Formula 1-217
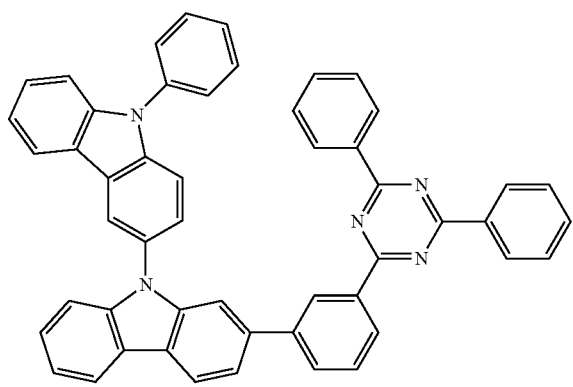 [SMILES: c1ccc(-c2nc(-c3ccccc3)nc(-c3cccc(-c4ccc5c6ccccc6n(-c6ccc7c(c6)c6ccccc6n7-c6ccccc6)c5c4)c3)n2)cc1]
Chemical Formula 1-218
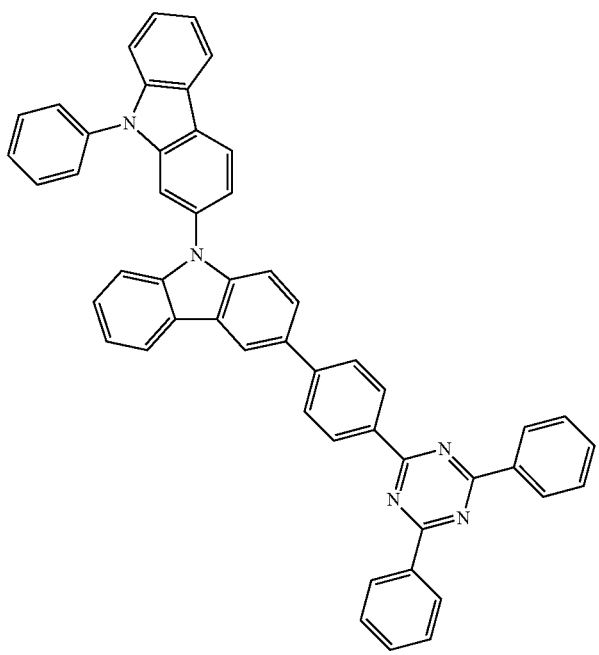 [SMILES: c1ccc(-c2nc(-c3ccccc3)nc(-c3ccc(-c4ccc5c(c4)c4ccccc4n5-c4ccc5c6ccccc6n(-c6ccccc6)c5c4)cc3)n2)cc1]

Chemical Formula 1-219
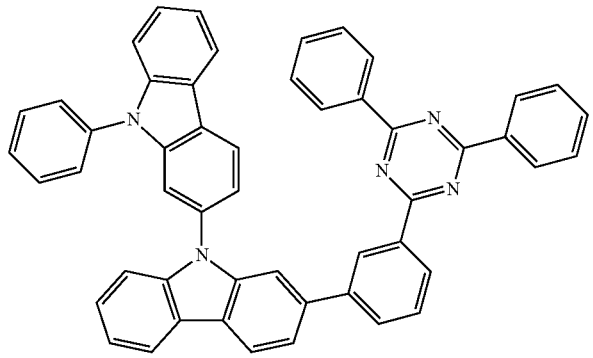 [SMILES: c1ccc(-c2nc(-c3ccccc3)nc(-c3cccc(-c4ccc5c6ccccc6n(-c6ccc7c8ccccc8n(-c8ccccc8)c7c6)c5c4)c3)n2)cc1]
Chemical Formula 1-220
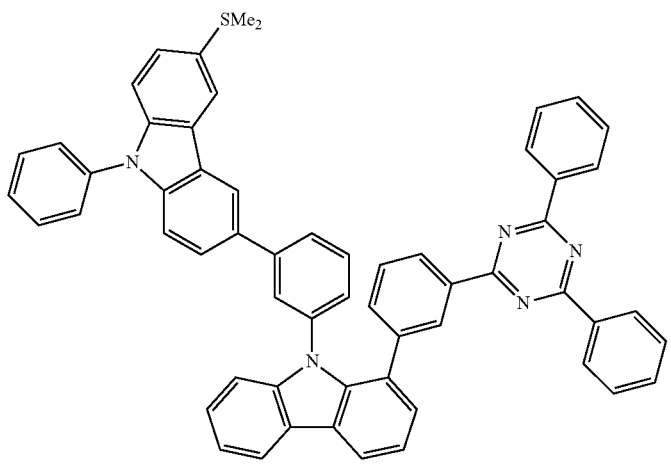
Chemical Formula 1-221
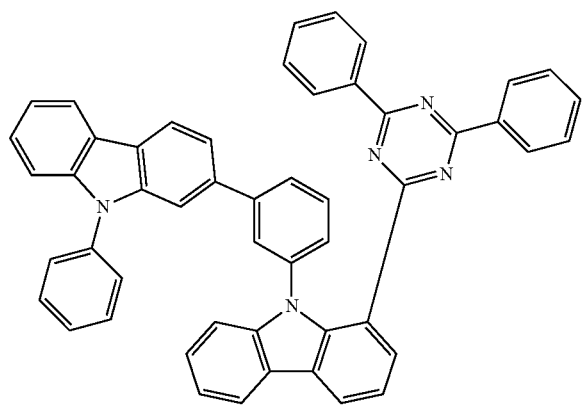 [SMILES: c1ccc(-c2nc(-c3ccccc3)nc(-c3cccc4c5ccccc5n(-c5cccc(-c6ccc7c8ccccc8n(-c8ccccc8)c7c6)c5)c34)n2)cc1]
Chemical Formula 1-222
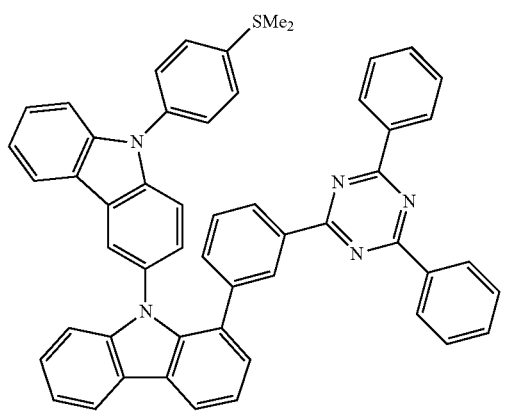

Chemical Formula 1-223
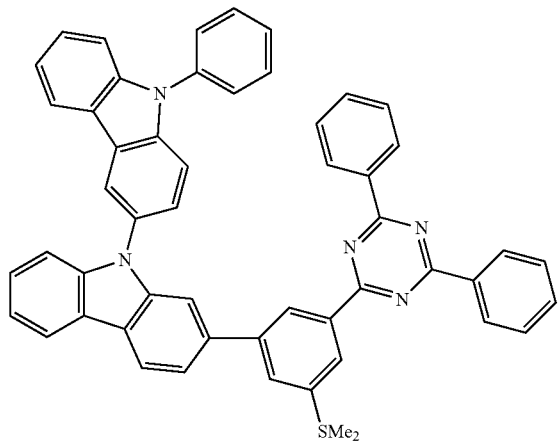
Chemical Formula 1-224
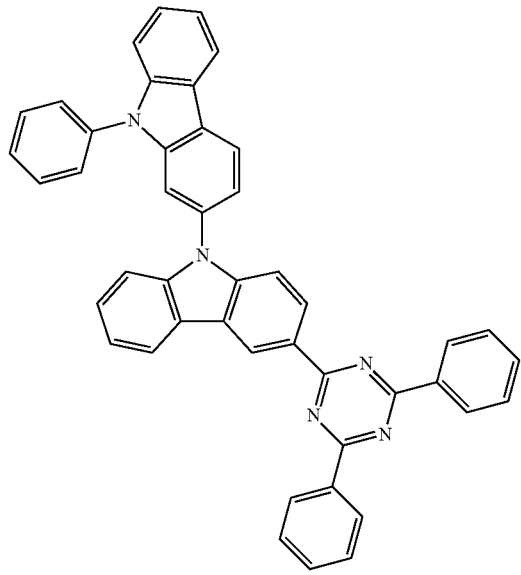 [SMILES: c1ccc(-c2nc(-c3ccccc3)nc(-c3ccc4c(c3)c3ccccc3n4-c3ccc4c5ccccc5n(-c5ccccc5)c4c3)n2)cc1]

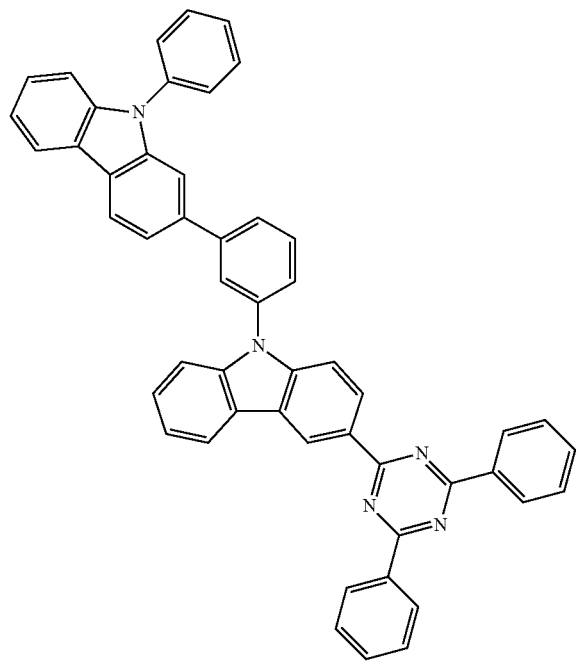 [SMILES: c1ccc(-c2nc(-c3ccccc3)nc(-c3ccc4c(c3)c3ccccc3n4-c3cccc(-c4ccc5c6ccccc6n(-c6ccccc6)c5c4)c3)n2)cc1]
Chemical Formula 1-225
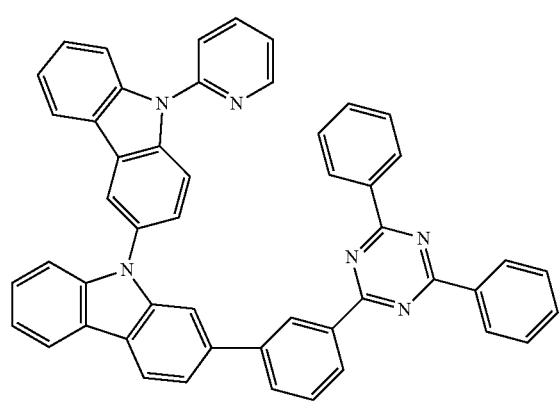 [SMILES: c1ccc(-c2nc(-c3ccccc3)nc(-c3cccc(-c4ccc5c6ccccc6n(-c6ccc7c(c6)c6ccccc6n7-c6ccccn6)c5c4)c3)n2)cc1]
Chemical Formula 1-226
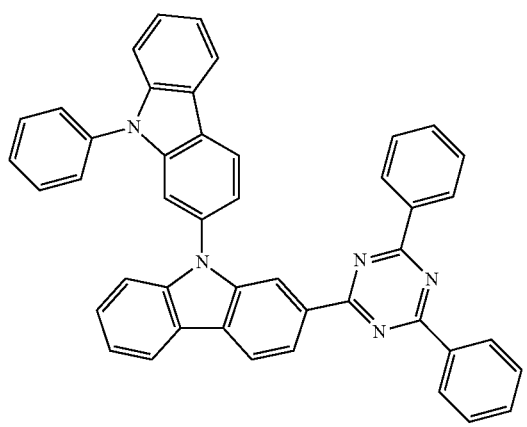 [SMILES: c1ccc(-c2nc(-c3ccccc3)nc(-c3ccc4c5ccccc5n(-c5ccc6c7ccccc7n(-c7ccccc7)c6c5)c4c3)n2)cc1]
Chemical Formula 1-227

Chemical Formula 1-228
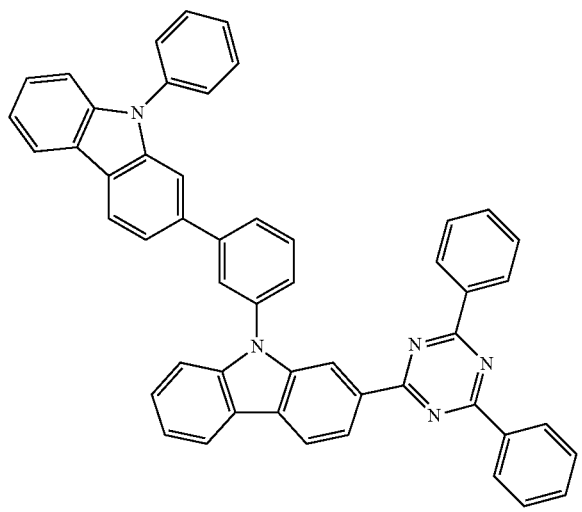 [SMILES: c1ccc(-c2nc(-c3ccccc3)nc(-c3ccc4c5ccccc5n(-c5cccc(-c6ccc7c8ccccc8n(-c8ccccc8)c7c6)c5)c4c3)n2)cc1]
Chemical Formula 1-229
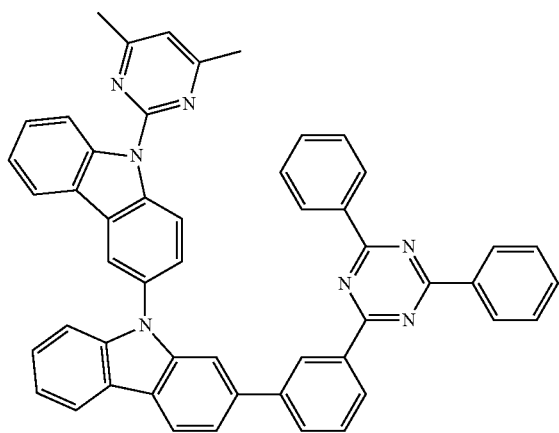 [SMILES: Cc1cc(C)nc(-n2c3ccccc3c3cc(-n4c5ccccc5c5ccc(-c6cccc(-c7nc(-c8ccccc8)nc(-c8ccccc8)n7)c6)cc54)ccc32)n1]
Chemical Formula 1-230
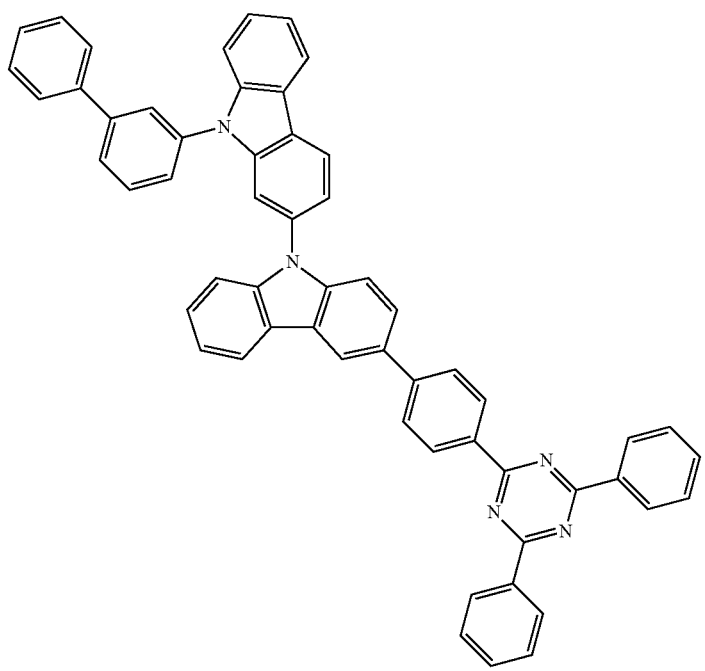 [SMILES: c1ccc(-c2cccc(-n3c4ccccc4c4ccc(-n5c6ccccc6c6cc(-c7ccc(-c8nc(-c9ccccc9)nc(-c9ccccc9)n8)cc7)ccc65)cc43)c2)cc1]

Chemical Formula 1-231
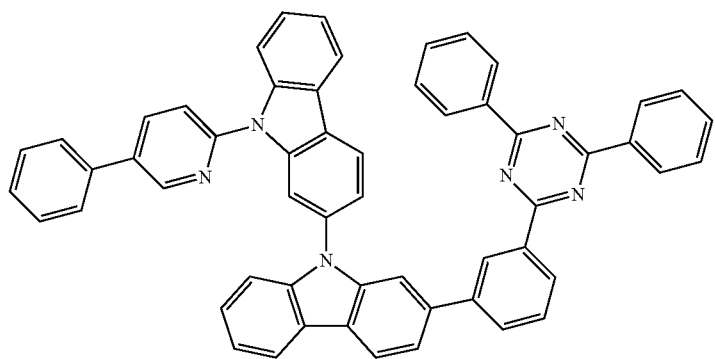 [SMILES: c1ccc(-c2ccc(-n3c4ccccc4c4ccc(-n5c6ccccc6c6ccc(-c7cccc(-c8nc(-c9ccccc9)nc(-c9ccccc9)n8)c7)cc65)cc43)nc2)cc1]
Chemical Formula 1-232
Chemical Formula 1-233

Chemical Formula 1-234

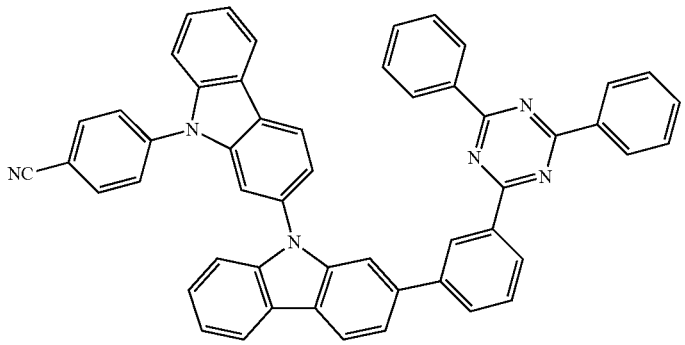 [SMILES: N#Cc1ccc(-n2c3ccccc3c3ccc(-n4c5ccccc5c5ccc(-c6cccc(-c7nc(-c8ccccc8)nc(-c8ccccc8)n7)c6)cc54)cc32)cc1]

The compounds represented by Chemical Formula 1 may be manufactured based on Preparation Examples as will be described later. According to the exemplary embodiment, the compounds may be manufactured by a method such as the following Reaction Formula 1 or Reaction Formula 2.

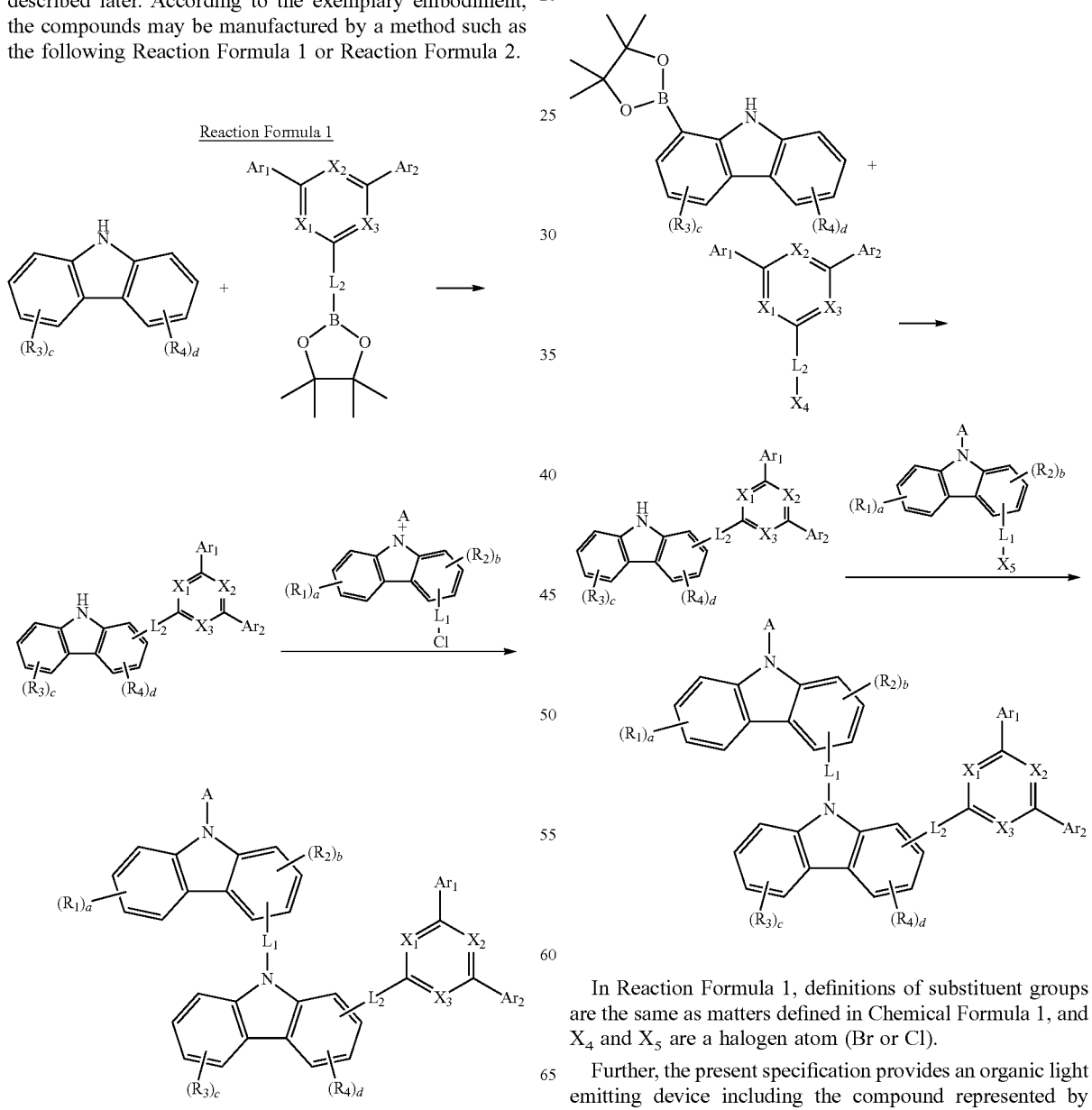

In Reaction Formula 1, definitions of substituent groups are the same as matters defined in Chemical Formula 1, and $X_4$ and $X_5$ are a halogen atom (Br or Cl).

Further, the present specification provides an organic light emitting device including the compound represented by Chemical Formula 1.

In the exemplary embodiment of the present specification, there is provided an organic light emitting device including: a first electrode; a second electrode provided to face the first electrode; and one or more organic material layers provided between the first electrode and the second electrode, in which one or more of the organic material layers include the compound of Chemical Formula 1.

The organic material layer of the organic light emitting device of the present specification may have a single layer structure, or a multilayered structure in which two or more organic material layers are laminated. For example, the organic light emitting device of the present invention may have a structure including a hole injection layer, a hole transport layer, a light emitting layer, an electron transport layer, an electron injection layer, and the like as the organic material layer. However, the structure of the organic light emitting device is not limited thereto, but may include a smaller number of organic layers.

In the exemplary embodiment of the present specification, the organic material layer includes the hole injection layer or the hole transport layer, and the hole injection layer or the hole transport layer includes the compound of Chemical Formula 1.

In another exemplary embodiment, the organic material layer includes the light emitting layer, and the light emitting layer includes the compound of Chemical Formula 1. Specifically, the compound of Chemical Formula 1 may be included as a host of a phosphorescent light emitting layer. In the present specification, the phosphorescent light emitting layer may further include a phosphorescent material. It is preferable that the phosphorescent material include a metal complex and the metal complex have a metal atom selected from Ir, Pt, Os, Au, Cu, Re, and Ru and a ligand.

Preferable specific examples of the metal complex will be described below.

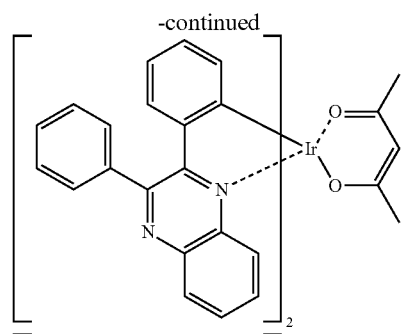

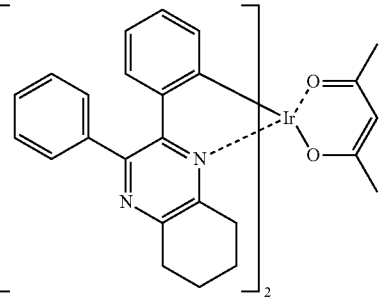

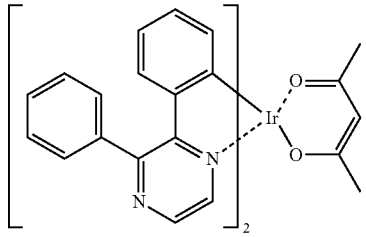

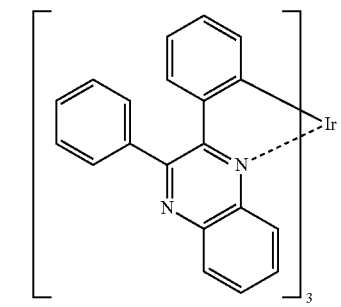

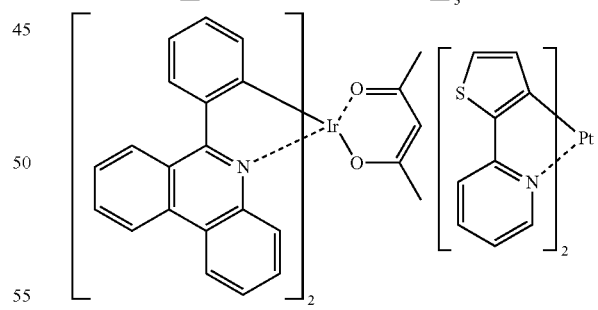

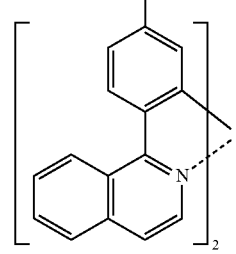

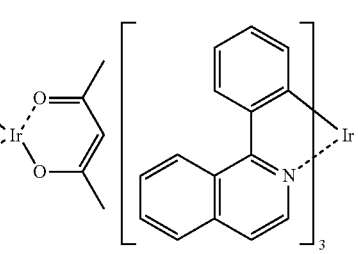

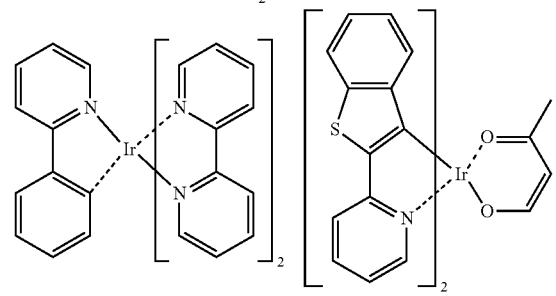

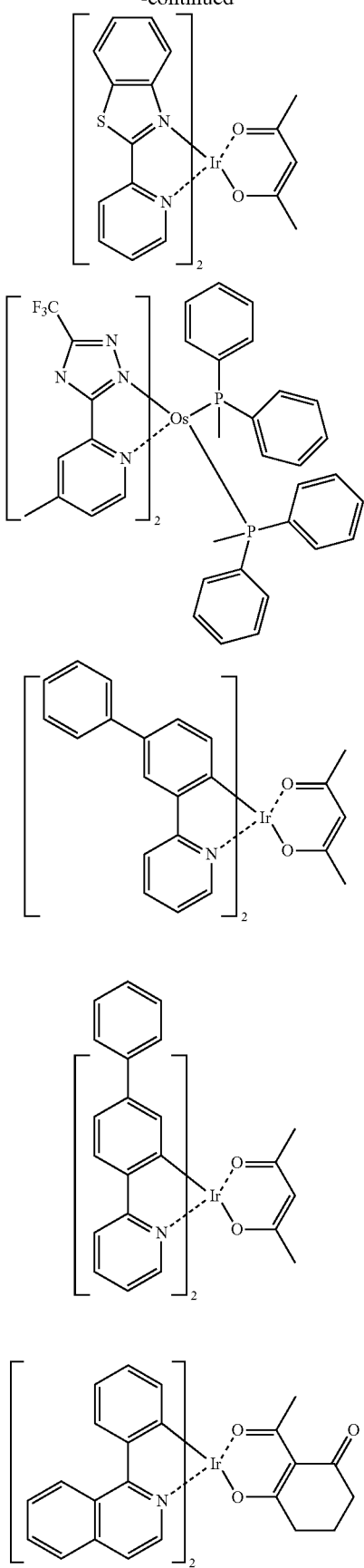
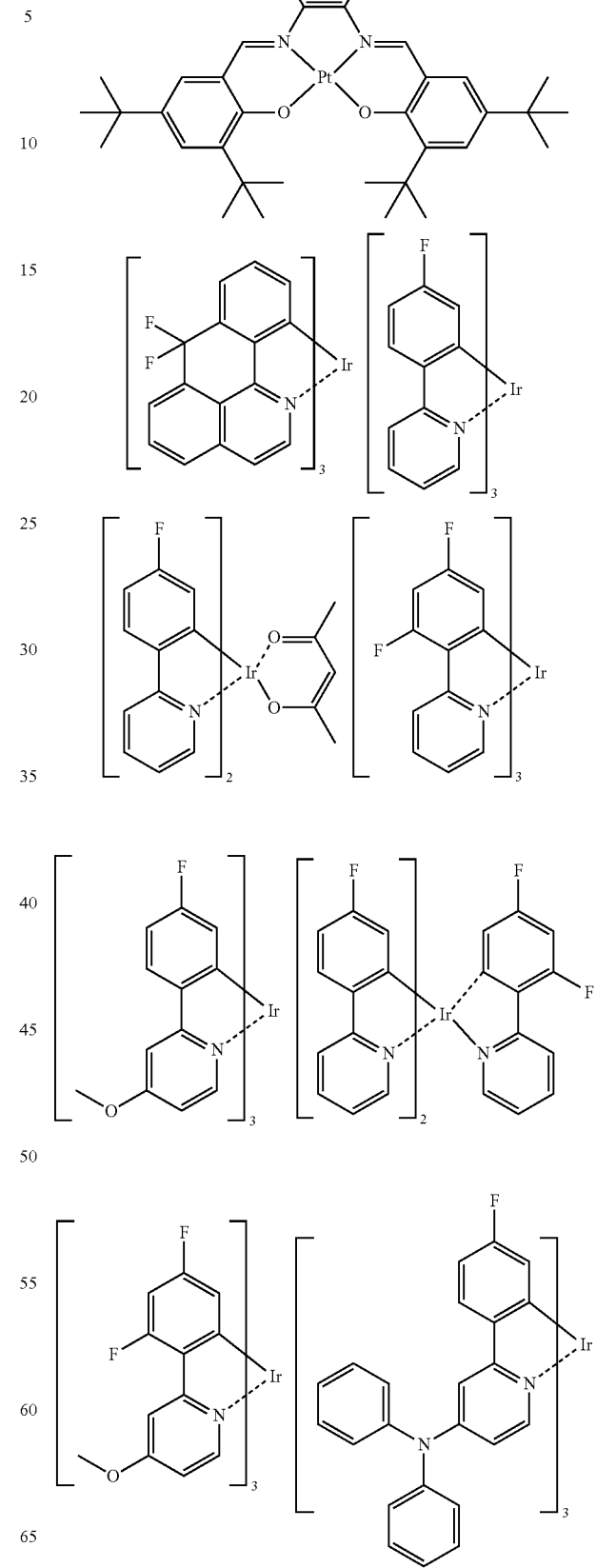

221
-continued
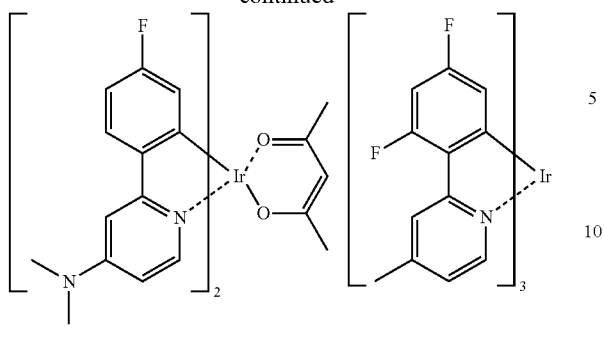
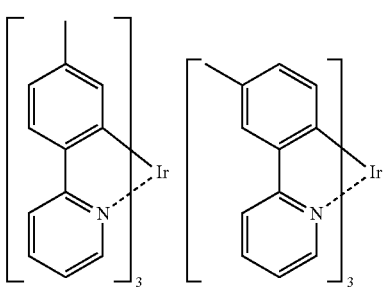
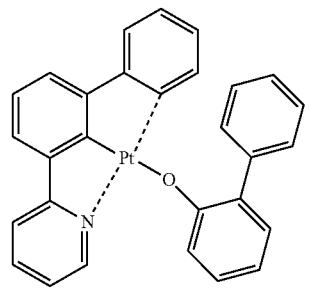
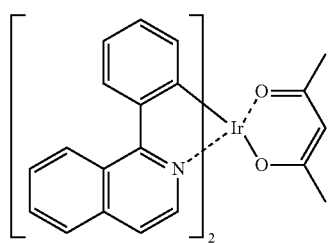
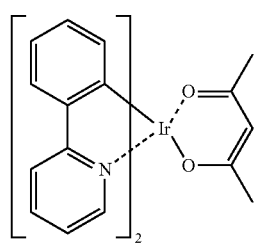
222
-continued
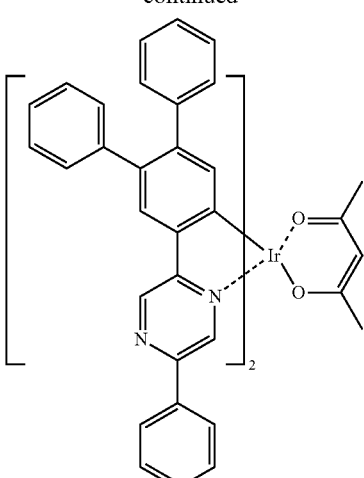
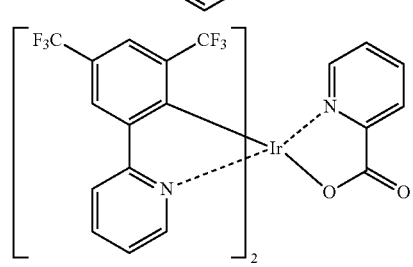
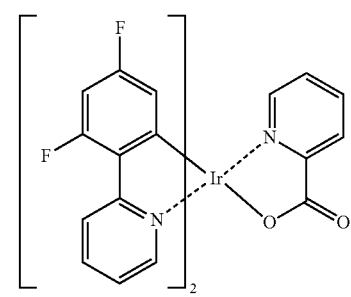
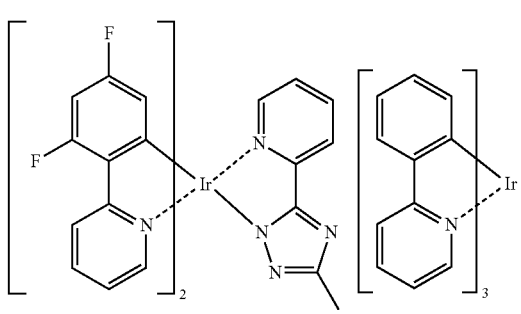
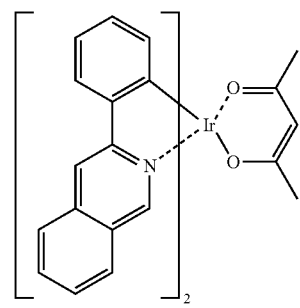

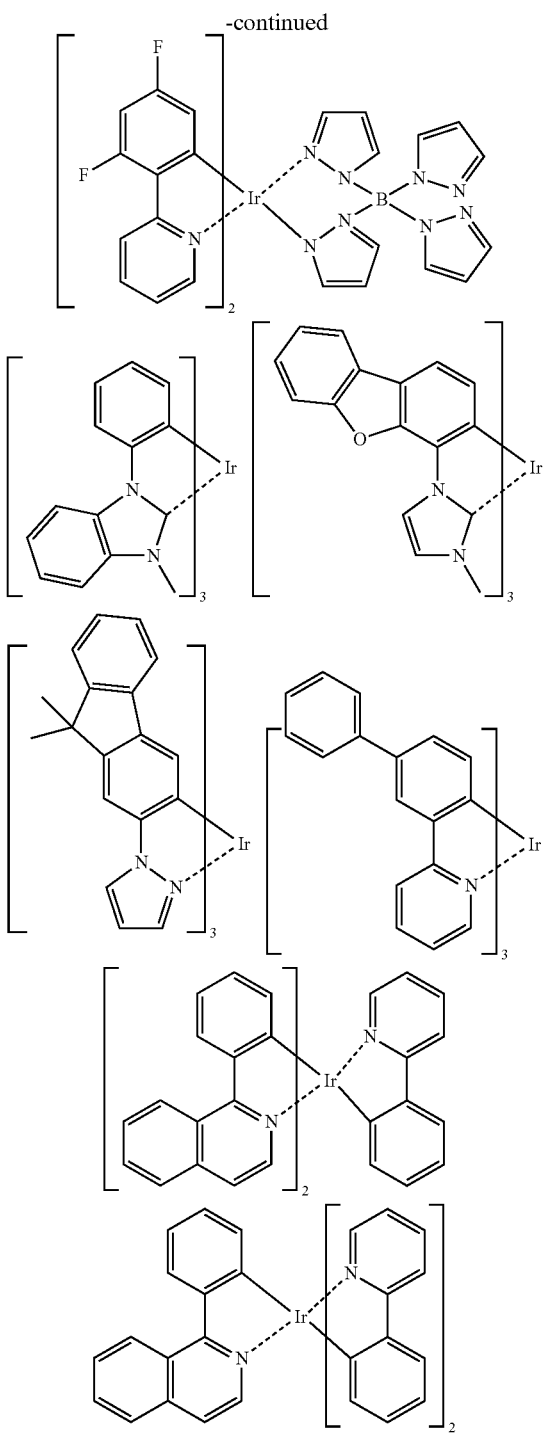

In the exemplary embodiment of the present specification, the organic material layer includes the electron transport layer or the electron injection layer, and the electron transport layer or the electron injection layer includes the compound of Chemical Formula 1.

In the exemplary embodiment of the present specification, the electron transport layer, the electron injection layer, or a layer simultaneously performing electron transporting and electron injection includes the compound of Chemical Formula 1.

In another exemplary embodiment, the organic material layer includes the light emitting layer and the electron transport layer, and the electron transport layer includes the compound of Chemical Formula 1.

In the exemplary embodiment of the present specification, the organic material layer further includes the hole injection layer or the hole transport layer including a compound including an arylamino group, a carbazole group, or a benzocarbazole group in addition to the organic material layer including the compound of Chemical Formula 1.

In the exemplary embodiment of the present specification, the organic material layer including the compound of Chemical Formula 1 includes the compound of Chemical Formula 1 as a host, and includes another organic compound, a metal, or a metal compound as a dopant.

In another exemplary embodiment, the organic light emitting device may be an organic light emitting device having a structure (normal type) where an anode, one or more organic material layers, and a cathode are sequentially laminated on a substrate.

In another exemplary embodiment, the organic light emitting device may be an organic light emitting device having an inverted direction structure (inverted type) where the cathode, one or more organic material layers, and the anode are sequentially laminated on the substrate.

For example, the structure of the organic light emitting device according to the exemplary embodiment of the present specification is illustrated in FIGS. 1 and 2.

FIG. 1 illustrates an example of an organic light emitting device including a substrate 1, an anode 2, a light emitting layer 3, and a cathode 4. In the aforementioned structure, the compound may be included in the light emitting layer.

FIG. 2 illustrates an example of an organic light emitting device including a substrate 1, an anode 2, a hole injection layer 5, a hole transport layer 6, a light emitting layer 7, an electron transport layer 8, and a cathode 4. In the aforementioned structure, the compound may be included in one or more layers of the hole injection layer, the hole transport layer, the light emitting layer, and the electron transport layer.

The organic light emitting device of the present specification may be manufactured by materials and methods known in the art, except that one or more of organic material layers include the compound of the present specification, that is, the compound of Chemical Formula 1.

In the case where the organic light emitting device includes a plurality of organic material layers, the organic material layers may be formed of the same material or different materials.

The organic light emitting device of the present specification may be manufactured by materials and methods known in the art, except that one or more of organic material layers include the compound of Chemical Formula 1, that is, the compound represented by Chemical Formula 1.

For example, the organic light emitting device of the present specification may be manufactured by sequentially laminating the first electrode, the organic material layer, and the second electrode on the substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming the organic material layer including the hole injection layer, the hole transport layer, the light emitting layer, and the electron transport layer thereon, and then depositing a material that can be used as the cathode thereon. In addition to this method, the organic light emitting device may be manufactured by sequentially depositing a cathode material, the organic material layer, and an anode material on the substrate.

Further, the compound of Chemical Formula 1 may be formed as the organic material layer by a vacuum deposition method or a solution coating method when the organic light emitting device is manufactured. Herein, the solution coating method means spin coating, dip coating, doctor blading, inkjet printing, screen printing, a spray method, roll coating, or the like, but is not limited thereto.

In addition to this method, the organic light emitting device may be manufactured by sequentially depositing a cathode material, an organic material layer, and an anode material on a substrate (International Patent Application Laid-Open No. WO 2003/012890). However, the manufacturing method is not limited thereto.

In the exemplary embodiment of the present specification, the first electrode is the anode, and the second electrode is the cathode.

In another exemplary embodiment, the first electrode is the cathode, and the second electrode is the anode.

It is preferable that the anode material be, in general, a material having a large work function so as to smoothly inject holes into the organic material layer. Specific examples of the anode material that may be used in the present invention include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

It is preferable that the cathode material be, in general, a material having a small work function so as to easily inject electrons into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection material is a layer injecting the holes from the electrode, and it is preferable that the hole injection material be a compound which has an ability of transporting the holes to have a hole injection effect in the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material be between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer receiving the holes from the hole injection layer and transporting the holes to the light emitting layer, and the hole transport material is a material that can receive the holes from the anode or the hole injection layer and transport the holes to the light emitting layer, and a material having large mobility to the holes is suitable. Specific examples thereof include an arylamine-based organic material, a conductive polymer, a block copolymer in which a conjugate portion and a non-conjugate portion are present together, and the like, but are not limited thereto.

The light emitting material is a material that can receive the holes and the electrons from the hole transport layer and the electron transport layer, respectively, and bond the holes and the electrons to emit light in a visible ray region, and is preferably a material having good quantum efficiency to fluorescence or phosphorescence. Specific examples thereof include a 8-hydroxy-quinoline aluminum complex ($Alq_3$); a carbazole-based compound; a dimerized styryl compound; BAlq; a 10-hydroxybenzoquinoline-metal compound; benzoxazole, benzthiazole, and benzimidazole-based compounds; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensation aromatic cycle derivative, a heterocycle-containing compound, or the like. Specific examples of the compensation aromatic cycle derivative include an anthracene derivative, a pyrene derivative, a naphthalene derivative, a pentacene derivative, a phenanthrene compound, a fluoranthene compound, and the like, and specific examples of the heterocycle-containing compound include a carbazole derivative, a dibenzofuran derivative, a ladder-type furan compound, a pyrimidine derivative, and the like, but the examples are not limited thereto.

Examples of the dopant material include an aromatic amine derivative, a styrylamine compound, a boron complex, a fluoranthene compound, a metal complex, and the like. Specifically, the aromatic amine derivative is a compensation aromatic cycle derivative having a substituted or unsubstituted arylamino group, examples thereof include pyrene, anthracene, chrysene, and periflanthene having the arylamino group, and the like, the styrylamine compound is a compound where at least one arylvinyl group is substituted in substituted or unsubstituted arylamine, and in the styrylamine compound, one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport material is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the related art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present specification may be a top emission type, a bottom emission type, or a both-sided emission type according to the used material.

In the exemplary embodiment of the present specification, the compound of Chemical Formula 1 may be included in an organic solar cell or an organic transistor in addition to the organic light emitting device.

Manufacturing of the compound represented by Chemical Formula 1 and the organic light emitting device including the same will be described in detail in the following Examples. However, the following Examples are set forth to illustrate the present specification, but the scope of the present specification is not limited thereto.

EXAMPLE

<Preparation Example 1> Preparation of Chemical Formula P1

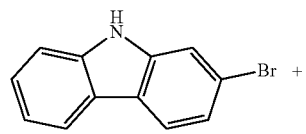

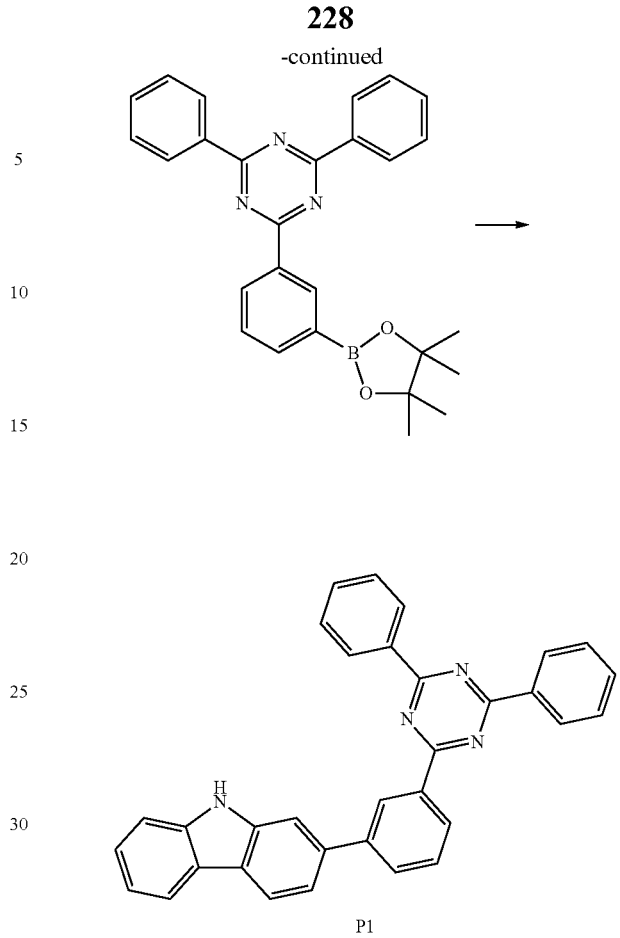

2-bromocarbazole (10.0 g, 40.6 mmol), 2,4-diphenyl-6-(3-(4,4,5,5-tetramethyl-1,3,2-dioxaborolane-2-yl)phenyl)-1,3,5-triazine (18.1 g, 41.5 mmol), and potassium carbonate (17.0 g, 123 mmol) were suspended in the mixture of tetrahydrofuran (100 mL) and water (50 mL). After nitrogen was charged, tetrakis(triphenylphosphine)palladium (0.9 g, 0.7 mmol) was applied to the suspension solution. Under nitrogen, the mixture was agitated in the reflux for about 12 hours. After the temperature was lowered to room temperature, the generated solid was filtered. The light yellow solid was precipitated in chloroform, agitated, filtered, and dried to obtain white solid P1 (17.8 g, 92%).

Compounds P2 to P40 were prepared according to the method of manufacturing compound P1 of Preparation Example 1. The structure, the shape, the yield, and MS thereof are arranged in the following Table.

| Preparation Example | Intermediate 1 | Intermediate 2 | Compound (Px) | Shape | Yield (%) | MS [M + H] |
|---|---|---|---|---|---|---|
| Preparation Example 2 (P2) | | | | White solid | 82 | 474 |
| Preparation Example 3 (P3) | | | | White solid | 90 | 474 |

| Intermediate 1 | Intermediate 2 | Compound (Px) | Shape | Yield (%) | MS [M + H] |
|---|---|---|---|---|---|
| Preparation Example 4 (P4) | | | White solid | 95 | 475 |
| Preparation Example 5 (P5) | | | White solid | 93 | 474 |

| | Intermediate 1 | Intermediate 2 | Compound (Px) | Shape | Yield (%) | MS [M + H] |
|---|---|---|---|---|---|---|
| Preparation Example 6 (P6) | 2-bromo-carbazole | 4,6-diphenyl-2-(4-(pinacolboryl)phenyl)pyrimidine | carbazol-2-yl-phenyl-diphenylpyrimidine | White solid | 88 | 474 |
| Preparation Example 7 (P7) | 2-bromo-carbazole | 2-(5-(pinacolboryl)pyridin-3-yl)-4,6-diphenyl-1,3,5-triazine | carbazol-2-yl-pyridinyl-diphenyltriazine | White solid | 85 | 476 |

| Preparation | Intermediate 1 | Intermediate 2 | Compound (Px) | Shape | Yield (%) | MS [M + H] |
|---|---|---|---|---|---|---|
| Preparation Example 8 (P8) | 2-bromocarbazole | triazine-pyridine-Bpin intermediate | triazine-pyridine-carbazole compound | White solid | 84 | 476 |
| Preparation Example 9 (P9) | 2-bromocarbazole | triazine-pyridine-Bpin intermediate | triazine-pyridine-carbazole compound | White solid | 87 | 476 |

-continued
| | Intermediate 1 | Intermediate 2 | Compound (Px) | Shape | Yield (%) | MS [M + H] |
|---|---|---|---|---|---|---|
| Preparation Example 10 (P10) | 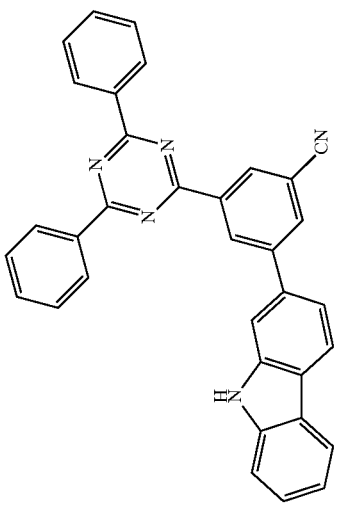 | 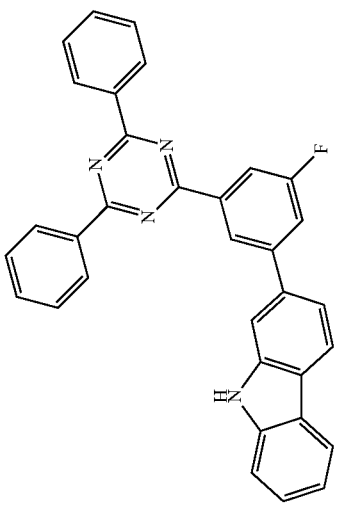 | 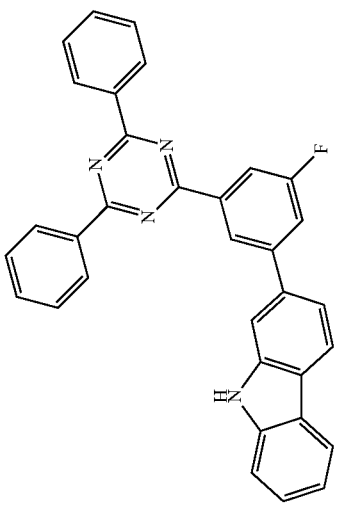 | White solid | 73 | 500 |
| Preparation Example 11 (P11) | 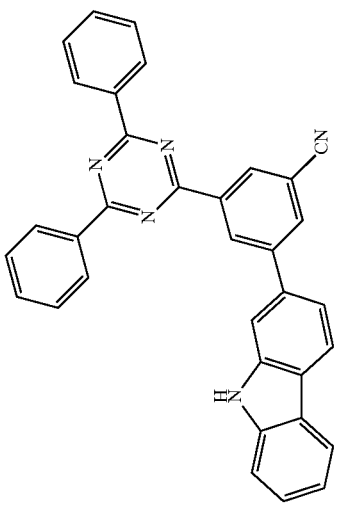 | 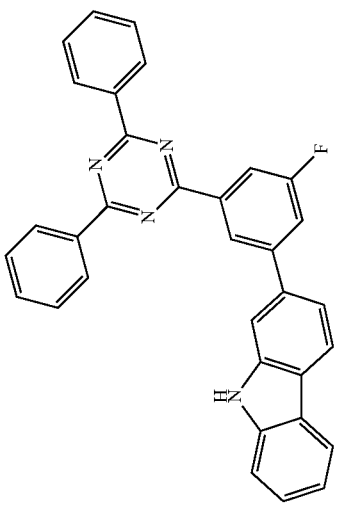 | 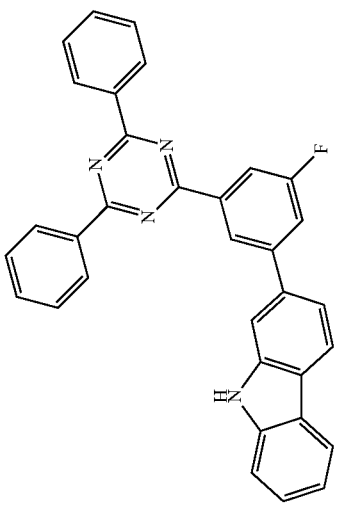 | White solid | 55 | 493 |

| Preparation Example | Intermediate 1 | Intermediate 2 | Compound (Px) | Shape | Yield (%) | MS [M+H] |
|---|---|---|---|---|---|---|
| Preparation Example 12 (P12) | 3-bromocarbazole | triazine-phenyl-Bpin intermediate | carbazole-phenyl-triazine compound | White solid | 67 | 475 |
| Preparation Example 13 (P13) | 3-bromocarbazole | pyrimidine-phenyl-Bpin intermediate | carbazole-phenyl-pyrimidine compound | White solid | 78 | 474 |

| | Intermediate 1 | Intermediate 2 | Compound (Px) | Shape | Yield (%) | MS [M + H] |
|---|---|---|---|---|---|---|
| Preparation Example 14 (P14) | | | | White solid | 81 | 474 |
| Preparation Example 15 (P15) | | | | White solid | 88 | 475 |

-continued
| | Intermediate 1 | Intermediate 2 | Compound (Px) | Shape | Yield (%) | MS [M + H] |
|---|---|---|---|---|---|---|
| Preparation Example 16 (P16) | 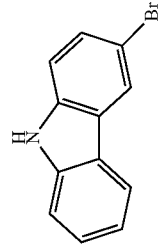 | 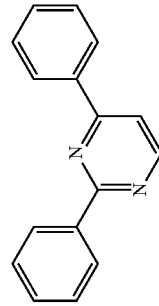 | 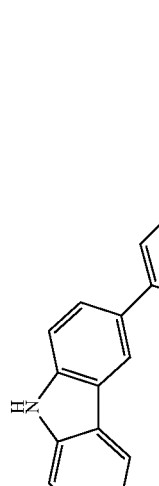 | White solid | 91 | 474 |
| Preparation Example 17 (P17) | 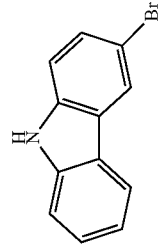 | 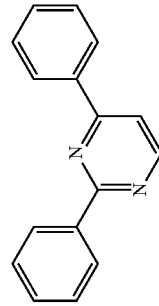 | 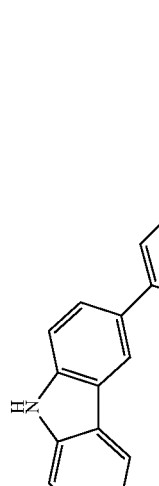 | White solid | 95 | 474 |

| Intermediate 1 | Intermediate 2 | Compound (Px) | Shape | Yield (%) | MS [M + H] |
|---|---|---|---|---|---|
| Preparation Example 18 (P18) | | | White solid | 89 | 476 |
| Preparation Example 19 (P19) | | | White solid | 77 | 476 |

| Preparation | Intermediate 1 | Intermediate 2 | Compound (Px) | Shape | Yield (%) | MS [M + H] |
|---|---|---|---|---|---|---|
| Preparation Example 20 (P20) | | | | White solid | 75 | 476 |
| Preparation Example 21 (P21) | | | | White solid | 59 | 500 |

| Preparation Example | Intermediate 1 | Intermediate 2 | Compound (Px) | Shape | Yield (%) | MS [M + H] |
|---|---|---|---|---|---|---|
| Preparation Example 22 (P22) | | | | White solid | 61 | 493 |
| Preparation Example 23 (P23) | | | | White solid | 81 | 475 |

| Preparation Example | Intermediate 1 | Intermediate 2 | Compound (Px) | Shape | Yield (%) | MS [M + H] |
|---|---|---|---|---|---|---|
| Preparation Example 24 (P24) | | | | White solid | 91 | 474 |
| Preparation Example 25 (P25) | | | | White solid | 90 | 474 |

-continued
| | Intermediate 1 | Intermediate 2 | Compound (Px) | Shape | Yield (%) | MS [M + H] |
|---|---|---|---|---|---|---|
| Preparation Example 26 (P26) | 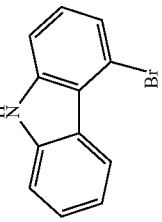 | 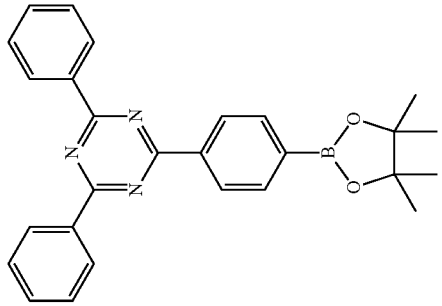 | 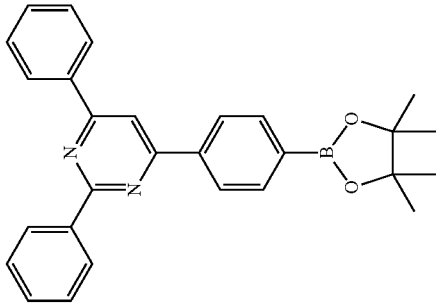 | White solid | 95 | 475 |
| Preparation Example 27 (P27) | 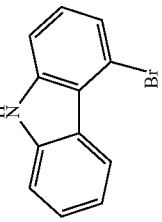 | 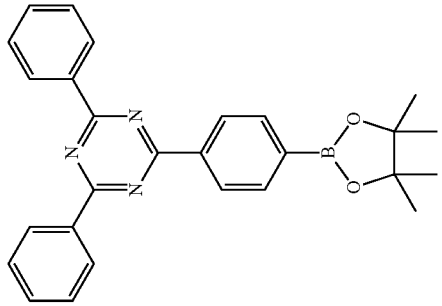 | 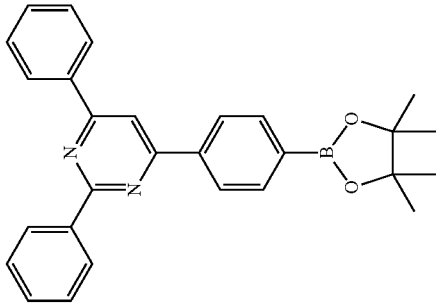 | White solid | 90 | 474 |

| | Intermediate 1 | Intermediate 2 | Compound (Px) | Shape | Yield (%) | MS [M + H] |
|---|---|---|---|---|---|---|
| Preparation Example 28 (P28) | 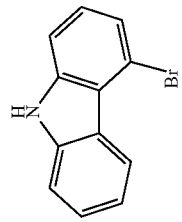 | 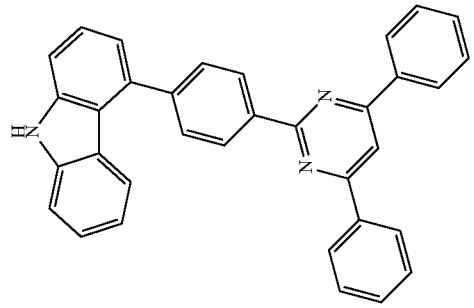 | 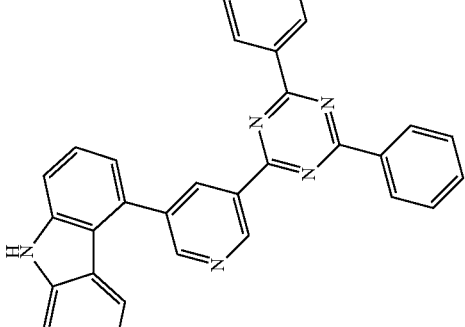 | White solid | 88 | 474 |
| Preparation Example 29 (P29) | 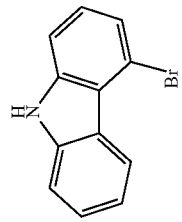 | 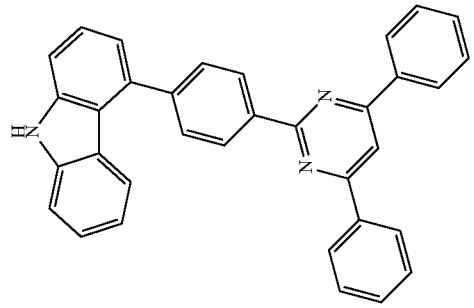 | 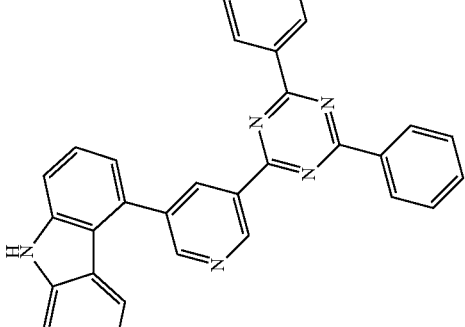 | White solid | 77 | 476 |

-continued
| Preparation Example | Intermediate 1 | Intermediate 2 | Compound (Px) | Shape | Yield (%) | MS [M + H] |
|---|---|---|---|---|---|---|
| Preparation Example 30 (P30) | 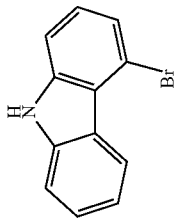 | 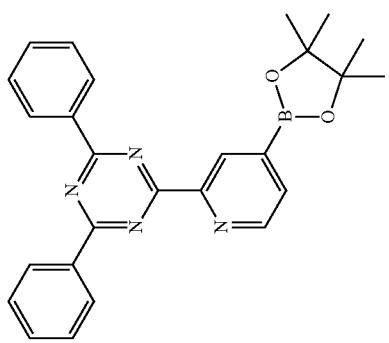 | 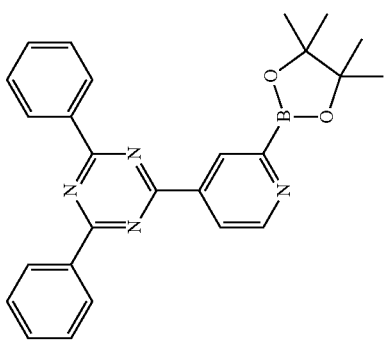 | White solid | 74 | 476 |
| Preparation Example 31 (P31) | 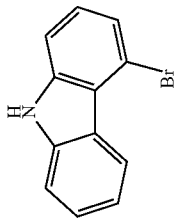 | 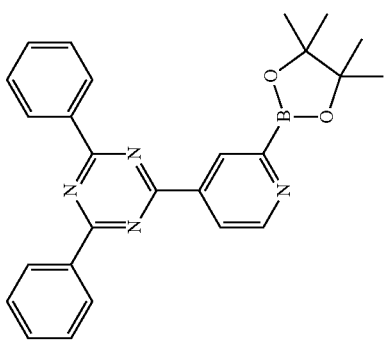 | 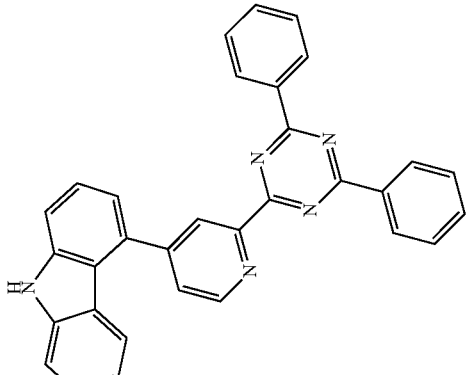 | White solid | 89 | 476 |

| Preparation | Intermediate 1 | Intermediate 2 | Compound (Px) | Shape | Yield (%) | MS [M + H] |
|---|---|---|---|---|---|---|
| Preparation Example 32 (P32) | 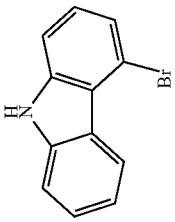 | 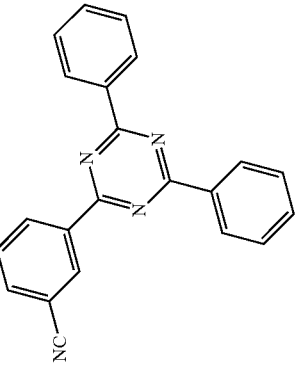 | 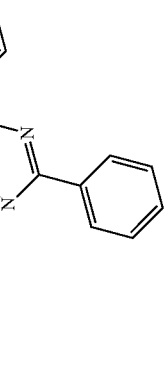 | White solid | 70 | 500 |
| Preparation Example 33 (P33) | 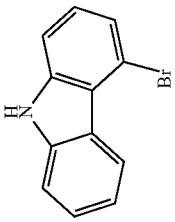 | 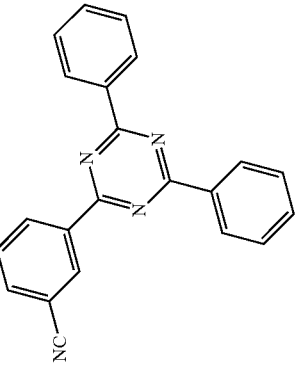 | 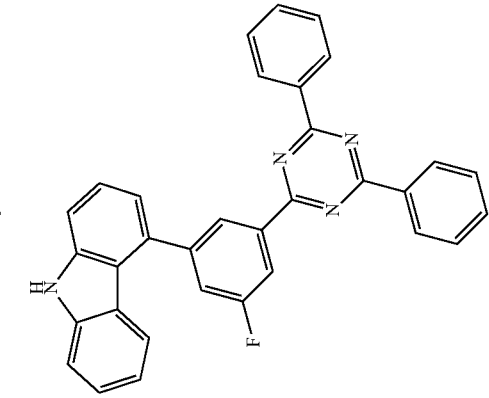 | White solid | 59 | 493 |

-continued

| Preparation Example | Intermediate 1 | Intermediate 2 | Compound (Px) | Shape | Yield (%) | MS [M + H] |
|---|---|---|---|---|---|---|
| Preparation Example 34 (P34) | | | | White solid | 60 | 550 |
| Preparation Example 35 (P35) | | | | White solid | 78 | 550 |

| Preparation Example | Intermediate 1 | Intermediate 2 | Compound (Px) | Shape | Yield (%) | MS [M + H] |
|---|---|---|---|---|---|---|
| Preparation Example 36 (P36) | | | | White solid | 56 | 591 |
| Preparation Example 37 (P37) | | | | White solid | 50 | 503 |

-continued

| Preparation Example | Intermediate 1 | Intermediate 2 | Compound (Px) | Shape | Yield (%) | MS [M + H] |
|---|---|---|---|---|---|---|
| Preparation Example 38 (P38) | 3-bromocarbazole | pyridyl-triazine-phenyl-Bpin | carbazole-phenyl-triazine(pyridyl)₂ | White solid | 41 | 477 |
| Preparation Example 39 (P39) | 1-bromocarbazole | phenyl-triazine-phenyl-Bpin | carbazole-phenyl-triazine(phenyl)₂ | White solid | 80 | 475 |

| Preparation Example | Intermediate 1 | Intermediate 2 | Compound (Px) | Shape | Yield (%) | MS [M + H] |
|---|---|---|---|---|---|---|
| Preparation Example 40 (P40) | carbazole-2-Bpin | 2-chloro-4,6-diphenyl-1,3,5-triazine | 2-(4,6-diphenyl-1,3,5-triazin-2-yl)-9H-carbazole | White solid | 41 | 477 |

<Preparation Example 41> Preparation of Chemical Formula 1-1

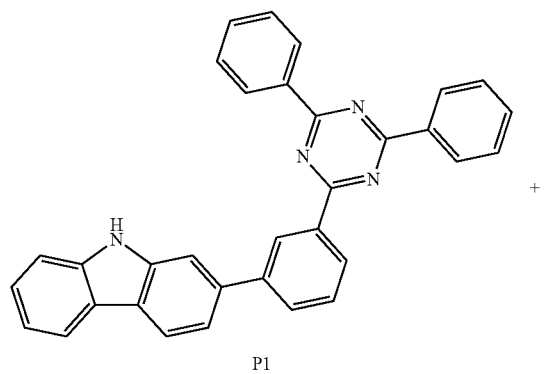

P1

+

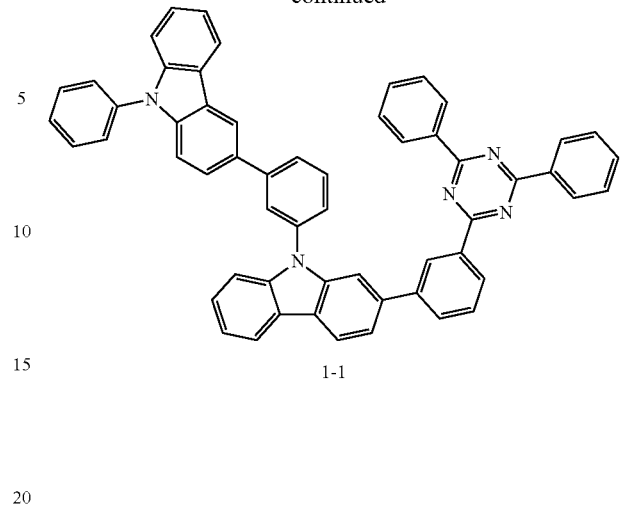

1-1

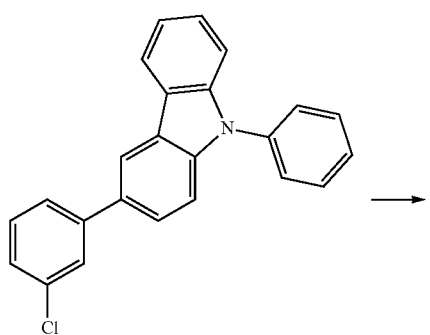

Compound P1 (8.2 g, 17.2 mmol), 3-(3-chlorophenyl)-9-phenyl-9H-carbazole (6.0 g, 16.9 mmol), bis(tri tertiary-butylphosphine)palladium (0.1 g, 0.2 mmol), and sodium tertiary-butoxide (2.8 g, 29.1 mmol) were mixed, and refluxed while being agitated in xylene (50 ml) under nitrogen for 6 hours. After the temperature was lowered to room temperature, the generated solid was filtered. The light yellow solid was dissolved by chloroform, magnesium sulfate and acid clay were put thereinto, followed by agitation and then filtration, and distillation was performed under a reduced pressure. Recrystallization was performed by using chloroform and ethyl acetate to obtain Chemical Formula 1-1 (8.8 g, 64%) that was the white solid compound.

The compounds of Chemical Formulas 1-2 to 1-231 were manufactured according to the method of manufacturing Chemical Formula 1-1 of Preparation Example 41. The structure, the shape, the yield, and MS thereof are arranged in the following Table.

| Intermediate 1 (Px) | Intermediate 2 | Chemical Formula | Shape | Yield (%) | MS [M + H] |
|---|---|---|---|---|---|
| Preparation Example 42 Chemical Formula 1-2 | P1 | | | White solid | 66 | 792 |

-continued
| | Intermediate 1 (Px) | Intermediate 2 | Chemical Formula | Shape | Yield (%) | MS [M + H] |
|---|---|---|---|---|---|---|
| Preparation Example 43 Chemical Formula 1-4 | P1 | 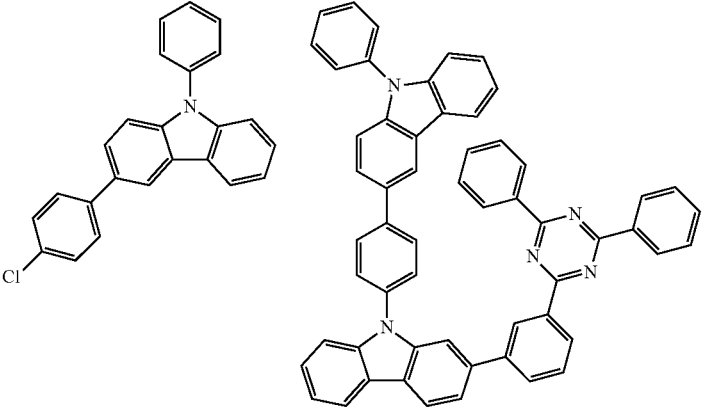 | 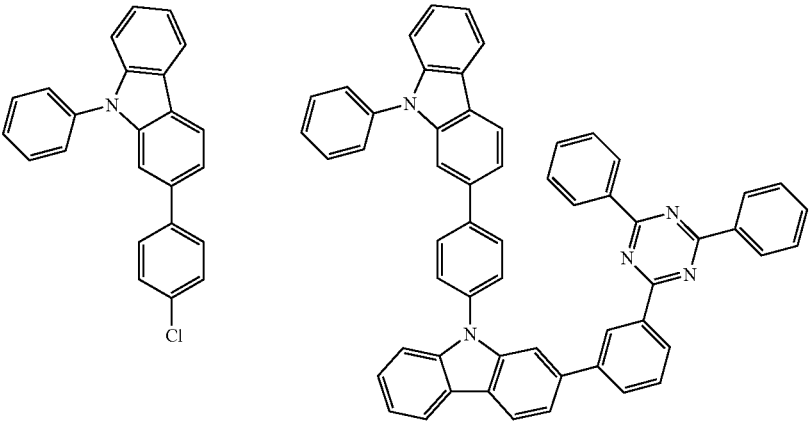 | Light yellow solid | 81 | 792 |
| Preparation Example 44 Chemical Formula 1-6 | P1 | 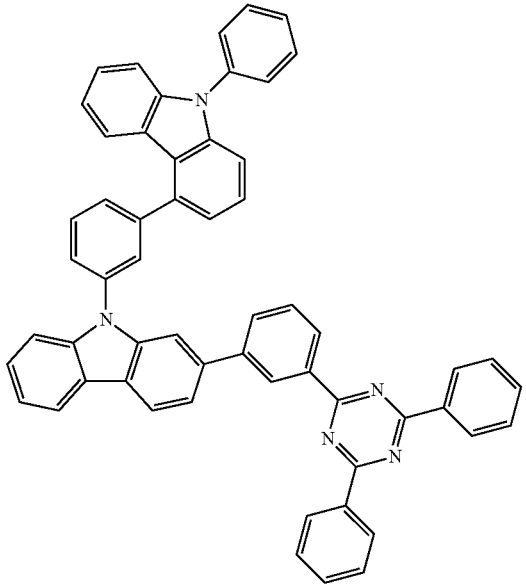 [SMILES: c1ccc(-c2nc(-c3ccccc3)nc(-c3cccc(-c4ccc5c6ccccc6n(-c6cccc(-c7cccc8c7c7ccccc7n8-c7ccccc7)c6)c5c4)c3)n2)cc1] | | Light yellow solid | 79 | 792 |
| Preparation Example 45 Chemical Formula 1-9 | P2 | | | White solid | 56 | 791 |

-continued

| Intermediate 1 (Px) | Intermediate 2 | Chemical Formula | Shape | Yield (%) | MS [M + H] |
|---|---|---|---|---|---|
| Preparation Example 46 Chemical Formula 1-11 | P3 | | White solid | 78 | 791 |
| Preparation Example 47 Chemical Formula 1-15 | P34 | | White solid | 85 | 867 |
| Preparation Example 48 Chemical Formula 1-18 | P34 | | White solid | 83 | 867 |
| Preparation Example 49 Chemical Formula 1-19 | P4 | | Light yellow solid | 66 | 792 |

-continued
| Intermediate 1 (Px) | Intermediate 2 | Chemical Formula | Shape | Yield (%) | MS [M + H] |
|---|---|---|---|---|---|
| Preparation Example 50 Chemical Formula 1-23 | P4 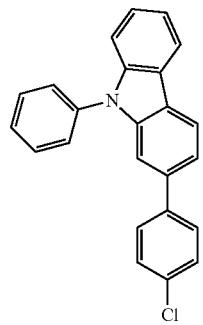 | 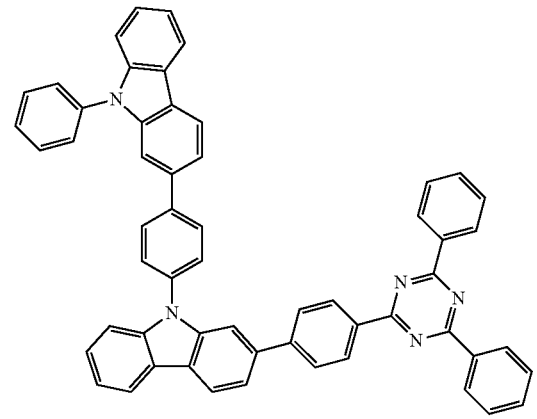 [SMILES: c1ccc(-c2nc(-c3ccccc3)nc(-c3ccc(-c4ccc5c6ccccc6n(-c6ccc(-c7ccc8c9ccccc9n(-c9ccccc9)c8c7)cc6)c5c4)cc3)n2)cc1] | Light yellow solid | 73 | 792 |
| Preparation Example 51 Chemical Formula 1-25 | P5 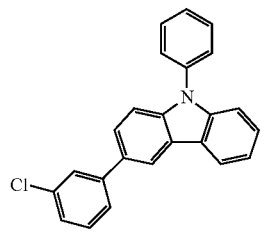 | 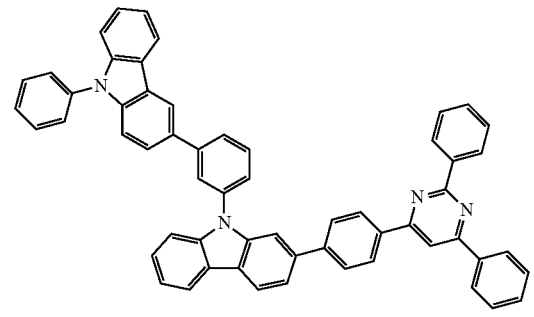 [SMILES: c1ccc(-c2cc(-c3ccc(-c4ccc5c6ccccc6n(-c6cccc(-c7ccc8c(c7)c7ccccc7n8-c7ccccc7)c6)c5c4)cc3)nc(-c3ccccc3)n2)cc1] | White solid | 66 | 791 |
| Preparation Example 52 Chemical Formula 1-29 | P5 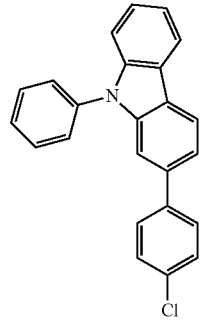 | 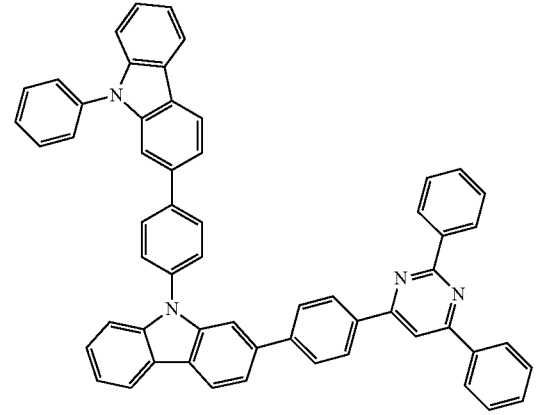 [SMILES: c1ccc(-c2cc(-c3ccc(-c4ccc5c6ccccc6n(-c6ccc(-c7ccc8c9ccccc9n(-c9ccccc9)c8c7)cc6)c5c4)cc3)nc(-c3ccccc3)n2)cc1] | Light yellow solid | 70 | 791 |
| Preparation Example 53 Chemical Formula 1-32 | P6 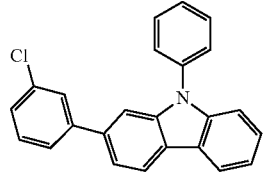 | 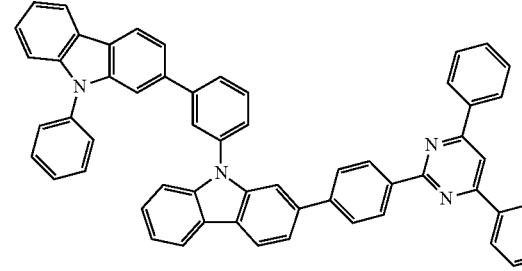 | White solid | 78 | 791 |

| Intermediate 1 (Px) | Intermediate 2 | Chemical Formula | Shape | Yield (%) | MS [M + H] |
|---|---|---|---|---|---|
| Preparation Example 57 Chemical Formula 1-37 | P7 | | White solid | 68 | 793 |
| Preparation Example 58 Chemical Formula 1-40 | P7 | | Light yellow solid | 79 | 793 |
| Preparation Example 56 Chemical Formula 1-41 | P7 | | White solid | 67 | 793 |

| Intermediate 1 (Px) | Intermediate 2 | Chemical Formula | Shape | Yield (%) | MS [M + H] |
|---|---|---|---|---|---|
| Preparation Example 57 Chemical Formula 1-46 | P8 | 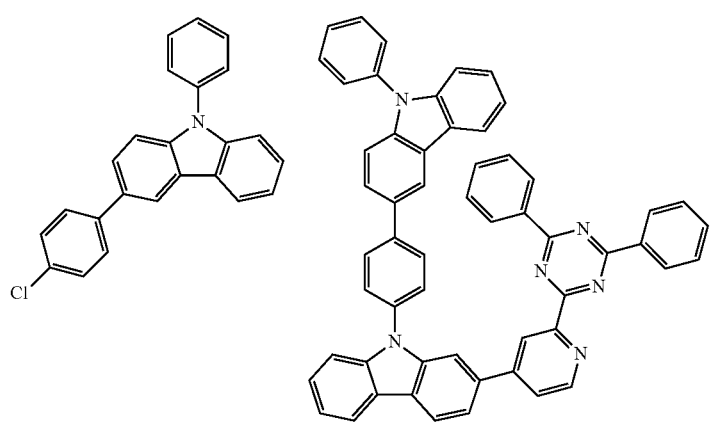 | Light yellow solid | 75 | 793 |
| Preparation Example 58 Chemical Formula 1-53 | P9 | 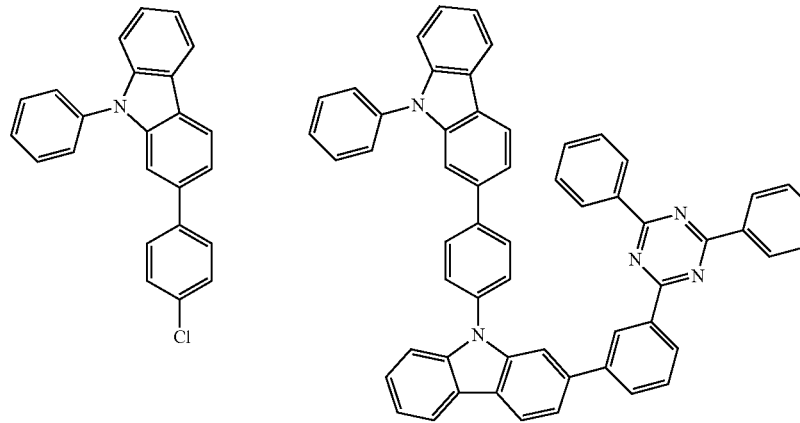 | White solid | 71 | 793 |
| Preparation Example 59 Chemical Formula 1-62 | P10 | 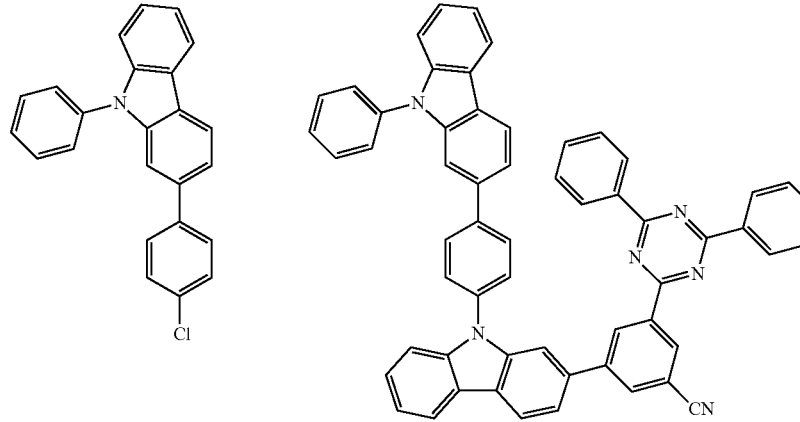 | White solid | 70 | 817 |

-continued
| Intermediate 1 (Px) | Intermediate 2 | Chemical Formula | Shape | Yield (%) | MS [M + H] |
|---|---|---|---|---|---|
| Preparation Example 60 Chemical Formula 1-63 | P11 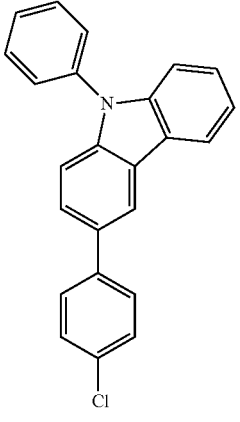 | 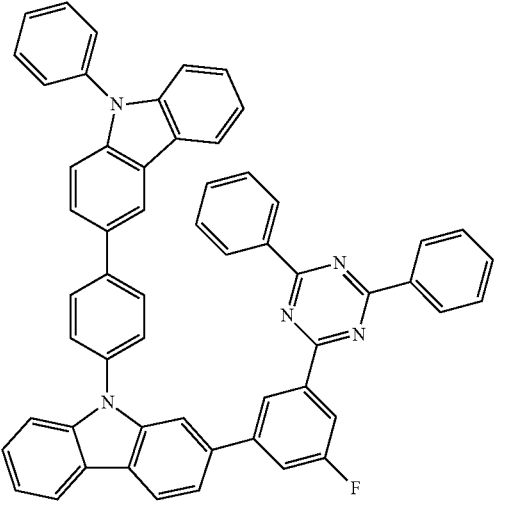 [SMILES: Fc1cc(-c2ccc3c4ccccc4n(-c4ccc(-c5ccc6c(c5)c5ccccc5n6-c5ccccc5)cc4)c3c2)cc(-c2nc(-c3ccccc3)nc(-c3ccccc3)n2)c1] | Light yellow solid | 82 | 810 |
| Preparation Example 61 Chemical Formula 1-69 | P1 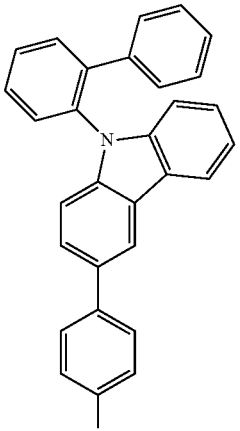 | 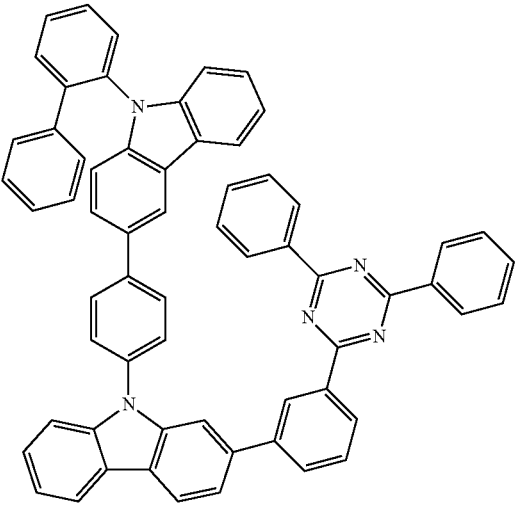 [SMILES: c1ccc(-c2nc(-c3ccccc3)nc(-c3cccc(-c4ccc5c6ccccc6n(-c6ccc(-c7ccc8c(c7)c7ccccc7n8-c7ccccc7-c7ccccc7)cc6)c5c4)c3)n2)cc1] | Light yellow solid | 71 | 868 |
| Preparation Example 62 Chemical Formula 1-70 | P12 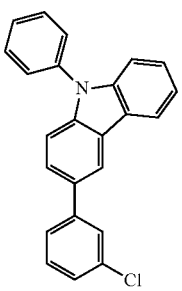 | 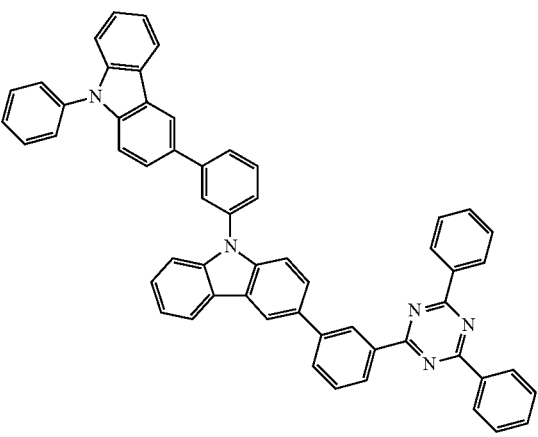 [SMILES: c1ccc(-c2nc(-c3ccccc3)nc(-c3cccc(-c4ccc5c(c4)c4ccccc4n5-c4cccc(-c5ccc6c(c5)c5ccccc5n6-c5ccccc5)c4)c3)n2)cc1] | Light yellow solid | 67 | 792 |

| Intermediate 1 (Px) | Intermediate 2 | Chemical Formula | Shape | Yield (%) | MS [M+H] |
|---|---|---|---|---|---|
| Preparation Example 63 Chemical Formula 1-71 | P12 | 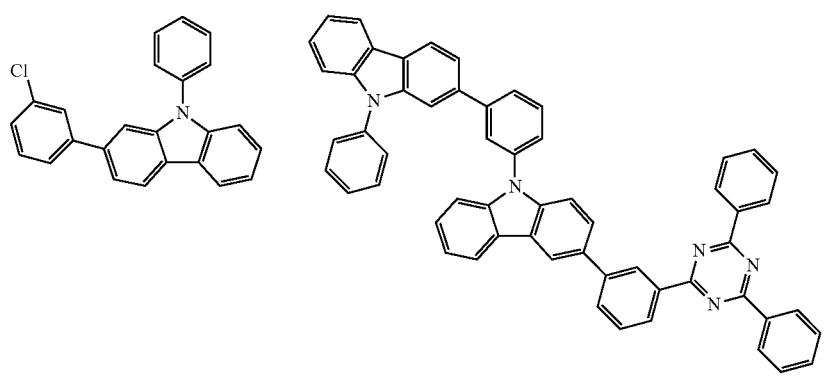 | White solid | 61 | 792 |
| Preparation Example 64 Chemical Formula 1-73 | P12 | 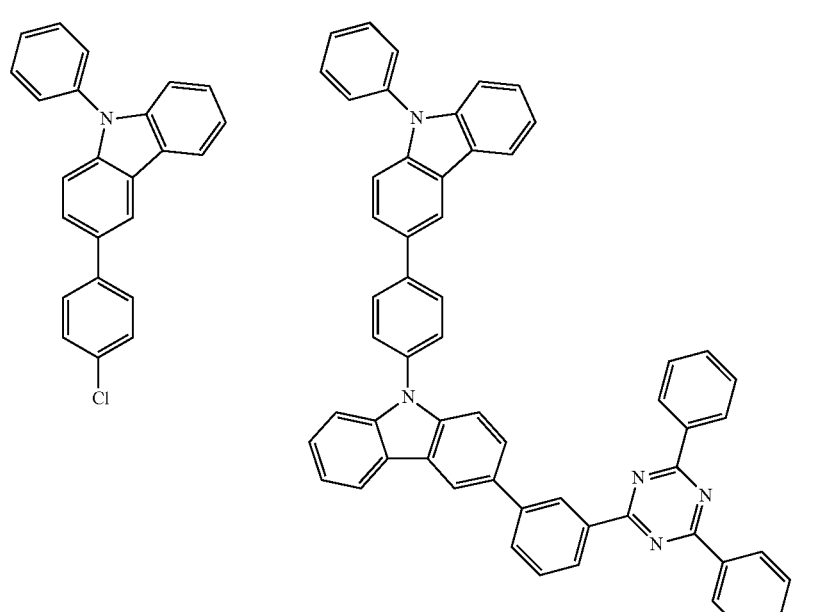 | Light yellow solid | 66 | 792 |

| Intermediate 1 (Px) | Intermediate 2 | Chemical Formula | Shape | Yield (%) | MS [M+H] |
|---|---|---|---|---|---|
| Preparation Example 65 Chemical Formula 1-74 | P12 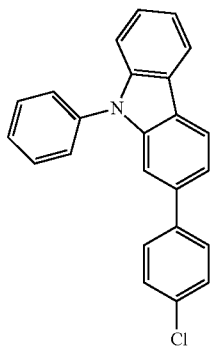 | 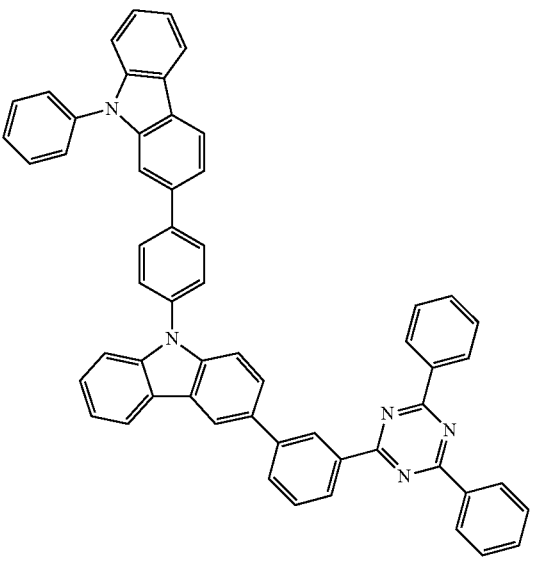 [SMILES: c1ccc(-c2nc(-c3ccccc3)nc(-c3cccc(-c4ccc5c(c4)c4ccccc4n5-c4ccc(-c5ccc6c7ccccc7n(-c7ccccc7)c6c5)cc4)c3)n2)cc1] | 흰색 고체 | 71 | 792 |
| Preparation Example 66 Chemical Formula 1-76 | P13 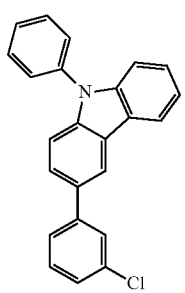 | 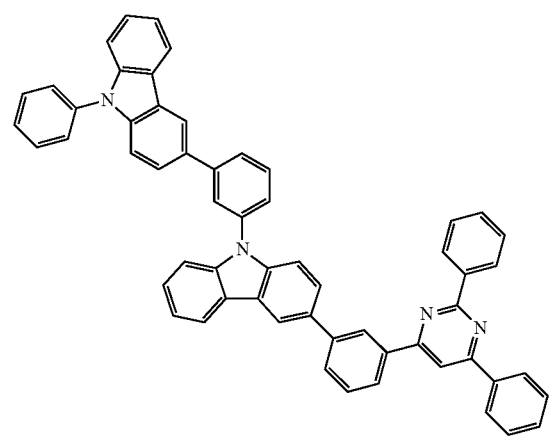 | Light yellow solid | 50 | 791 |

| Intermediate 1 (Px) | Intermediate 2 | Chemical Formula | Shape | Yield (%) | MS [M + H] |
|---|---|---|---|---|---|
| Preparation Example 67 Chemical Formula 1-80 | P14 | | Light yellow solid | 49 | 791 |
| Preparation Example 68 Chemical Formula 1-92 | P15 | | Light yellow solid | 78 | 792 |

| Intermediate 1 (Px) | Intermediate 2 | Chemical Formula | Shape | Yield (%) | MS [M+H] |
|---|---|---|---|---|---|
| Preparation Example 69 Chemical Formula 1-98 | P16 | | Light yellow solid | 78 | 791 |
| Preparation Example 70 Chemical Formula 1-105 | P17 | | Light yellow solid | 69 | 791 |

-continued
| Intermediate 1 (Px) | Intermediate 2 | Chemical Formula | Shape | Yield (%) | MS [M + H] |
|---|---|---|---|---|---|
| Preparation Example 71 Chemical Formula 1-109 | P18 | 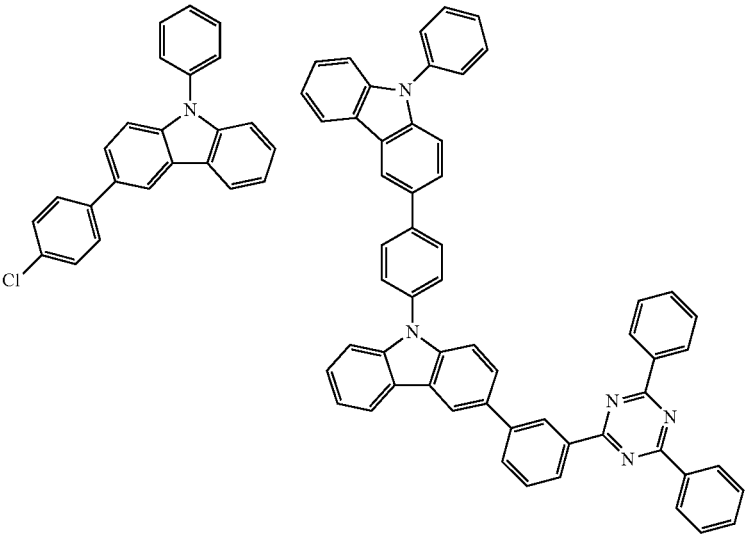 | Light yellow solid | 71 | 793 |
| Preparation Example 70 Chemical Formula 1-105 | P19 | 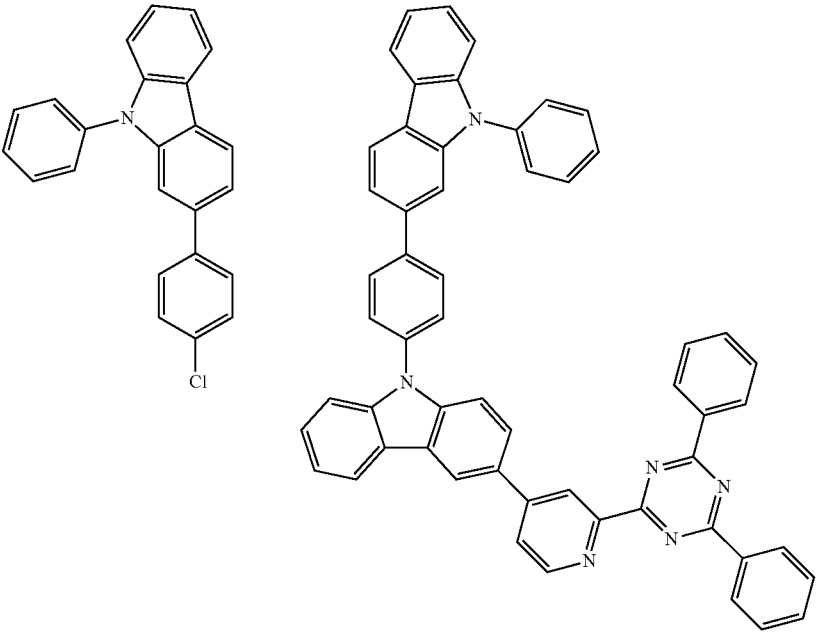 | Light yellow solid | 61 | 793 |

-continued
| Intermediate 1 (Px) | Intermediate 2 | Chemical Formula | Shape | Yield (%) | MS [M + H] |
|---|---|---|---|---|---|
| Preparation Example 71 Chemical Formula 1-109 | P20 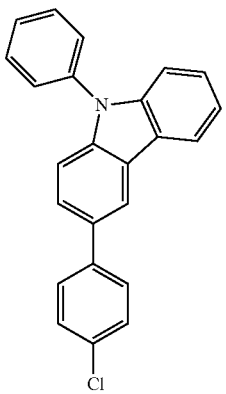 | 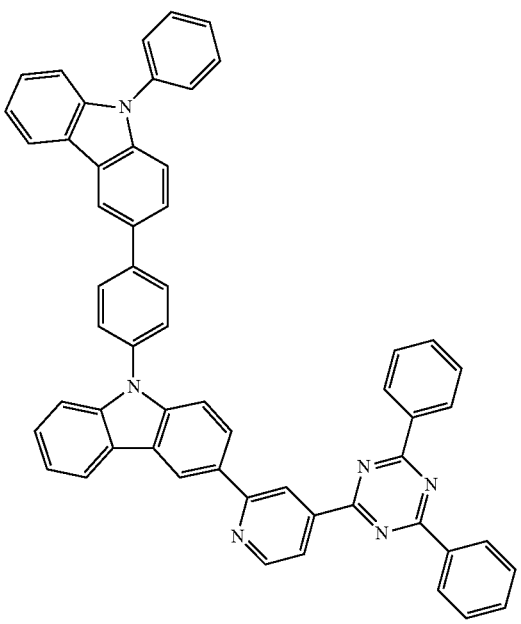 [SMILES: c1ccc(-c2nc(-c3ccccc3)nc(-c3cccc(-c4ccc5c(c4)c4ccccc4n5-c4ccc(-c5ccc6c(c5)c5ccccc5n6-c5ccccc5)cc4)c3)n2)cc1] | Light yellow solid | 65 | 793 |
| Preparation Example 74 Chemical Formula 1-124 | P37 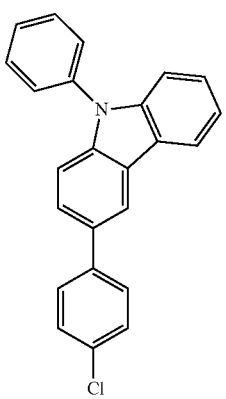 | 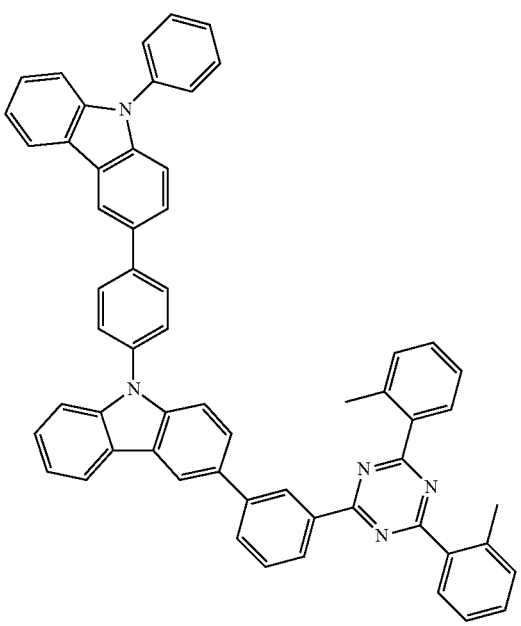 [SMILES: Cc1ccccc1-c1nc(-c2cccc(-c3ccc4c(c3)c3ccccc3n4-c3ccc(-c4ccc5c(c4)c4ccccc4n5-c4ccccc4)cc3)c2)nc(-c2ccccc2C)n1] | Light yellow solid | 62 | 820 |

| Intermediate 1 (Px) | Intermediate 2 | Chemical Formula | Shape | Yield (%) | MS [M + H] |
|---|---|---|---|---|---|
| Preparation Example 75 Chemical Formula 1-128 | P38 | 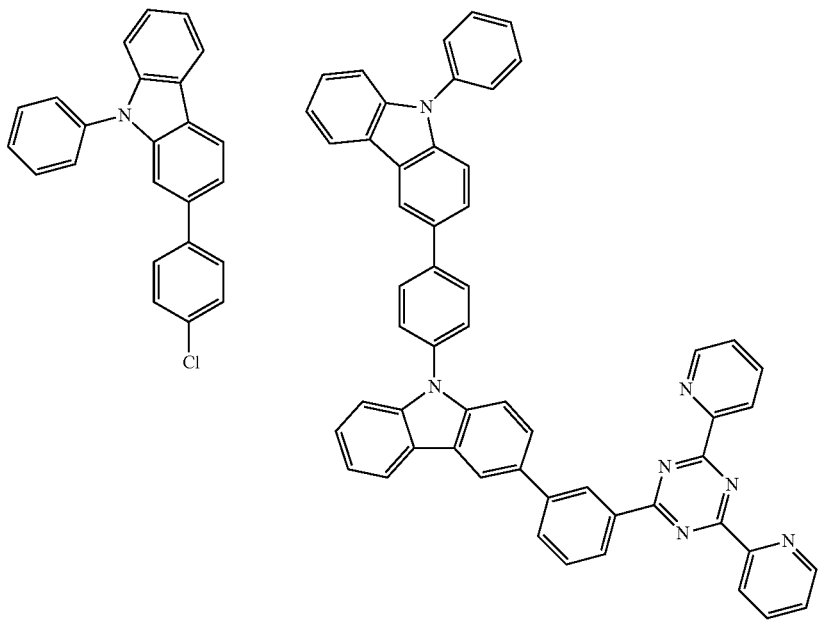 | Light yellow solid | 58 | 794 |
| Preparation Example 76 Chemical Formula 1-131 | P21 | 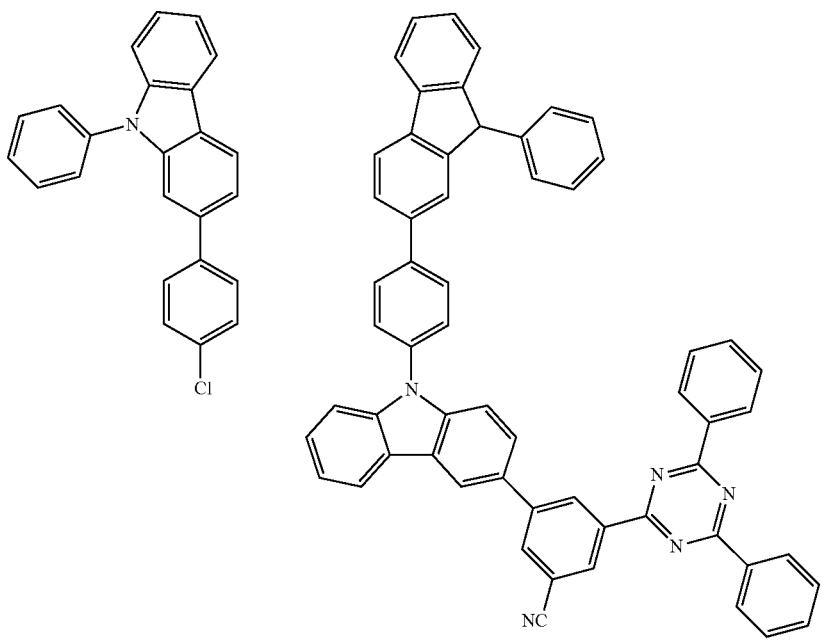 | Light yellow solid | 81 | 817 |

| Intermediate 1 (Px) | Intermediate 2 | Chemical Formula | Shape | Yield (%) | MS [M+H] |
|---|---|---|---|---|---|
| Preparation Example 77 Chemical Formula 1-132 | P22 | 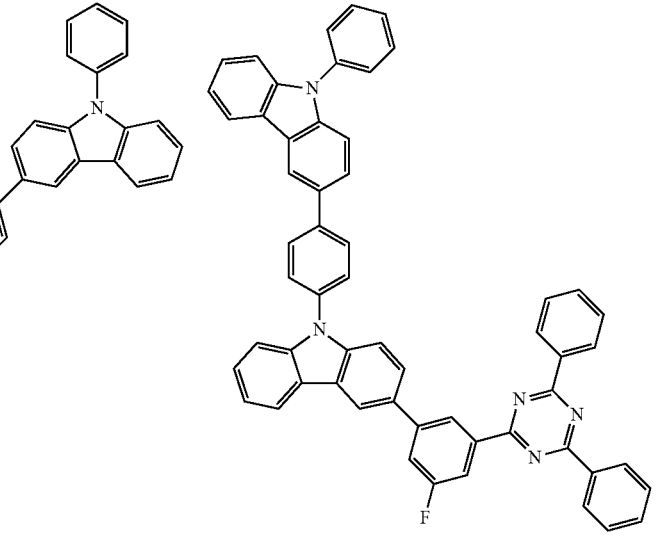 | Light yellow solid | 81 | 810 |
| Preparation Example 78 Chemical Formula 1-142 | P23 | 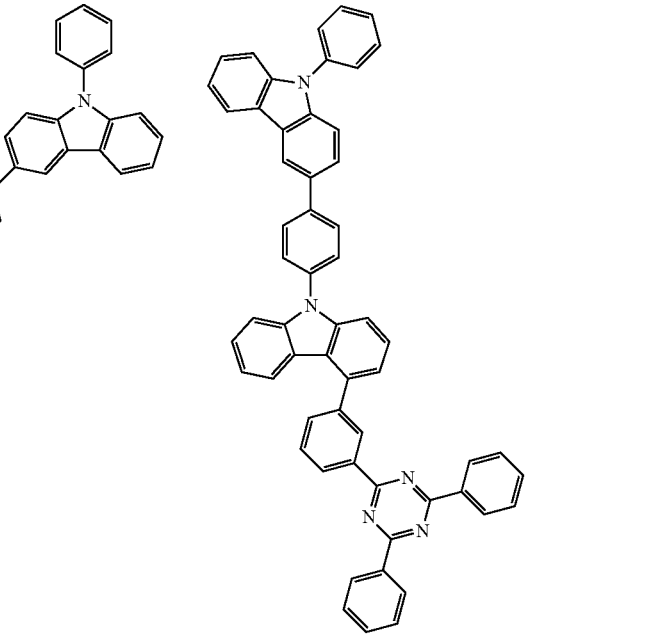 | Light yellow solid | 77 | 792 |

| Intermediate 1 (Px) | Intermediate 2 | Chemical Formula | Shape | Yield (%) | MS [M + H] |
|---|---|---|---|---|---|
| Preparation Example 79 Chemical Formula 1-147 | P24 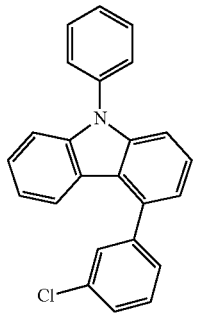 | 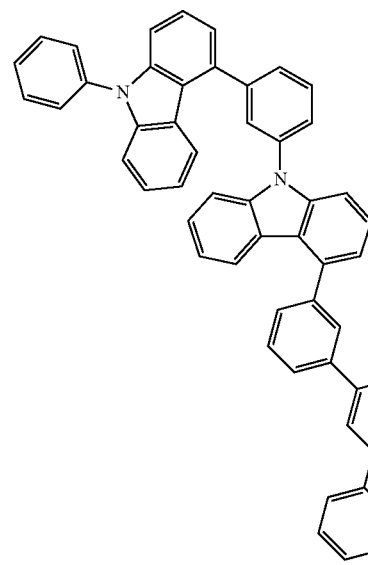 | White solid | 71 | 791 |
| Preparation Example 80 Chemical Formula 1-150 | P25 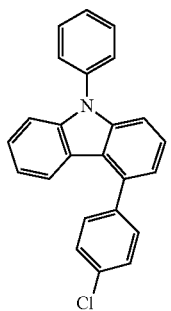 | 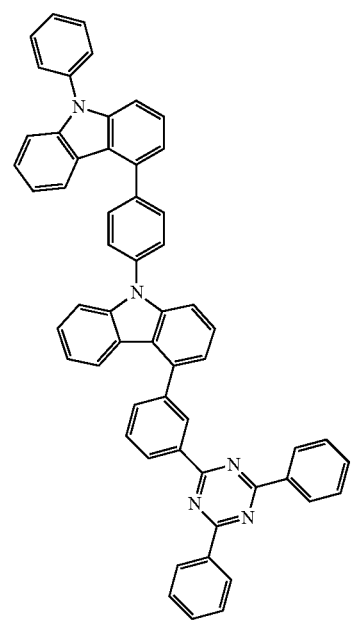 [SMILES: c1ccc(-c2nc(-c3ccccc3)nc(-c3cccc(-c4cccc5c4c4ccccc4n5-c4ccc(-c5cccc6c5c5ccccc5n6-c5ccccc5)cc4)c3)n2)cc1] | White solid | 66 | 791 |

| Intermediate 1 (Px) | Intermediate 2 | Chemical Formula | Shape | Yield (%) | MS [M + H] |
|---|---|---|---|---|---|
| Preparation Example 81 Chemical Formula 1-152 | P35 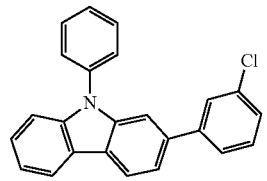 | 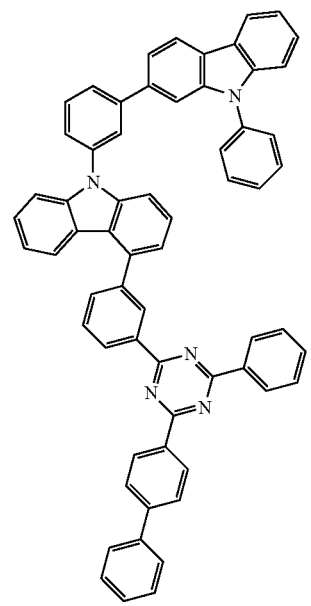 [SMILES: c1ccc(-c2ccc(-c3nc(-c4ccccc4)nc(-c4cccc(-c5cccc6c5c5ccccc5n6-c5cccc(-c6ccc7c8ccccc8n(-c8ccccc8)c7c6)c5)c4)n3)cc2)cc1] | White solid | 75 | 867 |
| Preparation Example 82 Chemical Formula 1-160 | P26 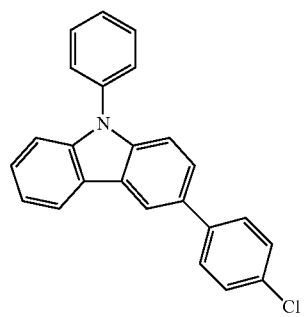 | 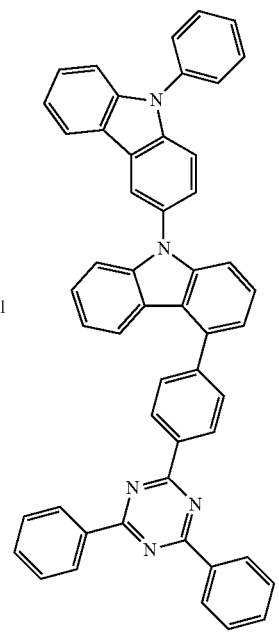 | Light yellow solid | 89 | 792 |

-continued
| Intermediate 1 (Px) | Intermediate 2 | Chemical Formula | Shape | Yield (%) | MS [M + H] |
|---|---|---|---|---|---|
| Preparation Example 83 Chemical Formula 1-165 | P27 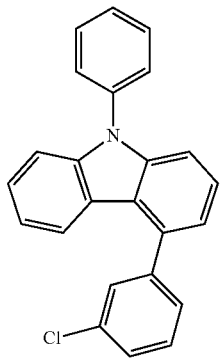 | 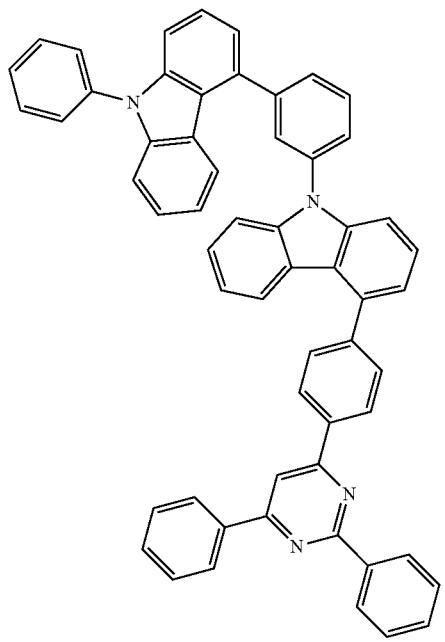 [SMILES: c1ccc(-c2cc(-c3ccc(-c4cccc5c4c4ccccc4n5-c4cccc(-c5cccc6c5c5ccccc5n6-c5ccccc5)c4)cc3)nc(-c3ccccc3)n2)cc1] | White solid | 60 | 791 |
| Preparation Example 84 Chemical Formula 1-173 | P28 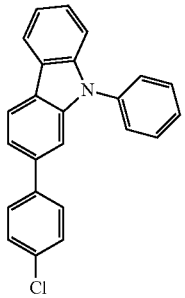 | 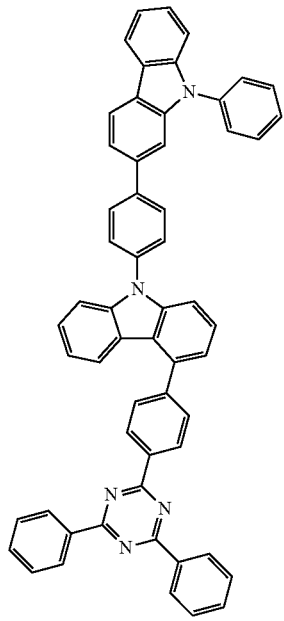 [SMILES: c1ccc(-c2nc(-c3ccccc3)nc(-c3ccc(-c4cccc5c4c4ccccc4n5-c4ccc(-c5ccc6c7ccccc7n(-c7ccccc7)c6c5)cc4)cc3)n2)cc1] | Light yellow solid | 78 | 791 |

| Intermediate 1 (Px) | Intermediate 2 | Chemical Formula | Shape | Yield (%) | MS [M+H] |
|---|---|---|---|---|---|
| Preparation Example 85 Chemical Formula 1-178 | P29 | 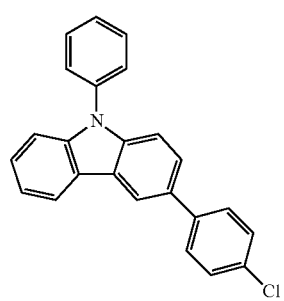 [SMILES: Clc1ccc(-c2ccc3c(c2)c2ccccc2n3-c2ccccc2)cc1] | Light yellow solid | 69 | 793 |
| Preparation Example 86 Chemical Formula 1-185 | P30 | 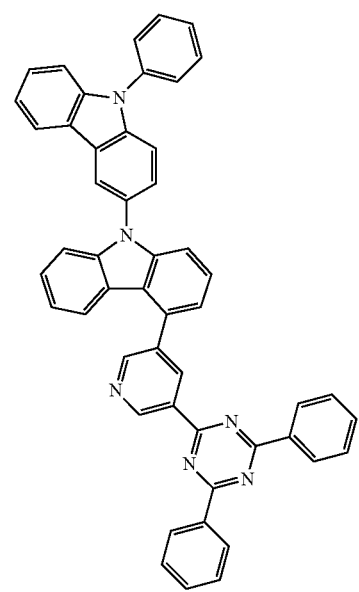 [SMILES: c1ccc(-c2nc(-c3ccccc3)nc(-c3cncc(-c4cccc5c4c4ccccc4n5-c4ccc5c(c4)c4ccccc4n5-c4ccccc4)c3)n2)cc1] | Light yellow solid | 65 | 793 |

-continued
| Intermediate 1 (Px) | Intermediate 2 | Chemical Formula | Shape | Yield (%) | MS [M + H] |
|---|---|---|---|---|---|
| Preparation Example 87 Chemical Formula 1-191 | P31 | 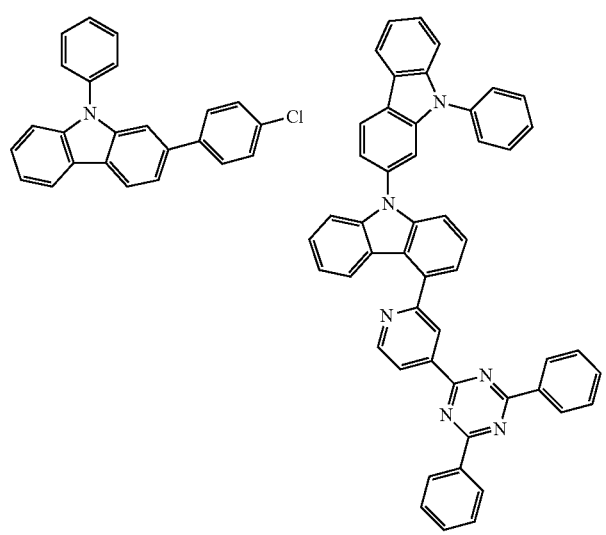 | Light yellow solid | 78 | 793 |
| Preparation Example 88 Chemical Formula 1-200 | P32 | 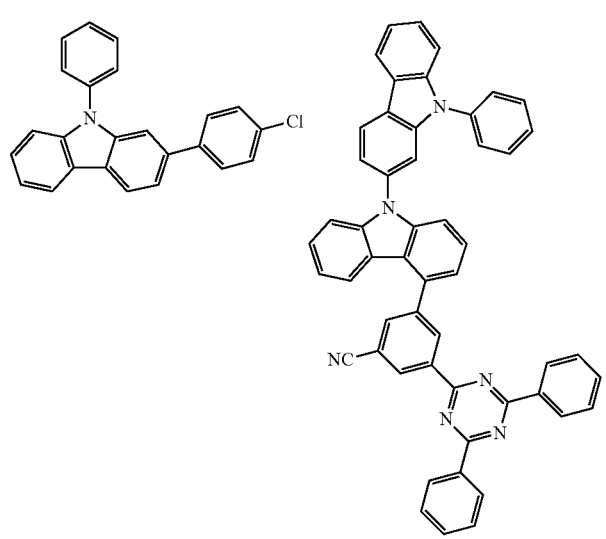 | Light yellow solid | 81 | 817 |

| Intermediate 1 (Px) | Intermediate 2 | Chemical Formula | Shape | Yield (%) | MS [M + H] |
|---|---|---|---|---|---|
| Preparation Example 89 Chemical Formula 1-201 | P33 | 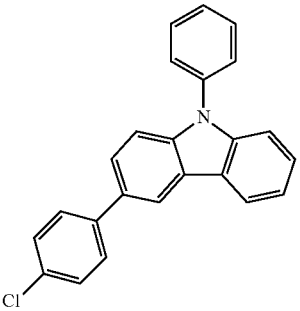 [SMILES: Clc1ccc(-c2ccc3c(c2)c2ccccc2n3-c2ccccc2)cc1] | Light yellow solid | 77 | 810 |
| Preparation Example 90 Chemical Formula 1-211 | P36 | 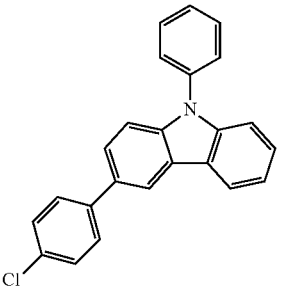 [SMILES: Clc1ccc(-c2ccc3c(c2)c2ccccc2n3-c2ccccc2)cc1] | Light yellow solid | 71 | 908 |
| Preparation Example 91 Chemical Formula 1-214 | P36 | 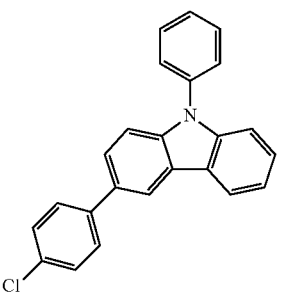 [SMILES: Clc1ccc(-c2ccc3c(c2)c2ccccc2n3-c2ccccc2)cc1] | Light yellow solid | 71 | 908 |

-continued
| Intermediate 1 (Px) | Intermediate 2 | Chemical Formula | Shape | Yield (%) | MS [M + H] |
|---|---|---|---|---|---|
| Preparation Example 92 Chemical Formula 1-219 | P1 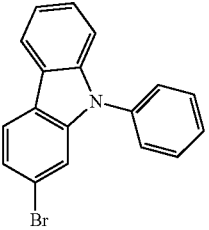 | 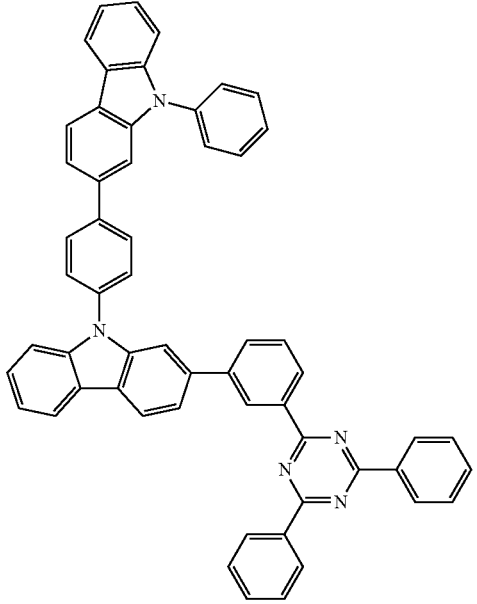 [SMILES: c1ccc(-c2nc(-c3ccccc3)nc(-c3cccc(-c4ccc5c6ccccc6n(-c6ccc(-c7ccc8c9ccccc9n(-c9ccccc9)c8c7)cc6)c5c4)c3)n2)cc1] | White solid | 69 | 716 |
| Preparation Example 93 Chemical Formula 1-221 | P40 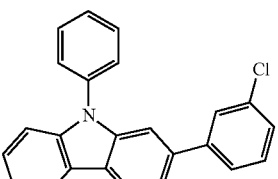 | 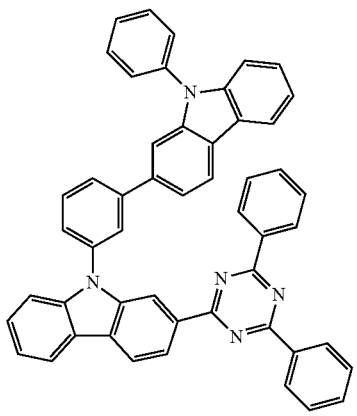 [SMILES: c1ccc(-c2nc(-c3ccccc3)nc(-c3ccc4c5ccccc5n(-c5cccc(-c6ccc7c8ccccc8n(-c8ccccc8)c7c6)c5)c4c3)n2)cc1] | Light yellow solid | 75 | 716 |

| Intermediate 1 (Px) | Intermediate 2 | Chemical Formula | Shape | Yield (%) | MS [M + H] |
|---|---|---|---|---|---|
| Preparation Example 94 Chemical Formula 1-227 | P40 | | yellow solid | 55 | 640 |
| Preparation Example 95 Chemical Formula 1-231 | P1 | | White solid | 55 | 793 |

FIGS. 3 to 16 illustrate data for confirming synthesis of main compounds.

Experimental Example 1

The glass substrate on which a thin film of ITO (indium tin oxide) was applied in a thickness of 1,500 Å was put into distilled water having the detergent dissolved therein and washed by the ultrasonic wave. In this case, the used detergent was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was finished, washing with ultrasonic waves was performed by solvents such as isopropyl alcohol, acetone, and methanol, and the ITO was dried and transported to the plasma washing machine. Further, the substrate was washed by using oxygen plasma for 5 minutes, and then transported to the vacuum deposition machine.

Hexanitrile hexaazatriphenylene (HAT) of the following Chemical Formula was thermally deposited under vacuum in a thicknesses of 500 Å on the ITO transparent electrode thus prepared to form the hole injection layer.

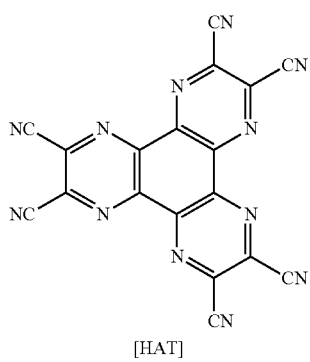

[HAT]

The NPB (N,N-bis-(1-naphthalenyl)-N,N-bis-phenyl-(1,1-biphenyl)-4,4-diamine) compound having the following structure was thermally deposited under vacuum in a thickness of 400 Å on the hole injection layer to form the hole transport layer.

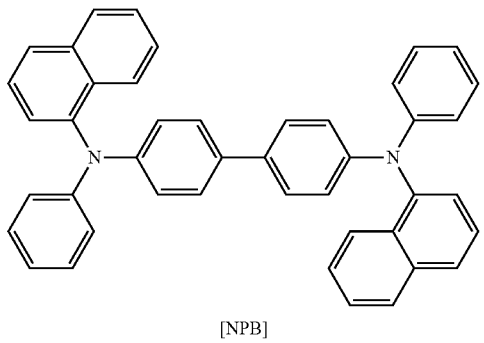

[NPB]

Subsequently, the compound of Chemical Formula 1-1 manufactured in Preparation Example 41 was deposited under vacuum in a film thickness of 300 Å with the Ir(ppy)$_3$ dopant at a concentration of 10% on the hole transport layer to form the light emitting layer.

The following electron transport material was deposited under vacuum in a thickness of 200 Å on the light emitting layer to form the electron injection and transport layer.

[Electron Transport Material]

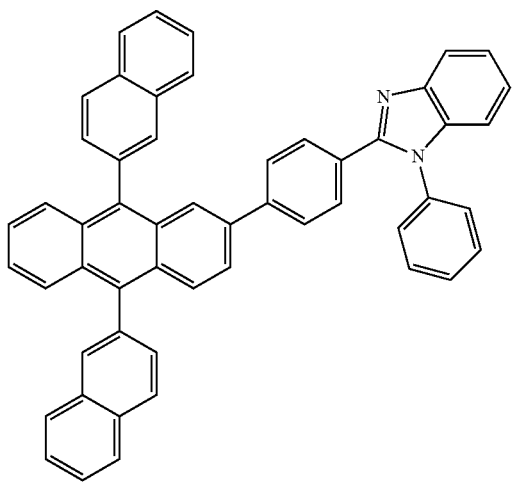 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

Lithium fluoride (LiF) in a thickness of 12 Å and aluminum in a thickness of 2,000 Å were subsequently deposited on the electron injection and transport layer to form the cathode.

In the aforementioned process, the deposition speed of the organic material was maintained at 0.4 to 0.7 Å/sec, the deposition speed of the lithium fluoride of the cathode was maintained at 0.3 Å/sec, the deposition speed of aluminum was maintained at 2 Å/sec, and the degree of vacuum during the deposition was maintained at $2 \times 10^{-7}$ to $5 \times 10^{-8}$ torr.

Experimental Example 2

The same experiment was performed, except that the compound of Chemical Formula 1-2 was used instead of the compound of Chemical Formula 1-1 in Experimental Example 1.

Experimental Example 3

The same experiment was performed, except that the compound of Chemical Formula 1-4 was used instead of the compound of Chemical Formula 1-1 in Experimental Example 1.

Experimental Example 4

The same experiment was performed, except that the compound of Chemical Formula 1-23 was used instead of the compound of Chemical Formula 1-1 in Experimental Example 1.

Experimental Example 5

The same experiment was performed, except that the compound of Chemical Formula 1-29 was used instead of the compound of Chemical Formula 1-1 in Experimental Example 1.

Experimental Example 6

The same experiment was performed, except that the compound of Chemical Formula 1-40 was used instead of the compound of Chemical Formula 1-1 in Experimental Example 1.

Experimental Example 7

The same experiment was performed, except that the compound of Chemical Formula 1-62 was used instead of the compound of Chemical Formula 1-1 in Experimental Example 1.

Experimental Example 8

The same experiment was performed, except that the compound of Chemical Formula 1-74 was used instead of the compound of Chemical Formula 1-1 in Experimental Example 1.

Experimental Example 9

The same experiment was performed, except that the compound of Chemical Formula 1-98 was used instead of the compound of Chemical Formula 1-1 in Experimental Example 1.

Experimental Example 10

The same experiment was performed, except that the compound of Chemical Formula 1-109 was used instead of the compound of Chemical Formula 1-1 in Experimental Example 1.

Experimental Example 11

The same experiment was performed, except that the compound of Chemical Formula 1-142 was used instead of the compound of Chemical Formula 1-1 in Experimental Example 1.

Experimental Example 12

The same experiment was performed, except that the compound of Chemical Formula 1-152 was used instead of the compound of Chemical Formula 1-1 in Experimental Example 1.

Experimental Example 13

The same experiment was performed, except that the compound of Chemical Formula 1-200 was used instead of the compound of Chemical Formula 1-1 in Experimental Example 1.

Experimental Example 14

The same experiment was performed, except that the compound of Chemical Formula 1-211 was used instead of the compound of Chemical Formula 1-1 in Experimental Example 1.

Experimental Example 15

The same experiment was performed, except that the compound of Chemical Formula 1-219 was used instead of the compound of Chemical Formula 1-1 in Experimental Example 1.

Experimental Example 16

The same experiment was performed, except that the compound of Chemical Formula 1-231 was used instead of the compound of Chemical Formula 1-1 in Experimental Example 1.

Comparative Example 1

The same experiment was performed, except that the following H1 was used instead of the compound of Chemical Formula 1-1 in Experimental Example 1.

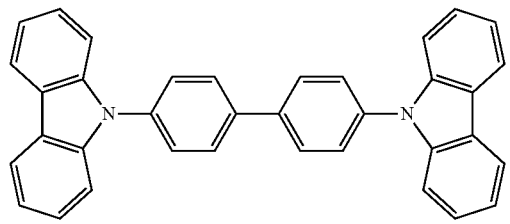

H1

In Experimental Examples 1 to 16 and Comparative Example 1, results of the devices manufactured by using each compound as the light emitting layer are described in Table 1.

TABLE 1

| No. | Host | Dopant | Doping concentration (%) | Driving voltage (V) @5,000 cd/m$^2$ | Light emitting efficiency (Cd/A) |
|---|---|---|---|---|---|
| Comparative Example 1 | H1 | Ir(ppy)$_3$ | 10 | 5.2 | 36 |
| Experimental Example 1 | Chemical Formula 1-1 | Ir(ppy)$_3$ | 10 | 4.7 | 40 |
| Experimental Example 2 | Chemical Formula 1-2 | Ir(ppy)$_3$ | 10 | 4.9 | 45 |
| Experimental Example 3 | Chemical Formula 1-4 | Ir(ppy)$_3$ | 10 | 4.5 | 44 |
| Experimental Example 4 | Chemical Formula 1-23 | Ir(ppy)$_3$ | 10 | 4.4 | 43 |
| Experimental Example 5 | Chemical Formula 1-29 | Ir(ppy)$_3$ | 10 | 4.7 | 42 |
| Experimental Example 6 | Chemical Formula 1-40 | Ir(ppy)$_3$ | 10 | 4.2 | 48 |
| Experimental Example 7 | Chemical Formula 1-62 | Ir(ppy)$_3$ | 10 | 4.3 | 44 |
| Experimental Example 8 | Chemical Formula 1-74 | Ir(ppy)$_3$ | 10 | 4.6 | 47 |
| Experimental Example 9 | Chemical Formula 1-98 | Ir(ppy)$_3$ | 10 | 4.8 | 46 |
| Experimental Example 10 | Chemical Formula 1-109 | Ir(ppy)$_3$ | 10 | 4.7 | 47 |
| Experimental Example 11 | Chemical Formula 1-142 | Ir(ppy)$_3$ | 10 | 4.7 | 41 |
| Experimental Example 12 | Chemical Formula 1-152 | Ir(ppy)$_3$ | 10 | 4.9 | 47 |
| Experimental Example 13 | Chemical Formula 1-200 | Ir(ppy)$_3$ | 10 | 4.4 | 40 |
| Experimental Example 14 | Chemical Formula 1-211 | Ir(ppy)$_3$ | 10 | 4.7 | 47 |

TABLE 1-continued

| No. | Host | Dopant | Doping concentration (%) | Driving voltage (V) @5,000 cd/m² | Light emitting efficiency (Cd/A) |
|---|---|---|---|---|---|
| Experimental Example 15 | Chemical Formula 1-219 | Ir(ppy)₃ | 10 | 4.1 | 49 |
| Experimental Example 16 | Chemical Formula 1-231 | Ir(ppy)₃ | 10 | 4.2 | 48 |

As confirmed in Table 1, Experimental Examples 1 to 16 show that the compound of the present specification can be used as the host of the green light emitting layer and exhibits the low voltage characteristic and improved efficiency as compared to Comparative Example 1.

EXPLANATION OF REFERENCE NUMERALS AND SYMBOLS

1: Substrate
2: Anode
3: Light emitting layer
4: Cathode
5: Hole injection layer
6: Hole transport layer
7: Light emitting layer
8: Electron transport layer

The invention claimed is:

1. A compound represented by the following Chemical Formula 1:

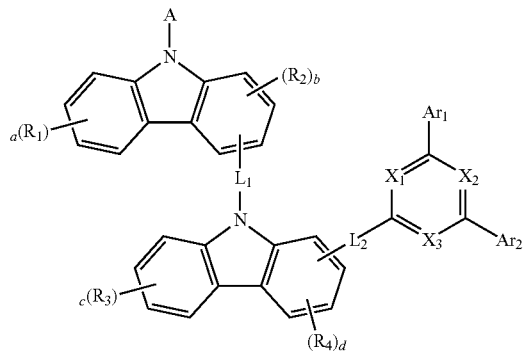

[Chemical Formula 1]

in Chemical Formula 1, $L_1$ is a direct bond, $L_2$ is a substituted or unsubstituted arylene group, $X_1$ is N, $X_2$ is N, and $X_3$ is N, A is hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted phenyl group; or a substituted or unsubstituted biphenyl group, $Ar_1$ and $Ar_2$ are the same as or different from each other, and are each independently hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted aryl group; a substituted or unsubstituted fluorenyl group; or a substituted or unsubstituted aromatic or aliphatic heterocyclic group including one or more of N, O, and S atoms, but do not include a carbazole group, $R_1$ to $R_4$ and $R_{11}$ to $R_{13}$ are the same as or different from each other, and are each independently hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted aryl group; a substituted or unsubstituted fluorenyl group; or a substituted or unsubstituted aromatic or aliphatic heterocyclic group including one or more of N, O, and S atoms, a and c are each an integer of 1 to 4, b and d are each an integer of 1 to 3, in the case where a is 2 or more, and $R_1$s are the same as or different from each other, in the case where b is 2 or more, $R_2$s are the same as or different from each other, in the case where c is 2 or more, $R_3$s are the same as or different from each other, and in the case where d is 2 or more, $R_4$s are the same as or different from each other.

2. The compound of claim 1, wherein Chemical Formula 1 is represented by the following Chemical Formula 2:

[Chemical Formula 2]

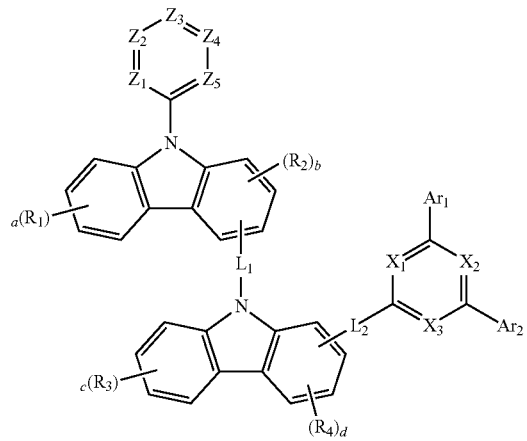

in Chemical Formula 2, $Z_1$ to $Z_5$ are the same as or different from each other, and are each independently $CR_5$, herein, $R_5$ is the same as definitions of $R_1$ to $R_4$, $R_5$s are the same as or different from each other, and a residual substituent group is the same as a matter defined in Chemical Formula 1.

3. The compound of claim 1, wherein A is a phenyl group unsubstituted or substituted by an alkyl group, a phenyl group, or a N-containing monocyclic six-membered heterocyclic group; or a biphenyl group unsubstituted or substituted by an alkyl group, a phenyl group, or a N-containing monocyclic six-membered heterocyclic group.

4. The compound of claim 1, wherein $L_2$ is a substituted or unsubstituted arylene group; or a substituted or unsubstituted divalent heterocyclic group including one or more of N, O, and S atoms.

5. The compound of claim 1, wherein the Structural Formula

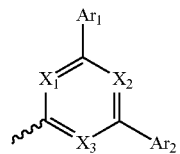

is selected from the following Structural Formulas:

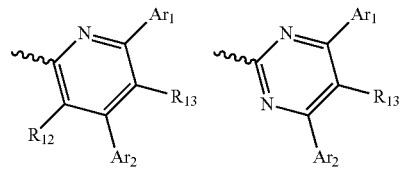

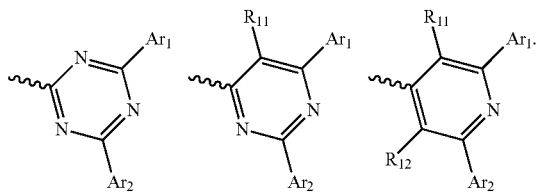

6. The compound of claim 1, wherein $Ar_1$ and $Ar_2$ are the same as or different from each other, and are each independently a phenyl group unsubstituted or substituted by an alkyl group, a phenyl group, or a N-containing heterocyclic group; fluorenyl unsubstituted or substituted by an alkyl group, a phenyl group, or a N-containing heterocyclic group; or a N-containing heterocyclic group unsubstituted or substituted by an alkyl group, a phenyl group, or a N-containing heterocyclic group.

7. The compound of claim 1, wherein Chemical Formula 1 is selected from Chemical Formulas of the following Table:

Chemical Formula 1-217

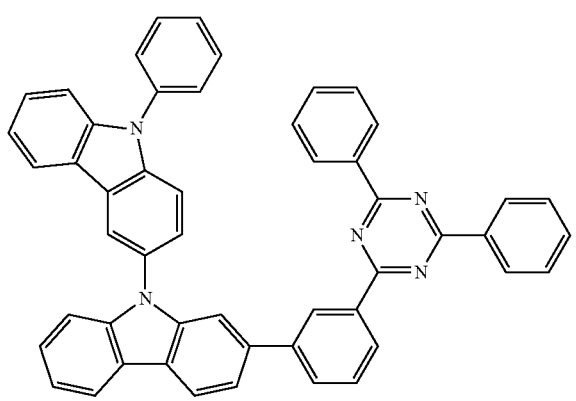 [SMILES: c1ccc(-c2nc(-c3ccccc3)nc(-c3cccc(-c4ccc5c6ccccc6n(-c6ccc7c(c6)c6ccccc6n7-c6ccccc6)c5c4)c3)n2)cc1]

Chemical Formula 1-218
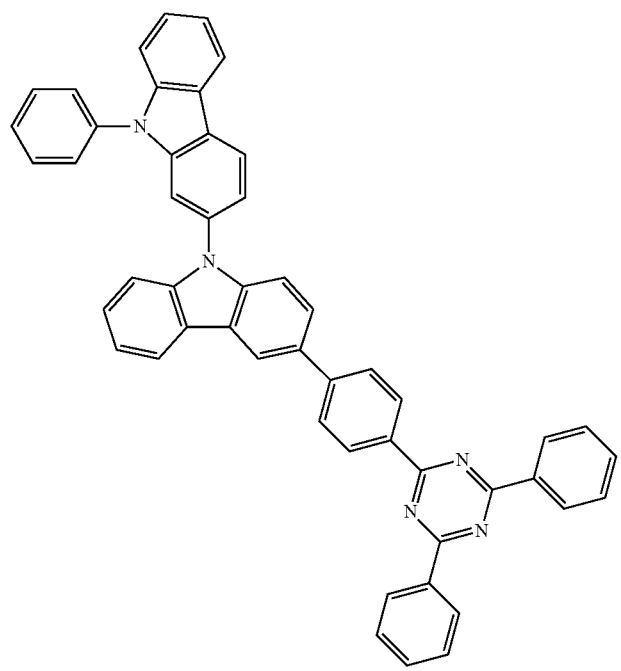 [SMILES: c1ccc(-c2nc(-c3ccccc3)nc(-c3ccc(-c4ccc5c(c4)c4ccccc4n5-c4ccc5c6ccccc6n(-c6ccccc6)c5c4)cc3)n2)cc1]
Chemical Formula 1-219
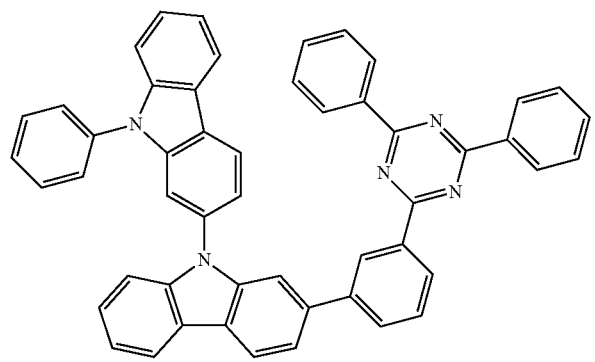 [SMILES: c1ccc(-c2nc(-c3ccccc3)nc(-c3cccc(-c4ccc5c6ccccc6n(-c6ccc7c8ccccc8n(-c8ccccc8)c7c6)c5c4)c3)n2)cc1]
Chemical Formula 1-223
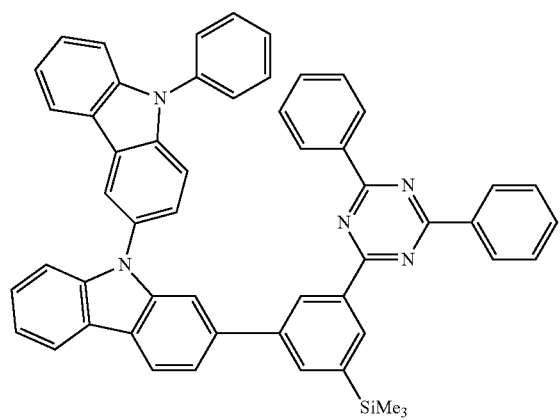 [SMILES: C[Si](C)(C)c1cc(-c2ccc3c4ccccc4n(-c4ccc5c(c4)c4ccccc4n5-c4ccccc4)c3c2)cc(-c2nc(-c3ccccc3)nc(-c3ccccc3)n2)c1]

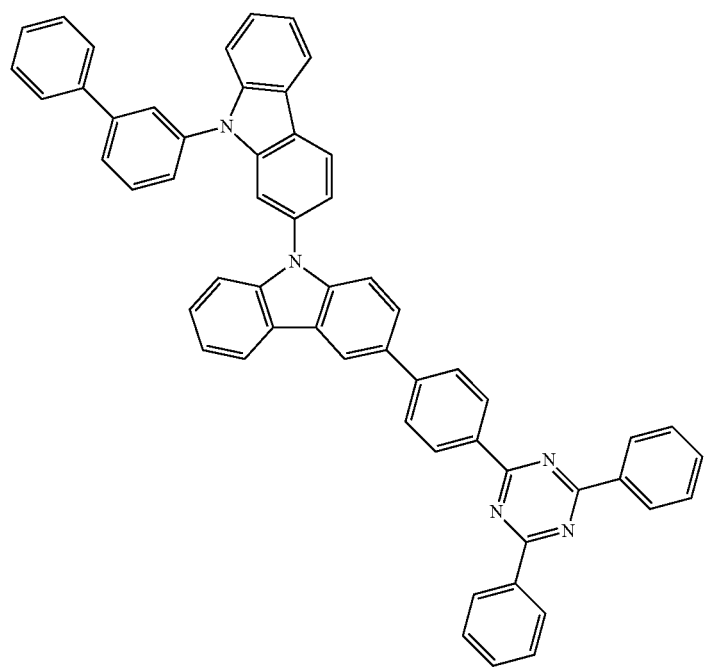 [SMILES: c1ccc(-c2cccc(-n3c4ccccc4c4ccc(-n5c6ccccc6c6cc(-c7ccc(-c8nc(-c9ccccc9)nc(-c9ccccc9)n8)cc7)ccc65)cc43)c2)cc1]
Chemical Formula 1-230
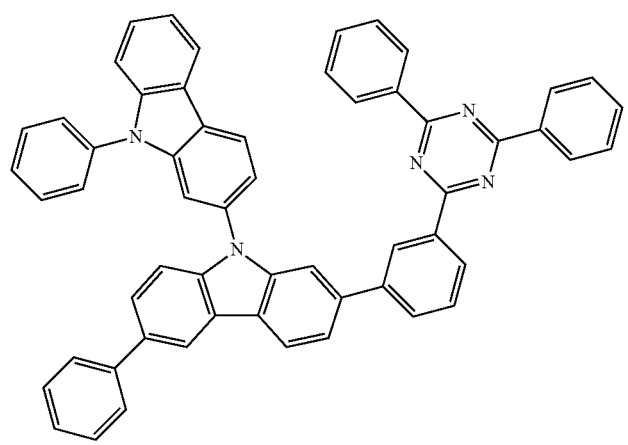 [SMILES: c1ccc(-c2ccc3c(c2)c2ccc(-c4cccc(-c5nc(-c6ccccc6)nc(-c6ccccc6)n5)c4)cc2n3-c2ccc3c4ccccc4n(-c4ccccc4)c3c2)cc1]
Chemical Formula 1-233
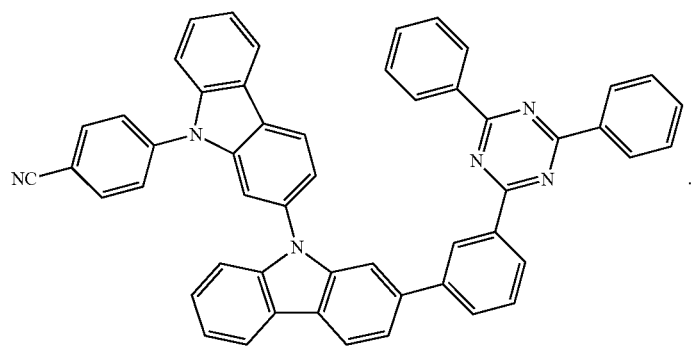 [SMILES: N#Cc1ccc(-n2c3ccccc3c3ccc(-n4c5ccccc5c5ccc(-c6cccc(-c7nc(-c8ccccc8)nc(-c8ccccc8)n7)c6)cc54)cc32)cc1]
Chemical Formula 1-234

8. An organic light emitting device comprising:
a first electrode;
a second electrode provided to face the first electrode; and
one or more organic material layers provided between the first electrode and the second electrode,
wherein one or more of the organic material layers include the compound according to claim 1.

9. The organic light emitting device of claim 8, wherein the organic material layer including the compound is a light emitting layer.

10. The organic light emitting device of claim 9, wherein the light emitting layer is a phosphorescent light emitting layer.

11. The organic light emitting device of claim 9, wherein the light emitting layer further includes a phosphorescent material.

\* \* \* \* \*